(12) United States Patent
Glick et al.

(10) Patent No.: US 10,532,088 B2
(45) Date of Patent: Jan. 14, 2020

(54) ADOPTIVE CELLULAR THERAPY USING AN AGONIST OF RETINOIC ACID RECEPTOR-RELATED ORPHAN RECEPTOR GAMMA AND RELATED THERAPEUTIC METHODS

(71) Applicant: Lycera Corporation, Ann Arbor, MI (US)

(72) Inventors: Gary D. Glick, Ann Arbor, MI (US); Peter L. Toogood, Ann Arbor, MI (US); Xiao Hu, Northville, MI (US); Thomas D. Aicher, Ann Arbor, MI (US); Laura Lee Celeste, Ann Arbor, MI (US); Xikui Liu, Ann Arbor, MI (US); Clarke B. Taylor, Ann Arbor, MI (US); Chad A. Van Huis, Hartland, MI (US)

(73) Assignee: Lycera Corporation, Ann Arbor, MA (US)

( * ) Notice: Subject to any disclaimer, the term of this patent is extended or adjusted under 35 U.S.C. 154(b) by 552 days.

(21) Appl. No.: 15/120,798

(22) PCT Filed: Feb. 27, 2015

(86) PCT No.: PCT/US2015/017977
§ 371 (c)(1),
(2) Date: Aug. 23, 2016

(87) PCT Pub. No.: WO2015/131035
PCT Pub. Date: Sep. 3, 2015

(65) Prior Publication Data
US 2017/0007686 A1 Jan. 12, 2017

Related U.S. Application Data

(60) Provisional application No. 61/945,431, filed on Feb. 27, 2014.

(51) Int. Cl.
| | | |
|---|---|---|
| *A61K 35/17* | (2015.01) |
| *A61K 31/4353* | (2006.01) |
| *A61K 31/437* | (2006.01) |
| *A61K 31/4375* | (2006.01) |
| *A61K 31/47* | (2006.01) |
| *A61K 31/4709* | (2006.01) |
| *A61K 31/538* | (2006.01) |
| *C12N 5/0783* | (2010.01) |
| *A61K 39/00* | (2006.01) |
| *A61K 35/15* | (2015.01) |
| *A61K 39/02* | (2006.01) |

(52) U.S. Cl.
CPC ........ *A61K 39/0011* (2013.01); *A61K 31/437* (2013.01); *A61K 31/4353* (2013.01); *A61K 31/4375* (2013.01); *A61K 31/47* (2013.01); *A61K 31/4709* (2013.01); *A61K 31/538* (2013.01); *A61K 35/15* (2013.01); *A61K 35/17* (2013.01); *A61K 39/0002* (2013.01); *A61K 39/02* (2013.01); *C12N 5/0636* (2013.01); *C12N 5/0646* (2013.01); *A61K 2039/5158* (2013.01); *A61K 2039/54* (2013.01); *C12N 2501/20* (2013.01); *C12N 2501/385* (2013.01); *C12N 2501/999* (2013.01); *C12N 2510/00* (2013.01)

(58) Field of Classification Search
CPC .. A61K 31/538; A61K 31/4709; A61K 31/47; A61K 31/4375; A61K 31/437; A61K 31/4353; A61K 35/17
See application file for complete search history.

(56) References Cited

U.S. PATENT DOCUMENTS

| | | |
|---|---|---|
| 3,803,184 A | 4/1974 | Njimi et al. |
| 3,936,478 A | 2/1976 | Takeshita et al. |
| 5,229,109 A | 7/1993 | Grimm et al. |
| 5,229,115 A | 7/1993 | Lynch |
| 5,583,152 A | 12/1996 | Bernstein et al. |
| 5,776,451 A | 7/1998 | Hsu et al. |
| 5,985,903 A | 11/1999 | Assmann et al. |
| 6,020,354 A | 2/2000 | Assmann et al. |
| 6,037,367 A | 3/2000 | Christensen, IV et al. |
| 6,160,001 A | 12/2000 | Assmann et al. |
| 6,172,092 B1 | 1/2001 | Assmann et al. |
| 6,180,643 B1 | 1/2001 | Zablocki et al. |
| 6,348,032 B1 | 2/2002 | Sperl et al. |
| 6,352,985 B1 | 3/2002 | Yamasaki et al. |
| 6,387,939 B1 | 5/2002 | Assmann et al. |
| 6,392,010 B1 | 5/2002 | Salvino et al. |
| 6,403,607 B1 | 6/2002 | Hidaka et al. |
| 6,440,973 B1 | 8/2002 | Zablocki et al. |
| 6,534,535 B1 | 3/2003 | Zhu et al. |
| 6,605,634 B2 | 8/2003 | Zablocki et al. |
| 6,638,960 B2 | 10/2003 | Assmann et al. |
| 6,683,091 B2 | 1/2004 | Asberom et al. |
| 6,828,344 B1 | 12/2004 | Seehra et al. |
| 7,084,176 B2 | 8/2006 | Morie et al. |
| 7,115,750 B1 | 10/2006 | Kato et al. |
| 7,138,401 B2 | 11/2006 | Kasibhatla et al. |

(Continued)

FOREIGN PATENT DOCUMENTS

| | | |
|---|---|---|
| EP | 0882718 A1 | 12/1998 |
| EP | 1531848 A2 | 5/2005 |

(Continued)

OTHER PUBLICATIONS

Restifo et al., Nat Rev Immunol. Mar. 22, 2012;12(4):269-281 (Year: 2012).*

(Continued)

Primary Examiner — Daniel C Gamett
(74) Attorney, Agent, or Firm — Dechert LLP

(57) ABSTRACT

The invention relates to medical therapy using an agonist of the retinoic acid receptor-related orphan receptor gamma (RORγ) and provides adoptive cellular therapies using an agonist of RORγ, populations of lymphocyte cells that have been exposed to an agonist of RORγ, populations of dendritic cells that have been exposed to an agonist of RORγ, pharmaceutical compositions, and methods for enhancing therapeutic effects of lymphocyte cells and/or dendritic cells in a patient by administering an agonist of RORγ to a patient.

37 Claims, 6 Drawing Sheets

(56) References Cited

U.S. PATENT DOCUMENTS

| | | |
|---|---|---|
| 7,329,675 B2 | 2/2008 | Cox et al. |
| 7,420,059 B2 | 9/2008 | O'Connor et al. |
| 7,482,342 B2 | 1/2009 | D'Orchymont et al. |
| 7,569,571 B2 | 8/2009 | Dong et al. |
| 7,652,043 B2 | 1/2010 | Beachy et al. |
| 7,696,200 B2 | 4/2010 | Ackermann et al. |
| 7,713,996 B2 | 5/2010 | Ackermann et al. |
| 7,741,495 B2 | 6/2010 | Liou et al. |
| 7,799,933 B2 | 9/2010 | Ceccarelli et al. |
| 7,973,135 B2 | 7/2011 | Liik et al. |
| 7,993,638 B2 | 8/2011 | Cai et al. |
| 7,998,736 B2 | 8/2011 | Morgan et al. |
| 8,067,608 B2 | 11/2011 | Beachy et al. |
| 8,383,099 B2 | 2/2013 | Dudley et al. |
| 8,389,738 B2 | 3/2013 | Kousaka et al. |
| 8,389,739 B1 | 3/2013 | Thacher et al. |
| 8,541,185 B2 | 9/2013 | Oved et al. |
| 8,741,812 B2 | 6/2014 | Javitt |
| 9,095,583 B2 | 8/2015 | Karstens et al. |
| 9,266,827 B2 | 2/2016 | Aicher et al. |
| 9,394,315 B2 | 7/2016 | Aicher et al. |
| 9,487,490 B2 | 11/2016 | Barr et al. |
| 9,512,111 B2 | 12/2016 | Glick et al. |
| 9,556,168 B2 | 1/2017 | Barr et al. |
| 9,603,838 B2 | 3/2017 | Karstens et al. |
| 9,657,033 B2 | 5/2017 | Aicher et al. |
| 9,663,502 B2 | 5/2017 | Aicher et al. |
| 9,663,522 B2 | 5/2017 | Barr et al. |
| 9,783,511 B2 | 10/2017 | Aicher et al. |
| 9,802,958 B2 | 10/2017 | Aicher et al. |
| 9,809,561 B2 | 10/2017 | Aicher et al. |
| 9,896,441 B2 | 2/2018 | Aicher et al. |
| 10,208,061 B2 | 2/2019 | Aicher et al. |
| 2005/0037925 A1 | 2/2005 | Tsukamoto et al. |
| 2006/0004000 A1 | 1/2006 | D'Orchymont et al. |
| 2006/0100230 A1 | 5/2006 | Bischoff et al. |
| 2007/0010537 A1 | 1/2007 | Hamamura et al. |
| 2007/0010670 A1 | 1/2007 | Hirata et al. |
| 2007/0049556 A1 | 3/2007 | Zhang et al. |
| 2007/0060567 A1 | 3/2007 | Ackermann et al. |
| 2007/0154487 A1 | 7/2007 | Littman et al. |
| 2007/0185136 A1 | 8/2007 | Courtemanche et al. |
| 2007/0191603 A1 | 8/2007 | Ackermann et al. |
| 2007/0197782 A1 | 8/2007 | Clough et al. |
| 2007/0219257 A1 | 9/2007 | Beachy et al. |
| 2007/0232661 A1 | 10/2007 | Beachy et al. |
| 2007/0281922 A1 | 12/2007 | Liu et al. |
| 2008/0027002 A1 | 1/2008 | Liik et al. |
| 2008/0027100 A1 | 1/2008 | McCormick et al. |
| 2008/0058386 A1 | 3/2008 | Liou et al. |
| 2008/0153805 A1 | 6/2008 | Ceccarelli et al. |
| 2008/0199486 A1 | 8/2008 | Argon et al. |
| 2008/0305169 A1 | 12/2008 | Miki et al. |
| 2009/0005410 A1 | 1/2009 | Charvat et al. |
| 2009/0042851 A1 | 2/2009 | Despeyroux et al. |
| 2009/0075973 A1 | 3/2009 | Newcom et al. |
| 2009/0131523 A1 | 5/2009 | Yosef |
| 2009/0247502 A1 | 10/2009 | Newcom et al. |
| 2009/0275586 A1 | 11/2009 | Govek et al. |
| 2010/0022515 A1 | 1/2010 | Alper et al. |
| 2010/0087376 A1 | 4/2010 | Kazantseva et al. |
| 2010/0130484 A1 | 5/2010 | Ackermann et al. |
| 2010/0234340 A1 | 9/2010 | Schunk et al. |
| 2010/0310533 A1 | 12/2010 | Yee |
| 2011/0053915 A1 | 3/2011 | Ivaschenko et al. |
| 2011/0112070 A1 | 5/2011 | Baldwin et al. |
| 2011/0118246 A1 | 5/2011 | Baldwin et al. |
| 2011/0130384 A1 | 6/2011 | Setoh et al. |
| 2011/0142814 A1 | 6/2011 | Zanin-Zhorov et al. |
| 2011/0151478 A1 | 6/2011 | Liik et al. |
| 2011/0178063 A1 | 7/2011 | Baldwin et al. |
| 2011/0229504 A1 | 9/2011 | Fritsche et al. |
| 2011/0236363 A1 | 9/2011 | Chang et al. |
| 2012/0135011 A1 | 5/2012 | Podack et al. |
| 2013/0039911 A1 | 2/2013 | Bedi et al. |
| 2013/0045191 A1 | 2/2013 | Weinschenk et al. |
| 2013/0102075 A1 | 4/2013 | Vera et al. |
| 2013/0102542 A1 | 4/2013 | Kazantseva et al. |
| 2014/0038942 A1 | 2/2014 | Karstens et al. |
| 2014/0088094 A1 | 3/2014 | Glick et al. |
| 2014/0186295 A1 | 7/2014 | Kupper et al. |
| 2014/0187504 A1 | 7/2014 | Chaturvedi |
| 2014/0187554 A1 | 7/2014 | Kamenecka et al. |
| 2014/0314795 A1 | 10/2014 | Riddell et al. |
| 2014/0343023 A1 | 11/2014 | Wolfrum et al. |
| 2015/0017120 A1 | 1/2015 | Wittrup et al. |
| 2015/0111877 A1 | 4/2015 | Aicher et al. |
| 2015/0126493 A1 | 5/2015 | Aicher et al. |
| 2015/0133437 A1 | 5/2015 | Aicher et al. |
| 2015/0191434 A1 | 7/2015 | Barr et al. |
| 2015/0210687 A1 | 7/2015 | Barr et al. |
| 2015/0218096 A1 | 8/2015 | Barr et al. |
| 2015/0218169 A1 | 8/2015 | Barr et al. |
| 2015/0297566 A1 | 10/2015 | Karstens et al. |
| 2016/0304476 A1 | 10/2016 | Aicher et al. |
| 2016/0304505 A1 | 10/2016 | Aicher et al. |
| 2016/0311787 A1 | 10/2016 | Aicher et al. |
| 2016/0318951 A1 | 11/2016 | Aicher et al. |
| 2017/0183331 A1 | 6/2017 | Aicher et al. |
| 2017/0190659 A1 | 7/2017 | Aicher et al. |
| 2017/0313722 A1 | 11/2017 | Aicher et al. |
| 2018/0030005 A1 | 2/2018 | Aicher et al. |
| 2018/0179224 A1 | 6/2018 | Aicher et al. |
| 2018/0208587 A1 | 7/2018 | Aicher et al. |
| 2018/0265502 A1 | 9/2018 | Aicher et al. |

FOREIGN PATENT DOCUMENTS

| | | |
|---|---|---|
| EP | 1768662 A2 | 4/2007 |
| EP | 1820515 A1 | 8/2007 |
| EP | 2038301 A2 | 3/2009 |
| EP | 2158327 A2 | 3/2010 |
| EP | 2181710 A1 | 5/2010 |
| EP | 2321407 A1 | 5/2011 |
| EP | 2462165 A1 | 6/2012 |
| EP | 2542590 A2 | 1/2013 |
| EP | 2547354 A2 | 1/2013 |
| EP | 2158327 B1 | 5/2013 |
| EP | 2649086 A1 | 10/2013 |
| EP | 2688594 A2 | 1/2014 |
| EP | 2689010 A1 | 1/2014 |
| EP | 2825197 A1 | 1/2015 |
| JP | 6-250441 A | 9/1994 |
| JP | 2000-511558 A | 9/2000 |
| JP | 2004307487 A | 11/2004 |
| JP | 2006-512357 A | 4/2006 |
| JP | 2013-541597 A | 11/2013 |
| JP | 2017-507950 A | 3/2017 |
| JP | 2018-515491 A | 6/2018 |
| WO | WO-92/13856 A1 | 8/1992 |
| WO | WO-97/01561 A1 | 1/1997 |
| WO | WO-97/48697 A1 | 12/1997 |
| WO | WO-98/22457 A1 | 5/1998 |
| WO | WO-00/17202 A1 | 3/2000 |
| WO | WO-01/012600 A1 | 2/2001 |
| WO | WO-02/14361 A2 | 2/2002 |
| WO | WO-2002/058622 A2 | 8/2002 |
| WO | WO-02/100819 A1 | 12/2002 |
| WO | WO-03/014075 A2 | 2/2003 |
| WO | WO-03/104428 A2 | 12/2003 |
| WO | WO-2004/056820 A1 | 7/2004 |
| WO | WO-2004/056830 A1 | 7/2004 |
| WO | WO-05/028434 A2 | 3/2005 |
| WO | WO-2005/030225 A2 | 4/2005 |
| WO | WO-2005/033048 A2 | 4/2005 |
| WO | WO-2005/033288 A2 | 4/2005 |
| WO | WO-2005/037834 A1 | 4/2005 |
| WO | WO-2005/058847 A1 | 6/2005 |
| WO | WO-2005/084208 A2 | 9/2005 |
| WO | WO-2005/120558 A2 | 12/2005 |

(56) References Cited

FOREIGN PATENT DOCUMENTS

| WO | WO-2006/007486 A2 | 1/2006 |
|---|---|---|
| WO | WO-2006/057460 A1 | 6/2006 |
| WO | WO-2006/065495 A2 | 6/2006 |
| WO | WO-2006/115509 A2 | 11/2006 |
| WO | WO-2007/010259 A1 | 1/2007 |
| WO | WO-2007/024944 A1 | 3/2007 |
| WO | WO-2007/031429 A1 | 3/2007 |
| WO | WO-2007/093507 A1 | 8/2007 |
| WO | WO-2007/125405 A2 | 11/2007 |
| WO | WO-2007/138998 A1 | 12/2007 |
| WO | WO-2008/003703 A1 | 1/2008 |
| WO | WO-2008/008923 A2 | 1/2008 |
| WO | WO-2008/045664 A2 | 4/2008 |
| WO | WO-2008/062740 A1 | 5/2008 |
| WO | WO-2008/074692 A1 | 6/2008 |
| WO | WO-2008/097428 A2 | 8/2008 |
| WO | WO-2008/150827 A1 | 12/2008 |
| WO | WO-2008/151200 A2 | 12/2008 |
| WO | WO-2009/032667 A1 | 3/2009 |
| WO | WO-2009/035997 A2 | 3/2009 |
| WO | WO-2009/077956 A2 | 6/2009 |
| WO | WO-2009/147187 A1 | 12/2009 |
| WO | WO-2009/149819 A1 | 12/2009 |
| WO | WO-2009/149820 A1 | 12/2009 |
| WO | WO-2009/157196 A1 | 12/2009 |
| WO | WO-2010/017827 A1 | 2/2010 |
| WO | WO-2010/030947 A1 | 3/2010 |
| WO | WO-2010/038901 A1 | 4/2010 |
| WO | WO-2010/057101 A2 | 5/2010 |
| WO | WO-2010/058023 A1 | 5/2010 |
| WO | WO-2010/059602 A2 | 5/2010 |
| WO | WO-2010/071853 A1 | 6/2010 |
| WO | WO-2010/102958 A1 | 9/2010 |
| WO | WO-2010/117425 A1 | 10/2010 |
| WO | WO-2010/123139 A1 | 10/2010 |
| WO | WO-2010/125082 A1 | 11/2010 |
| WO | WO-2011/017303 A1 | 2/2011 |
| WO | WO-2011/019634 A2 | 2/2011 |
| WO | WO-2011/059839 A1 | 5/2011 |
| WO | WO-2011/067364 A1 | 6/2011 |
| WO | WO-2011/067365 A1 | 6/2011 |
| WO | WO-2011/067366 A1 | 6/2011 |
| WO | WO-2011/109059 A1 | 9/2011 |
| WO | WO-2011/109789 A2 | 9/2011 |
| WO | WO-2011/113819 A2 | 9/2011 |
| WO | WO-2011/115892 A1 | 9/2011 |
| WO | WO-2012/020100 A2 | 2/2012 |
| WO | WO-2012/032065 A1 | 3/2012 |
| WO | WO-2012/032067 A1 | 3/2012 |
| WO | WO-2012/037108 A1 | 3/2012 |
| WO | WO-2012/064744 A2 | 5/2012 |
| WO | WO-2012/079000 A1 | 6/2012 |
| WO | WO-2012/127464 A2 | 9/2012 |
| WO | WO-2012/129394 A2 | 9/2012 |
| WO | WO-2012/129514 A1 | 9/2012 |
| WO | WO-2012/139775 A1 | 10/2012 |
| WO | WO-2012/129394 A9 | 11/2012 |
| WO | WO-2012/178108 A1 | 12/2012 |
| WO | WO-2013/045431 A1 | 4/2013 |
| WO | WO-2013/074916 A1 | 5/2013 |
| WO | WO-2013/135588 A1 | 9/2013 |
| WO | WO-2013/167136 A1 | 11/2013 |
| WO | WO-2013/169588 A1 | 11/2013 |
| WO | WO-2013/169704 A2 | 11/2013 |
| WO | WO-2013/169864 A2 | 11/2013 |
| WO | WO-2013/176740 A1 | 11/2013 |
| WO | WO-2014/028669 A1 | 2/2014 |
| WO | WO-2014/031174 A1 | 2/2014 |
| WO | WO-2014/095757 A1 | 6/2014 |
| WO | WO-2014/201378 A1 | 12/2014 |
| WO | WO-2014/201378 A9 | 1/2015 |
| WO | WO-2015/131035 A1 | 9/2015 |
| WO | WO-2015/171610 A2 | 11/2015 |
| WO | WO-2016/179343 A1 | 11/2016 |

OTHER PUBLICATIONS

Garcia-Hernandez, M. et al. "Adoptive Transfer of Tumor-Specific Tc17 Effector T Cells Controls the Growth of B16 Melanoma in Mice," *J. Immunology*. (2010) vol. 184, No. 8, pp. 4215-4227.

Yang, S. M. and Murray, W. V. "Microwave assisted ring-opening of epoxides with N-biaryl sulfonamides in the synthesis of matrix metalloproteinase-9 inhibitors," *Tetrahedron Lett*. (2008) vol. 49, No. 5, pp. 835-839.

CAS Registry No. 1012413-39-6; STN Entry Date: Apr. 6, 2008; Chemical name: Benzenesulfonamide, N-[4-[(2-fluorophenyl)methoxy]phenyl]-N-methyl-.

CAS Registry No. 632292-33-2; STN Entry Date: Dec. 30, 2003; Chemical name: 2-[[1,2,3,4-tetrahydro-1-[(4-methylphenyl)sulfonyl]-6-quinolinyl]methyl]-1H-isoindole-1,3(2H)-dione.

Zhu, W. et al. "Potent 11β-Hydroxylase Inhibitors with Inverse Metabolic Stability in Human Plasma and Hepatic S9 Fractions to Promote Wound Healing," *J. Med. Chem*. (2014) vol. 57, No. 18, pp. 7811-7817.

Zhao, S.-H. et al. "3,4-Dihydro-2H-benzo[1,4]oxazine Derivatives as 5-HT$_6$ Receptor Antagonists," *Bioorg. Med. Chem. Lett*. (2007) vol. 17, pp. 3504-3507.

Tavares, F. X. et al. "Potent, Selective, and Orally Efficacious Antagonists of Melanin-Concentrating Hormone Receptor 1," *J. Med. Chem*. (2006) vol. 49, No. 24, pp. 7095-7107.

International Search Report and Written Opinion for International Application No. PCT/US2015/017977 dated Jun. 23, 2015 (10 pages).

Zhang et al., "Increasing Human Th17 Differentiation Through Activation of Orphan Nuclear Receptor Retinoid Acid-Related Orphan Receptor γ (RORγ) by a Class of Aryl Amide Compounds," Molecular Pharmacology, vol. 82, pp. 583-590 (2012).

English Abstract JP6-250441 published 1994 (1 page).

English Abstract of JP2004307487A published 2004 (2 pages).

International Search Report and Written Opinion for PCT/US2011/059788 dated May 23, 2012 (23 pages).

International Search Report and Written Opinion for PCT/US2013/040085 dated Oct. 23, 2013 (9 pages).

Annunziato et al., "Type 17 T helper cells-origins, features and possible roles in rheumatic disease," 5 Nat. Rev. Rheumatol. 325-31 (2009).

Boaventura et al., "Human mucosal leishmaniasis: Neutrophils infiltrate areas of tissue damage that express high levels of Th17-related cytokines," 40 Eur. J. Immunol. 2830-36 (2010).

Buonocore et al., "Innate lymphoid cells drive interleukin-23-dependent innate intestinal pathology," 464 Nature 1371-75 (2010).

Eberl et al., "An essential function for the nuclear receptor RORγt in the generation of fetal lymphoid tissue inducer cells," 5(1) Nat. Immunol. 64-73 (2004).

Figueroa-Vega et al., "Increased Circulating Pro-Inflammatory Cytokines and Th17 Lymphocytes in Hashimoto's Thyroiditis," 95(2) J. Clin. Endocrinol. Metab. 953-62 (2010).

Gennaro (ed.), Remington: The Science and Practice of Pharmacy, 20th edition (2000).

He et al., "RORγt, a Novel Isoform of an Orphan Receptor, Negatively Regulates Fas Ligand Expression and IL-2 Production in T Cells," 9 Immunity 797-806 (1998).

Hirose et al., "RORγ: the third member of ROR/RZR orphan receptor subfamily that is highly expressed in skeletal muscle," 205 Biochem. Biophys. Res. Comm. 1976-83 (1994).

Hueber et al., "Cutting Edge: Mast Cells Express IL-17A in Rheumatoid Arthritis Synovium," 184 J. Immunol. 3336-40 (2010).

Ivanov et al., "The Orphan Nuclear Receptor RORγt Directs the Differentiation Program of Proinflammatory IL-17+ T Helper Cells," 126 *Cell* 1121-33 (2006).

Jia et al., "The T helper type 17/regulatory T cell imbalance in patients with acute Kawasaki disease," 162 Clin. Exp. Immunol. 131-37 (2010).

Jin et al., "Structural Basis for Hydroxycholesterols as Natural Ligands of Orphan Nuclear Receptor RORγ," *Mol. Endocrinol*. (2010) vol. 24, No. 5, pp. 923-929.

(56) References Cited

OTHER PUBLICATIONS

Kastelein et al., "Discovery and Biology of IL-23 and IL-27: Related but Functionally Distinct Regulators of Inflammation," 25 Annu. Rev. Immunol. 221-42 (2007).
Kurebayashi et al., "Selective LXXLL peptides antagonize transcriptional activation by the retinoid-related orphan receptor RORγ," 315 Biochem. Biophys. Res. Comm. 919-27 (2004).
Louten et al., "Development and function of TH17 cells in health and disease," 123(5) J. Allergy Clin. Immunol. 1004-11 (2009).
Miossec et al., "Interleukin-17 and Type 17 Helper T Cells," 361(9) New Eng. J. Med. 888-98 (2009).
Sun et al., "Requirement for RORγ in Thymocyte Survival and Lymphoid Organ Development," 288 Science 2369-72 (2000).
Sutton et al., "Interleukin-1 and IL-23 Induce Innate IL-17 Production from γδ T Cells, Amplifying Th17 Responses and Autoimmunity," 31 Immunity 331-41 (2009).
Wang et al., "Identification of SR1078, a Synthetic Agonist for the Orphan Nuclear Receptors RORα and RORγ," 5(11) ACS Chem. Biol. 1029-34 (2010).
Xie et al., "RORγt Recruits Steroid Receptor Coactivators to Ensure Thymocyte Survival," 175(6) J. Immunol. 3800-09 (2005).
Yang et al., "T Helper 17 Lineage Differentiation is programmed by Orphan Nuclear Receptors RORα and RORγ," 28 Immunity 29-39 (2008).
André et al., "Disruption of retinoid-related orphan receptor β changes circadian behaviour, causes retinal degeneration and leads to vacillans phenotype in mice," 17(14) The EMBO J. 3867-77 (1998).
Becker-André et al., "Identification of nuclear receptor mRNAs by RT-PCR amplification of conserved zinc-finger motif sequences," 194(3) Biochem. Biophys. Res. Comm. 1371-79 (1993).
Burris et al., "Targeting Orphan Nuclear Receptors for Treatment of Metabolic Diseases and Autoimmunity," 19(1) Chem. Biol. 51-59 (2012).
Cai, et al., "Pivotal Role of Dermal IL-17-Producing γδ T Cells in Skin Inflammation", Immunity (2011) vol. 35, pp. 596-610.
Carlberg et al., "RZRs, a new family of retinoid-related orphan receptors that function as both monomers and homodimers," 8 Mol. Endocrinol. 757-70 (1994).
D. van der Heijde, et al., "Secukinumab Provides Significant and Sustained Inhibition of Joint Structural Damage in a Phase III Study of Active Psoriatic Arthritis" Arthritis & Rheumatology Brief Report, Accepted Article DOI: 10.1002/art.39685, American College of Rheumatology, (2016) pp. 1-27.
Baeten, et al., "Secukinumab, an Interleukin-17A Inhibitor, in Ankylosing Spondylitis", The New England Journal of Medicine, (2015) vol. 373, pp. 2534-2548.
Dussault et al., "Orphan nuclear receptor RORα-deficient mice display the cerebellar defects of *staggerer*," 70 Mech. Develop. 147-53 (1998).
Giguère et al., "Isoform-specific amino-terminal domains dictate DNA-binding properties of RORα, a novel family of orphan hormone nuclear receptors," 8 Genes & Develop. 538-53 (1994).
Huh et al., "Small molecule inhibitors of RORγt: Targeting Th17 cells and other applications," 42 Eur. J. Immunol. 2232-2237 (2012).
Krueger, "A welcome surprise in psoriasis", Nature Medicine, (2012) vol. 18, No. 12, pp. 1750-1751.
Leonardi, et al., "Anti-Interleukin-17 Monoclonal Antibody Ixekizumab in Chronic Plaque Psoriasis", The New England Journal of Medicine, (2012) vol. 366, Iss. 13, pp. 1-10.
Martinez, "Th17-biased RORγt transgenic mice become susceptible to a viral model for multiple sclerosis", Brain, Behavior, and Immunity, (2014) vol. 43, pp. 86-97.
Medvedev et al., "Cloning of a cDNA encoding the murine orphan receptor RZR/RORγ and characterization of its response element," 181 Gene 199-206 (1996).
Nakajima, et al., "IL-17A as an Inducer for Th2 Immune Responses in Murine Atopic Dermatitis Models", Journal of Investigative Dermatology, (2014) vol. 134, pp. 2122-2130.

Ortiz et al., "TOR: a new orphan receptor expressed in the thymus that can modulate retinoid and thyroid hormone signals," 9 Mol. Endocrinol. 1679-91 (1995).
Papp, et al. "Brodalumab, an Anti-Interleukin-17-Receptor Antibody for Psoriasis", The New England Journal of Medicine, (2012) vol. 366, Iss. 13, 9 pgs.
Skepner, J. et al. "Pharmacologic Inhibition of RORγt Regulates Th17 Signature Gene Expression and Suppresses Cutaneous Inflammation In Vivo," downloaded from the Internet at http://www.jimmunol.org/cgi/doi/10.4049/jimmunol.1302190 on Feb. 17, 2014, published in final edited form in *J. Immunol.* (2014) vol. 192, No. 6, pp. 2564-2575.
Smith, "The Bench-to-Bedside Story of IL-17 and the Therapeutic Efficacy of its Targeting in Spondyloarthritis", Curr Rheumatol Rep. (2016) vol. 18, pp. 1-10.
Solt et al., "Action of RORs and their ligands in (patho)physiology," 23(12) Trends in Endocrinology and Metabolism. 619-627 (2012).
Tlustochowicz, et al. "Efficacy and Safety of Subcutaneous and Intravenous Loading Dose Regimens of Secukinumab in Patients with Active Rheumatoid Arthritis: Results from a Randomized Phase II Study" The Journal of Rheumatology, (2016) vol. 43, No. 3, pp. 495-503.
Villey et al., "RORγT, a thymus-specific isoform of the orphan nuclear receptor RORγ/TOR, is up-regulated by signaling through the pre-T cell receptor and binds to the TEA promoter," 29 Eur. J. Immunol. 4072-80 (1999).
Wiesenberg et al., "Transcriptional activation of the nuclear receptor RZRα by the pineal gland hormone melatonin and identification of CGP 52608 as a synthetic ligand," 23(3) Nucl. Acids Res. 327-33 (1995).
Xiao, et al., "Small-Molecule RORγt Antagonists Inhibit T Helper 17 Cell Transcriptional Network by Divergent Mechanisms", Immunity (2014) vol. 40, pp. 477-489.
Arisawa et al., "Development of Isomerization and Cycloisomerization with Use of a Ruthenium Hydride with N-Heterocyclic Carbene and Its Application to the Synthesis of Heterocycles," 71 J. Org. Chem. 4255-61 (2006).
Berge et al., "Pharmaceutical salts," 66(1) J. Pharm. Sci. 1-19 (1977).
Bhagawanth et al., "Room-Temperature Pd-Catalyzed Amidation of Aryl Bromides Using tert-Butyl Carbamate," 74 J. Org. Chem. 4634-37 (2009).
Boger et al., "Regiocontrolled Nucleophilic Addition to Selectively Activated p-Quinone Diimines: Alternative Preparation of a Key Intermediate Employed in the Preparation of the CC-1065 Left-Hand Subunit," 55 J. Org. Chem. 1379-90 (1990).
Carroll et al., "Synthesis, Nicotinic Acetylcholine Receptor Binding, and Antinociceptive Properties of 2-exo-2-(2',3'-Disubstituted 5'-pyridinyl)-y-azabicyclo[2.2.1]heptanes: Epibatidine Analogues," 45 J. Med. Chem. 4755-61 (2002).
Chang et al., "7-Aroyl-aminoindoline-1-sulfonamides as a Novel Class of Potent Antitubulin Agents," 49 J. Med. Chem. 6656-59 (2006).
Colbon et al., "Double Arylation of Allyl Alcohol via a One-Pot Heck Arylation—Isomerization—Acylation Cascade," 13 Org. Lett. 5456-59 (2011).
De et al., Methods in Molecular Biology 1184, second edition, Human Press (2014).
Gould, "Salt selection for basic drugs," 33 Int'l J. Pharmaceutics 201-217 (1986).
Grasa et al., "Amination Reactions of Aryl Halides with Nitrogen-Containing Reagents Mediated by Palladium/Imidazolium Salt Systems," 66 J. Org. Chem. 7729-37 (2001).
Greene & Wuts, Protective Groups in Organic Synthesis, 2d Edition (1991).
Guimond et al., "Rhodium(III)-Catalyzed Isoquinolone Synthesis: The N-O Bond as a Handle for C-N Bond Formation and Catalyst Turnover," 132(20) J. Am. Chem. Soc. 6908-09 (2010).
Hanessian et al., "A versatile protocol for the stereocontrolled elaboration of vicinal secondary and tertiary centers of relevance to natural product synthesis," 52(6) J. Org. Chem. 1170-72 (1987).

(56) References Cited

OTHER PUBLICATIONS

Hauser et al., "Relative Ease of Cyclization of 2-, 3-, and 4-Aminopyridine Derivatives. Synthesis of Naphthyridines," 15 J. Org. Chem. 1224-32 (1950).
International Search Report and Written Opinion for PCT/US2013/039422 dated Oct. 11, 2013 (9 pages).
International Search Report and Written Opinion for PCT/US2013/039839 dated Oct. 18, 2013 (8 pages).
Ishikura et al., "An Efficient Synthesis of 3-Heteroarylpyridines via Diethyl-(3-pyridyl)-borane," Synthesis 936-38 (1984).
Jayashree et al., "Design and synthesis of 2-quinolones as antioxidants and antimicrobials: a rational approach," 19 Med. Chem. Res. 193-209 (2010).
Jiang et al., "Synthesis and Cytotoxicity Evaluation of Novel Indolylpyrimidines and Indolylpyrazines as Potential Antitumor Agents," 9 Bioorg. Med. Chem. 1149-54 (2001).
Li et al., "Chemical Libraries via Sequential C-H Functionalization of Phenols," 10 J. Comb. Chem. 170-74 (2008).
Li et al., "Synthesis and Resolution of a Novel Chiral Diamine Ligand and Application to Asymmetric Lithiation-Substitution," 2 Org. Lett. 875-78 (2000).
Liu et al., "1-Sulfonylindazoles as potent and selective 5-HT6 ligands," 19 Bioorg. Med. Chem. Lett. 2413-15 (2009).
Murase et al., "A New Concise Synthesis of Arcyriacyanin A and Its Unique Inhibitory Activity against a Panel of Human Cancer Cell Line," 48(1) Chem. Pharm. Bull. 81-84 (2000).
Ninomiya et al., "Phosphorous in Organic Synthesis—VII: Diphenyl Phosphorazidate (DPPA). A New Convenient Reagent for a Modified Curtius Reaction," 30 Tetrahedron 2151-57 (1975).
Nyrkova et al., "Synthesis of a New Heterocyclic System—3,4-Diazaphenoxazine," 1(9) J. Org. Chem. USSR, 1711-14, translating 1(9) Zh. Org. Khimii, 1688-91 (1965).
Santilli et al., "Synthesis of 5,6,7,8-Tetrahydro-5-oxopyrido[2,3-d] pyrimidine-6-carbonitriles and -6-carboxylic Acid Esters," 12 J. Het. Chem. 311-16 (1975).
Skraup, "Eine Synthese des Chinolins," 13 Berichte 2086-87 (1880).
Stefko et al., "General and Modular Synthesis of Isomeric 5-Substituted Pyridin-2-yl and 6-Substituted Pyridin-3-yl C-Ribonucleosides Bearing Diverse Alkyl, Aryl, Hetaryl, Amino, Carbamoyl, and Hydroxy Groups," 76 J. Org. Chem. 6619-35 (2011).
STN Columbus, pp. 1-40 (2011).
Takano et al., "A new synthesis of a steroid side chain via stereocontrolled protonation: synthesis of (−)-desmosterol," 14 J. Chem. Soc., Chem. Commun. 760-61 (1983).
Van Heerden et al., "Dibutylboron triflate promoted conjugate addition of benzylic and allylic organocopper reagents to chiral α,β-unsaturated N-acyl imidazolidinones" 38(10) Tet. Lett. 182-124 (1997).
Wang et al., "Synthesis of new carbon-11-labeled 7-aroyl-aminoindoline-1-sulfonamides as potential PET agents for imaging of tubulin polymerization in cancers," 51(1) J. Label. Compd. Radiopharm. 6-11 (2008).
Yeh et al., "Practical Cu-catalyzed amination of functionalized heteroaryl halides," 47(34) Tetrahedron Lett. 6011-16 (2006).
Zhu et al., "The Direct Formulation of Functionalized Alkyl(aryl)zinc halides by Oxidative Addition of Highly Reactive Zinc with Organic Halides and Their Reactions with Acid Chlorides, α,β-Unsaturated Ketones, and Allylic, Aryl, and Vinyl Halides," 56 J. Org. Chem. 1445-53 (1991).
International Search Report and Written Opinion for PCT/US2014/071663 dated Apr. 17, 2015 (6 pages).
International Search Report and Written Opinion for PCT/US2014/071671 dated Apr. 28, 2015 (10 pages).
International Search Report and Written Opinion for PCT/US2014/071656 dated Mar. 12, 2015 (8 pages).
Yang, T. et al. "Discovery of Tertiary Amine and Indole Derivatives as Potent RORγt Inverse Agonists," ACS Med. Chem. Lett. (2014) vol. 5, pp. 65-68.
Jun., C. H. "Adoptive T cell therapy for cancer in the clinic," J. Clin. Invest. (2007) vol. 117, No. 6, pp. 1466-1476.
Zhu, J. et al. "Differentiation of Effector CD4 T Cell Populations," Author manuscript available in PMC on Nov. 20, 2012, published in final edited form in Annu. Rev. Immunol. (2010) vol. 28, pp. 445-489.
Martin-Orozco, N. et al. "Th17 cells promote cytotoxic T cell activation in tumor immunity," Author manuscript available in PMC on Nov. 20, 2010, published in final edited form in Immunity (2009) vol. 31, pp. 787-798.
Pardoll, D. M. "The blockade of immune checkpoints in cancer immunotherapy," Nature Rev. Cancer (2012) vol. 12, pp. 252-264.
Restifo, N. P. et al. "Adoptive immunotherapy for cancer: harnessing the T cell response," Nature Rev. Immunol. (2012) vol. 12, pp. 269-281.
Drug Discovery & Development "Lycera's Oral Immunotherapy May Have Anti-Cancer Activity," Dated Nov. 7, 2014. (2 pages).
Lycera "Lycera Announces Research Showing Promising Anti-Cancer Activity of Novel, Oral Immunotherapy Candidates," Press release dated Feb. 9, 2015. (2 pages).
X. Hu et al. in Poster Presentation Entitled "Novel, Synthetic RORgamma Agonist Compounds as a Potential Anti-Cancer Approach" at Society for Immunotherapy of Cancer (SITC) Meeting 2014, Nov. 6-9, 2014.
Huang, Z. et al. "Retinoid-related orphan receptor γt is a potential therapeutic target for controlling inflammatory autoimmunity," Expert Opin. Ther. Targets (2007) vol. 11, No. 6, pp. 737-743.
Wang et al., "Modulation of Retinoic Acid Receptor-related Orphan Receptor α and γ Activity by 7-Oxygenated Sterol Ligands," J. Biol. Chem. (2010) vol. 285, No. 7, pp. 5013-5025.
Bai et al., "Sulfation of 25-hydroxycholesterol by SULT2B1b decreases cellular lipids via the LXR/SREBP-1c signaling pathway in human aortic endothelial cells," Atherosclerosis, vol. 214, pp. 350-356 (author's manuscript pp. 1-14) (2011).
Bensinger et al., "LXR signaling couples sterol metabolism to proliferation in the acquired immune response," Cell, vol. 134, pp. 97-111 (2008).
Brown et al., "Oxysterols and atherosclerosis," Atherosclerosis, vol. 142, pp. 1-28 (1999).
Chen et al., "Enzymatic reduction of oxysterols impairs LXR signaling in cultured cells and the livers of mice," Cell Metab., vol. 5, pp. 73-79 (2007).
Cheng et al., "Increased cholesterol content in Gammadelta (γδ) T lymphocytes differentially regulates their activation," PLoS ONE 8, pp. 1-9 (2013).
Cook et al., "24-hydroxycholesterol sulfation by human cytosolic sulfotransferases: formation of monosulfates and disulfates, molecular modeling, sulfatase sensitivity, and inhibition of liver X receptor activation," Drug Metab. Dispos., vol. 37, pp. 2069-2078 (2009).
Hanyu et al., "Cholesterol sulfate induces expression of the skin barrier protein filaggrin in normal human epidermal keratinocytes through induction of RORα," Biochem. Biophys. Res. Commun., vol. 428, pp. 99-104 (2012).
Hu et al., "Sterol metabolism controls $T_H17$ differentiation by generating endogenous RORγ agonists," Nature Chemical Biology, vol. 11, pp. 141-147 (2015).
Iida et al., "Tumor-Infiltrating CD4+Th17 Cells Produce IL-17 in Tumor Microenvironment and Promote Tumor Progression in Human Gastric Cancer," Oncology Reports, vol. 25, pp. 1271-1277 (2011).
Ikonen, "Cellular cholesterol trafficking and compartmentalization," Nat. Rev. Mol. Cell Biol., vol. 9, pp. 125-138 (2008).
Kallen et al., "Crystal structure of the human RORα ligand binding domain in complex with cholesterol sulfate at 2.2 Å," J. Biol. Chem., vol. 279, pp. 14033-14038 (2004).
Kidani et al., "The sterol regulatory element binding proteins are essential for the metabolic programming of effector T cells and adaptive immunity," Nat. Immunol., vol. 14, pp. 489-499 (2013).
Liao et al., "Association Between Th17-Related Cytokines and Risk of Non-Small Cell Lung Cancer Among Patients With or Without Chronic Obstructive Pulmonary Disease," Cancer, pp. 3122-3129 (2015).
Ma et al., "25-Hydroxycholesterol-3-sulfate regulates macrophage lipid metabolism via the LXR/SREBP-1 signaling pathway," Am. J. Physiol. Endocrinol. Metab., vol. 295, pp. E1369-E1379 (2008).

(56) References Cited

OTHER PUBLICATIONS

Solt et al., "Identification of a selective RORγ ligand that suppresses $T_H17$ cells and stimulates T regulatory cells," *ACS Chem. Biol.*, vol. 7, pp. 1515-1519 (2012).

Song et al., "Auto-oxidized cholesterol sulfates are antagonistic ligands of liver X receptors: implications for the development and treatment of atherosclerosis," *Steroids*, vol. 66, pp. 473-479 (2001).

Spann et al., "Regulated accumulation of desmosterol integrates macrophage lipid metabolism and inflammatory responses," *Cell*, vol. 151, pp. 138-152 (2012).

Spann et al., "Sterols and oxysterols in immune cell function," *Nat. Immunol.*, vol. 14, pp. 893-900 (2013).

Wang et al., "A second class of nuclear receptors for oxysterols: Regulation of RORα and RORγ activity by 24S-hydroxycholesterol (cerebrosterol)," *Biochim. Biophys. Acta*, vol. 1801, pp. 917-923 (2010).

Yang et al., "Sterol intermediates from cholesterol biosynthetic pathway as liver X receptor ligands," *J. Biol. Chem.*, vol. 281, pp. 27816-27826 (2006).

Arellano et al., "Clinical uses of GM-CSF, a critical appraisal and update," *Biologics: Targets & Therapy*, vol. 2, pp. 13-27 (2008).

Chang et al., "Synthetic RORγt Agonists Enhance Protective Immunity," ACS Chem. Biol., Just Accepted Manuscript—DOI: 10.1021/acschembio.5b00899—Publication Date (Web): Jan. 19, 2016, (30 pages).

Chen et al., "Th1-, Th2-, and Th17-associated cytokine expression in hypopharyngeal carcinoma and clinical significance," *Eur Arch Otorhinolaryngol*, DOI: 10.1007/s00405-015-3779-2, 8 pages, (2015).

Codarri et al., "RORγt drives production of the cytokine GM-CSF in helper T cells, which is essential for the effector phase of autoimmune neuroinflammation," *Nature Immunology*, vol. 12, pp. 560-568, (2011).

Gnerlich et al., "Induction of Th17 Cells in the Tumor Microenvironment Improves Survival in a Murine Model of Pancreatic Cancer," *The Journal of Immunology*, vol. 185, pp. 4063-4071, (2010).

Hinrichs et al., "Type 17 CD8+ T cells display enhanced antitumor immunity," *Blood*, vol. 114, pp. 596-599, (2009).

Hu et al. in "RORγ Agonists as a Novel Immunotherapy Approach for Cancer" in American Association for Cancer Research Annual Meeting in Philadelphia, Pennsylvania, Apr. 21, 2015, Poster Session: Novel Immunomodulators, Abstract No. 4273.

Kryczek et al., "Phenotype, distribution, generation, and functional and clinical relevance of Th17 cells in the human tumor environments," *The American Society of Hematology*, vol. 114, pp. 1141-1149, (2009).

Ma et al., "Contribution of IL-17-producing γδ T cells to the efficacy of anticancer chemotherapy," *J. Exp. Med.*, vol. 208, pp. 491-503, (2011).

Munegowda et al., "Th17 and Th17-stimulated CD8 + T cells play a distinct role in Th17-induced preventive and therapeutic antitumor immunity," *Cancer Immunol Immunother*, vol. 60, (2011), one page, Abstract only.

Muranski et al., "Tumor-specific Th17-polarized cells eradicate large established melanoma," *Blood*, vol. 112, pp. 362-373, (2008).

Nelson et al., "The Inducible Costimulator Augments Tc17 Cell Responses to Self and Tumor Tissue," *The Journal of Immunology*, vol. 194, pp. 1737-1747, (2015).

Nunez et al., "T helper type 17 cells contribute to anti-tumour immunity and promote the recruitment of T helper type 1 cells to the tumour," *Immunology*, vol. 139, pp. 61-71, (2012).

Soroosh et al., "Oxysterols are agonist ligands of RORγt and drive Th17 cell differentiation," PNAS, vol. 111, pp. 12163-12168, (2014).

\* cited by examiner (A)

(B)

(A)

(B)

(A)

(B)

(A)

(B)

(A)

(B)

(A)

(B)

US 10,532,088 B2

ADOPTIVE CELLULAR THERAPY USING AN AGONIST OF RETINOIC ACID RECEPTOR-RELATED ORPHAN RECEPTOR GAMMA AND RELATED THERAPEUTIC METHODS

CROSS-REFERENCE TO RELATED APPLICATIONS

This application is the national stage of International (PCT) Patent Application Serial No. PCT/US2015/017977, filed Feb. 27, 2015 which claims the benefit of and priority to U.S. Provisional Patent Application Ser. No. 61/945,431, filed Feb. 27, 2014, the contents of which are hereby incorporated by reference in their entirety.

FIELD OF THE INVENTION

The invention relates to medical therapy using an agonist of the retinoic acid receptor-related orphan receptor gamma (RORγ) and provides adoptive cellular therapies using an agonist of RORγ, populations of lymphocyte cells that have been exposed to an agonist of RORγ, populations of dendritic cells that have been exposed to an agonist of RORγ, pharmaceutical compositions, and methods for enhancing the therapeutic effects of lymphocyte cells and/or dendritic cells in a patient by administering an agonist of RORγ to the patient.

BACKGROUND

Cancer, bacterial infections, fungal infections, and immune disorders continue to be a significant health problem despite the substantial research efforts and scientific advances reported in the literature. Some of the most frequently diagnosed cancers include prostate cancer, breast cancer, and lung cancer. Prostate cancer is the most common form of cancer in men. Breast cancer remains a leading cause of death in women. Lung cancer is a leading cause of cancer death worldwide, responsible for over one million deaths annually according to a study from year 2008. Lung cancer is often attributed to long-term exposure to tobacco smoke, but genetic factors and exposure to asbestos and air pollution have been reported as factors contributing to the development of lung cancer. Another cancer, melanoma, is a form of skin cancer in which over one-hundred thousand new cases are diagnosed each year in the United States according to the American Cancer Society. Current treatment options for these cancers are not effective for all patients and/or can have substantial adverse side effects. Another unmet need associated with cancer therapy is treatment of chronic infections in patients with a weakened immune system due to receiving radiation therapy, chemotherapy, and/or other anti-cancer therapies. Such chronic infections include bacterial, fungal, and viral infections.

In addition to the unmet needs in cancer therapy, various bacterial infections are becoming a more significant health concern due to the increase in bacterial infections resistant to current antibiotic therapies. One example is *Staphylococcus aureus*. It has been reported that multiple strains of *Staphylococcus aureus* have become resistant to multiple antibiotic medications commonly used to treat patients suffering from *Staphylococcus aureus* infections.

Another unmet medical need is for improved therapies to treat fungal infections. Fungal infections have been reported to afflict over one billion people each year, with infections by *candida* being one of the most common fungal infections in humans.

Adoptive cellular therapy has been investigated as a treatment option for patients suffering from cancer and other medical disorders. Restifo and coworkers recently reviewed progress in using adoptively transferred T cells to treat cancer. Restifo et al. in *Nat. Rev. Immunol.* (2012) vol. 12(4), pages 269-281. Recent efforts using adoptive cellular therapy to treat cancer build from earlier reports, such as U.S. Pat. Nos. 5,229,15 and 5,776,451, describing exposing lymphocyte cells to certain interleukins and then administering the resulting lymphocyte cells to a patient. More recent reports such as U.S. Pat. No. 7,998,736 and International Patent Application Publication No. WO 2012/129451 describe, for example, using T cells that have been modified to express certain proteins. Despite the research devoted to developing adoptive cellular therapy for treatment of medical disorders, improved methods and compositions are needed. For instance, methods for improving the potency of adoptively transferred cells and increasing the longevity of adoptively transferred cells would make adoptive cellular therapy a more attractive treatment modality.

The present invention addresses the need for improved methods and compositions for adoptive cellular therapy and provides other benefits associated with using an agonist of RORγ in medical therapy.

SUMMARY

The invention provides medical therapies using an agonist of the retinoic acid receptor-related orphan receptor gamma (RORγ). Aspects of the invention include adoptive cellular therapy using an agonist of RORγ, populations of lymphocyte cells that have been exposed to an agonist of RORγ, populations of dendritic cells that have been exposed to an agonist of RORγ, pharmaceutical compositions, and methods for enhancing the therapeutic effects of lymphocyte cells and/or dendritic cells in a patient by administering an agonist of RORγ to a patient. The medical therapies, populations of lymphocyte cells, populations of dendritic cells, and pharmaceutical compositions are particularly useful in treating cancer, bacterial infections, fungal infections, and immune disorders. Particularly preferred is treatment of cancer, such as ovarian cancer, melanoma, colorectal cancer, lung cancer, breast cancer, prostate cancer, pancreatic cancer, renal cell carcinoma, leukemia, a B-cell lymphoma, and non-Hodgkin lymphoma, using a T cell that has been exposed to an agonist of RORγ. The medical therapies are contemplated to provide benefits to humans as well as veterinary animals. Various aspects and embodiments of the invention are described in more detail below.

One aspect of the invention provides a method of delivering to a patient a RORγ agonist treated cell selected from the group consisting of a lymphocyte cell and dendritic cell. The method comprises administering to a patient in need thereof a pharmaceutical composition comprising said cell that has been exposed ex vivo to an agonist of RORγ. The lymphocyte cell may be, for example, a T cell or a natural killer cell, and such cells may be further characterized according to whether the cell is autologous or allogenic. Potential benefits of treating lymphocyte cells with a RORγ agonist include, for example, improved cytotoxicity toward diseased tissue/pathogens in the patient, increased longevity of lymphocyte cells upon administration to the patient, and increased expansion of lymphocyte cells (i.e., increasing the number of lymphocyte cells) during culture ex vivo. Attributes that may also be observed upon treating lymphocyte cells with a RORγ agonist include, for example, a decrease in the formation of suppressive T cells, an increase in production of cytokines, and/or an increase in production of chemokines. The patient may be suffering from cancer, a bacterial infection, a fungal infection, an immune disorder, or other medical disorder.

Another aspect of the invention provides a method of preparing a population of cells that have been exposed ex vivo to an agonist of RORγ, where the cells are lymphocyte cells or dendritic cells. The method comprises exposing a population of cells selected from the group consisting of lymphocyte cells and dendritic cells ex vivo to an agonist of RORγ to thereby provide said population of cells that have been exposed ex vivo to an agonist of RORγ. The population of cells may be part of a composition that comprises, for example, other types of cells. Additionally, the method may optionally further comprise obtaining cells from a patient for use in the culturing step, or obtaining cells from a subject that produces cells allogenic to the cells of a patient that will receive the RORγ agonist treated cells, for use in the culturing step. When the cells are lymphocyte cells, the lymphocyte cells may be obtained from, for example, blood, cancer tissue, bone marrow, the spleen, a lymph node, or the thymus. In certain embodiments, the lymphocyte cells are obtained from cancer tissue or a lymph node.

Another aspect of the invention provides a method of treating a medical disorder. The method comprises administering to a patient in need thereof a cell that has been exposed ex vivo to an agonist of RORγ to treat the medical disorder, wherein the cell is a lymphocyte cell or dendritic cell. Exemplary medical disorders include, for example, cancer, bacterial infections, fungal infections, and immune disorders. The method embraces combination therapy, such as combination therapy using another agent to enhance the efficacy of the lymphocyte cell and/or an agent having independent efficacy in treating the medical disorder. For instance, when the patient suffers from cancer, there are numerous anti-cancer agents described in the literature, and these are contemplated for use in combination with a cell (e.g., a lymphocyte cell or dendritic cell) that has been exposed ex vivo to an agonist of RORγ. The methods may also be used in combination with surgical procedures that remove cancerous tissue.

Another aspect of the invention provides a method of increasing the immune benefit of a vaccination. The method comprises administering to a patient in need thereof a cell that has been exposed ex vivo to an agonist of RORγ to increase the immune benefit of vaccination, wherein the patient has received vaccination or will receive vaccination during the time period over which said cell exerts physiological activity, and the cell is a lymphocyte cell or a dendritic cell. The vaccination may enhance immunity against, for example, a cancer, viral infection, immune disorder, or other medical disorder. Exemplary embodiments pertain to enhancing immunity against a cancer, particularly in those patients that have undergone surgery to remove cancerous tissue.

Another aspect of the invention provides a population of lymphocyte cells that have been exposed ex vivo to an agonist of RORγ. The population may be characterized by the presence and/or quantity of particular types of cells in the population. For example, in certain embodiments, the population comprises one or more of the following: T cells and natural killer cells. In yet other embodiments, the population is characterized by (i) a majority of lymphocyte cells in the population are T cells, (ii) a majority of lymphocyte cells in the population are CD8$^+$ T cells, CD4$^+$ T cells, T$_H$17 cells, or a combination thereof, or (iii) a majority of lymphocyte cells in the population are natural killer cells. In yet other embodiments, the population is characterized by: (i) a majority of lymphocyte cells in the population are T cells, (ii) a majority of lymphocyte cells in the population are CD8$^+$ T cells, CD4$^+$ T cells, T$_H$17 cells, or a combination thereof, (iii) a majority of lymphocyte cells in the population are Tc17 cells, (iv) a majority of lymphocyte cells in the population are natural killer cells, or (v) a majority of lymphocyte cells in the population are natural killer T cells, γδ T cells, or a combination thereof.

Another aspect of the invention provides a population of dendritic cells that have been exposed ex vivo to an agonist of RORγ.

Pharmaceutical compositions are provided, such as a pharmaceutical composition comprising a population of cells described herein and a pharmaceutically acceptable carrier. The pharmaceutical compositions are useful in the therapeutic methods.

Another aspect of the invention relates to therapeutic methods in which an RORγ agonist is administered to a patient in an amount sufficient to elicit a therapeutic benefit from a population of lymphocyte cells and/or dendritic cells in the patient. In certain embodiments, the population is a population of lymphocyte cells in the patient. Without being bound by a particular theory, the RORγ agonist contacts lymphocyte cells in the patient and increases the therapeutic benefit of the population of lymphocyte cells, wherein the RORγ agonist contacted lymphocyte cells treat the medical disorder. In such a therapeutic approach, lymphocyte cells in the patient preferably have a receptor specific for the medical disorder to be treated. One aspect of this therapeutic approach is a method of treating a medical disorder, wherein the method comprises administering to a patient, in need thereof having a population of lymphocyte cells featuring a receptor specific for the medical disorder, an agonist of RORγ in an amount sufficient to elicit a therapeutic benefit from said population of lymphocyte cells to thereby treat the disorder. Another aspect of this therapeutic approach provides a method of treating a medical disorder, wherein the method comprises administering to a patient in need thereof an agonist of RORγ in an amount sufficient to increase a therapeutic benefit of a population of lymphocyte cells in the patient to thereby treat the disorder, and wherein the patient has been administered a lymphocyte cell or will be administered a lymphocyte cell during the time period over which said agonist of RORγ exerts physiological activity.

DETAILED DESCRIPTION

Figure 1:
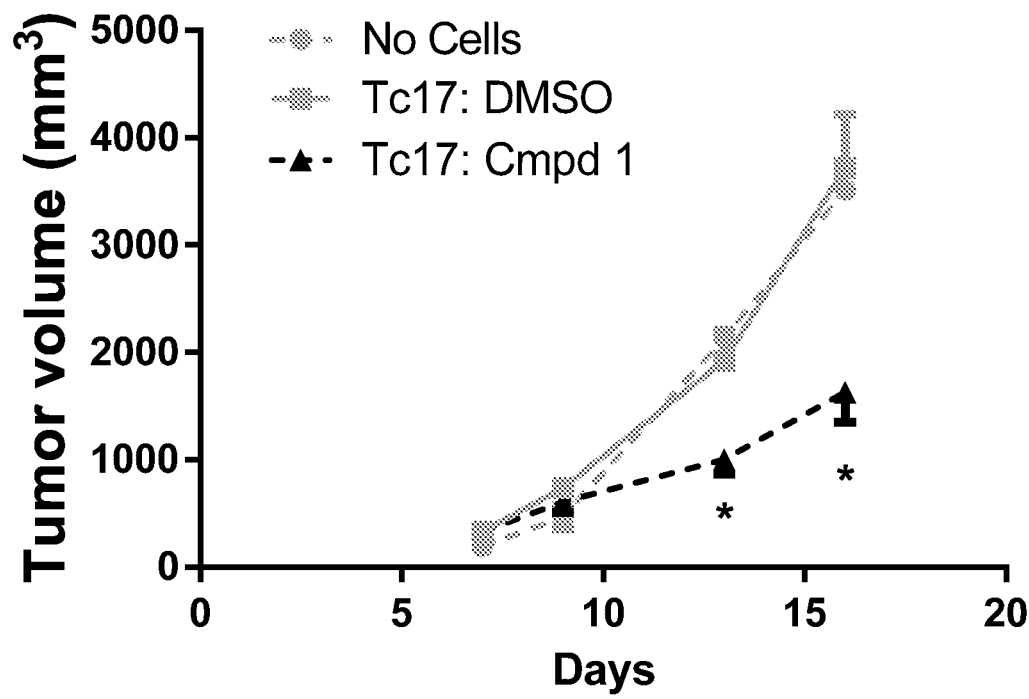
FIG. 1 provides line graphs of results from an assay evaluating change in tumor volume over time in mice bearing EG7 tumors that have been exposed to Tc17 cells, where the Tc17 cells have been exposed ex vivo to an RORγ agonist, as further described in Example 5. Part A provides results for tumors exposed to Tc17 cells previously exposed ex vivo to RORγ agonist compound 1 at a concentration of 10 μM, and provides results from control assays where * indicates p<0.004 vs. DMSO treated Tc17 cells. Part B provides results for tumors exposed to Tc17 cells previously exposed ex vivo to RORγ agonist compound 2 at a concentration of 5 μM, and provides results from control assays where * indicates p<0.002 vs. DMSO treated Tc17 cells.
Figure 1:
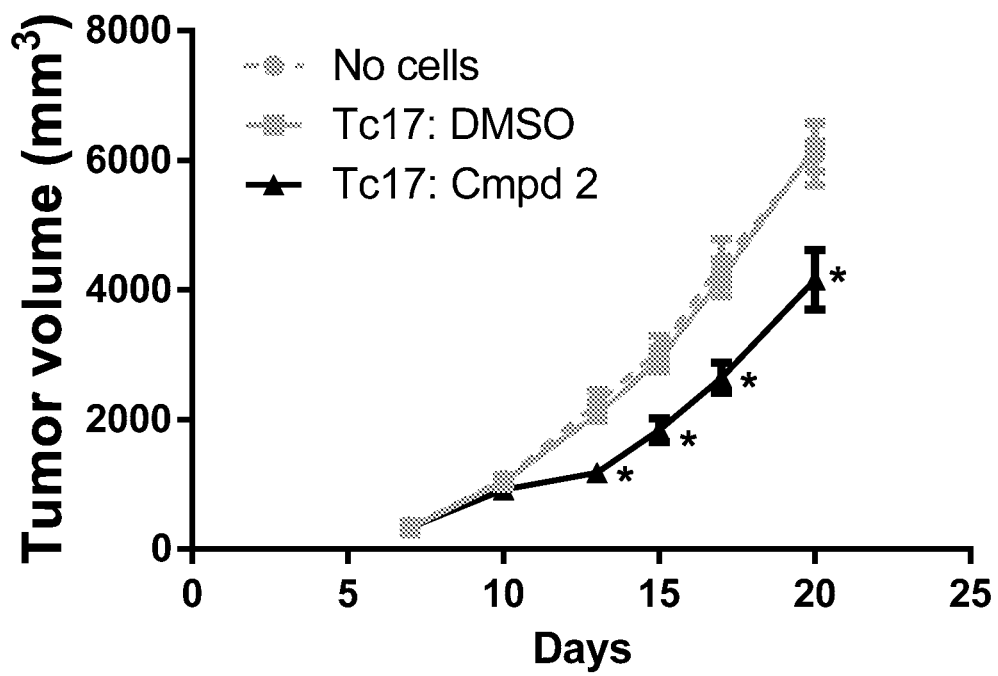

The invention provides medical therapies using an agonist of the retinoic acid receptor-related orphan receptor gamma (RORγ). Aspects of the invention include adoptive cellular therapy using an agonist of RORγ, populations of lymphocyte cells that have been exposed to an agonist of RORγ, populations of dendritic cells that have been exposed to an agonist of RORγ, pharmaceutical compositions, and methods for enhancing the therapeutic effects of lymphocyte cells and/or dendritic cells in a patient by administering an agonist of RORγ to a patient. The medical therapies, populations of lymphocyte cells, populations of dendritic cells, and pharmaceutical compositions are particularly useful in treating cancer, bacterial infections, fungal infections, and immune disorders. Particularly preferred is treatment of cancer, such as ovarian cancer, melanoma, colorectal cancer, lung cancer, breast cancer, prostate cancer, pancreatic cancer, renal cell carcinoma, leukemia, a B-cell lymphoma, and non-Hodgkin lymphoma, using a T cell that has been exposed to an agonist of RORγ. Potential benefits of treating lymphocyte cells with a RORγ agonist include, for example, improved cytotoxicity toward diseased tissue/pathogens in the patient, increased longevity of lymphocyte cells upon administration to the patient, and increased expansion of lymphocyte cells (i.e., increasing the number of lymphocyte cells) during culture ex vivo. Attributes that may be observed upon treating lymphocyte cells with a RORγ agonist include, for example, a decrease in the formation of suppressive T cells, an increase in production of cytokines, and/or an increase in production of chemokines.

The practice of the invention employs, unless otherwise indicated, conventional techniques of organic chemistry, pharmacology, molecular biology (including recombinant techniques), cell biology, biochemistry, and immunology. Such techniques are explained in the literature, such as in "Comprehensive Organic Synthesis" (B. M. Trost & I. Fleming, eds., 1991-1992); "Handbook of experimental immunology" (D. M. Weir & C. C. Blackwell, eds.); "Current protocols in molecular biology" (F. M. Ausubel et al., eds., 1987, and periodic updates); and "Current protocols in immunology" (J. E. Coligan et al., eds., 1991), each of which is herein incorporated by reference in its entirety.

Various aspects of the invention are set forth below in sections; however, aspects of the invention described in one particular section are not to be limited to any particular section. Further, when a variable is not accompanied by a definition, the previous definition of the variable controls.

I. General Features of Therapeutic Methods Using Adoptive Cellular Transfer

One aspect of the invention provides medical therapy using adoptive cellular transfer of lymphocyte cells and/or dendritic cells, in each instance the cells having been exposed to an agonist of RORγ. The medical therapy is useful in treating cancer, bacterial infections, fungal infections, and immune disorders. In adoptive cellular transfer, cells are obtained from a source (typically the patient in need of treatment), cultured ex vivo with an agent, and then the resulting cells are administered to the patient in need of therapy. The culturing typically subjects the cells to conditions whereby the cells increase in number (i.e., expansion) and/or acquire features providing improved therapeutic benefit. Described herein are methods and compositions in which lymphocyte cells and/or dendritic cells are treated ex vivo with an agonist of RORγ, and the resulting cells are administered to a patient. The agonist of RORγ is desirably a small organic molecule, but may be any agent that has an agonist effect on RORγ. General features of the therapeutic methods and compositions are described below, and more specific embodiments of the lymphocyte cells, dendritic cells, procedures for isolating and culturing cells, administering cells to a patient, medical disorders to be treated, and RORγ agonists are described in Sections II-VII below.

Exemplary Methods of Delivering a RORγ Agonist Treated Cell to a Patient

One aspect of the invention provides a method of delivering to a patient a RORγ agonist treated cell selected from the group consisting of a lymphocyte cell and dendritic cell. The method comprises administering to a patient in need thereof a pharmaceutical composition comprising said cell that has been exposed ex vivo to an agonist of RORγ.

The method may further comprise a culturing step. In such embodiments, the method further comprises culturing a cell (i.e., the lymphocyte cell or dendritic cell) with an agonist of RORγ to provide the cell that has been exposed ex vivo to an agonist of RORγ. The culturing may comprise exposing the cell to a cytokine (e.g., IL-1β, IL-2, IL-6, IL-7, IL-10, IL-12, IL-15, IL-18, IL-21, IL-23, or transforming growth factor beta). During the culturing step, the cell may be exposed to an antigen associated with a medical disorder. Although not to be bound by theory, cells having an receptor specific to an antigen associated with a medical disorder can provide a more effective therapy than cells lacking such a receptor. Accordingly, in certain embodiments, the culturing step comprises exposing the cell to an antigen associated with a medical disorder. The antigen may be an antigen presenting cell. Alternatively, the antigen may comprise cancer tissue. Further, as described below, the cell may be genetically altered to express a receptor specific to an antigen associated with a medical disorder.

The cell may be autologous or allogenic. Autologous cells are cells obtained from the patient whom will receive the cell exposed ex vivo to an agonist of RORγ. As such, in certain embodiments, the method may further comprise obtaining a cell from said patient, for use in the culturing step. Alternatively, the cells may be allogenic, i.e., obtained from a subject that produces cells allogenic to cells of the patient. In such embodiments, the method may further comprise obtaining a cell from a subject that produces cells allogenic to lymphocyte cells of the patient, for use in the culturing step.

In certain embodiments, the cell is a lymphocyte cell. Lymphocyte cells can be obtained from human or animal tissues according to procedures described in the literature. In certain embodiments, the lymphocyte cell is obtained from blood, cancer tissue, bone marrow, the spleen, a lymph node, or the thymus. In certain other embodiments, the lymphocyte cell is obtained from a population of peripheral blood mononuclear cells, such as human peripheral blood mononuclear cells. In certain other embodiments, the lymphocyte cell is obtained from a lymph node in proximity to a tumor or site of infection. In certain other embodiments, the lymphocyte cell is obtained from cancer tissue. In yet other embodiments, the lymphocyte cell is a tumor-infiltrating-lymphocyte cell.

Cells can be characterized according to the presence of a receptor for an antigen specific for a medical disorder. In certain embodiments, the cell expresses a receptor for an antigen specific for a medical disorder. As indicate above, such cells may provide more effective therapies for treating disease since the cells are more likely to target tissue specific to the disease to be treated. In certain embodiments, the medical disorder is a cancer, bacterial infection, fungal infection, or immune disorder. In yet other embodiments, the cell may express a receptor that, while not specific for a medical disorder, has utility in enhancing cell efficacy in treating the disorder.

Various types of lymphocyte cells have been described in the literature for use in adoptive cellular transfer. In certain embodiments, the lymphocyte cell is a T cell. In certain other embodiments, the lymphocyte cell is a CD8$^+$ T cell, CD4$^+$ T cell, or $T_H17$ cell. In certain other embodiments, the lymphocyte cell is a CD8$^+$ T cell, CD4$^+$ T cell, or a combination thereof. In certain other embodiments, the lymphocyte cell is a natural killer cell. In certain other embodiments, the lymphocyte cell is a Tc17 cell, natural killer T cell, or γδ T cell. In yet other embodiments, the lymphocyte cell is a genetically altered lymphocyte cell.

Cells may be administered to the patient according to procedures described in the literature. In certain embodiments, the administering comprises injecting into the patient the pharmaceutical composition. The injecting may be intravenous injection or injection directly into diseased tissue, such as a tumor. In yet other embodiments, the injecting may be subcutaneous injection into the patient.

The therapeutic method embraces combination therapies, such as administering (i) an agent that enhances the efficacy of the cell exposed to an agonist of RORγ and/or (ii) an agent having independent efficacy in treating the target medical disorder. In certain embodiments, the method further comprises administering to the patient one or more agents selected from the group consisting of a cytokine and an agonist of RORγ. The therapeutic methods described herein can be used in combination with radiation therapy, surgery, and other medical techniques.

The therapeutic methods are contemplated to provide medical benefits to human patients, such as adult human patients and pediatric human patients. The therapeutic methods are also contemplated to provide medical benefits to animal patients, such as veterinary animals.

Exemplary Methods of Preparing a Population of Cells Exposed Ex Vivo to an Agonist of RORγ

One aspect of the invention provides a method of preparing a population of cells that have been exposed ex vivo to an agonist of RORγ, where the cells are lymphocyte cells and/or dendritic cells. The method comprises exposing a population of cells selected from the group consisting of lymphocyte cells and dendritic cells ex vivo to an agonist of RORγ to thereby provide said population of cells that have been exposed ex vivo to an agonist of RORγ. The population of cells may be used in therapeutic methods described herein.

The exposing step may comprise culturing a population of cells with an agonist of RORγ for a duration of time sufficient to increase the number of cells in the population. The culturing may comprise exposing the cell to a cytokine (e.g., IL-1β, IL-2, IL-6, IL-7, IL-10, IL-12, IL-15, IL-18, IL-21, IL-23, or transforming growth factor beta). Further during the culturing step, the cell may optionally be exposed to an antigen associated with a medical disorder. Accordingly, in certain embodiments, the culturing step comprises exposing the cell to an antigen associated with a medical disorder. The antigen may be an antigen presenting cell. Alternatively, the antigen may comprise cancer tissue.

The cell may be autologous or allogenic. Autologous cells are cells obtained from the patient whom will receive the cell exposed ex vivo to an agonist of RORγ. As such, in certain embodiments, the method may further comprise obtaining a cell (i.e., a lymphocyte or dendritic cell) from said patient for use in the culturing step. Alternatively, the cells may be allogenic, i.e., obtained from subject that produces cells allogenic to cells of the patient. In such embodiments, the method may further comprise obtaining a cell from a subject that produces cells allogenic to cells of the patient, for use in the culturing step.

In certain embodiments, the cell is a lymphocyte cell. Lymphocyte cells can be obtained from human or animal tissues according to procedures described in the literature. In certain embodiments, the lymphocyte cell is obtained from blood, cancer tissue, bone marrow, the spleen, a lymph node, or the thymus. In certain other embodiments, the lymphocyte cell is obtained from a population of peripheral blood mononuclear cells, such as human peripheral blood mononuclear cells. In certain other embodiments, the lymphocyte cell is obtained from a lymph node in proximity to a tumor or site of infection. In certain other embodiments, the lymphocyte cell is obtained from cancer tissue. In yet other embodiments, the lymphocyte cell is a tumor-infiltrating-lymphocyte cell.

Cells can be characterized according to the presence of a receptor for an antigen specific for a medical disorder. In certain embodiments, the cell expresses a receptor for an antigen specific for a medical disorder. As indicated above, such cells may provide more effective therapies for treating disease since the cells are more likely to target tissue specific to the disease to be treated. In certain embodiments, the medical disorder is a cancer, bacterial infection, fungal infection, or immune disorder. In yet other embodiments, the cell may express a receptor that, while not specific for a medical disorder, has utility in enhancing cell efficacy in treating the disorder.

Various types of lymphocyte cells have been described in the literature for use in adoptive cellular transfer. In certain embodiments, the lymphocyte cell is a T cell. In certain other embodiments, the lymphocyte cell is a $CD8^+$ T cell, $CD4^+$ T cell, or $T_H17$ cell. In certain other embodiments, the lymphocyte cell is a $CD8^+$ T cell, $CD4^+$ T cell, or a combination thereof. In certain other embodiments, the lymphocyte cell is a natural killer cell. In certain other embodiments, the lymphocyte cell is a Tc17, natural killer T cell, or γδ T cell. In yet other embodiments, the lymphocyte cell is a genetically altered lymphocyte cell.

Cells may be administered to the patient according to procedures described in the literature. In certain embodiments, the administering comprises injecting into the patient the pharmaceutical composition. The injecting may be intravenous injection or injection directly into diseased tissue, such as a tumor.

Exemplary Methods of Treating a Medical Disorder

One aspect of the invention provides a method of treating a medical disorder. The method comprises administering to a patient in need thereof a cell that has been exposed ex vivo to an agonist of RORγ to treat the medical disorder, wherein the cell is a lymphocyte cell or dendritic cell. The medical disorder can be, for example, a cancer, bacterial infection, fungal infection, or immune disorder. Additional exemplary medical disorders are described in, for example, Section VI. In certain embodiments, the medical disorder is a cancer selected from the group consisting of a solid tumor, lymphoma, and leukemia. In certain other embodiments, the medical disorder is a cancer selected from the group consisting of ovarian cancer, melanoma, colorectal cancer, lung cancer, breast cancer, prostate cancer, pancreatic cancer, renal cell carcinoma, leukemia, a B-cell lymphoma, and non-Hodgkin lymphoma.

The therapeutic method can be further characterized according to, for example, the cells used, the agonist of RORγ, and/or the administration of additional therapeutic agents such as a cytokine or lymphodepleting agent.

As explained above, cells can be characterized according to the presence of a receptor for an antigen specific for the medical disorder. In certain embodiments, the method uses a cell expressing a receptor for an antigen specific for the medical disorder. In yet other embodiments, the cell may express a receptor that, while not specific for a medical disorder, has utility in enhancing cell efficacy in treating the disorder.

The cell may be autologous or allogenic. In certain embodiments, the cells are autologous. In certain other embodiments, the are allogenic.

In certain embodiments, the cell is a lymphocyte cell. Various types of lymphocyte cells have been described in the literature for use in adoptive cellular transfer. In certain embodiments, the lymphocyte cell is a T cell. In certain other embodiments, the lymphocyte cell is a $CD8^+$ T cell, $CD4^+$ T cell, or $T_H17$ cell. In certain other embodiments, the lymphocyte cell is a $CD8^+$ T cell, $CD4^+$ T cell, or a combination thereof. In certain other embodiments, the lymphocyte cell is a natural killer cell. In certain other embodiments, the lymphocyte cell is a Tc17 cell, natural killer T cell, or γδ T cell. In yet other embodiments, the lymphocyte cell is a genetically altered lymphocyte cell. In still other embodiments, the lymphocyte cell is a tumor-infiltrating-lymphocyte cell. In certain embodiments, the lymphocyte cell is a tumor-infiltrating-lymphocyte cell, and the medical disorder is a tumor.

The therapeutic method embraces combination therapies, such as administering (i) an agent that enhances the efficacy of the cell (i.e., a lymphocyte cell or dendritic cell) exposed to an agonist of RORγ and/or (ii) an agent having independent efficacy in treating the target medical disorder. In certain embodiments, the method further comprises administering to the patient one or more agents selected from the group consisting of a cytokine and an agonist of RORγ. In yet other embodiments, the method further comprises administering to the patient a lymphodepleting agent. The lymphodepleting agent may comprise, for example, cyclophosphamide, fludarabine, or a combination thereof. Additional exemplary combination therapies are described in Section VIII.

The therapeutic methods are contemplated to provide medical benefits to human patients, such as adult human patients and pediatric human patients. The therapeutic methods are also contemplated to provide medical benefits to animal patients, such as veterinary animals.

The agonist of RORγ may be an agonist of RORγ described in Section VII herein. In certain embodiments, the agonist of RORγ is a small organic molecule. In certain other embodiments, the agonist of RORγ is a compound of Formula I described herein.

Exemplary Methods of Increasing Immune Benefit of Vaccination

One aspect of the invention provides a method of increasing the immune benefit of a vaccination. The method comprises administering to a patient in need thereof a cell that has been exposed ex vivo to an agonist of RORγ to increase the immune benefit of vaccination, wherein the patient has received vaccination or will receive vaccination during the time period over which said lymphocyte cell exerts physiological activity, and the cell is a lymphocyte cell or a dendritic cell.

The vaccination may be vaccination against a cancer, such as solid tumor or one of the medical disorders described in Section VI. In certain embodiments, the patient has previously undergone surgery to remove cancerous tissue.

The method can be further characterized according to the type of cell used. For example, the cell may be autologous or allogenic. In certain embodiments, the cells are autologous. In certain other embodiments, the cells are allogenic. In certain embodiments, the cell is a lymphocyte cell. In certain embodiments, the lymphocyte cell is a T cell. In certain embodiments, the lymphocyte cell is a $CD8^+$ T cell, $CD4^+$ T cell, or $T_H17$ cell. In certain other embodiments, the lymphocyte cell is a $CD8^+$ T cell, $CD4^+$ T cell, or a combination thereof. In certain other embodiments, the lymphocyte cell is a natural killer cell. In certain other embodiments, the lymphocyte cell is a Tc17, natural killer T cell, or γδ T cell. In still other embodiments, the lymphocyte cell is a tumor-infiltrating-lymphocyte cell. In certain embodiments, the lymphocyte cell is a tumor-infiltrating-lymphocyte cell, and the vaccination is vaccination against a tumor.

The therapeutic method embraces combination therapies, such as administering agents that enhance the efficacy of a cell (i.e., a lymphocyte cell or dendritic cell) exposed to an agonist of RORγ. Accordingly, in certain embodiments, the method further comprises administering to the patient one or more agents selected from the group consisting of a cytokine and an agonist of RORγ.

The therapeutic methods are contemplated to provide medical benefits to human patients, such as adult human patients and pediatric human patients. The therapeutic methods are also contemplated to provide medical benefits to animal patients, such as veterinary animals.

The agonist of RORγ may be an agonist of RORγ described in Section VII herein. In certain embodiments, the agonist of RORγ is a small organic molecule. In certain other embodiments, the agonist of RORγ is a compound of Formula I described herein.

Exemplary Population of Lymphocyte Cells Exposed Ex Vivo to an Agonist of RORγ

One aspect of the invention provides a population of lymphocyte cells that have been exposed ex vivo to an agonist of RORγ. The population may be characterized by the presence and/or quantity of particular types of cells in the population. For example, in certain embodiments, the population comprises one or more of the following: T cells and natural killer cells. In certain other embodiments, a majority of lymphocyte cells in the population are T cells. In certain other embodiments, a majority of lymphocyte cells in the population are CD8$^+$ T cells, CD4$^+$ T cells, $T_H17$ cells, or a combination thereof. In yet other embodiments, a majority of lymphocyte cells in the population are natural killer cells. In yet other embodiments, a single type of lymphocyte cell (e.g., a T cell, CD8$^+$ T cell, CD4$^+$ T cell, $T_H17$ cell, Tc17 cell, natural killer T cell, or γδ T cell) comprises at least 60%, 70% 80%, 90% or 95% of the cells in the population. In yet other embodiments, the population is characterized by: (i) a majority of lymphocyte cells in the population are T cells, (ii) a majority of lymphocyte cells in the population are CD8$^+$ T cells, CD4$^+$ T cells, $T_H17$ cells, or a combination thereof, (iii) a majority of lymphocyte cells in the population are Tc17 cells, (iv) a majority of lymphocyte cells in the population are natural killer cells, or (v) a majority of lymphocyte cells in the population are natural killer T cells, γδ T cells, or a combination thereof. In yet other embodiments, a majority of lymphocyte cells in the population are CD8$^+$ T cells, CD4$^+$ T cells, or a combination thereof. In yet other embodiments, the population is characterized by a majority of lymphocyte cells in the population are Tc17 cells, CD4+Th0 T lymphocyte cells, Th17-polarized CD4+ T lymphocyte cells, CD8+Tc17 T lymphocyte cells, or a combination thereof.

The population of cells can be further characterized according to the abundance of lymphocyte cells having a receptor for an antigen specific for a medical disorder. In certain embodiments, a majority of lymphocyte cells in the population comprise a receptor for an antigen specific for a medical disorder. In yet other embodiments, at least 60%, 70% 80%, 90% or 95% of the cells in the population have a receptor for an antigen specific for a medical disorder. The medical disorder may be a medical disorder described in Section VI. In certain embodiments, the medical disorder is a cancer, bacterial infection, fungal infection, or immune disorder. In certain other embodiments, the medical disorder is a cancer selected from the group consisting of solid tumor, lymphoma, and leukemia. In yet other embodiments, the medical disorder is a cancer selected from the group consisting of ovarian cancer, melanoma, colorectal cancer, lung cancer, breast cancer, prostate cancer, pancreatic cancer, renal cell carcinoma, leukemia, a B-cell lymphoma, and non-Hodgkin lymphoma.

The population of cells can also be characterized according to the origin of the lymphocyte cells. In certain embodiments, the lymphocyte cells are derived from blood, cancer tissue, bone marrow, the spleen, a lymph node, or the thymus. In certain other embodiments, the lymphocyte cells are obtained from a population of peripheral blood mononuclear cells, such as human peripheral blood mononuclear cells. In certain other embodiments, a majority of lymphocyte cells in the population are tumor-infiltrating-lymphocyte cells. In yet other embodiments, a majority of the lymphocyte cells are derived from a lymph node in proximity to a tumor or site of infection. In yet other embodiments, a majority of the lymphocyte cells are derived from cancer tissue.

Exemplary Population of Dendritic Cells Exposed Ex Vivo to an Agonist of RORγ

One aspect of the invention provides a population of dendritic cells that have been exposed ex vivo to an agonist of RORγ. The population of cells can be further characterized according to the abundance of cells having a receptor for an antigen specific for a medical disorder. In certain embodiments, a majority of cells in the population comprise a receptor for an antigen specific for a medical disorder. In yet other embodiments, at least 60%, 70% 80%, 90% or 95% of the cells in the population have a receptor for an antigen specific for a medical disorder. The medical disorder may be a medical disorder described in Section VI. In certain embodiments, the medical disorder is a cancer, bacterial infection, fungal infection, or immune disorder. In certain other embodiments, the medical disorder is a cancer selected from the group consisting of solid tumor, lymphoma, and leukemia. In yet other embodiments, the medical disorder is a cancer selected from the group consisting of ovarian cancer, melanoma, colorectal cancer, lung cancer, breast cancer, prostate cancer, pancreatic cancer, renal cell carcinoma, leukemia, a B-cell lymphoma, and non-Hodgkin lymphoma.

Exemplary Pharmaceutical Compositions Comprising Cells

One aspect of the invention provides a pharmaceutical composition comprising a population of cells described herein and a pharmaceutically acceptable carrier. Exemplary pharmaceutically acceptable carriers include, for example, aqueous and non-aqueous, isotonic sterile injection solutions, which can contain anti-oxidants, buffers, bacteriostats, and solutes that render the formulation isotonic with blood, and aqueous and non-aqueous sterile suspensions that can include suspending agents, solubilizers, thickening agents, stabilizers, and preservatives, and other pharmaceutically acceptable carriers described in Section X below and/or in the literature. In certain preferred embodiments, the cells are lymphocyte cells.

Exemplary Methods for Increasing the Longevity of RORγ Agonist Treated Lymphocyte Cell One contemplated benefit of exposing a lymphocyte cell to an agonist of RORγ is increasing the longevity of the lymphocyte cell, particularly increasing the longevity of the lymphocyte cell after administration to a patient. Accordingly, one aspect of the invention provides a method for increasing the longevity of the lymphocyte cell. The method comprises exposing a lymphocyte cell ex vivo to an agonist of RORγ in an amount sufficient to increase the longevity of the lymphocyte cell. In certain embodiments, the exposing a lymphocyte cell ex vivo to an agonist of RORγ results in at least a 5%, 10%, 20%, 30% or 50% increase in longevity of the lymphocyte cell relative to the life of the lymphocyte cell without having been exposed to the agonist of RORγ.

II. Exemplary Lymphocyte Cells for Use in Medical Therapy

Lymphocyte cells may be obtained from the patient to be treated or may be obtained from a subject that produces lymphocyte cells allogenic to lymphocyte cells of the patient to receive the lymphocyte cells. Lymphocyte cells are white blood cells involved in immune function in a patient. Lymphocyte cells can be a T cell, natural killer cell, or a B cell. The therapeutic methods embrace using a T cell, natural killer cell, B cell, and combinations thereof. In certain embodiments, the lymphocyte cell is a T cell or a natural killer cell. In yet other embodiments, the lymphocyte cell may be a type of T cell referred to as a natural killer T cell. Lymphocyte cells may be further characterized according to features described below.

Lymphocyte cells may be characterized according to whether they are a tumor infiltrating lymphocyte, naïve T lymphocyte, memory T lymphocyte, effector T lymphocyte, $CD8^+$ T cell, $CD4^+$ T cell, $CD4^+/CD8^+$ double positive T lymphocyte, $CD28^+CD8^+$ T cell, or $T_H17$ cell. $CD8^+$ T cells can be separated into naïve $CD8^+$ T cells, memory $CD8^+$ T cells, and effector $CD8^+$ T cells, according to cell surface antigens characteristic to each type of cell. Whether a cell or cell population is positive for a particular cell surface marker can be determined by flow cytometry using staining with a specific antibody for the surface marker and an isotype matched control antibody. A cell population negative for a marker refers to the absence of significant staining of the cell population with the specific antibody above the isotype control, and positive refers to uniform staining of the cell population above the isotype control. For instance, $CD4^+$ T helper cells can be sorted into naive, central memory, and effector cells by identifying cell populations that have cell surface antigens. In certain embodiments, central memory CD4+ T cells are CD62L positive and CD45RO positive. In certain embodiments, effector $CD4^+$ T cells are CD62L and CD45RO negative. In yet other embodiments, the lymphocyte cell is a Th1 cell, Tc1 cell, Th0 cell, or Tc0 cell.

In certain embodiments, the lymphocyte cell is a $CD8^+$ T cell, which is optionally further characterized according to the whether the $CD8^+$ T cell is a naïve $CD8^+$ T cell, a memory $CD8^+$ T cell, or an effector $CD8^+$ T cell. In certain embodiments, the lymphocyte cell is a memory $CD8^+$ T cell, which may be further characterized according to whether the cell is CD62L positive or CD45RO positive. In certain other embodiments, the lymphocyte cell is an effector $CD8^+$ T cell, which may be further characterized according to whether the cell is CD62L negative or CD45RO negative.

In yet other embodiments, the lymphocyte cell is a CD4+Th0 T lymphocyte, Th17– polarized CD4+ T lymphocyte, or CD8+Tc17 T lymphocyte. In still other embodiments, the lymphocyte cell is a memory T cell present in CD62L+ or CD62L– subsets of CD8+ peripheral blood lymphocytes. In certain embodiments, the central memory T cells may be CD45RO+, CD62L+, CD8+ T cells. In certain embodiments, effector T cells are negative for CD62L, CCR7, CD28, and CD127, and positive for granzyme B and perforin.

T cells can be characterized according to identity of a T cell receptor located on the surface of the T cell. The T cell receptor is a disulfide-linked membrane-anchored heterodimer that normally consists of highly variable alpha (α) and beta (β) chains expressed as part of a complex with the invariant CD3 chain molecules. T cells expressing this receptor are referred to as α:β (or αβ) T cells. A minority of T cells express an alternate receptor, formed by variable gamma (γ) and delta (δ) chains, and such T cells are referred as γδ T cells.

One subtype of T cells is natural killer T (NKT) cells. NKT cells are a heterogeneous group of T cells that share properties of both T cells and natural killer NK cells. Many NKT cells recognize the non-polymorphic CD1d molecule, an antigen-presenting molecule that binds self- and foreign lipids and glycolipids.

Other subtypes of T cells include, for example, $CD8^+$ T cells, $CD4^+$ T cells, Tc17 cells, natural killer T cells, and γδ T cells. Still other subtypes of T cells include, for example, $CD4^-$ $CD8^-$ T cells and $CD28^+CD8^+$ T cells.

Preferably the lymphocyte cell comprises a receptor specific for an antigen of a medical condition. The receptor can be the endogenous lymphocyte cell receptor, i.e., the antigen-specific lymphocyte cell receptor that is endogenous (i.e., native to) the lymphocyte. In such instances, the lymphocyte comprising the endogenous lymphocyte cell receptor can be a lymphocyte cell that was isolated from the patient, which is known to express the particular medical condition-specific antigen. Alternatively, the lymphocyte comprising the endogenous lymphocyte cell receptor can be a lymphocyte cell that was isolated from a subject that produces allogenic lymphocyte cells (i.e., lymphocyte cells that are histocompatible with the patient that will receive the lymphocyte cells). In certain embodiments, the subject from which lymphocyte cells are obtained may be immunized prior to obtaining the lymphocyte cells, so that the lymphocyte cells to be administered to the patient will have specificity for the medical disorder to be treated.

The antigen of a disease recognized by the endogenous lymphocyte cell receptor can be any antigen which is characteristic of the disease. For example, the antigen may be, for example, a tumor antigen, such as gp100, MART-1, TRP-1, TRP-2, tyrosinase, NY-ESO-1, MAGE-1, or MAGE-3.

Lymphocyte cells may also be characterized according to the presence of a phenotypic marker of activation for tumor reactivity, such as the presence of 4-1BBL. Populations of lymphocyte cells enriched for such a phenotypic marker may provide therapeutic advantages.

Lymphocyte cells may also be characterized according to the level of expression of the RORγ. In certain embodiments, the lymphocyte cell may be induced to express or engineered to express RORγ, thereby increasing the amount of RORγ.

Genetically Altered Lymphocyte Cells

The lymphocyte cell may be a genetically modified lymphocyte cell, such as a genetically modified lymphocyte cell described in, for example, International Patent Application Publication No. WO 2012/129514, which is hereby incorporated by reference. Genetic modification of the lymphocyte may improve the efficacy of therapy by promoting the viability and/or function of transferred lymphocyte cells, provide a genetic marker to permit selection and/or evaluation of in vivo survival or migration, or may incorporate functions that improve the safety of immunotherapy, for example, by making the cell susceptible to negative selection in vivo. The lymphocyte may be genetically modified so that the lymphocyte cell expresses certain proteins, such as a survival cytokine (e.g., granulocyte-macrophage colony-stimulating factor) and/or receptor for an antigen (e.g., a tumor antigen).

Accordingly, in embodiments, lymphocyte cells are modified with chimeric antigen receptors (CAR). The CARs may comprise a single-chain antibody fragment (scFv) that is derived from the variable heavy (VH) and variable light (VL) chains of a monoclonal antibody (mAb) linked to the TCR $CD3^+$ chain that mediates T-cell activation and cytotoxicity. Costimulatory signals can also be provided through the CAR by fusing the costimulatory domain of CD28 or 4-1 BB to the $CD3^+$ chain. CARs are specific for cell surface molecules independent from HLA, thus overcoming the limitations of TCR-recognition including HLA-restriction and low levels of HLA-expression on tumor cells.

CARs can be constructed with a specificity for a particular cell surface marker by utilizing antigen binding fragments or antibody variable domains of, for example, antibody molecules. The antigen binding molecules can be linked to one or more cell signaling modules. In embodiments, cell signaling modules include CD3 transmembrane domain, CD3 intracellular signaling domains, and CD 28 transmembrane domains. In certain embodiments, the intracellular signaling domain comprises a CD28 transmembrane and signaling domain linked to a CD3 intracellular domain. In yet other embodiments, the cell signaling module may comprise ICOS or 4-1BB.

The CARs may be specific for cell surface expressed antigens associated with pathogens or cancer cells. In certain embodiments, the CAR is specific for a HIV antigen, HCV antigen, HBV antigen, CMV antigen, or tumor antigen such as orphan tyrosine kinase receptor ROR1, tEGFR, Her2, L1-CAM, CD19, CD20, CD22, mesothelin, and CEA. In certain embodiments, the CAR is specific for a fungal infection, such as the CAR described by Kumaresan et al. in Proc. Natl. Acad. Sci. USA (2014) vol. 111(29), pages 10660-10665 in which T cells express a chimeric CD28 and CD3-ξ (abbreviated as "D-CAR"), which is hereby incorporated by reference.

In yet other embodiments, the CAR contains an antigen binding domain, a costimulatory domain, and a CD3 ξ signaling domain. The costimulatory domain used in combination with the CD3 ξ signaling domain can mimic the two-signal model of T cell activation. The CAR antigen binding domain can be an antibody or antibody fragment, such as, for example, a Fab or an scFv. Non-limiting examples of anti-cancer antibodies include, for example: trastuzumab, bevacizumab, rituximab, pertuzumab, cetuximab, IMC-1C11, EMD 7200, SGN-30, SGN-15, SGN-33 (a humanized antibody targeted to CD33 antigen), SGN-40 (a humanized monoclonal antibody targeted to CD40 antigen), SGN-35 (a genetically engineered monoclonal antibody targeted to a CD30 antigen), SGN-70 (a humanized antibody targeted to CD70 antigen), SGN-75 (a conjugate comprising SGN70 antibody), and SGN-17/19 (a fusion protein containing antibody and enzyme conjugated to melphalan prodrug).

Various infection techniques have been developed which utilize recombinant infectious virus particles for gene delivery to cells. The viral vectors which have been used in this way include virus vectors derived from simian virus 40, adenoviruses, adeno-associated virus (AAV), lentiviral vectors, and retroviruses. Thus, gene transfer and expression methods are numerous but essentially function to introduce and express genetic material in mammalian cells. Retroviral vectors provide a highly efficient method for gene transfer into eukaryotic cells. Moreover, retroviral integration takes place in a controlled fashion and results in the stable integration of one or a few copies of the new genetic information per cell.

It can be useful to include in the T cells a positive marker that enables selection of cells of the negative selectable phenotype in vitro. The positive selectable marker may be a gene which, upon being introduced into the host cell, expresses a dominant phenotype permitting positive selection of cells carrying the gene. Genes of this type are known in the art and include, for example, hygromycin-B phosphotransferase gene (hph) which confers resistance to hygromycin B, the amino glycoside phosphotransferase gene (neo or aph) from Tn5 which codes for resistance to the antibiotic G418, the dihydrofolate reductase (DHFR) gene, the adenosine daminase gene (ADA), and the multi-drug resistance (MDR) gene.

III. Exemplary Procedures for Isolating and Culturing Lymphocyte Cells

Exemplary procedures for isolating and culturing lymphocyte cells are described in herein below. Further details for isolating and culturing lymphocyte cells can be found in the literature, such as in U.S. Pat. Nos. 5,229,109; 5,229,115; 5,776,451; and 7,998,736; each of which is hereby incorporated by reference.

Isolation of Lymphocyte Cells from a Patient

Lymphocyte cells can be isolated from, for example, blood, cancer tissue, bone marrow, the spleen, a lymph node, and the thymus. Desirably, the lymph node is in proximity to a tumor or site of infection. In certain embodiments, the lymphocyte cell is a tumor-antigen specific T cell isolated from a tumor, such as a tumor in the patient to be treated with a population T cells that have been exposed to an agonist of RORγ.

Culturing Lymphocyte Cells

Lymphocyte cells are cultured ex vivo in the presence of an agonist of RORγ. Exemplary culture media and conditions include, for example, RPMI 1640, 25 mM HEPES, 2 mM L-glutamine, penicillin (50 U/mL), streptomycin (50 mg/mL) and 10% human serum as culture media where the temperature is approximately 37° C. and cells are cultured for up to several days, as further described in, for example, U.S. Patent Application Publication No. 2010/0310533.

In certain embodiments, the culturing is performed under conditions such that the number of lymphocyte cells increases (i.e., expanded). Ex vivo expansion of lymphocyte cells can be carried out in accordance with known techniques, such as those described in U.S. Pat. No. 6,040,177. To illustrate, the desired population of lymphocyte cells may be expanded by adding an initial lymphocyte cell population to a culture medium in vitro, and then adding to the culture medium feeder cells, such as non-dividing peripheral blood mononuclear cells (PBMC), (e.g., such that the resulting population of cells contains at least about 5, 10, 20, or 40 or more PBMC feeder cells for each lymphocyte in the initial population to be expanded); and incubating the culture (e.g., for a time sufficient to expand the number of lymphocyte cells). The non-dividing feeder cells can comprise gamma-irradiated PBMC feeder cells. The PBMCs may be optionally irradiated with gamma rays in the range of about 3000 to 3600 rads. The culture can typically be incubated under temperature conditions favorable for growth of lymphocyte cells, such as at temperature of at least about 25 degrees Celsius, and more preferably at least about 30 degrees Celsius or about 37 degrees Celsius.

Exposing Lymphocyte Cells to Additional Agents (e.g., Cytokines)

Lymphocyte cells may be exposed to a growth factor or other agent during the culturing step. For example, lymphocyte cells may be exposed to a cytokine. The cytokine may be, for example, IL-1β, IL-2, IL-6, IL-7, IL-10, IL-12, IL-15, IL-18, IL-21, IL-23, or transforming growth factor beta. In certain embodiments, the cytokine may be, for example, IL-1β, IL-2, IL-6, IL-21, IL-23, or transforming growth factor beta. In yet other embodiments, the cytokine may be a Th17 cytokine. The concentration of cytokine used in the culturing step may be, for example, in the range of (a)

about 0.1 ng of cytokine per mL of culture media to (b) about 100 ng of cytokine per mL of culture media.

In yet other embodiments, lymphocyte cells may be exposed to anti-CD2, anti-CD3, and/or anti-CD28 antibody to stimulate the lymphocyte cells, thereby promoting expansion of the lymphocyte cells. Procedures have been reported in the literature for stimulating T cells using, for example, anti-CD3/CD28 beads. See, for example, Trickett et al. in *J. Immunol. Methods*. (2003) vol. 275(1-2), pages 251-255. Alternatively, or in addition to, lymphocyte cells may be exposed to an anti-ICOS or another co-stimulatory antibody.

In yet other embodiments, the lymphocyte cells may be exposed to an anti-IFNγ and/or anti-IL-4 antibody. In still other embodiments, the lymphocyte cells may be exposed to (i) an anti-CD2, anti-CD3, or anti-T cell receptor antibody and (ii) one or more of an anti-CD28, anti-ICOS, anti-CD137 (4-1BB), or anti-CD27 antibody, or B71.Fc, B72.Fc, ICOSL.Fc, or 4-1BBL.Fc.

The concentration of antibody used in the culturing step may be, for example, in the range of (a) about 0.1 μg of antibody per mL of culture media to (b) about 100 μg of antibody per mL of culture media.

In yet other embodiments, the lymphocyte cells may be transfected with a plasmid expressing RORγ.

Exposing Lymphocyte Cells to an Antigen Ex Vivo

Lymphocyte cells may be cultured ex vivo with an antigen in order to produce lymphocyte cells that target a particular antigen when the cultured lymphocyte cells are administered to a patient. When the medical disorder to be treated is a cancer, the antigen may be cancer tissue, such as cancer tissue comprising a polypeptide, total RNA, lysed cancer cells, or apoptotic cancer bodies. The antigen may also be an antigen presenting cell, such as an autologous dendritic cell, a monocyte, an EBV-transformed B cell line, an allogeneic EBV transformed B cell line expressing the shared restricting allele, or an artificial antigen presenting cell.

Characterization of Cells after Culturing with Agonist of RORγ

After cells have been cultured with an agonist of RORγ, the cells may be analyzed for changes in the amount of IL-17A produced by the cells. For example, after the cells have been cultured with an agonist of RORγ, an aliquot of the cells may be treated with phorbol 12-myristate 13-acetate (PMA, 100 ng/mL) and ionomycin (1 μg/mL) in the presence of protein transporter inhibitor brefeldin A (3 μg/mL) for 5 hours. The resulting cells are intracellularly stained for IL-17A and analyzed by flow cytometer to determine the amount of IL-17A produced by the cells. Desirably, the cells cultured with an agonist of RORγ produce a greater amount of IL-17A relative to analagous cells that have not undergone treatment with an agonist of RORγ. In certain embodiments, the increase in IL-17A production is at least about 5%, 10%, 25%, 50%, 75%, or 100%.

As an alternative to the above procedure, media from differentiation culture (used when culturing cells with an agonist of RORγ) may be analyzed (such as using an ELISA assay) to determine the amount of IL-17A in the media. Desirably, the amount of IL-17A in the media is greater due to the increased production of IL-17A by cells cultured with an agonist of RORγ. In certain embodiments, the increase in the amount of IL-17A is at least about 5%, 10%, 25%, 50%, 75%, or 100% by weight.

IV. Exemplary Dendritic Cells for Use in Medical Therapy

Dendritic cells are potent antigen-presenting cells, typically of bone marrow origin, that are integral in the stimulation of primary and secondary T-cell and B-cell responses. Dendritic cells can be obtained from, for example, peripheral blood, umbilical cord blood, or bone marrow using methods described in the literature. See, for example, Bernhard et al. in *Cancer Res.* (1995) vol. 55, page 1099; and Chang et al. in *Clin. Cancer Res.* (2002) vol. 8, page 1021.

In certain embodiments, dendritic cells are obtained from CD34+ hematopoietic progenitor cells derived from bone marrow or granulocyte-colony stimulating factor-mobilized peripheral blood, such as described by Bernhard et al. in *Cancer Res.* (1995) vol. 55, page 1099. In other embodiments, dendritic cells are derived and expanded from CD34+ hematopoietic progenitor cells in umbilical cord blood by inducing dendritic cell differentiation and proliferation with GM-CSF plus TNF-alpha, such as described in, for example, Caux et al. in *Nature* (Lond.) (1992), vol. 360, pages 258-261. In other embodiments, dendritic cells are obtained from CD14+ monocytes, such as described by Chang et al. in *Clin. Cancer Res.* (2002) vol. 8, page 1021.

Populations of patient-derived cells containing a high percentage of dendritic cells may be used in certain embodiments. Such populations may comprise, for example, at least about 50%, 60%, 70%, 80%, 90%, or more dendritic cells. Other cells in the population may be, for example, red blood cells.

The dendritic cells may be modified, such as the modified dendritic cells described in, for example, U.S. Pat. No. 8,597,946 and International Patent Application Publication Nos. WO 2008/066749 and WO 2009/114547, each of which is hereby incorporated by reference. Further description of exemplary dendritic cells can be found in, for example, International Patent Application Publication Nos. WO 2002/087626, WO 2002/044338, and WO 2002/083879, each of which is hereby incorporated by reference. In certain embodiments, the dendritic cells express ROR-gamma.

V. Administering Cells to a Patient

Cells may be administered to a patient using procedures described in the literature for adoptive cellular transfer. Exemplary administration procedures involve injecting a cell (e.g., a lymphocyte cell or dendritic cell) into a patient, such as by intravenous injection. The cell or a population of cells may be formulated in a pharmaceutical composition suitable for injection into the patient.

The dosage of cells to be administered can be determined by a practitioner of ordinary skill. In particular, any suitable number of lymphocyte cells can be administered to the patient. While a single lymphocyte is capable of expanding and providing a benefit, it is preferable to administer at least $10^3$, more preferably at least $10^5$, even more preferably at least $10^8$ and optionally $10^{12}$ or more lymphocyte cells. In certain embodiments, from about $10^8$ to about $10^{12}$ lymphocyte cells are administered to a patient. It is understood that administration of excessive quantities of lymphocyte cells (e.g., more than $10^{15}$ or $10^{18}$ lymphocyte cells) may exceed the ability of certain patients to support them, thereby leading to undesirable effects. In certain embodiments, at least $10^3$, $10^5$, $10^8$, $10^{12}$ or more dendritic cells are administered to a patient.

VI. Exemplary Medical Disorders for Treatment

It is contemplated that the therapeutic methods can provide medical benefits to subjects suffering from a medical disorder such as a cancer, bacterial infection, fungal infection, or immune disorder. The methods may also be useful in increasing immunogenicity against an opportunistic infection or as a vaccine adjuvant. Additionally, the therapeutic methods can provide medical benefits in combination therapy.

Cancer

The disorder may be cancer. In certain embodiments, the cancer is a solid tumor or leukemia. In certain other embodiments, the cancer is colon cancer, pancreatic cancer, breast cancer, ovarian cancer, prostate cancer, squamous cell carcinoma, basal cell carcinoma, adenocarcinoma, sweat gland carcinoma, sebaceous gland carcinoma, lung cancer, leukemia, bladder cancer, stomach cancer, cervical cancer, testicular cancer, skin cancer, rectal cancer, thyroid cancer, kidney cancer, uterus cancer, esophagus cancer, liver cancer, an acoustic neuroma, oligodendroglioma, meningioma, neuroblastoma, or retinoblastoma. In certain other embodiments, the cancer is small cell lung cancer, non-small cell lung cancer, melanoma, cancer of the central nervous system tissue, brain cancer, Hodgkin's lymphoma, non-Hodgkin's lymphoma, cutaneous T-Cell lymphoma, cutaneous B-Cell lymphoma, or diffuse large B-Cell lymphoma. In certain other embodiments, the cancer is breast cancer, colon cancer, small-cell lung cancer, non-small cell lung cancer, prostate cancer, renal cancer, ovarian cancer, leukemia, melanoma, or cancer of the central nervous system tissue. In certain other embodiments, the cancer is colon cancer, small-cell lung cancer, non-small cell lung cancer, renal cancer, ovarian cancer, renal cancer, or melanoma.

In certain embodiments, the non-Hodgkin's lymphoma is a B-cell lymphoma, such as a diffuse large B-cell lymphoma, primary mediastinal B-cell lymphoma, follicular lymphoma, small lymphocytic lymphoma, mantle cell lymphoma, marginal zone B-cell lymphoma, extranodal marginal zone B-cell lymphoma, nodal marginal zone B-cell lymphoma, splenic marginal zone B-cell lymphoma, Burkitt lymphoma, lymphoplasmacytic lymphoma, hairy cell leukemia, or primary central nervous system (CNS) lymphoma.

In certain embodiments, the non-Hodgkin's lymphoma is a T-cell lymphoma, such as a precursor T-lymphoblastic lymphoma, peripheral T-cell lymphoma, cutaneous T-cell lymphoma, angioimmunoblastic T-cell lymphoma, extranodal natural killer/T-cell lymphoma, enteropathy type T-cell lymphoma, subcutaneous panniculitis-like T-cell lymphoma, anaplastic large cell lymphoma, or peripheral T-cell lymphoma.

In certain embodiments, the leukemia is chronic lymphocytic leukemia, acute myelogenous leukemia, chronic myelogenous leukemia, or acute lymphoblastic leukemia.

In yet other embodiments, the cancer is a vascularized tumor, squamous cell carcinoma, adenocarcinoma, small cell carcinoma, melanoma, glioma, neuroblastoma, sarcoma (e.g., an angiosarcoma or chondrosarcoma), astrocytic tumor, bartholin gland carcinoma, basal cell carcinoma, biliary cancer, bone cancer, bone marrow cancer, bronchial cancer, bronchial gland cancer, carcinoid, cholangiocarcinoma, chondrosarcoma, choriod plexus papilloma/carcinoma, gastric antrum cancer, gastric fundus cancer, gastrinoma, glioblastoma, glucagonoma, heart cancer, hemangioblastomas, hemangioendothelioma, hemangiomas, hepatic adenoma, hepatic adenomatosis, hepatobiliary cancer, hepatocellular carcinoma, Hodgkin's disease, ileum cancer, insulinoma, intraepithelial neoplasia, interepithelial squamous cell neoplasia, intrahepatic bile duct cancer, invasive squamous cell carcinoma, jejunum cancer, joint cancer, Kaposi's sarcoma, chronic lymphocytic leukemia, chronic myeloid leukemia, clear cell carcinoma, connective tissue cancer, cystadenoma, digestive system cancer, duodenum cancer, endocrine system cancer, endodermal sinus tumor, endometrial hyperplasia, endometrial stromal sarcoma, endometrioid adenocarcinoma, endothelial cell cancer, ependymal cancer, epithelial cell cancer, Ewing's sarcoma, eye and orbit cancer, female genital cancer, focal nodular hyperplasia, gallbladder cancer, pelvic cancer, large cell carcinoma, large intestine cancer, leiomyosarcoma, lentigo maligna melanomas, lymphoma, male genital cancer, malignant melanoma, malignant mesothelial tumors, medulloblastoma, medulloepithelioma, meningeal cancer, mesothelial cancer, metastatic carcinoma, mouth cancer, mucoepidermoid carcinoma, multiple myeloma, muscle cancer, nasal tract cancer, nervous system cancer, small intestine cancer, smooth muscle cancer, soft tissue cancer, somatostatin-secreting tumor, spine cancer, squamous cell carcinoma, striated muscle cancer, submesothelial cancer, superficial spreading melanoma, T cell leukemia, tongue cancer, undifferentiated carcinoma, ureter cancer, urethra cancer, urinary bladder cancer, urinary system cancer, uterine cervix cancer, uterine corpus cancer, uveal melanoma, vaginal cancer, verrucous carcinoma, VIPoma, vulva cancerneuroepithelial adenocarcinoma nodular melanoma, non-epithelial skin cancer, non-Hodgkin's lymphoma, oat cell carcinoma, oligodendroglial cancer, oral cavity cancer, osteosarcoma, papillary serous adenocarcinoma, penile cancer, pharynx cancer, pituitary tumors, plasmacytoma, pseudosarcoma, pulmonary blastoma, rectal cancer, renal cell carcinoma, respiratory system cancer, retinoblastoma, rhabdomyosarcoma, sarcoma, serous carcinoma, sinus cancer, larynx cancer, parotid cancer, bilary tract cancer, thyroid cancer, acral lentiginous melanoma, actinic keratoses, acute lymphocytic leukemia, acute myeloid leukemia, adenoid cycstic carcinoma, adenomas, adenosarcoma, adenosquamous carcinoma, anal canal cancer, anal cancer, or anorectum cancer.

Additional exemplary cancers include fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, epithelial carcinoma, glioma, astrocytoma, medulloblastoma, and hemangioblastoma.

In certain embodiments, the cancer is a neuroblastoma, meningioma, hemangiopericytoma, multiple brain metastases, glioblastoma multiforms, glioblastoma, brain stem glioma, poor prognosis malignant brain tumor, malignant glioma, anaplastic astrocytoma, anaplastic oligodendroglioma, neuroendocrine tumor, rectal adeno carcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T cell lymphoma, cutaneous B-Cell lymphoma, diffuse large B-Cell lymphoma, low grade follicular lymphoma, metastatic melanoma, localized melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unrespectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, or leiomyoma.

In certain embodiments, the methods may be used to treat a cancer selected from the group consisting of ovarian cancer, melanoma, colorectal cancer, lung cancer, breast cancer, prostate cancer, pancreatic cancer, renal cell carcinoma, leukemia, a B-cell lymphoma, and non-Hodgkin lymphoma. In certain other embodiments, the cancer is selected from the group consisting of a solid tumor, a lymphoma, and a leukemia. In certain other embodiments, the cancer expresses RORγ. In certain other embodiments, the cancer does not express RORγ. In yet other embodiments, the cancer is a metastatic cancer.

The therapeutic methods described herein using lymphocyte cells and/or an agonist of RORγ may be used in combination with surgery, such as surgery to remove cancerous tissue. As described in Section IX, the therapeutic methods may also be used in combination with other therapeutic agents, such as radiation and/or chemotherapy when treating cancer.

Efficacy of the RORγ agonist treated lymphocyte cells to treat a particular cancer may be evaluated using procedures described in the literature for testing the anti-cancer efficacy of activated lymphocyte cells, such as procedures described in U.S. Pat. No. 5,229,115.

Vaccination Adjuvant

Another aspect of the invention provides for enhancing the efficacy of vaccination. The method comprises administering to a patient in need thereof an agonist of RORγ to thereby enhance the efficacy of vaccination. Preferrably, the agonist of RORγ is administered at a time such that the vaccine and agonist of RORγ are each present in a clinically beneficial amount in the patient.

Vaccination remains a primary mechanism of inhibiting the spread of infectious agents. Exemplary vaccines include, for example, tumor vaccines, viral vaccines (DNA, RNA or retroviral), and bacterial vaccines.

Bacterial Infections

Bacterial infections may be treated using the therapeutic methods described herein. The bacterial infection can be characterized according to classifications known in the art. For example, in certain embodiments, the bacterial infection is a gram-positive bacterial infection, such as a gram-positive cocci bacterial infection or a gram-positive bacilli bacterial infection. In other embodiments, the bacterial infection is a gram-negative bacterial infection, such as a gram-negative cocci bacterial infection or a gram-negative bacilli bacterial infection. The bacterial infection can also be characterized according to whether it is caused by anaerobic or aerobic bacteria. Accordingly, in certain embodiments, the bacterial infection is an anaerobic bacterial infection. In certain other embodiments, the bacterial infection is an aerobic bacterial infection.

A variety of bacteria are contemplated to be susceptible to the therapeutic methods. Representative bacteria include Staphylococci species, e.g., *S. aureus*; Enterococci species, e.g., *E. faecalis* and *E. faecium*; Streptococci species, e.g., *S. pyogenes* and *S. pneumoniae*; *Escherichia* species, e.g., *E. coli*, including enterotoxigenic, enteropathogenic, enteroinvasive, enterohemorrhagic and enteroaggregative *E. coli* strains; *Haemophilus* species, e.g., *H. influenza*; and *Moraxella* species, e.g., *M. catarrhalis*. Other examples include *Mycobacteria* species, e.g., *M. tuberculosis, M. avian-intracellulare, M. kansasii, M. bovis, M. africanum, M. genavense, M. leprae, M. xenopi, M. simiae, M. scrofulaceum, M. malmoense, M. celatum, M. abscessus, M. chelonae, M. szulgai, M. gordonae, M. haemophilum, M. fortuni* and *M. marinum*; *Corynebacteria* species, e.g., *C. diphtheriae*; *Vibrio* species, e.g., *V. cholerae*; *Campylobacter* species, e.g., *C. jejuni*; *Helicobacter* species, e.g., *H. pylori*; *Pseudomonas* species, e.g., *P. aeruginosa*; *Legionella* species, e.g., *L. pneumophila*; *Treponema* species, e.g., *T. pallidum*; *Borrelia* species, e.g., *B. burgdorferi*; *Listeria* species, e.g., *L. monocytogenes*; *Bacillus* species, e.g., *B. cereus*; *Bordatella* species, e.g., *B. pertussis*; *Clostridium* species, e.g., *C. perfringens, C. tetani, C. difficile* and *C. botulinum*; *Neisseria* species, e.g., *N. meningitidis* and *N. gonorrhoeae*; *Chlamydia* species, e.g., *C. psittaci, C. pneumoniae* and *C. trachomatis*; *Rickettsia* species, e.g., *R. rickettsii* and *R. prowazekii*; *Shigella* species, e.g., *S. sonnei*; *Salmonella* species, e.g., *S. typhimurium*; *Yersinia* species, e.g., *Y. enterocolitica* and *Y. pseudotuberculosis*; *Klebsiella* species, e.g., *K. pneumoniae*; *Mycoplasma* species, e.g., *M. pneumoniae*; *Trypanosoma brucei*; and *citrobacter rodentium*. The bacterial infection may be an infection of mucoepithelial barriers, an intracellular infection (e.g., *francisella tularenis*), or an extracellular infection.

In certain embodiments, the compounds described herein are used to treat a subject suffering from a bacterial infection selected from the group consisting of *S. aureus, E. faecalis, E. faecium, S. pyogenes, S. pneumonia*, and *P. aeruginosa*.

In certain embodiments, the disorder is a fungal infection. Exemplary fungi that may be treated include, for example, *Acremonium, Absidia* (e.g., *Absidia corymbifera*), *Alternaria, Aspergillus* (e.g., *Aspergillus clavatus, Aspergillus flavus, Aspergillus fumigatus, Aspergillus nidulans, Aspergillus niger, Aspergillus terreus*, and *Aspergillus versicolor*), *Aureobasidium, Basidiobolus, Blastomyces* (e.g., *Blastomyces dermatitidis*), *Candida* (e.g., *Candida albicans, Candida glabrata, Candida guilliermondii, Candida kefir, Candida krusei, Candida lusitaniae, Candida parapsilosis, Candida pseudotropicalis, Candida stellatoidea, Candida tropicalis, Candida utilis, Candida lipolytica, Candida famata* and *Candida rugosa*), *Cephalosporium, Chaetomium, Chrysosporium, Cladosporium* (e.g., *Cladosporium carrionii* and *Cladosporium trichloides*), *Coccidioides* (e.g., *Coccidioides immitis*), *Conidiobolus, Coprinus, Corynespora, Cryptococcus* (e.g., *Cryptococcus neoformans*), *Curvularia, Cunninghamella* (e.g., *Cunninghamella elegans*), *Exophiala* (e.g., *Exophiala dermatitidis* and *Exophiala spinifera*), *Epidermophyton* (e.g., *Epidermophyton floccosum*), *Fonsecaea* (e.g., *Fonsecaea pedrosoi*), *Fusarium* (e.g., *Fusarium solani*), *Geotrichum* (e.g., *Geotrichum candiddum* and *Geotrichum clavatum*), *Hendersonula, Histoplasma, Leptosphaeria, Loboa, Madurella, Malassezia* (e.g., *Malassezia furfur*), *Microsporum* (e.g., *Microsporum canis* and *Microsporum gypseum*), *Mycocentrospora, Mucor, Neotestudina, Paecilomyces, Paracoccidioides* (e.g., *Paracoccidioides brasiliensis*), *Penicillium* (e.g., *Penicillium marneffei*), *Phialophora, Pneumocystis* (e.g., *Pneumocystis carinii*), *Pseudallescheria* (e.g., *Pseudallescheria boydii*), *Rhinosporidium, Rhizomucor, Rhizopus* (e.g., *Rhizopus microsporus* var. *rhizopodiformis* and *Rhizopus oryzae*), *Saccharomyces* (e.g., *Saccharomyces cerevisiae*), *Scopulariopsis, Sporothrix* (e.g., *Sporothrix schenckii*), *Trichophyton* (e.g., *Trichophyton mentagrophytes* and *Trichophyton rubrum*), *Trichosporon* (e.g., *Trichosporon asahii, Trichosporon* beigelii and *Trichosporon cutaneum*), and *Wangiella*. In certain other embodiments, the fungal infection is a mucocutaneous candidiasis infection, such as chronic infection by mucocutaneous candidiasis.

Immune Disorders/Conditions

Immune disorders may be treated using therapeutic methods described herein. In certain embodiments, the disorder is an immune deficiency disorder. Exemplary immune deficiency disorders include, for example, a human immunodeficiency viral infection, a patient with a deficient immune system due to chemotherapy, or a patient recovering from surgery who has a deficient immune system. In certain other embodiments, the disorder is an opportunistic infection resulting from an HIV infection.

In certain other embodiments, the immune disorder is the immunodeficiency known as Job's syndrome (also known as Hyper-Immunoglobulin E Syndrome (HIES)). In yet other embodiments, the immune disorder is an immunodeficiency associated with a mutation of the Jak gene or a mutation of STAT3 gene.

In certain embodiments, the present methods may be applied to the reconstitution of a patient's immune system after chemotherapy and/or irradiation. As described in, for example, Avigan, D. et al. *Bone Marrow Transplantation* (2000) 26, 169-176, patients may exhibit abnormalities and deficiencies in their immune responses for many months after high-dose chemotherapy. Because chemotherapy and irradiation may severely comprise the immune system of a patient, the immunity-augmenting effects of the present are contemplated to be beneficial to patients who are immunocompromised after chemotherapy and/or radiation therapy.

Autoimmune polyendocrine syndrome type 1 (APS-1), also known as autoimmune polyendocrinopathy-candidiasis-ectodermal dystrophy (APECED), Whitaker syndrome, or candidiasis-hypoparathyroidism-Addison's disease-syndrome, is a subtype of autoimmune polyendocrine syndrome, in which multiple endocrine glands dysfunction as a result of autoimmunity. Thus, patients suffering from APECED are contemplated to benefit from the present methods.

Therapeutic methods described herein may be used to treat neutropenia. Neutropenia is a granulocyte disorder generally characterized by an abnormally low number of neutrophils.

Fungal Infection

A fungal infection may be treated using therapeutic methods described herein. Exemplary fungi that may be treated include, for example, *Acremonium, Absidia* (e.g., *Absidia corymbifera*), *Alternaria, Aspergillus* (e.g., *Aspergillus clavatus, Aspergillus flavus, Aspergillus fumigatus, Aspergillus nidulans, Aspergillus niger, Aspergillus terreus*, and *Aspergillus versicolor*), *Aureobasidium, Basidiobolus, Blastomyces* (e.g., *Blastomyces dermatitidis*), *Candida* (e.g., *Candida albicans, Candida glabrata, Candida guilliermondii, Candida kefyr, Candida krusei, Candida lusitaniae, Candida parapsilosis, Candida pseudotropicalis, Candida stellatoidea, Candida tropicalis, Candida utilis, Candida lipolytica, Candida famata* and *Candida rugosa*), *Cephalosporium, Chaetomium, Chrysosporium, Cladosporium* (e.g., *Cladosporium carrionii* and *Cladosporium trichloides*), *Coccidioides* (e.g., *Coccidioides immitis*), *Conidiobolus, Coprinus, Corynespora, Cryptococcus* (e.g., *Cryptococcus neoformans*), *Curvularia, Cunninghamella* (e.g., *Cunninghamella elegans*), *Exophiala* (e.g., *Exophiala dermatitidis* and *Exophiala spinifera*), *Epidermophyton* (e.g., *Epidermophyton floccosum*), *Fonsecaea* (e.g., *Fonsecaea pedrosoi*), *Fusarium* (e.g., *Fusarium solani*), *Geotri-* *chum* (e.g., *Geotrichum candiddum* and *Geotrichum clavatum*), *Hendersonula, Histoplasma, Leptosphaeria, Loboa, Madurella, Malassezia* (e.g., *Malassezia furfur*), *Microsporum* (e.g., *Microsporum canis* and *Microsporum gypseum*), *Mycocentrospora, Mucor, Neotestudina, Paecilomyces, Paracoccidioides* (e.g., *Paracoccidioides brasiliensis*), *Penicillium* (e.g., *Penicillium marneffei*), *Phialophora, Pneumocystis* (e.g., *Pneumocystis carinii*), *Pseudallescheria* (e.g., *Pseudallescheria boydii*), *Rhinosporidium, Rhizomucor, Rhizopus* (e.g., *Rhizopus microsporus* var. *rhizopodiformis* and *Rhizopus oryzae*), *Saccharomyces* (e.g., *Saccharomyces cerevisiae*), *Scopulariopsis, Sporothrix* (e.g., *Sporothrix schenckii*), *Trichophyton* (e.g., *Trichophyton mentagrophytes* and *Trichophyton rubrum*), *Trichosporon* (e.g., *Trichosporon asahii, Trichosporon beigelii* and *Trichosporon cutaneum*), and *Wangiella*.

Additional Medical Disorders

Therapeutic methods described herein may be used to treat a circadian rhythm disorder. In addition, the therapeutic methods described herein may be used to treat a sleep disorder associated with a disruption of circadian rhythm in a patient.

VII. Exemplary RORγ Agonists

The RORγ agonist is an agent that promotes RORγ activity, such as by binding to and activating RORγ or by increasing expression of RORγ in a patient or population of cells. The RORγ agonist may be, for example, a small organic molecule, polypeptide, or nucleic acid. Various RORγ agonists are reported in the literature, such as in International Patent Application Publication No. WO 2013/169864; Zhang et al. in *Mol. Pharmacol.* (2012) vol. 82, pages 583-590; and Wang et al. in *ACS Chem. Biol.* (2010), vol. 5, pages 1029-1034; each of which is hereby incorporated by reference. Exemplary RORγ agonists are also described below.

Tetrahydro[1,8]naphthyridine and Related RORγ Agonists

In certain embodiments, the RORγ agonist is a generic or specific compound described in International Patent Application Publication No. WO 2013/169864, such as a compound represented by Formula I:

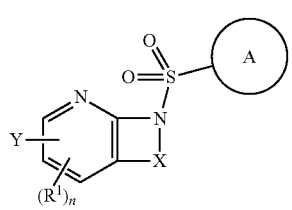

(I)

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-6}$alkyl, $C_{1-6}$haloalkyl, $C_{1-6}$hydroxyalkyl, $C_{1-6}$alkoxy, $C_{1-6}$haloalkoxy, —N($R^4$)($R^5$), —CO$_2R^6$, —C(O)$R^6$, —CN, —$C_{1-4}$alkylene-$C_{1-4}$alkoxy, —$C_{1-4}$alkylene-N($R^4$)($R^5$), —$C_{1-4}$alkylene-CO$_2R^6$, —O—$C_{1-6}$alkylene-N($R^4$)($R^5$), —N($R^4$)C(O)—$C_{1-6}$alkylene-N($R^4$)($R^5$), —S(O)$_p C_{1-6}$alkyl, —SO$_2$N($R^4$)($R^5$), —N($R^4$)SO$_2$ ($C_{1-6}$alkyl), —C(O)N($R^4$)($R^5$), and —N($R^4$)C(O)N($R^4$)($R^5$);

X is —O—[C(R⁶)(R⁷)]—[C(R⁶)₂]ₘ-ψ, —O—C(R⁶)₂—C(R⁶)(R⁷)—C(R⁶)₂-ψ, —O—C(R⁶)₂—C(R⁶)(R⁷)-ψ, —C(R⁶)₂—[C(R⁶)(R⁷)]—[C(R⁶)₂]m-ψ, —C(O)—[C(R⁶)(R⁷)]—[C(R⁶)₂]m-ψ, —C(R⁶)₂—N(R⁸)—[C(R⁶)(R⁷)]—[C(R⁶)₂]m-ψ, —C(R⁶)=N-ψ, —C(R⁶)₂C(R⁶)=N-ψ, —N=C(R⁶)-ψ, or —N=C(R⁶)C(R⁶)₂-ψ; wherein ψ is a bond to the sulfonamide ring nitrogen atom in Formula I;

Y is —N(R²)(R³) or —O-aralkyl, wherein said aralkyl is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N(R⁴)(R⁵), —CN, —CO₂—$C_{1-6}$alkyl, —C(O)—$C_{1-6}$alkyl, —C(O)N(R⁴)(R⁵), —S(O)$_p$$C_{1-6}$alkyl, —SO₂N(R⁴)(R⁵), and —N(R⁴)SO₂($C_{1-6}$alkyl);

R¹ represents independently for each occurrence hydrogen, halogen, or $C_{1-6}$alkyl;

R² is —C(O)-aryl, —C(O)-aralkyl, —C(O)—[C(R⁶)₂]ₘ-cycloalkyl, —C(O)—[C(R⁶)₂]ₘ-heterocyclyl, —C(O)—$C_{1-6}$alkyl, —C(O)—$C_{1-6}$alkylene-$C_{1-6}$alkoxyl, —C(O)—$C_{1-6}$alkylene-cycloalkyl, or —C(O)—$C_{1-6}$alkylene-heterocycloalkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N(R⁴)(R⁵), —CN, —CO₂—$C_{1-6}$alkyl, —C(O)—$C_{1-6}$alkyl, —C(O)N(R⁴)(R⁵), —S(O)$_p$$C_{1-6}$alkyl, —SO₂N(R⁴)(R⁵), and —N(R⁴)SO₂($C_{1-6}$alkyl);

R³ is hydrogen or $C_{1-6}$alkyl;

R⁴ and R⁵ each represent independently for each occurrence hydrogen or $C_{1-6}$alkyl; or R⁴ and R⁵ taken together with the nitrogen atom to which they are attached form a 3-7 membered heterocyclic ring;

R⁶ represents independently for each occurrence hydrogen or $C_{1-6}$alkyl;

R⁷ is hydrogen, hydroxyl, $C_{1-6}$hydroxyalkyl, $C_{1-6}$alkyl, $C_{1-6}$haloalkyl, —CO₂R⁶, $C_{1-6}$alkylene-CO₂R⁶, $C_{1-4}$hydroxyalkylene-CO₂R⁶, —N(R⁴)(R⁵), $C_{1-6}$alkylene-N(R⁴)(R⁵), $C_{1-6}$hydroxyalkylene-N(R⁴)(R⁵), —N(R⁴)C(O)R⁹, $C_{1-6}$alkylene-N(R⁴)C(O)R⁹, $C_{1-6}$alkylene-C(O)N(R⁴)(R⁵), —N(R⁴)CO₂—$C_{1-6}$alkyl, or $C_{1-6}$alkylene-N(R⁴)(C(O)N(R⁴)(R⁵); or R⁷ is heterocycloalkyl or $C_{1-4}$alkylene-heterocycloalkyl, wherein the heterocycloalkyl is optionally substituted with 1, 2, or 3 substituents independently selected from the group consisting of oxo, halogen, hydroxyl, $C_{1-6}$alkyl, $C_{1-6}$haloalkyl, $C_{1-6}$hydroxyalkyl, $C_{1-6}$alkoxy, and $C_{1-6}$haloalkoxy;

R⁸ is hydrogen, $C_{1-6}$alkyl, or —C(O)—$C_{1-6}$alkyl;

R⁹ is hydrogen, $C_{1-6}$alkyl, $C_{1-6}$hydroxyalkyl, $C_{1-6}$alkylene-N(R⁴)(R⁵), or $C_{1-6}$alkylene-N(R⁴)C(O)—$C_{1-6}$alkyl;

n is 1 or 2; and m and p each represent independently for each occurrence 0, 1, or 2.

In certain embodiments, A is aryl or heteroaryl; each of which is optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is aryl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is phenyl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is phenyl optionally substituted with 1, 2, or 3 substituents independently selected from the group consisting of halogen and $C_{1-6}$haloalkyl. In certain embodiments, at least one substituent is attached at the meta-position of the phenyl ring.

In certain other embodiments, A is heteroaryl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy.

In certain embodiments, A is heterocycloalkyl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain embodiments, A is piperidine or pyrrolidine, each of which is optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy.

In certain embodiments, X is —O—[C(R⁶)(R⁷)]—[C(R⁶)₂]ₘ-ψ. In certain other embodiments, X is —C(R⁶)₂—[C(R⁶)(R⁷)]—[C(R⁶)₂]ₘ-ψ. In certain other embodiments, X is —C(O)—[C(R⁶)(R⁷)]—[C(R⁶)₂]ₘ-ψ. In certain other embodiments, X is —C(R⁶)₂—N(R⁸)—[C(R⁶)(R⁷)]—[C(R⁶)₂]ₘ-ψ. In certain other embodiments, X is —C(R⁶)=N-ψ.

In certain embodiments, Y is —N(R²)(R³). In certain embodiments, Y is —O— aralkyl optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N(R⁴)(R⁵), —CN, —CO₂—$C_{1-6}$alkyl, —C(O)—$C_{1-6}$alkyl, —C(O)N(R⁴)(R⁵), —S(O)$_p$$C_{1-6}$alkyl, —SO₂N(R⁴)(R⁵), and —N(R⁴)SO₂($C_{1-6}$alkyl). In certain other embodiments, Y is —O-aralkyl optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N(R⁴)(R⁵), —CN, —CO₂—$C_{1-6}$alkyl, and —C(O)—$C_{1-6}$alkyl. In certain other embodiments, Y is —O— benzyl optionally substituted with 1, 2, or 3 substituents independently selected from the group consisting of halogen, $C_{1-6}$alkyl, and $C_{1-6}$haloalkyl.

In certain embodiments, R¹ is hydrogen.

In certain embodiments, R² is —C(O)-aryl or —C(O)-aralkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, and $C_{1-6}$haloalkyl. In certain other embodiments, R² is —C(O)-aryl or —C(O)-aralkyl; each of which is substituted with 2 substituents independently selected from the group consisting of halogen, hydroxyl, $C_{1-6}$alkoxy, $C_{1-6}$haloalkoxy, $C_{1-6}$alkyl, and $C_{1-6}$haloalkyl, and said substituents are located at the ortho-positions of the aromatic ring. In certain other embodiments, R² is —C(O)-phenyl or —C(O)-benzyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, and $C_{1-6}$haloalkyl. In certain other embodiments, R² is —C(O)-phenyl or —C(O)-benzyl; each of which is optionally substituted with 1, 2, or 3 substituents independently selected from the group consisting of halogen, $C_{1-6}$alkyl, and $C_{1-6}$haloalkyl. In certain other embodiments, R² is represented by:

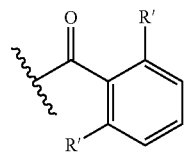

wherein each R' is independently halogen, hydroxyl, $C_{1-6}$alkoxy, $C_{1-6}$haloalkoxy, $C_{1-6}$alkyl, or $C_{1-6}$haloalkyl. In certain other embodiments, $R^2$ is represented by:

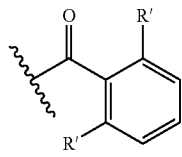

wherein each R' is independently halogen, $C_{1-6}$alkyl, or $C_{1-6}$haloalkyl.

In certain other embodiments, $R^2$ is represented by:

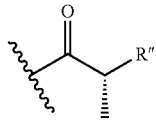

wherein R" is $C_{1-6}$alkyl, aryl, or heterocyclyl, each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N($R^4$)($R^5$), —CN, —$CO_2$—$C_{1-6}$alkyl, —C(O)—$C_{1-6}$alkyl, —C(O)N($R^4$)($R^5$), —S(O)$_p$$C_{1-6}$alkyl, —$SO_2$N($R^4$)($R^5$), and —N($R^4$)$SO_2$($C_{1-6}$alkyl). In certain embodiments, R" is phenyl optionally substituted with 1, 2, or 3 substituents independently selected from the group consisting of halogen, $C_{1-6}$alkyl, and $C_{1-6}$haloalkyl.

In certain embodiments, $R^3$ is hydrogen.

In certain embodiments, $R^7$ is hydrogen. In certain other embodiments, $R^7$ is hydroxyl, $C_{1-6}$hydroxyalkyl, $C_{1-6}$alkyl, $C_{1-6}$haloalkyl, —$CO_2R^6$, $C_{1-6}$alkylene-$CO_2R^6$, $C_{1-4}$hydroxyalkylene-$CO_2R^6$, —N($R^4$)($R^5$), $C_{1-6}$alkylene-N($R^4$)($R^5$), $C_{1-6}$hydroxyalkylene-N($R^4$)($R^5$), —N($R^4$)C(O)$R^9$, $C_{1-6}$alkylene-N($R^4$)C(O)$R^9$, $C_{1-6}$alkylene-C(O)N($R^4$)($R^5$), —N($R^4$)$CO_2$—$C_{1-6}$alkyl, or —N($R^4$)C(O)$R^9$. In certain other embodiments, $R^7$ is $C_{1-6}$hydroxyalkyl, $C_{1-6}$alkyl, $C_{1-6}$alkylene-$CO_2R^6$, —N($R^4$)($R^5$), $C_{1-6}$alkylene-N($R^4$)($R^5$), or $C_{1-6}$alkylene-N($R^4$)C(O)$R^9$. In certain other embodiments, $R^7$ is $C_{1-3}$hydroxyalkyl, methyl, ethyl, or $C_{1-3}$alkylene-N(H)C(O)—$C_{1-4}$alkyl.

In certain other embodiments, $R^7$ is heterocycloalkyl or $C_{1-4}$alkylene-heterocycloalkyl, wherein the heterocycloalkyl is optionally substituted with 1, 2, or 3 substituents independently selected from the group consisting of oxo, halogen, hydroxyl, $C_{1-6}$alkyl, $C_{1-6}$haloalkyl, $C_{1-6}$hydroxyalkyl, $C_{1-6}$alkoxy, and $C_{1-6}$haloalkoxy.

In other embodiments, the RORγ agonist is a compound represented by Formula II:

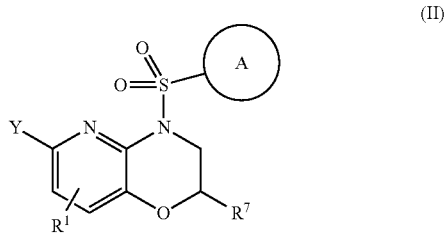

(II)

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-6}$alkyl, $C_{1-6}$haloalkyl, $C_{1-6}$hydroxyalkyl, $C_{1-6}$alkoxy, $C_{1-6}$haloalkoxy, —N($R^4$)($R^5$), —$CO_2R^6$, —C(O)$R^6$, —CN, —$C_{1-4}$alkylene-$C_{1-4}$alkoxy, and —$C_{1-4}$alkylene-N($R^4$)($R^5$);

Y is —N($R^2$)($R^3$) or —O-aralkyl, wherein said aralkyl is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N($R^4$)($R^5$), —CN, —$CO_2$—$C_{1-6}$alkyl, —C(O)—$C_{1-6}$alkyl, —C(O)N($R^4$)($R^5$), —S(O)$_p$$C_{1-6}$alkyl, —$SO_2$N($R^4$)($R^5$), and —N($R^4$)$SO_2$($C_{1-6}$alkyl); $R^1$ is hydrogen, halogen, or $C_{1-6}$alkyl;

$R^2$ is —C(O)-aryl, —C(O)-aralkyl, —C(O)—[C($R^6$)$_2$]$_m$-cycloalkyl, —C(O)—[C($R^6$)$_2$]$_m$-heterocyclyl, —C(O)—$C_{1-8}$alkyl, —C(O)—$C_{1-6}$alkylene-$C_{1-6}$alkoxyl, —C(O)—$C_{1-6}$alkylene-cycloalkyl, or —C(O)—$C_{1-6}$alkylene-heterocycloalkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N($R^4$)($R^5$), —CN, —$CO_2$—$C_{1-6}$alkyl, —C(O)—$C_{1-6}$alkyl, —C(O)N($R^4$)($R^5$), —S(O)$_p$$C_{1-6}$alkyl, —$SO_2$N($R^4$)($R^5$), and —N($R^4$)$SO_2$($C_{1-6}$alkyl);

$R^3$ is hydrogen or $C_{1-6}$alkyl;

$R^4$ and $R^5$ each represent independently for each occurrence hydrogen or $C_{1-6}$alkyl; or $R^4$ and $R^5$ taken together with the nitrogen atom to which they are attached form a 3-7 membered heterocyclic ring;

$R^6$ represents independently for each occurrence hydrogen or $C_{1-6}$alkyl; $R^7$ is hydrogen, hydroxyl, $C_{1-6}$hydroxyalkyl, $C_{1-6}$alkyl, $C_{1-6}$haloalkyl, —$CO_2R^6$, $C_{1-6}$alkylene-$CO_2R^6$, $C_{1-4}$hydroxyalkylene-$CO_2R^6$, —N($R^4$)($R^5$), $C_{1-6}$alkylene-N($R^4$)($R^5$), $C_{1-6}$hydroxyalkylene-N($R^4$)($R^5$), —N($R^4$)C(O)$R^9$, $C_{1-6}$alkylene-N($R^4$)C(O)$R^9$, $C_{1-6}$alkylene-C(O)N($R^4$)($R^5$), —N($R^4$)$CO_2$—$C_{1-6}$alkyl, or $C_{1-6}$alkylene-N($R^4$)(C(O)N($R^4$)($R^5$); or $R^7$ is heterocycloalkyl or $C_{1-4}$alkylene-heterocycloalkyl, wherein the heterocycloalkyl is optionally substituted with 1, 2, or 3 substituents independently selected from the group consisting of oxo, halogen, hydroxyl, $C_{1-6}$alkyl, $C_{1-6}$haloalkyl, $C_{1-6}$hydroxyalkyl, $C_{1-6}$alkoxy, and $C_{1-6}$haloalkoxy;

$R^9$ is hydrogen, $C_{1-6}$alkyl, $C_{1-6}$hydroxyalkyl, $C_{1-6}$alkylene-N($R^4$)($R^5$), or $C_{1-6}$alkylene-N($R^4$)C(O)—$C_{1-6}$alkyl; and m and p each represent independently for each occurrence 0, 1, or 2.

In certain embodiments, A is aryl or heteroaryl; each of which is optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is aryl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is phenyl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain other embodiments, A is phenyl optionally substituted with 1, 2, or 3 substituents independently selected from the group consisting of halogen and $C_{1-6}$haloalkyl. In certain embodiments, at least one substituent is attached at the meta-position of the phenyl ring.

In certain other embodiments, A is heterocycloalkyl optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy. In certain embodiments, A is piperidine or pyrrolidine, each of which is optionally substituted with 1, 2, or 3 substituents independently selected from the group consisting of halogen, $C_{1-6}$alkyl, $C_{1-6}$haloalkyl, $C_{1-6}$alkoxy, and $C_{1-6}$haloalkoxy.

In certain embodiments, Y is —N($R^2$)($R^3$). In certain embodiments, Y is —O— aralkyl optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N($R^4$)($R^5$), —CN, —$CO_2$—$C_{1-6}$alkyl, —C(O)—$C_{1-6}$alkyl, —C(O)N($R^4$)($R^5$), —S(O)$_p$$C_{1-6}$alkyl, —$SO_2$N($R^4$)($R^5$), and —N($R^4$)$SO_2$($C_{1-6}$alkyl). In certain other embodiments, Y is —O-aralkyl optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N($R^4$)($R^5$), —CN, —$CO_2$—$C_{1-6}$alkyl, and —C(O)—$C_{1-6}$alkyl. In certain other embodiments, Y is —O— benzyl optionally substituted with 1, 2, or 3 substituents independently selected from the group consisting of halogen, $C_{1-6}$alkyl, and $C_{1-6}$haloalkyl.

In certain embodiments, $R^1$ is hydrogen.

In certain embodiments, $R^2$ is —C(O)-aryl or —C(O)-aralkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, and $C_{1-6}$haloalkyl. In certain other embodiments, $R^2$ is —C(O)-aryl or —C(O)-aralkyl; each of which is substituted with 2 substituents independently selected from the group consisting of halogen, hydroxyl, $C_{1-6}$alkoxy, $C_{1-6}$haloalkoxy, $C_{1-6}$alkyl, and $C_{1-6}$haloalkyl, and said substituents are located at the ortho-positions of the aromatic ring. In certain other embodiments, $R^2$ is —C(O)-phenyl or —C(O)-benzyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, and $C_{1-6}$haloalkyl. In certain other embodiments, $R^2$ is —C(O)-phenyl or —C(O)-benzyl; each of which is optionally substituted with 1, 2, or 3 substituents independently selected from the group consisting of halogen, $C_{1-6}$alkyl, and $C_{1-6}$haloalkyl. In certain other embodiments, $R^2$ is represented by:

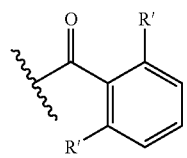

wherein each R' is independently halogen, hydroxyl, $C_{1-6}$alkoxy, $C_{1-6}$haloalkoxy, $C_{1-6}$alkyl, or $C_{1-6}$haloalkyl. In certain other embodiments, $R^2$ is represented by:

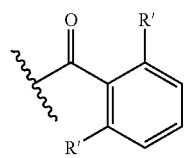

wherein each R' is independently halogen, $C_{1-6}$alkyl, or $C_{1-6}$haloalkyl.

In certain embodiments, $R^2$ is represented by:

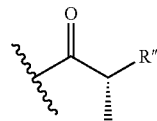

wherein R" is $C_{1-6}$alkyl, aryl, or heterocyclyl, each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N($R^4$)($R^5$), —CN, —$CO_2$—$C_{1-6}$alkyl, —C(O)—$C_{1-6}$alkyl, —C(O)N($R^4$)($R^5$), —S(O)$_p$$C_{1-6}$alkyl, —$SO_2$N($R^4$)($R^5$), and —N($R^4$)$SO_2$($C_{1-6}$alkyl). In certain embodiments, R" is phenyl optionally substituted with 1, 2, or 3 substituents independently selected from the group consisting of halogen, $C_{1-6}$alkyl, and $C_{1-6}$haloalkyl.

In certain embodiments, $R^3$ is hydrogen.

In certain embodiments, $R^7$ is hydrogen. In certain other embodiments, $R^7$ is hydroxyl, $C_{1-6}$hydroxyalkyl, $C_{1-6}$alkyl, $C_{1-6}$haloalkyl, —$CO_2R^6$, $C_{1-6}$alkylene-$CO_2R^6$, $C_{1-4}$hydroxyalkylene-$CO_2R^6$, —N($R^4$)($R^5$), $C_{1-6}$alkylene-N($R^4$)($R^5$), $C_{1-6}$hydroxyalkylene-N($R^4$)($R^5$), —N($R^4$)C(O)$R^9$, $C_{1-6}$alkylene-N($R^4$)C(O)$R^9$, $C_{1-6}$alkylene-C(O)N($R^4$)($R^5$), —N($R^4$)$CO_2$—$C_{1-6}$alkyl, or —N($R^4$)C(O)$R^9$. In certain other embodiments, $R^7$ is $C_{1-6}$hydroxyalkyl, $C_{1-6}$alkyl, $C_{1-6}$alkylene-$CO_2R^6$, $C_{1-6}$alkylene-N($R^4$)($R^5$), or $C_{1-6}$alkylene-N($R^4$)C(O)$R^9$. In certain other embodiments, $R^7$ is $C_{1-3}$hydroxyalkyl, methyl, ethyl, or $C_{1-3}$alkylene-N(H)C(O)—$C_{1-4}$alkyl.

In other embodiments, the RORγ agonist is a compound represented of Formula V:

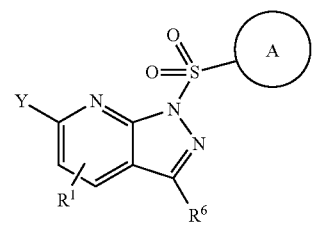

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-6}$alkyl, $C_{1-6}$haloalkyl, $C_{1-6}$hydroxyalkyl, $C_{1-6}$alkoxy, $C_{1-6}$haloalkoxy, —N($R^4$)($R^5$), —$CO_2R^6$, —C(O)$R^6$, —CN, —$C_{1-4}$alkylene-$C_{1-4}$alkoxy, and —$C_{1-4}$alkylene-N($R^4$)($R^5$);

Y is —N($R^2$)($R^3$) or —O-aralkyl, wherein said aralkyl is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N($R^4$)($R^5$), —CN, —$CO_2$—$C_{1-6}$alkyl, —C(O)—$C_{1-6}$alkyl, —C(O)N($R^4$)($R^5$), —S(O)$_p$$C_{1-6}$alkyl, —$SO_2$N($R^4$)($R^5$), and —N($R^4$)$SO_2$($C_{1-6}$alkyl);

$R^1$ is hydrogen, halogen, or $C_{1-6}$alkyl;

$R^2$ is —C(O)-aryl, —C(O)-aralkyl, —C(O)—[C($R^6$)$_2$]$_m$-cycloalkyl, —C(O)—[C($R^6$)$_2$]$_m$-heterocyclyl, —C(O)—$C_{1-8}$alkyl, —C(O)—$C_{1-6}$alkylene-$C_{1-6}$alkoxyl, —C(O)—

$C_{1-6}$alkylene-cycloalkyl, or —C(O)—$C_{1-6}$alkylene-heterocycloalkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N($R^4$)($R^5$), —CN, —$CO_2$—$C_{1-6}$alkyl, —C(O)—$C_{1-6}$alkyl, —C(O)N($R^4$)($R^5$), —S(O)$_p$$C_{1-6}$alkyl, —$SO_2$N($R^4$)($R^5$), and —N($R^4$)$SO_2$($C_{1-6}$alkyl);

$R^3$ is hydrogen or $C_{1-6}$alkyl;

$R^4$ and $R^5$ each represent independently for each occurrence hydrogen or $C_{1-6}$alkyl; or $R^4$ and $R^5$ taken together with the nitrogen atom to which they are attached form a 3-7 membered heterocyclic ring;

$R^6$ represents independently for each occurrence hydrogen or $C_{1-6}$alkyl; and m and p each represent independently for each occurrence 0, 1, or 2.

The definitions of variables in the Formulae above encompass multiple chemical groups. The application contemplates embodiments where, for example, i) the definition of a variable is a single chemical group selected from those chemical groups set forth above, ii) the definition is a collection of two or more of the chemical groups selected from those set forth above, and iii) the compound is defined by a combination of variables in which the variables are defined by (i) or (ii).

In certain other embodiments, the RORγ agonist is one of the compounds listed in Tables 1-3 below or a pharmaceutically acceptable salt thereof

TABLE 1

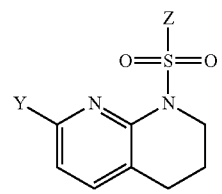

| No. | Y | Z |
|---|---|---|
| I-1 | 2-Cl, 6-CF₃ benzamide | 4-F phenyl |
| I-2 | 2-F, 6-CF₃ benzamide | 3-Cl phenyl |
| I-3 | 2,6-bis(CF₃) benzamide | 3-cyclopropyl phenyl |
| I-4 | 2-Cl, 6-F benzamide | 4-F phenyl |
| I-5 | 2,6-diF benzamide | 3-Cl phenyl |
| I-6 | 2,6-diCl benzamide | 3-cyclopropyl phenyl |
| I-7 | 4-Cl phenylacetamide | 4-F phenyl |
| I-8 | nicotinamide (pyridin-3-yl) | 3-Cl phenyl |
| I-9 | (R)-2-phenylacetamide | 3-cyclopropyl phenyl |
| I-10 | cyclohexanecarboxamide | 4-F phenyl |

TABLE 1-continued

| No. | Y | Z |
|---|---|---|
| I-11 | 2-Cl, 6-CF₃-benzamide | 3-CF₃-phenyl |
| I-12 | 2-F, 6-CF₃-benzamide | 3,4-difluorophenyl |
| I-13 | 2-CF₃, 6-Cl-benzamide | 3-CF₃-phenyl |
| I-14 | 2-Cl, 6-F-benzamide | 3,4-difluorophenyl |
| I-15 | 2,6-difluorobenzamide | 4-CF₃-phenyl |
| I-16 | 2,6-dichlorobenzamide | 3,4-difluorophenyl |
| I-17 | (4-chlorophenyl)acetamide | 3-CF₃-phenyl |
| I-18 | nicotinamide (pyridin-3-yl-carboxamide) | 3,4-difluorophenyl |
| I-19 | (R)-2-phenylpropanamide | 3-CF₃-phenyl |
| I-20 | cyclohexanecarboxamide | 3,4-difluorophenyl |
| I-21 | 2-Cl, 6-CF₃-benzamide | 1-methyl-1H-pyrazol-4-yl |
| I-22 | 2-F, 6-CF₃-benzamide | 1-methyl-1H-imidazol-4-yl |
| I-23 | 2-CF₃, 6-Cl-benzamide | 5-fluoropyridin-2-yl |
| I-24 | 2-Cl, 6-F-benzamide | 1-methylpiperidin-4-yl |

TABLE 1-continued

| No. | Y | Z |
|---|---|---|
| I-25 | 2,6-difluorobenzamide | 1-methylpyrrolidin-3-yl |
| I-26 | 2,6-dichlorobenzamide | 1-methyl-1H-pyrazol-4-yl |
| I-27 | 2-(4-chlorophenyl)acetamide | 1-methyl-1H-imidazol-4-yl |
| I-28 | nicotinamide | 5-fluoropyridin-2-yl |
| I-29 | (S)-2-phenylpropanamide | piperidin-1-yl |
| I-30 | cyclohexanecarboxamide | 1-methylpyrrolidin-3-yl |
| I-31 | isobutyramide | 3-methoxyphenyl |
| I-32 | isobutyramide | 4-fluorophenyl |
| I-33 | isobutyramide | 3-chlorophenyl |
| I-34 | (S)-2-methoxypropanamide | 3-methoxyphenyl |
| I-35 | (S)-2-methoxypropanamide | 3-chlorophenyl |
| I-36 | (S)-2-((cis)-octahydropentalen-2-yl)propanamide | 3-chlorophenyl |
| I-37 | (S)-2-((cis)-octahydropentalen-2-yl)propanamide | 3-methoxyphenyl |
| I-38 | 2-chloro-6-(trifluoromethyl)benzamide | 3-methoxyphenyl |
| I-39 | 2-fluoro-6-(trifluoromethyl)benzamide | cis-octahydrocyclopenta[c]pyrrol-2-yl |

TABLE 1-continued

| No. | Y | Z |
|---|---|---|
| I-40 | 2-Cl, 6-CF3 benzamide | 5-methyl-2-(hydroxymethyl)piperidin-1-yl |
| I-41 | 2,6-dichlorobenzyloxy | 4-fluorophenyl |
| I-42 | 2,6-dichlorobenzyloxy | 4-(trifluoromethyl)phenyl |
| I-43 | 2,6-dichlorobenzyloxy | 3,4-difluorophenyl |
| I-44 | benzyloxy | 1-methyl-1H-pyrazol-4-yl |
| I-45 | benzyloxy | hexahydrocyclopenta[c]pyrrol-2(1H)-yl |

TABLE 2

| No. | Y | A-B | Z |
|---|---|---|---|
| II-1 | 2-Cl, 6-CF3 benzamide | 5,6,7,8-tetrahydro-1,8-naphthyridinyl | 4-fluorophenyl |
| II-2 | 2-F, 6-CF3 benzamide | 5,6,7,8-tetrahydro-1,8-naphthyridinyl | 3-(trifluoromethyl)phenyl |

TABLE 2-continued

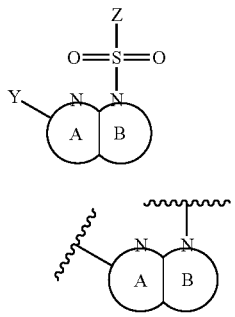

| No. | Y | | Z |
|---|---|---|---|
| II-3 | 2,6-difluorobenzamide | 5,6,7,8-tetrahydro-1,8-naphthyridin-2-yl (N8) | 3,4-difluorophenyl |
| II-4 | 2,6-dichlorobenzamide | 5,6,7,8-tetrahydro-1,8-naphthyridin-2-yl (N8) | 1-methyl-1H-pyrazol-4-yl |
| II-5 | 2,6-dichlorobenzamide | 5,6,7,8-tetrahydro-1,8-naphthyridin-2-yl (N8) | 4-methylpiperidin-1-yl |
| II-6 | 2-chloro-6-(trifluoromethyl)benzamide | 5,6,7,8-tetrahydro-1,8-naphthyridin-2-yl (N8) | 1-methylpyrrolidin-3-yl |
| II-7 | 2-chloro-6-(trifluoromethyl)benzamide | 6-(hydroxymethyl)-5,6,7,8-tetrahydro-1,8-naphthyridin-2-yl | 4-fluorophenyl |
| II-8 | 2-fluoro-6-(trifluoromethyl)benzamide | 6-(hydroxymethyl)-5,6,7,8-tetrahydro-1,8-naphthyridin-2-yl | 3-(trifluoromethyl)phenyl |
| II-9 | 2,6-difluorobenzamide | 6-(acetamidomethyl)-5,6,7,8-tetrahydro-1,8-naphthyridin-2-yl (N(H)C(O)CH3) | 3,4-difluorophenyl |

TABLE 2-continued
| No. | Y | | Z |
|---|---|---|---|
| II-10 | 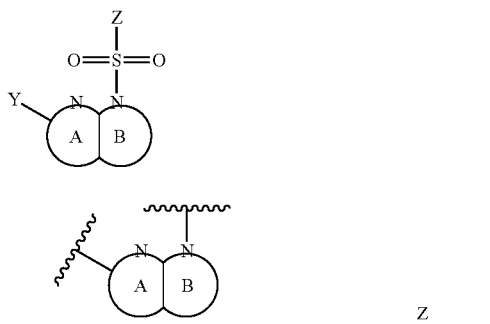 | 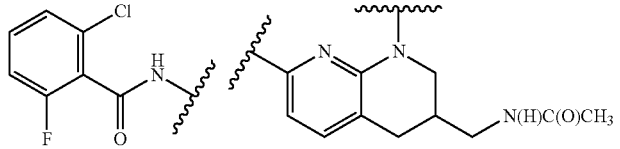 | 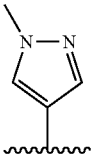 |
| II-11 | 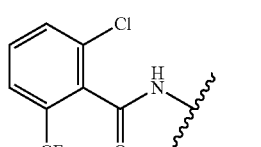 |  | 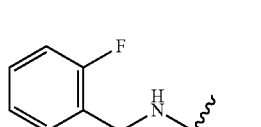 |
| II-12 | 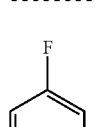 | 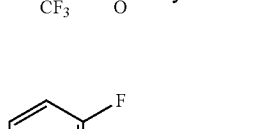 | 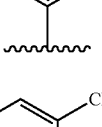 |
| II-13 | 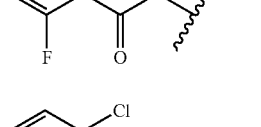 | 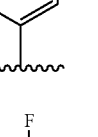 | 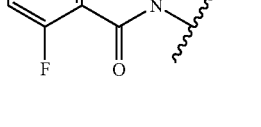 |
| II-14 | 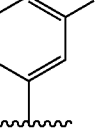 | 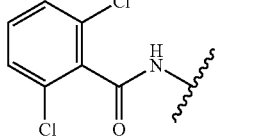 | 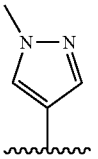 |
| II-15 | | | |
| II-16 | | | |

TABLE 2-continued

| No. | Y | | Z |
|---|---|---|---|
| II-17 | 2-F, 6-CF3 benzamide | 6-yl pyrido-oxazine, 2-CH2OH | 4-fluorophenyl |
| II-18 | 2,6-difluoro benzamide | 6-yl pyrido-oxazine, 2-CH2OH | 3-CF3-phenyl |
| II-19 | 2-Cl, 6-F benzamide | 6-yl pyrido-oxazine, 2-CH2OH | 3,4-difluorophenyl |
| II-20 | 2,6-dichloro benzamide | 6-yl pyrido-oxazine, 2-CH2N(H)C(O)CH3 | 1-methyl-1H-pyrazol-4-yl |
| II-21 | 2-Cl, 6-CF3 benzamide | 6-yl pyrido-oxazine, 2-CH2N(H)C(O)CH3 | 4-methylpiperidin-1-yl |
| II-22 | 2-F, 6-CF3 benzamide | 6-yl pyrido-oxazine, 2-CH2N(H)C(O)CH3 | 4-fluorophenyl |
| II-23 | 2,6-difluoro benzamide | 6-yl pyrido-oxazine, 2-methyl | 3-CF3-phenyl |

TABLE 2-continued

| No. | Y | | Z |
|---|---|---|---|
| II-24 | 2,6-dichloro-fluorobenzamide 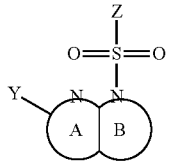 | pyrido-oxazine 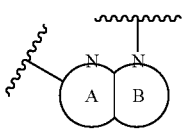 | 3,4-difluorophenyl 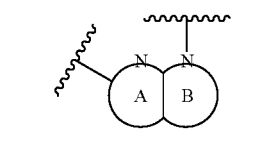 |
| II-25 | 2,6-dichlorobenzamide 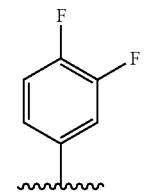 [SMILES: *c1ccc(F)c(F)c1] | pyrido-oxazine 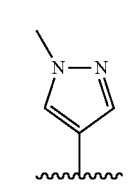 | 1-methylpyrazol-4-yl 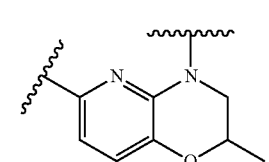 |
| II-26 | 2-chloro-6-CF3-benzamide  | naphthyridinone 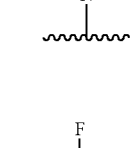 | N-piperidinyl 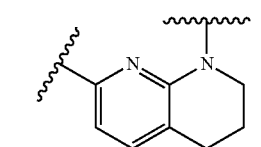 |
| II-27 | 2-fluoro-6-CF3-benzamide 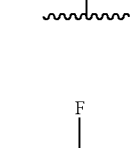 | naphthyridinone 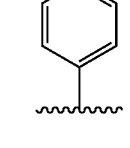 | 4-fluorophenyl 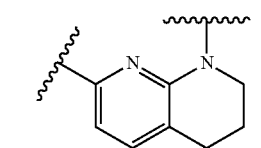 |
| II-28 | 2,6-difluorobenzamide 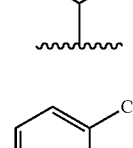 | naphthyridinone 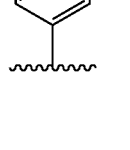 | 3-CF3-phenyl 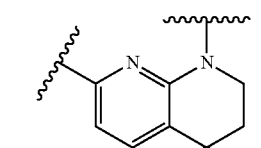 [SMILES: *c1ccc2c(n1)N(*)CCC2] |
| II-29 | 2-chloro-6-fluorobenzamide 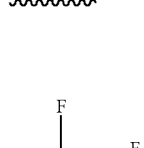 | naphthyridinone 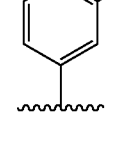 | 3,4-difluorophenyl 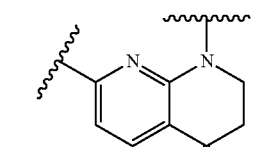 [SMILES: *c1ccc2c(n1)N(*)CCC2] |

TABLE 2-continued

| No. | Y | | Z |
|---|---|---|---|
| II-30 | 2,6-dichlorophenyl-C(O)NH- | 7,8-dihydro-5-oxo-1,8-naphthyridinyl | 1-methyl-1H-pyrazol-4-yl |
| II-31 | 2-chloro-6-(trifluoromethyl)phenyl-C(O)NH- | 7,8-dihydro-5-oxo-1,8-naphthyridinyl | 1-methylpiperidin-4-yl |
| II-32 | 2,6-dichlorophenyl-C(O)NH- | 5-methyl-2,3,4,5-tetrahydropyrido[2,3-b][1,4]diazepinyl | 1-methyl-1H-pyrazol-4-yl |
| II-33 | 2-chloro-6-(trifluoromethyl)phenyl-C(O)NH- | 5-methyl-2,3,4,5-tetrahydropyrido[2,3-b][1,4]diazepinyl | 3-chlorophenyl |
| II-34 | 2-fluoro-6-(trifluoromethyl)phenyl-C(O)NH- | 5-acetyl-2,3,4,5-tetrahydropyrido[2,3-b][1,4]diazepinyl | 4-fluorophenyl |
| II-35 | 2,6-difluorophenyl-C(O)NH- | 5-acetyl-2,3,4,5-tetrahydropyrido[2,3-b][1,4]diazepinyl | 3-(trifluoromethyl)phenyl |

TABLE 3

| No. | Compound |
|---|---|
| III-1 | |
| III-2 | |
| III-3 | |
| III-4 | |
| III-5 | |

TABLE 3-continued

| No. | Compound |
|---|---|
| III-6 | |
| III-7 | |
| III-8 | |
| III-9 | |
| III-10 | |

TABLE 3-continued

| No. | Compound |
|---|---|
| III-11 | |
| III-12 | |
| III-13 | |
| III-14 | |
| III-15 | |
| III-16 | |
| III-17 | |
| III-18 | |
| III-19 | |
| III-20 | |

TABLE 3-continued

| No. | Compound |
|---|---|
| III-21 | (structure) |
| III-22 | (structure) |
| III-23 | (structure) |
| III-24 | (structure) |
| III-25 | (structure) |
| III-26 | (structure) |
| III-27 | (structure) |
| III-28 | (structure) |
| III-29 | (structure) |
| III-30 | (structure) |

TABLE 3-continued

| No. | Compound |
|---|---|
| III-31 | (structure) |
| III-32 | (structure) |
| III-33 | (structure) |
| III-34 | (structure) |
| III-35 | (structure) |
| III-36 | (structure) |
| III-37 | (structure) |
| III-38 | (structure) |
| III-39 | (structure) |
| III-40 | (structure) |

TABLE 3-continued

| No. | Compound |
|---|---|
| III-41 | |
| III-42 | |
| III-43 | |
| III-44 | |
| III-45 | |
| III-46 | |
| III-47 | |
| III-48 | |
| III-49 | |
| III-50 | |

TABLE 3-continued

| No. | Compound |
|-----|----------|
| III-51 | |
| III-52 | |
| III-53 | |
| III-54 | |
| III-55 | |
| III-56 | |
| III-57 | |
| III-58 | |

Methods for preparing the above compounds are described in, for example, WO 2013/169864.

Tetrahydroquinoline Sulfonamide and Related RORγ Agonists

In certain embodiments, the RORγ agonist is one of the generic or specific tetrahydroquinoline sulfonamide or related RORγ agonist compounds depicted below, such as the family of compounds represented by Formula I*:

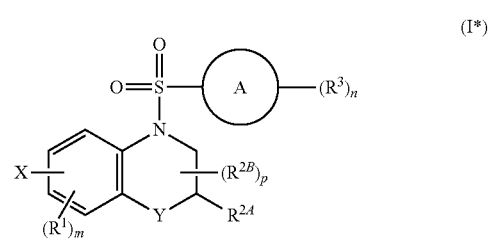

(I*)

or a pharmaceutically acceptable salt thereof; wherein:

A is phenylene, 5-6 membered heteroarylene, or $C_{3-6}$ heterocycloalkylene;

$R^1$ represents independently for each occurrence halogen, $C_{1-6}$ alkyl, $C_{1-6}$ haloalkyl, or $C_3$-6 cycloalkyl;

$R^{2A}$ is one of the following:

(i) hydrogen, $C_{1-6}$ alkyl, $C_{1-3}$ haloalkyl, $C_{3-6}$ cycloalkyl, —($C_{1-6}$ alkylene)-($C_{3-6}$ cycloalkyl), —O—($C_{1-6}$ alkylene)-$CO_2R^4$, —O—($C_{1-6}$ alkylene)-C(O)—($C_{1-6}$ alkyl), —N(R⁴)—(C₁₋₆ alkylene)-CO₂R⁴, or —N(R⁴)—(C₁₋₆ alkylene)-C(O)—(C₁₋₆ alkyl), wherein the C₁₋₆ alkyl, C₃₋₆ cycloalkyl, and C₁₋₆ alkylene are optionally substituted with 1 or 2 substituents independently selected from the group consisting of —CO₂R⁴, —C(O)N(R⁴)(R⁵), —C(O)—N(R⁴)—(C₁₋₄ alkylene)-CO₂R⁴, —N(R⁴)C(O)R⁸, —CN, halogen, hydroxyl, C₁₋₆ alkoxy, C₁₋₆ haloalkoxy, C₁₋₆ haloalkyl, —N(R⁴)(R⁵), —N(R⁴)C(O)N(R⁴)(R⁵), —N(R⁴)CO₂R⁹, —N(R⁴)S(O)₂R⁹, and —N(R⁴)S(O)₂N(R⁴)(R⁵); or (ii) —CO₂R⁴, —N(R⁴)C(O)R⁹, —N(R⁴)CO₂R⁹, —N(R⁴)C(O)N(R⁴)(R⁵), —N(R⁴)C(O)N(R⁴)(heteroaryl), —N(R⁴)S(O)₂R⁹, —N(R⁴)(R⁵), or —OH;

R²ᴮ is C₁₋₆ alkyl or C₁₋₃ haloalkyl;

R³ represents independently for each occurrence hydrogen, C₁₋₆ haloalkyl, halogen, hydroxyl, C₁₋₆ alkyl, C₃₋₆ cycloalkyl, C₁₋₆ alkoxy, C₁₋₆ haloalkoxy, —N(R⁴)(R⁸), —O—(C₁₋₆ hydroxyalkyl), or —O—(C₁₋₆ alkylene)-CO₂R⁴; or two vicinal occurrences of R³ are taken together with intervening atoms to form a 4-6 membered ring;

R⁴ and R⁵ each represent independently for each occurrence hydrogen, C₁₋₆ alkyl, or C₃₋₆ cycloalkyl; or an occurrence of R⁴ and R⁵ attached to the same nitrogen atom are taken together with the nitrogen atom to which they are attached to form a 3-8 membered heterocyclic ring;

R⁶ and R⁷ each represent independently for each occurrence hydrogen, fluoro, or C₁₋₆ alkyl, or R⁶ and R⁷ are taken together with the carbon atom to which they are attached to form a 3-6 membered carbocyclic ring; or R⁶ and a vicinal occurrence of R²ᴮ are taken together to form a bond;

R⁸ represents independently for each occurrence C₁₋₆ alkyl, C₃₋₆ cycloalkyl, —(C₁₋₆ alkylene)-(C₃₋₆ cycloalkyl), or aryl, each of which is optionally substituted with 1, 2, or 3 substituents independently selected from the group consisting of halogen, hydroxyl, or —CO₂R⁴; or R⁸ is —CO₂R⁴;

R⁹ represents independently for each occurrence C₁₋₆ alkyl, C₃₋₆ cycloalkyl, —(C₁₋₆ alkylene)-(C₃₋₆ cycloalkyl), C₁₋₆ haloalkyl, or C₁₋₆ hydroxyalkyl;

X is one of the following:
(i) —O-aralkyl, —O-heteroaralkyl, —O-phenyl, —O-heteroaryl, —O—(partially unsaturated bicyclic carbocyclyl), —O—(C₁₋₆ alkylene)-(C₃₋₆ cycloalkyl), —O—(C₃₋₆ cycloalkyl), —N(R⁴)-aralkyl, —N(R⁴)-phenyl, —N(R⁴)-(partially unsaturated bicyclic carbocyclyl), or —N(R⁴)—(C₁₋₆ alkylene)-(C₃₋₆ cycloalkyl), each of which is optionally substituted with 1, 2, or 3 substituents independently selected from the group consisting of halogen, C₁₋₆ haloalkyl, C₁₋₆ alkyl, C₃₋₆ cycloalkyl, C₁₋₆ alkoxy, C₁₋₆ haloalkoxy, —S—(C₁₋₆ alkyl), hydroxyl, cyano, —C(O)R⁹, and —SO₂R⁹;

(ii) —S-aralkyl, —S-heteroaralkyl, —S-phenyl, —S-heteroaryl, —S-(partially unsaturated bicyclic carbocyclyl), —S—(C₁₋₆ alkylene)-(C₃₋₆ cycloalkyl), or —S—(C₃₋₆ cycloalkyl), each of which is optionally substituted with 1, 2, or 3 substituents independently selected from the group consisting of halogen, C₁₋₆ haloalkyl, C₁₋₆ alkyl, C₃₋₆ cycloalkyl, C₁₋₆ alkoxy, C₁₋₆ haloalkoxy, —S—(C₁₋₆ alkyl), hydroxyl, cyano, —C(O)R⁹, and —SO₂R⁹;

(iii) —(C₂₋₆ alkenylene)-phenyl, —(C₂₋₆ alkenylene)-heteroaryl, —(C₂₋₆ alkenylene)-(partially unsaturated 8-10 membered bicyclic ring containing 0-3 heteroatoms), —(C₁₋₆ alkylene)-phenyl, —(C₁₋₆ alkylene)-heteroaryl, —(C₁₋₆ alkylene)-(partially unsaturated bicyclic heterocyclyl), —(C₁₋₆ alkylene)-(partially unsaturated bicyclic oxo-heterocyclyl), —(C₁₋₆ alkylene)-(C₃-C₆ cycloalkyl), -(5-6 membered heterocycloalkylene)-phenyl, or —(C₃₋₆ cycloalkylene)-phenyl, each of which is optionally substituted with 1, 2, or 3 substituents independently selected from the group consisting of halogen, C₁₋₆ haloalkyl, C₁₋₆ alkyl, C₃₋₆ cycloalkyl, C₁₋₆ alkoxy, C₁₋₆ haloalkoxy, —S—(C₁₋₆ alkyl), hydroxyl, cyano, —C(O)R⁹, and —SO₂R⁹;

(iv) —(C₂₋₆ alkenylene)-(C₁₋₆ alkyl), —(C₂₋₆ alkenylene)-(C₃₋₆ cycloalkyl), or

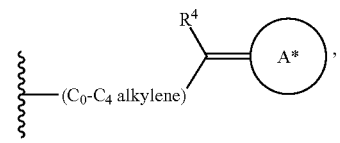

each of which is optionally substituted with 1, 2, or 3 substituents independently selected from the group consisting of halogen, C₁₋₆ haloalkyl, C₁₋₆ alkyl, C₃₋₆ cycloalkyl, C₁₋₆ alkoxy, C₁₋₆ haloalkoxy, —S—(C₁₋₆ alkyl), hydroxyl, cyano, —CO₂R⁴, and —SO₂R⁹, wherein A* is a 5-8 membered, partially saturated carbocyclic or heterocyclic ring; or (v) —(C₁₋₆ alkylene)-Z¹ or —(C₂₋₆ alkenylene)-Z¹, wherein Z¹ is —O-aralkyl, —O— heteroaralkyl, —O-phenyl, —O-heteroaryl, —O— (partially unsaturated bicyclic carbocyclyl), —O—(C₁₋₆ alkylene)-(C₃₋₆ cycloalkyl), —O—(C₃₋₆ cycloalkyl), —N(R⁴)-aralkyl, —N(R⁴)-phenyl, —N(R⁴)-(partially unsaturated bicyclic carbocyclyl), —N(R⁴)—(C₁₋₆ alkylene)-(C₃₋₆ cycloalkyl), or —N(R⁴)—(C₃₋₆ cycloalkyl), each of which is optionally substituted with 1, 2, or 3 substituents independently selected from the group consisting of halogen, C₁₋₆ haloalkyl, C₁₋₆ alkyl, C₃₋₆ cycloalkyl, C₁₋₆ alkoxy, C₁₋₆ haloalkoxy, —S—(C₁₋₆ alkyl), hydroxyl, cyano, —C(O)R⁹, and —SO₂R⁹;

Y is —C(R⁶)(R⁷)—, —O—, —C(O)—, or —S(O)ₚ—;

m and p each represent independently for each occurrence 0, 1, or 2; and n is 1, 2, or 3.

In certain embodiments, A is phenylene or 5-6 membered heteroarylene.

In certain embodiments, R¹ represents independently for each occurrence halogen or C₁₋₆ alkyl. In certain other embodiments, R¹ is fluoro, chloro, methyl, or trifluoromethyl.

In certain embodiments, R²ᴬ is C₁₋₆ alkyl substituted with 1 or 2 substituents independently selected from the group consisting of —CO₂R⁴, —C(O)N(R⁴)(R⁵), —C(O)—N(R⁴)—(C₁₋₄ alkylene)-CO₂R⁴, —N(R⁴)C(O)R⁸, —CN, halogen, hydroxyl, C₁₋₆ alkoxy, C₁₋₆haloalkoxy, C₁₋₆haloalkyl, —N(R⁴)(R⁵), —N(R⁴)C(O)N(R⁴)(R⁵), —N(R⁴)CO₂R⁹, —N(R⁴)S(O)₂R⁹, and —N(R⁴)S(O)₂N(R⁴)(R⁵).

In certain embodiments, R³ represents independently for each occurrence hydrogen, C₁₋₆ haloalkyl, halogen, hydroxyl, C₁₋₆ alkyl, C₃₋₄ cycloalkyl, C₁₋₆ alkoxy, or C₁₋₆ haloalkoxy.

In certain embodiments, R⁴ and R⁵ each represent independently for each occurrence hydrogen, C₁₋₆ alkyl, or C₃₋₆ cycloalkyl; or an occurrence of R⁴ and R⁵ attached to the same nitrogen atom are taken together with the nitrogen atom to which they are attached to form a 3-8 membered heterocyclic ring, wherein the heterocyclic ring is substituted with 1, 2, or 3 substituents independently selected from the group consisting of halogen, C₁₋₆ haloalkyl, C₁₋₆ alkyl, C₃₋₆ cycloalkyl, C₁₋₆ alkoxy, C₁₋₆ haloalkoxy, hydroxyl, cyano, oxo, —CO$_2$R$^{10}$, —C(O)R$^9$, —SO$_2$R$^9$, —N(R$^{10}$)C(O)—R$^{12}$, and —C(O)N(R$^{10}$)(R$^{11}$); wherein R$^{10}$ and R$^{11}$ each represent independently for each occurrence hydrogen, fluoro, or C$_{1-6}$ alkyl, or R$^{10}$ and R$^{11}$ are taken together with the carbon atom to which they are attached to form a 3-6 membered carbocyclic ring; and R$^{12}$ is C$_{1-6}$ alkyl, C$_{3-6}$ cycloalkyl, —(C$_{1-6}$ alkylene)-(C$_{3-6}$ cycloalkyl), or aryl, each of which is optionally substituted with 1, 2, or 3 substituents independently selected from the group consisting of halogen, hydroxyl, or —CO$_2$R$^{10}$.

In certain embodiments, X is —O-aralkyl, —O-heteroaralkyl, —O-phenyl, —O— heteroaryl, —O-(partially unsaturated bicyclic carbocyclyl), —O—(C$_{1-6}$alkylene)-(C$_{3-6}$cycloalkyl), —O—(C$_{3-6}$ cycloalkyl), —N(R$^4$)-aralkyl, —N(R$^4$)-phenyl, —N(R$^4$)-(partially unsaturated bicyclic carbocyclyl), or —N(R$^4$)—(C$_{1-6}$alkylene)-(C$_{3-6}$cycloalkyl), each of which is optionally substituted with 1, 2, or 3 substituents independently selected from the group consisting of halogen, C$_{1-6}$ haloalkyl, C$_{1-6}$ alkyl, C$_{3-6}$ cycloalkyl, C$_{1-6}$ alkoxy, C$_{1-6}$ haloalkoxy, —S—(C$_{1-6}$ alkyl), hydroxyl, cyano, —C(O)R$^9$, and —SO$_2$R$^9$.

In certain embodiments, X is —S-aralkyl, —S-heteroaralkyl, —S-phenyl, —S-heteroaryl, —S-(partially unsaturated bicyclic carbocyclyl), —S—(C$_{1-6}$alkylene)-(C$_{3-6}$cycloalkyl), or —S—(C$_{3-6}$ cycloalkyl), each of which is optionally substituted with 1, 2, or 3 substituents independently selected from the group consisting of halogen, C$_{1-6}$ haloalkyl, C$_{1-6}$ alkyl, C$_{3-6}$ cycloalkyl, C$_{1-6}$ alkoxy, C$_{1-6}$ haloalkoxy, —S—(C$_{1-6}$ alkyl), hydroxyl, cyano, —C(O)R$^9$, and —SO$_2$R$^9$.

In certain embodiments, X is —(C$_{2-6}$ alkenylene)-phenyl, —(C$_{2-6}$ alkenylene)-heteroaryl, —(C$_{2-6}$ alkenylene)-(partially unsaturated 8-10 membered bicyclic ring containing 0-3 heteroatoms), —(C$_{1-6}$ alkylene)-phenyl, —(C$_{1-6}$ alkylene)-heteroaryl, —(C$_{1-6}$ alkylene)-(partially unsaturated bicyclic heterocyclyl), —(C$_{1-6}$ alkylene)-(partially unsaturated bicyclic oxo-heterocyclyl), —(C$_{1-6}$ alkylene)-(C$_3$-C$_6$ cycloalkyl), -(5-6 membered heterocycloalkylene)-phenyl, or —(C$_{3-6}$ cycloalkylene)-phenyl, each of which is optionally substituted with 1, 2, or 3 substituents independently selected from the group consisting of halogen, C$_{1-6}$ haloalkyl, C$_{1-6}$ alkyl, C$_{3-6}$ cycloalkyl, C$_{1-6}$ alkoxy, C$_{1-6}$ haloalkoxy, —S—(C$_{1-6}$ alkyl), hydroxyl, cyano, —C(O)R$^9$, and —SO$_2$R$^9$.

In certain embodiments, X is —(C$_{2-6}$ alkenylene)-(C$_{1-6}$ alkyl), —(C$_{2-6}$ alkenylene)-(C$_{3-6}$ cycloalkyl), or

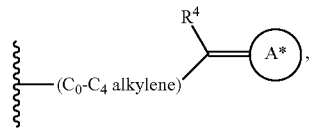

each of which is optionally substituted with 1, 2, or 3 substituents independently selected from the group consisting of halogen, C$_{1-6}$ haloalkyl, C$_{1-6}$ alkyl, C$_{3-6}$ cycloalkyl, C$_{1-6}$ alkoxy, C$_{1-6}$haloalkoxy, —S—(C$_{1-6}$ alkyl), hydroxyl, cyano, —C(O)R$^9$, and —SO$_2$R$^9$, wherein A* is a 5-8 membered, partially saturated carbocyclic or heterocyclic ring.

In certain embodiments, X is —(C$_{1-6}$ alkylene)-Z$^1$ or —(C$_{2-6}$ alkenylene)-Z$^1$, wherein Z$^1$ is —O-aralkyl, —O-heteroaralkyl, —O-phenyl, —O-heteroaryl, —O-(partially unsaturated bicyclic carbocyclyl), —O—(C$_{1-6}$ alkylene)-(C$_{3-6}$ cycloalkyl), —O—(C$_{3-6}$ cycloalkyl), —N(R$^4$)-aralkyl, —N(R$^4$)-phenyl, —N(R$^4$)-(partially unsaturated bicyclic carbocyclyl), —N(R$^4$)—(C$_{1-6}$alkylene)-(C$_{3-6}$ cycloalkyl), or —N(R$^4$)—(C$_{3-6}$cycloalkyl), each of which is optionally substituted with 1, 2, or 3 substituents independently selected from the group consisting of halogen, C$_{1-6}$ haloalkyl, C$_{1-6}$ alkyl, C$_{3-6}$ cycloalkyl, C$_{1-6}$ alkoxy, C$_{1-6}$ haloalkoxy, —S—(C$_{1-6}$ alkyl), hydroxyl, cyano, —C(O)R$^9$, and —SO$_2$R$^9$.

In certain embodiments, X is attached on the phenyl at the position located para to group Y.

In certain embodiments, Y is —C(R$^6$)(R$^7$)—. In certain other embodiments, Y is —O—. In yet other embodiments, Y is —S(O)$_p$—.

The definitions of variables in Formula I* above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii), e.g., such as where A is phenylene and R$^3$ is selected from the group consisting of C$_{1-6}$ haloalkyl, halogen, hydroxyl, and C$_{1-6}$ alkyl.

In certain other embodiments, the compound is a compound represented by Formula I-1:

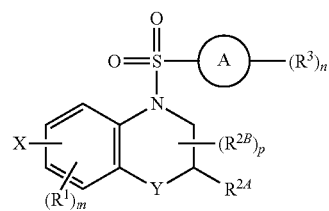

(I-1)

or a pharmaceutically acceptable salt thereof; wherein:

A is phenylene, 5-6 membered heteroarylene, or C$_{3-6}$heterocycloalkylene;

R$^1$ represents independently for each occurrence halogen, C$_{1-6}$ alkyl, C$_{1-6}$haloalkyl, or C$_{3-6}$ cycloalkyl;

R$^{2A}$ is hydrogen, C$_{1-6}$ alkyl, C$_{3-6}$ cycloalkyl, —O—(C$_{1-6}$alkylene)-CO$_2$R$^4$, —O—(C$_{1-6}$ alkylene)-C(O)—(C$_{1-6}$ alkyl), —N(R$^4$)—(C$_{1-6}$ alkylene)-CO$_2$R$^4$, or —N(R$^4$)—(C$_{1-6}$ alkylene)-C(O)—(C$_{1-6}$ alkyl), wherein the C$_{1-6}$ alkyl, C$_{3-6}$ cycloalkyl, and C$_{1-6}$ alkylene are optionally substituted with 1 or 2 substituents independently selected from the group consisting of —CO$_2$R$^4$, —N(R$^4$)C(O)(C$_{1-6}$ alkyl), —CN, halogen, hydroxyl, C$_{1-6}$ alkoxy, C$_{1-6}$haloalkoxy, C$_{1-6}$haloalkyl, —N(R$^4$)(R$^5$), —N(R$^4$)C(O)N(R$^4$)(R$^5$), —N(R$^4$)CO$_2$—(C$_{1-6}$ alkyl), —N(R$^4$)S(O)$_2$—(C$_{1-6}$ alkyl), and —N(R$^4$)S(O)$_2$N(R$^4$)(R$^5$); or R$^{2A}$ is —CO$_2$R$^4$ or —N(R$^4$)C(O)(C$_{1-6}$ alkyl);

R$^{2B}$ is C$_{1-6}$ alkyl, C$_{1-3}$haloalkyl, or fluoro;

R$^3$ represents independently for each occurrence hydrogen, C$_{1-6}$ haloalkyl, halogen, hydroxyl, C$_{1-6}$ alkyl, C$_{1-6}$ alkoxy, C$_{1-6}$haloalkoxy, or —O—(C$_{1-6}$ alkylene)-OH; or two vicinal occurrences of R$^3$ are taken together with intervening atoms to form a 4-6 membered ring;

R$^4$ and R$^5$ each represent independently for each occurrence hydrogen, C$_{1-6}$ alkyl, or C$_{3-6}$ cycloalkyl; or an occurrence of R$^4$ and R$^5$ attached to the same nitrogen atom are taken together with the nitrogen atom to which they are attached to form a 3-7 membered heterocyclic ring;

$R^6$ and $R^7$ each represent independently for each occurrence hydrogen or $C_{1-6}$ alkyl, or $R^6$ and $R^7$ are taken together with the carbon atom to which they are attached to form a 3-6 membered carbocyclic ring; or $R^6$ and $R^{2A}$ are taken together to form a bond;

X is one of the following:
(i) —O-aralkyl, —O-heteroaralkyl, —O-phenyl, —O-heteroaryl, —O-(partially unsaturated bicyclic carbocyclyl), —O—($C_{1-6}$ alkylene)-($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), or —N($R^4$)—($C_{1-6}$alkylene)-($C_{3-6}$cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$haloalkoxy, hydroxyl, and cyano;

(ii) —($C_{2-6}$ alkenylene)-phenyl, —($C_{2-6}$ alkenylene)-heteroaryl, —($C_{1-6}$ alkylene)-phenyl, —($C_{1-6}$ alkylene)-heteroaryl, —($C_{1-6}$ alkylene)-(partially unsaturated bicyclic heterocyclyl), —($C_{1-6}$ alkylene)-(partially unsaturated bicyclic oxo-heterocyclyl), -(5-6 membered heterocycloalkylene)-phenyl, or —($C_{3-6}$ cycloalkylene)-phenyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$haloalkoxy, hydroxyl, and cyano; or (iii) —($C_{1-6}$ alkylene)-$Z^1$ or —($C_{2-6}$ alkenylene)-$Z^1$, wherein $Z^1$ is —O-aralkyl, —O— heteroaralkyl, —O-phenyl, —O-heteroaryl, —O-(partially unsaturated bicyclic carbocyclyl), —O—($C_{1-6}$ alkylene)-($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), —N($R^4$)—($C_{1-6}$alkylene)-($C_{3-6}$cycloalkyl), or —N($R^4$)—($C_{3-6}$cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$haloalkoxy, hydroxyl, and cyano;

Y is —C($R^6$)($R^7$)—, —O—, —C(O)—, or —S(O)$_p$—;

m and p each represent independently for each occurrence 0, 1, or 2; and n is 1, 2, or 3.

In certain embodiments, A is phenylene or 5-6 membered heteroarylene.

In certain embodiments, $R^1$ represents independently for each occurrence halogen or $C_{1-6}$ alkyl.

In certain embodiments, Y is —C($R^6$)($R^7$)—. In certain other embodiments, Y is —O—. In yet other embodiments, Y is —S(O)$_p$—.

The definitions of variables in Formula I-1 above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii), e.g., such as where A is phenylene and $R^3$ is selected from the group consisting of $C_{1-6}$ haloalkyl, halogen, hydroxyl, and $C_{1-6}$ alkyl.

In certain other embodiments, the compound is a compound represented by Formula I-2:

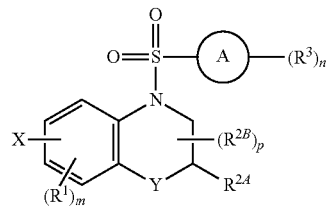

(I-2)

or a pharmaceutically acceptable salt thereof; wherein:

A is phenylene, 5-6 membered heteroarylene, or $C_{3-6}$ heterocycloalkylene;

$R^1$ represents independently for each occurrence halogen, $C_{1-6}$ alkyl, $C_{1-6}$haloalkyl, or $C_{3-6}$ cycloalkyl;

$R^{2A}$ is hydrogen, $C_{1-6}$ alkyl, $C_{3-6}$ cycloalkyl, —O—($C_{1-6}$ alkylene)-$CO_2R^4$, —O—($C_{1-6}$ alkylene)-C(O)—($C_{1-6}$ alkyl), —N($R^4$)—($C_{1-6}$ alkylene)-$CO_2R^4$, or —N($R^4$)—($C_{1-6}$ alkylene)-C(O)—($C_{1-6}$ alkyl), wherein the $C_{1-6}$ alkyl, $C_{3-6}$ cycloalkyl, and $C_{1-6}$ alkylene are optionally substituted with 1 or 2 substituents independently selected from the group consisting of —$CO_2R^4$, —N($R^4$)C(O)($C_{1-6}$ alkyl), —CN, halogen, hydroxyl, $C_{1-6}$ alkoxy, $C_{1-6}$haloalkoxy, $C_{1-6}$haloalkyl, —N($R^4$)($R^5$), —N($R^4$)C(O)N($R^4$)($R^5$), —N($R^4$)$CO_2$—($C_{1-6}$ alkyl), —N($R^4$)S(O)$_2$—($C_{1-6}$ alkyl), and —N($R^4$)S(O)$_2$N($R^4$)($R^5$); or $R^{2A}$ is —$CO_2R^4$ or —N($R^4$)C(O)($C_{1-6}$ alkyl);

$R^{2B}$ is $C_{1-6}$ alkyl or $C_{1-3}$haloalkyl;

$R^3$ represents independently for each occurrence hydrogen, $C_{1-6}$ haloalkyl, halogen, hydroxyl, $C_{1-6}$ alkyl, $C_{1-6}$ alkoxy, $C_{1-6}$haloalkoxy, or —O—($C_{1-6}$ alkylene)-OH; or two vicinal occurrences of $R^3$ are taken together with intervening atoms to form a 4-6 membered ring;

$R^4$ and $R^5$ each represent independently for each occurrence hydrogen, $C_{1-6}$ alkyl, or $C_{3-6}$ cycloalkyl; or an occurrence of $R^4$ and $R^5$ attached to the same nitrogen atom are taken together with the nitrogen atom to which they are attached to form a 3-7 membered heterocyclic ring;

$R^6$ and $R^7$ each represent independently for each occurrence hydrogen or $C_{1-6}$ alkyl, or $R^6$ and $R^7$ are taken together with the carbon atom to which they are attached to form a 3-6 membered carbocyclic ring; or $R^6$ and a vicinal occurrence of $R^{2B}$ are taken together to form a bond;

X is one of the following:
(i) —O-aralkyl, —O-heteroaralkyl, —O-phenyl, —O-heteroaryl, —O-(partially unsaturated bicyclic carbocyclyl), —O—($C_{1-6}$ alkylene)-($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), or —N($R^4$)—($C_{1-6}$alkylene)-($C_{3-6}$cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, hydroxyl, and cyano;

(ii) —($C_{2-6}$ alkenylene)-phenyl, —($C_{2-6}$ alkenylene)-heteroaryl, —($C_{1-6}$ alkylene)-phenyl, —($C_{1-6}$ alkylene)-heteroaryl, —($C_{1-6}$ alkylene)-(partially unsaturated bicyclic heterocyclyl), —($C_{1-6}$ alkylene)-(partially unsaturated bicyclic oxo-heterocyclyl), -(5-6 membered heterocycloalkylene)-phenyl, or —($C_{3-6}$ cycloalkylene)-phenyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$haloalkoxy, hydroxyl, and cyano; or (iii) —($C_{1-6}$ alkylene)-$Z^1$ or —($C_{2-6}$ alkenylene)-$Z^1$, wherein $Z^1$ is —O-aralkyl, —O— heteroaralkyl, —O-phenyl, —O-heteroaryl, —O-(partially unsaturated bicyclic carbocyclyl), —O—($C_{1-6}$ alkylene)-($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), —N($R^4$)—($C_{1-6}$alkylene)-($C_{3-6}$cycloalkyl), or —N($R^4$)—($C_{3-6}$cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$haloalkoxy, hydroxyl, and cyano;

Y is —C($R^6$)($R^7$)—, —O—, —C(O)—, or —S(O)$_p$—;

m and p each represent independently for each occurrence 0, 1, or 2; and n is 1, 2, or 3.

In certain embodiments, A is phenylene or 5-6 membered heteroarylene.

In certain embodiments, $R^1$ represents independently for each occurrence halogen or $C_{1-6}$ alkyl.

In certain embodiments, Y is —C($R^6$)($R^7$)—. In certain other embodiments, Y is —O—. In yet other embodiments, Y is —S(O)$_p$—.

The definitions of variables in Formula I-2 above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii), e.g., such as where A is phenylene and $R^3$ is selected from the group consisting of $C_{1-6}$ haloalkyl, halogen, hydroxyl, and $C_{1-6}$ alkyl.

In certain embodiments, the compound is represented by Formula I-A:

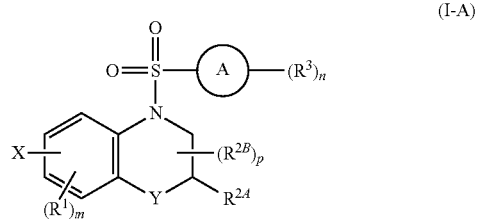

(I-A)

or a pharmaceutically acceptable salt thereof; wherein:

A is phenylene or a 5-6 membered heteroarylene;

$R^1$ represents independently for each occurrence halogen, $C_{1-6}$ alkyl, or $C_{3-6}$ cycloalkyl;

$R^{2A}$ is hydrogen, $C_{1-6}$ alkyl or $C_{3-6}$ cycloalkyl, wherein the $C_{1-6}$ alkyl or $C_{3-6}$ cycloalkyl are optionally substituted with 1 or 2 substituents independently selected from the group consisting of —CO$_2$R$^4$, —N(R$^4$)C(O)(C$_{1-6}$ alkyl), —CN, halogen, hydroxyl, $C_{1-6}$alkoxy, $C_{1-6}$ haloalkoxy, $C_{1-6}$haloalkyl, and —N(R$^4$)(R$^5$); or $R^{2A}$ is —CO$_2$R$^4$ or —N(R$^4$)C(O)(C$_{1-6}$ alkyl);

$R^{2B}$ is $C_{1-6}$ alkyl or $C_{1-3}$haloalkyl;

$R^3$ represents independently for each occurrence hydrogen, $C_{1-6}$ haloalkyl, halogen, hydroxyl, $C_{1-6}$ alkyl, $C_{1-6}$alkoxy, $C_{1-6}$ haloalkoxy, or —O—(C$_{1-6}$ alkylene)-OH; or two vicinal occurrences of $R^3$ are taken together with intervening atoms to form a 4-6 membered ring;

$R^4$ and $R^5$ each represent independently for each occurrence hydrogen, $C_{1-6}$ alkyl, or $C_{3-6}$ cycloalkyl; or an occurrence of $R^4$ and $R^5$ attached to the same nitrogen atom are taken together with the nitrogen atom to which they are attached to form a 3-7 membered heterocyclic ring;

$R^6$ and $R^7$ each represent independently for each occurrence hydrogen or $C_{1-6}$ alkyl, or $R^6$ and $R^7$ are taken together with the carbon atom to which they are attached to form a 3-6 membered carbocyclic ring; or $R^6$ and $R^{2A}$ are taken together to form a bond;

X is one of the following:

(i) —O-aralkyl, —O-heteroaralkyl, —O-phenyl, —O-heteroaryl, —O-(partially unsaturated bicyclic carbocyclyl), —O—(C$_{1-6}$ alkylene)-(C$_{3-6}$ cycloalkyl), —N(R$^4$)-aralkyl, —N(R$^4$)-phenyl, —N(R$^4$)-(partially unsaturated bicyclic carbocyclyl), or —N(R$^4$)—(C$_{1-6}$ alkylene)-(C$_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$haloalkoxy;

(ii) —(C$_{2-6}$ alkenylene)-phenyl, —(C$_{2-6}$ alkenylene)-heteroaryl, —(C$_{1-6}$ alkylene)-phenyl, —(C$_{1-6}$ alkylene)-heteroaryl, —(C$_{1-6}$ alkylene)-(partially unsaturated bicyclic heterocyclyl), —(C$_{1-6}$ alkylene)-(partially unsaturated bicyclic oxo-heterocyclyl), or -(5-6 membered heterocycloalkylene)-phenyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy; or (iii) —(C$_{1-6}$ alkylene)-$Z^1$ or —(C$_{2-6}$ alkenylene)-$Z^1$, wherein $Z^1$ is —O-aralkyl, —O— heteroaralkyl, —O-phenyl, —O-heteroaryl, —O-(partially unsaturated bicyclic carbocyclyl), —O—(C$_{1-6}$ alkylene)-(C$_{3-6}$ cycloalkyl), —O—(C$_{3-6}$ cycloalkyl), —N(R$^4$)-aralkyl, —N(R$^4$)-phenyl, —N(R$^4$)-(partially unsaturated bicyclic carbocyclyl), or —N(R$^4$)—(C$_{1-6}$alkylene)-(C$_{3-6}$cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy;

Y is —C(R$^6$)(R$^7$)—, —O—, or —C(O)—;

m and p are independently 0, 1, or 2; and n is 1, 2, or 3.

In certain embodiments, A is phenylene. In certain other embodiments, A is a 5-6 membered heteroarylene. In yet other embodiments, -A-($R^3$)$_n$ is one of the following:

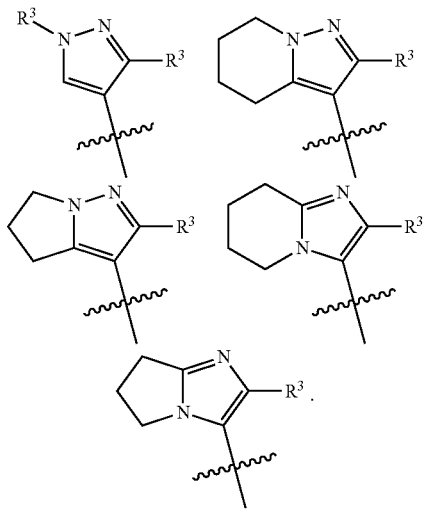

In certain embodiments, $R^1$ represents independently for each occurrence halogen, methyl, or cyclopropyl.

In certain embodiments, $R^{2A}$ is $C_{1-6}$ alkyl optionally substituted with 1 or 2 substituents independently selected from the group consisting of —$CO_2R^4$, —$N(R^4)C(O)(C_{1-6}$ alkyl), —CN, halogen, hydroxyl, $C_{1-6}$ alkoxy, $C_{1-6}$ haloalkoxy, and —$N(R^4)(R^5)$. In certain other embodiments, $R^{2A}$ is $C_{1-6}$ alkyl substituted with 1 or 2 substituents independently selected from the group consisting of —$CO_2R^4$, —$N(R^4)C(O)(C_{1-6}$ alkyl), —CN, hydroxyl, and $C_{1-6}$ alkoxy. In certain other embodiments, $R^{2A}$ is —$CO_2R^4$.

In certain embodiments, $R^{2B}$ is $C_{1-6}$ alkyl. In certain embodiments, $R^{2B}$ is methyl.

In certain embodiments, n is 1. In certain other embodiments, n is 1 or 2.

In certain embodiments, $R^3$ represents independently for each occurrence $C_{1-6}$ haloalkyl, halogen, $C_{1-6}$ alkyl, $C_{1-6}$ alkoxy, or —O—$(C_{1-6}$ alkylene)-OH. In certain other embodiments, $R^3$ is trifluoromethyl, fluoro, chloro, or methoxy. In certain other embodiments, $R^3$ is trifluoromethyl.

In certain embodiments, $R^4$ and $R^5$ each represent independently for each occurrence hydrogen or $C_{1-6}$ alkyl.

In certain embodiments, X is —O-aralkyl, —O-heteroaralkyl, —O-phenyl, —O— heteroaryl, —O-(partially unsaturated bicyclic carbocyclyl), —O—$(C_{1-6}$alkylene)-$(C_{3-6}$cycloalkyl), —$N(R^4)$-aralkyl, —$N(R^4)$-phenyl, —$N(R^4)$-(partially unsaturated bicyclic carbocyclyl), or —$N(R^4)$—$(C_{1-6}$ alkylene)-$(C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$haloalkoxy. In certain other embodiments, X is —O—aralkyl, —O-phenyl, —O-(partially unsaturated bicyclic carbocyclyl), —O—$(C_{1-6}$ alkylene)-$(C_{3-6}$ cycloalkyl), —$N(R^4)$-aralkyl, —$N(R^4)$-phenyl, —$N(R^4)$-(partially unsaturated bicyclic carbocyclyl), or —$N(R^4)$—$(C_{1-6}$alkylene)-$(C_{3-6}$cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$haloalkoxy. In certain other embodiments, X is —O— aralkyl or —$N(R^4)$-aralkyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$haloalkoxy. In certain other embodiments, X is —O—$(C_{1-6}$ alkylene)-phenyl or —$N(R^4)$—$(C_{1-6}$alkylene)-phenyl, each of which is substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy, where at least one substituent is present at the ortho position on the phenyl group in variable X. In certain other embodiments, X is —O— benzyl or —$N(R^4)$-benzyl, each of which is substituted with 1 or 2 substituents independently selected from the group consisting of chloro, bromo, and fluoro.

In certain embodiments, X is —$(C_{2-6}$ alkenylene)-phenyl, —$(C_{2-6}$ alkenylene)-heteroaryl, —$(C_{1-6}$ alkylene)-phenyl, —$(C_{1-6}$ alkylene)-heteroaryl, —$(C_{1-6}$ alkylene)-(partially unsaturated bicyclic heterocyclyl), —$(C_{1-6}$ alkylene)-(partially unsaturated bicyclic oxo-heterocyclyl), or -(5-6 membered heterocycloalkylene)-phenyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$haloalkoxy. In certain other embodiments, X is —$(C_{2-6}$ alkenylene)-phenyl, —$(C_{1-6}$ alkylene)-phenyl, —$(C_{1-6}$ alkylene)-heteroaryl, —$(C_{1-6}$ alkylene)-(partially unsaturated bicyclic heterocyclyl), —$(C_{1-6}$ alkylene)-(partially unsaturated bicyclic oxo-heterocyclyl), or -(5-6 membered heterocycloalkylene)-phenyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy. In certain other embodiments, X is —$(C_{2-6}$ alkenylene)-phenyl, —$(C_{1-6}$ alkylene)-phenyl, or —$(C_{1-6}$ alkylene)-heteroaryl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$haloalkoxy.

In certain embodiments, X is —$(C_{1-6}$ alkylene)-$Z^1$ or —$(C_{2-6}$ alkenylene)-$Z^1$, wherein $Z^1$ is —O-aralkyl, —O-heteroaralkyl, —O-phenyl, —O-heteroaryl, —O-(partially unsaturated bicyclic carbocyclyl), —O—$(C_{1-6}$ alkylene)-$(C_{3-6}$ cycloalkyl), —O—$(C_{3-6}$ cycloalkyl), —$N(R^4)$-aralkyl, —$N(R^4)$-phenyl, —$N(R^4)$-(partially unsaturated bicyclic carbocyclyl), or —$N(R^4)$—$(C_{1-6}$alkylene)-$(C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$haloalkoxy. In certain other embodiments, X is —$(C_{1-6}$ alkylene)-$Z^1$, wherein $Z^1$ is —O-aralkyl, —O-phenyl, —O-(partially unsaturated bicyclic carbocyclyl), —O—$(C_{1-6}$alkylene)-$(C_{3-6}$ cycloalkyl), —O—$(C_{3-6}$ cycloalkyl), —$N(R^4)$-aralkyl, —$N(R^4)$-phenyl, —$N(R^4)$-(partially unsaturated bicyclic carbocyclyl), or —$N(R^4)$—$(C_{1-6}$alkylene)-$(C_{3-6}$cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$haloalkoxy.

In certain embodiments, Y is —$C(R^6)(R^7)$—.

In certain embodiments, $R^6$ and $R^7$ are independently hydrogen or methyl.

In certain embodiments, Y is —$C(R^6)(R^7)$—, $R^6$ and $R^7$ are independently hydrogen or methyl, and X is attached at the 7-position of the 1,2,3,4-tetrahydroquinolinyl ring.

In certain embodiments, Y is —O—.

In certain embodiments, X is attached at the 6-position of the 3,4-dihydro-2H-benzo[b][1,4]oxazinyl ring.

In certain embodiments, m is 0 or 1. In certain other embodiments, m is 1.

In certain embodiments, p is 0. In certain other embodiments, p is 1.

The definitions of variables in Formula I-A above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii), e.g., such as where A is phenylene and $R^3$ is selected from the group consisting of $C_{1-6}$ haloalkyl, halogen, hydroxyl, and $C_{1-6}$ alkyl.

In certain other embodiments, the compound is represented by Formula I-B:

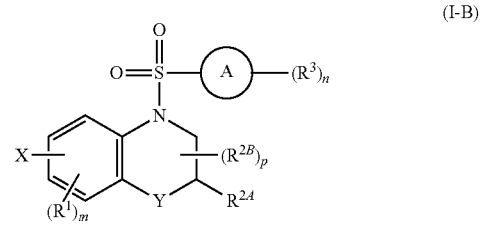

(I-B)

or a pharmaceutically acceptable salt thereof; wherein:
A is phenylene;
$R^1$ represents independently for each occurrence halogen, methyl, ethyl, or cyclopropyl;
$R^{2A}$ is $C_{1-6}$ alkyl substituted with 1 or 2 substituents independently selected from the group consisting of —CO$_2$R$^4$, —N(R$^4$)C(O)(C$_{1-6}$ alkyl), —CN, halogen, hydroxyl, C$_{1-6}$ alkoxy, C$_{1-6}$ haloalkoxy, C$_{1-6}$haloalkyl, and —N(R$^4$)(R$^5$);

R$^{2B}$ is methyl or ethyl;

R$^3$ represents independently for each occurrence C$_{1-3}$ haloalkyl, halogen, and C$_{1-3}$ alkyl;

R$^4$ and R$^5$ each represent independently for each occurrence hydrogen or methyl;

R$^6$ and R$^7$ each represent independently for each occurrence hydrogen, methyl, or ethyl;

X is attached at the meta or para position on the phenyl group relative to variable Y, and X is one of the following:
- (i) —O—(C$_{1-6}$ alkylene)-phenyl, —O-(partially unsaturated bicyclic carbocyclyl), or —O—(C$_{1-6}$ alkylene)-(C$_{3-6}$ cycloalkyl), each of which is optionally substituted with 1, 2, or 3 substituents independently selected from the group consisting of halogen, C$_{1-6}$ haloalkyl, C$_{1-6}$ alkyl, and C$_{1-6}$ alkoxy;
- (ii) —(C$_{2-6}$ alkenylene)-phenyl or —(C$_{1-6}$ alkylene)-phenyl, each of which is optionally substituted with 1, 2, or 3 substituents independently selected from the group consisting of halogen, C$_{1-6}$ haloalkyl, C$_{1-6}$ alkyl, C$_{3-6}$ cycloalkyl, C$_{1-6}$ alkoxy, and C$_{1-6}$ haloalkoxy; or
- (iii) —(C$_{1-6}$ alkylene)-Z$^1$, wherein Z$^1$ is —O-aralkyl, —O-phenyl, —O-(partially unsaturated bicyclic carbocyclyl), —O—(C$_{1-6}$alkylene)-(C$_{3-6}$cycloalkyl), —O—(C$_{3-6}$ cycloalkyl), —N(R$^4$)-aralkyl, —N(R$^4$)-phenyl, —N(R$^4$)-(partially unsaturated bicyclic carbocyclyl), or —N(R$^4$)—(C$_{1-6}$alkylene)-(C$_{3-6}$cycloalkyl), each of which is optionally substituted with 1, 2, or 3 substituents independently selected from the group consisting of halogen, C$_{1-6}$ haloalkyl, C$_{1-6}$ alkyl, and C$_{1-6}$ alkoxy;

Y is —C(R$^6$)(R$^7$)— or —O—;

m and p are independently 0 or 1; and n is 1 or 2.

In certain embodiments, X is —O—(C$_{1-6}$ alkylene)-phenyl optionally substituted with 1 or 2 substituents independently selected from the group consisting of halogen, C$_{1-6}$ haloalkyl, and C$_{1-6}$ alkyl.

In certain embodiments, Y is —C(R$^6$)(R$^7$)—.

The definitions of variables in Formula I-B above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

In certain other embodiments, the compound is a compound defined by one of the following formulae where variables X and Z are as defined in Table 4, or a pharmaceutically acceptable salt thereof

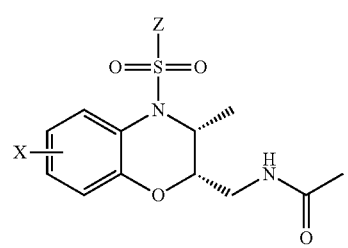

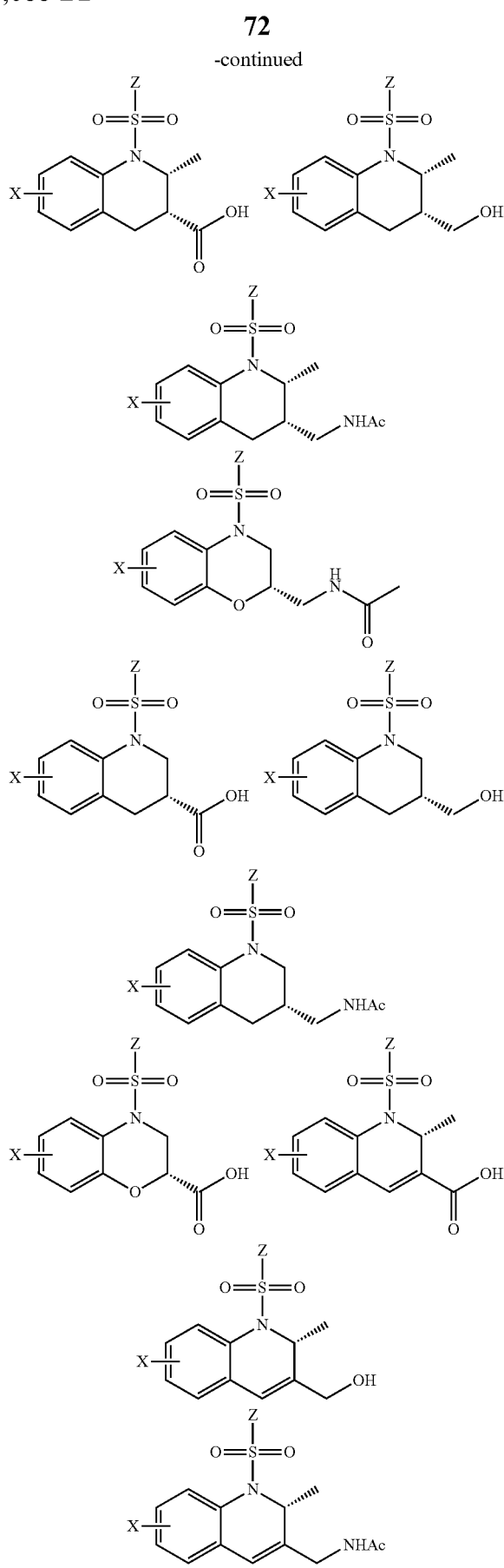

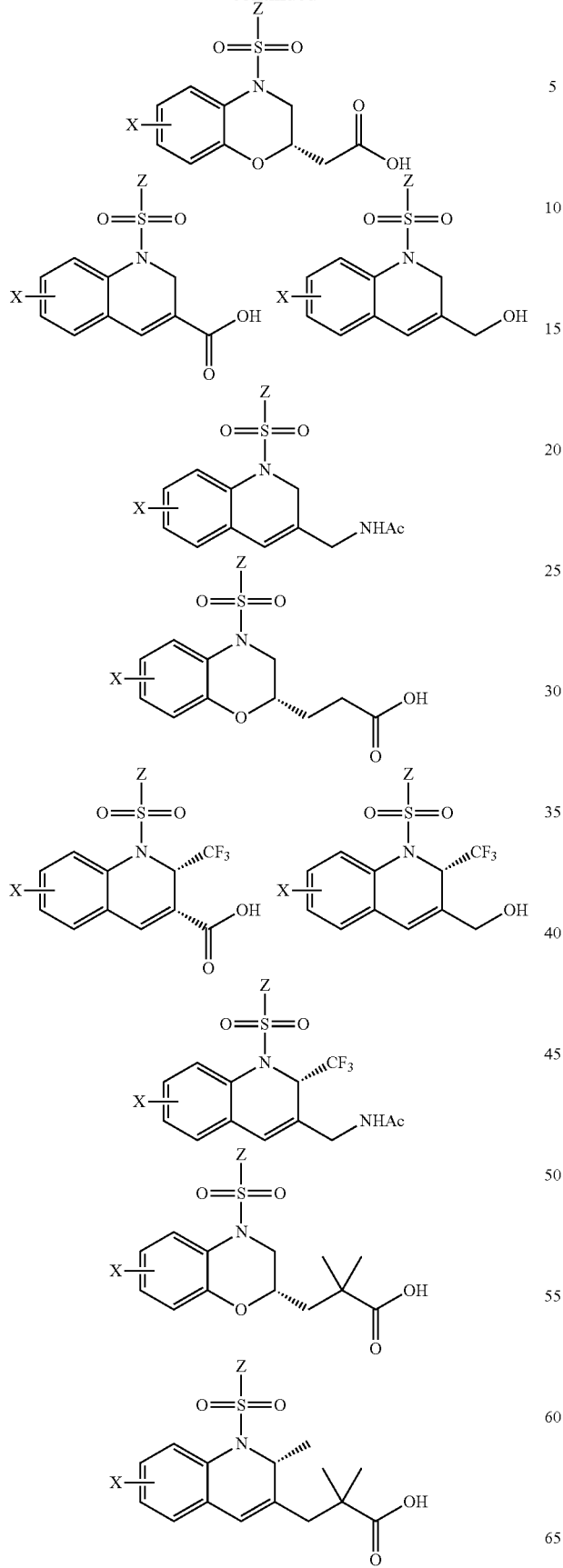
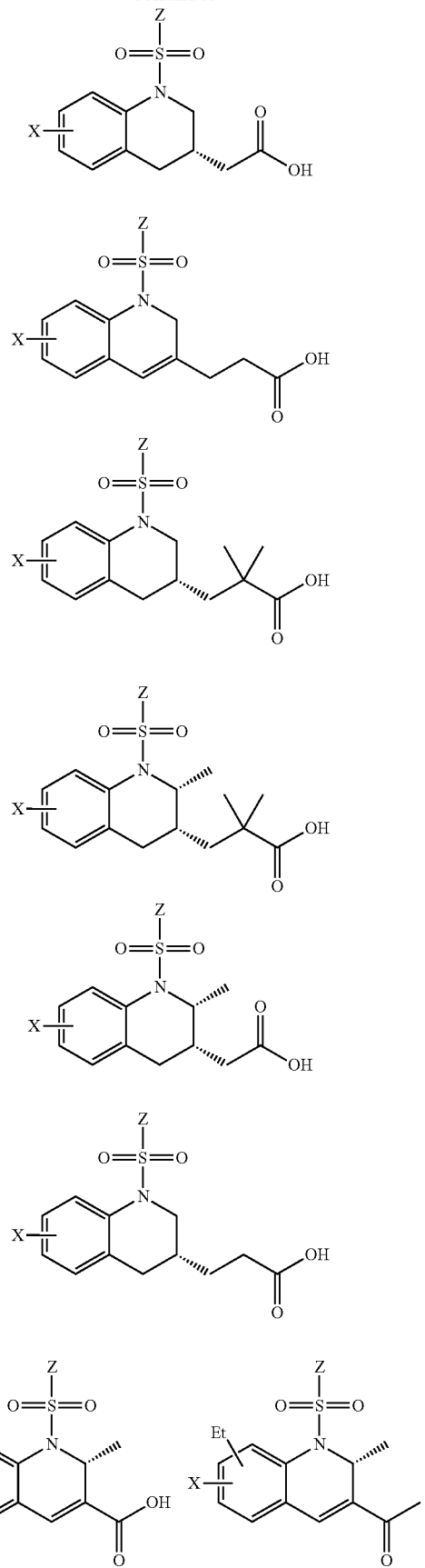

75
-continued
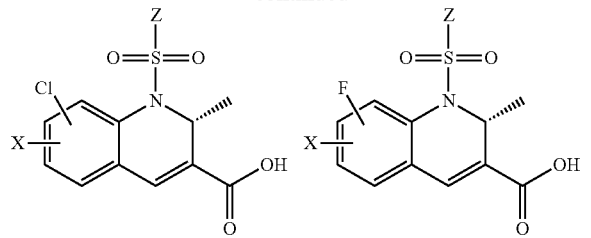
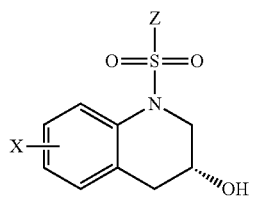
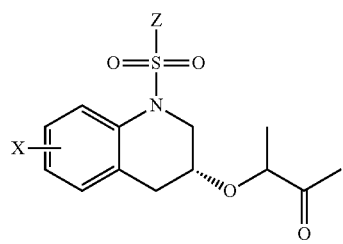
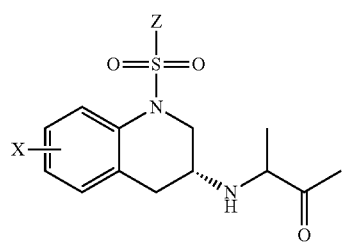
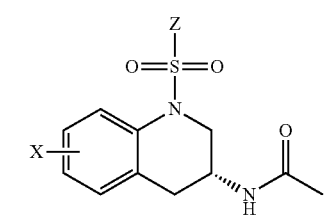
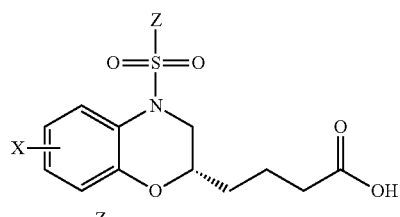
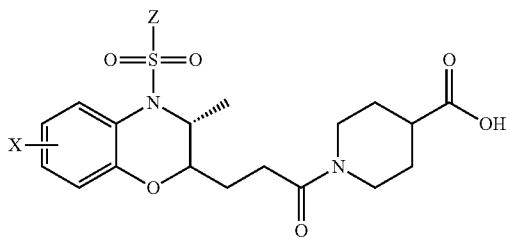
76
-continued
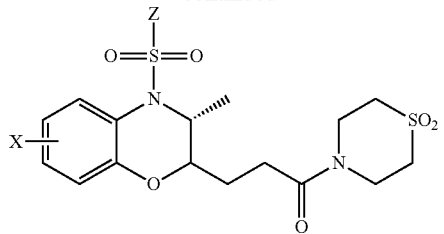
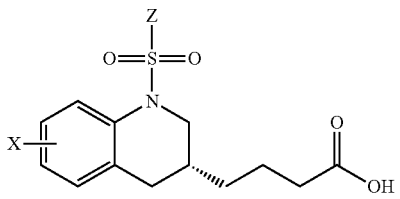
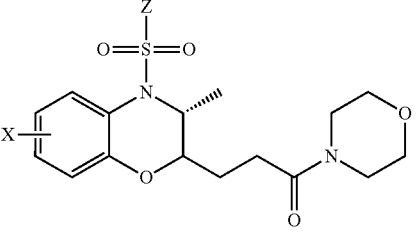
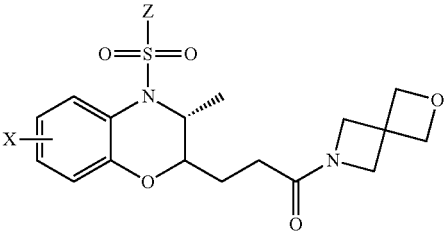
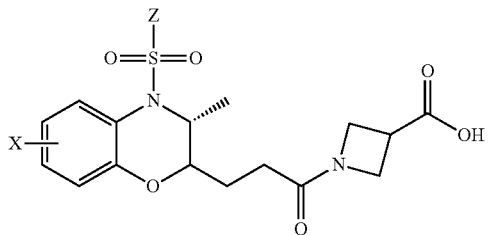
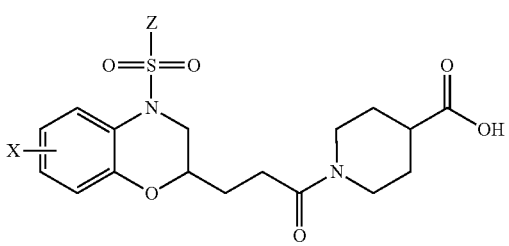
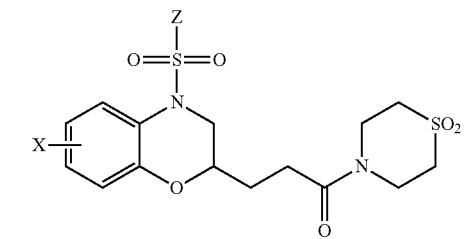

77
-continued
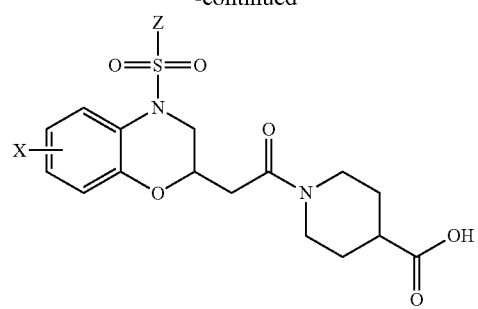
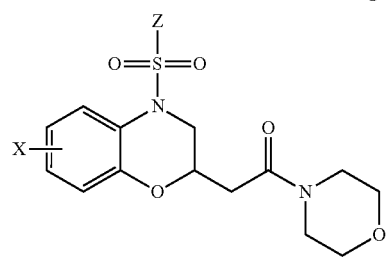
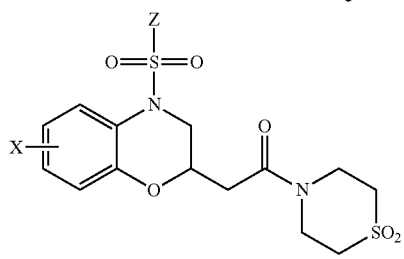
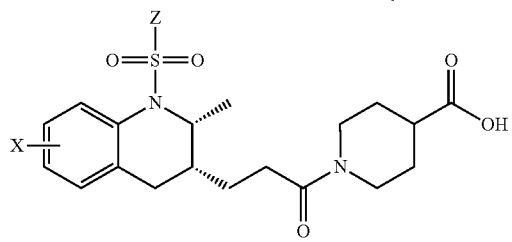
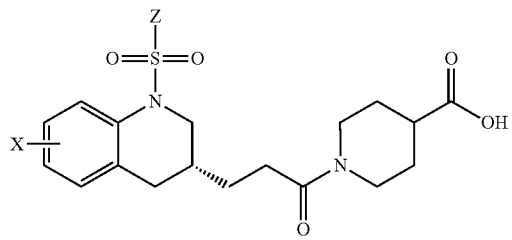
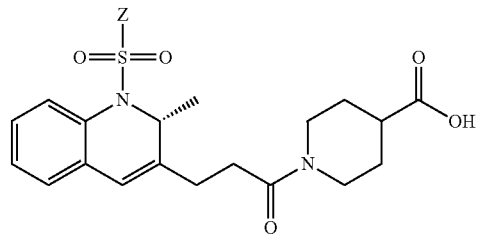
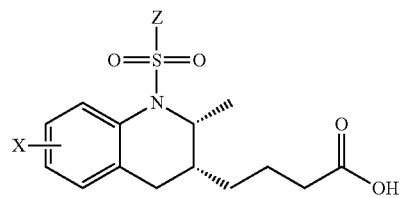
78
-continued
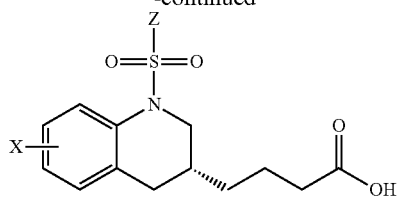
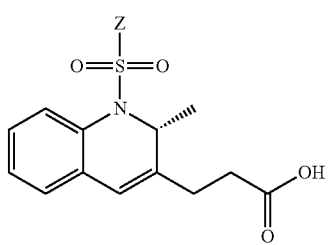
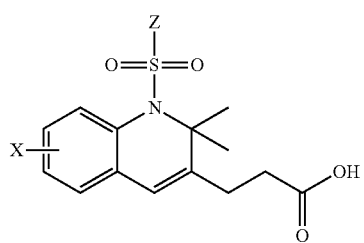
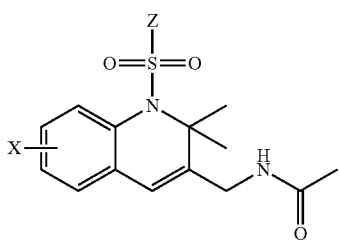
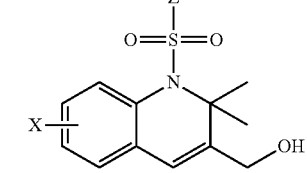
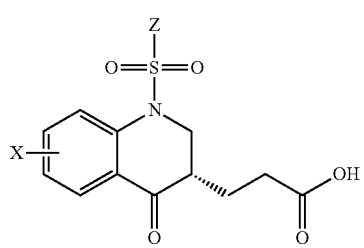
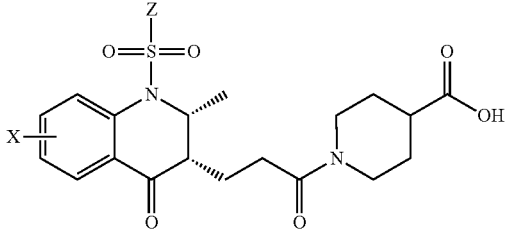

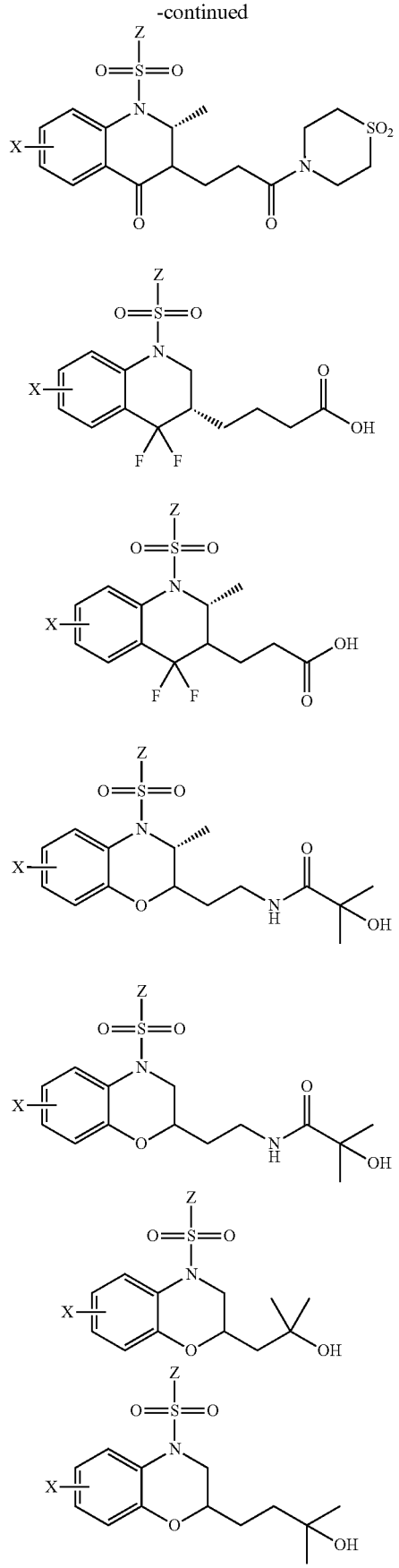

TABLE 4-continued

| No. | X | Z |
|---|---|---|
| IV-10 | 2-chloro-6-fluorobenzyl amino | 4-fluoro-3-methoxyphenyl |
| IV-11 | 1-(2-chloro-6-fluorophenyl)-1-methylvinyl | 4-fluoro-3-methoxyphenyl |
| IV-12 | cyclohexylmethoxy | 4-fluoro-3-methoxyphenyl |
| IV-13 | indan-1-yloxy | 4-fluoro-3-methoxyphenyl |
| IV-14 | indan-1-yl methyl | 4-fluoro-3-methoxyphenyl |
| IV-15 | 1,2,3,4-tetrahydronaphthalen-1-yloxy | 4-fluoro-3-methoxyphenyl |
| IV-16 | 7-chloroindan-1-yloxy | 4-fluoro-3-methoxyphenyl |
| IV-17 | indan-1-ylamino | 4-fluoro-3-methoxyphenyl |
| IV-18 | 2-(2-chloro-6-fluorophenyl)-2-methylcyclopropyl | 4-fluoro-3-methoxyphenyl |
| IV-19 | 1-(2-chloro-6-fluorophenyl)propylidene | 4-fluoro-3-methoxyphenyl |
| IV-20 | 1-(2-chloro-6-fluorophenyl)-2,2,2-trifluoroethylidene | 4-fluoro-3-methoxyphenyl |
| IV-21 | indan-1-ylidenemethyl | 4-fluoro-3-methoxyphenyl |
| IV-22 | 2-(2-chloro-6-fluorophenyl)-1-methylvinyl | 4-fluoro-3-methoxyphenyl |
| IV-23 | 1-(2-chloro-6-fluorophenyl)-2-methylpropenyl | 4-fluoro-3-methoxyphenyl |
| IV-24 | 1,2,3,4-tetrahydronaphthalen-2-yl | 4-fluoro-3-methoxyphenyl |
| IV-25 | indan-2-yl | 4-fluoro-3-methoxyphenyl |

TABLE 4-continued
| No. | X | Z |
|---|---|---|
| IV-26 | 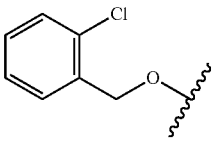 [SMILES: *OCc1ccccc1Cl] | 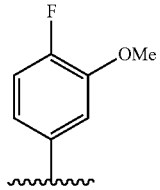 [SMILES: *c1ccc(F)c(OC)c1] |
| IV-27 | 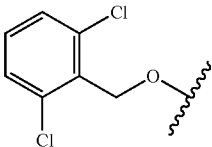 | 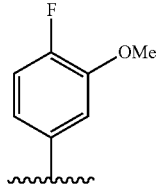 [SMILES: *c1ccc(F)c(OC)c1] |
| IV-28 | 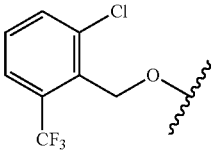 [SMILES: *OCc1c(Cl)cccc1C(F)(F)F] | 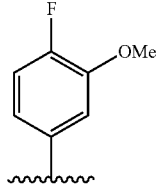 [SMILES: *c1ccc(F)c(OC)c1] |
| IV-29 | 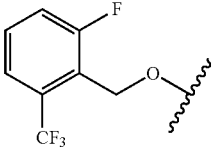 | 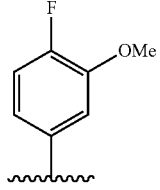 [SMILES: *c1ccc(F)c(OC)c1] |
| IV-30 | 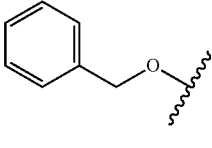 [SMILES: *OCc1ccccc1] | 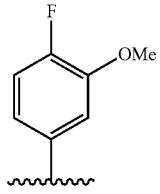 |
| IV-31 | 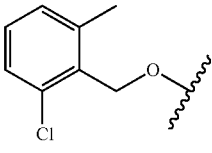 [SMILES: *OCc1c(C)cccc1Cl] | 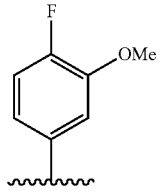 [SMILES: *c1ccc(F)c(OC)c1] |
| IV-32 | 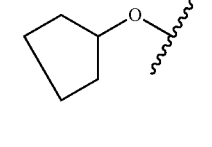 [SMILES: *OC1CCCC1] | 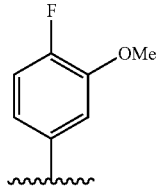 [SMILES: *c1ccc(F)c(OC)c1] |
| IV-33 | 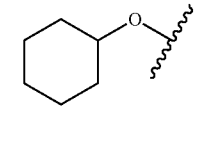 [SMILES: *OC1CCCCC1] | 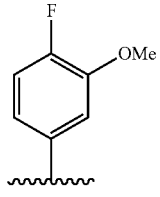 [SMILES: *c1ccc(F)c(OC)c1] |
| IV-34 | 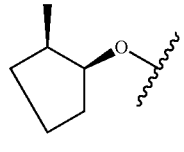 [SMILES: *O[C@H]1CCC[C@H]1C] | 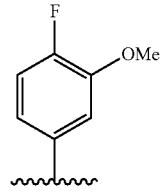 |
| IV-35 | 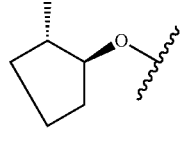 | 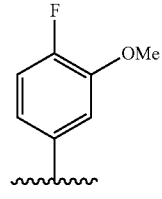 |
| IV-36 | 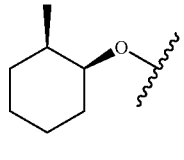 [SMILES: *O[C@H]1CCCC[C@H]1C] | 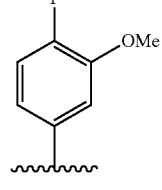 |
| IV-37 | 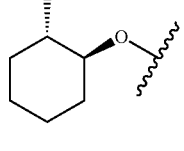 | 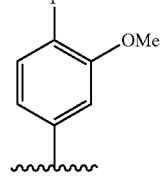 |
| IV-38 | 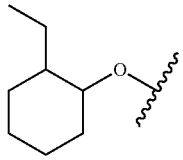 [SMILES: *OC1CCCCC1CC] | 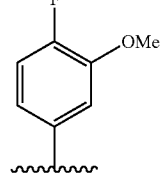 |
| IV-39 | 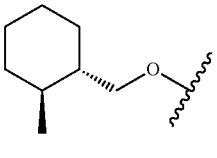 [SMILES: *OC[C@H]1CCCC[C@@H]1C] | 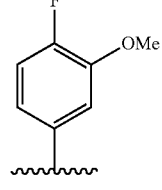 |
| IV-40 | 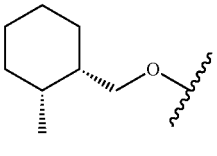 [SMILES: *OC[C@H]1CCCC[C@H]1C] | 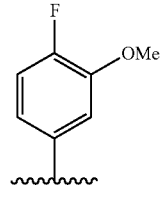 |
| IV-41 | 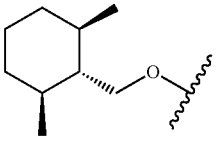 [SMILES: *OC[C@H]1[C@H](C)CCC[C@@H]1C] | 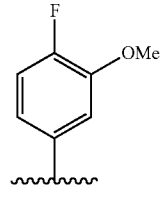 |

TABLE 4-continued

| No. | X | Z |
|---|---|---|
| IV-42 | (norbornyl-CH2-O-) | 4-F, 3-OMe phenyl |
| IV-43 | (norbornyl-CH2-O-) | 4-F, 3-OMe phenyl |
| IV-44 | (3-methylcyclopentyl-O-) | 4-F, 3-OMe phenyl |
| IV-45 | (3-isopropylcyclopentyl-O-) | 4-F, 3-OMe phenyl |
| IV-46 | (3,3-dimethylcyclopentyl-O-) | 4-F, 3-OMe phenyl |
| IV-47 | (3-methylcyclopentyl-O-) | 4-F, 3-OMe phenyl |
| IV-48 | (3-methylcyclopentyl-O-) | 4-F, 3-OMe phenyl |
| IV-49 | (2,6-dichlorobenzyl-O-) | 5-CF3-pyridin-3-yl |

TABLE 4-continued

| No. | X | Z |
|---|---|---|
| IV-50 | (2-F, 6-Cl-benzyl-NH-) | 5-CF3-pyridin-3-yl |
| IV-51 | (2,6-dichlorobenzyl-O-) | 1-methylimidazol-4-yl |
| IV-52 | (2-F, 6-Cl-benzyl-NH-) | 1-methylimidazol-4-yl |
| IV-53 | (2-F, 6-Cl-styryl-) | 5-methylpyridin-3-yl |
| IV-54 | (indan-1-yl-O-) | 5-methylpyridin-3-yl |
| IV-55 | (2-F, 6-Cl-styryl-) | 1-isopropylimidazol-4-yl |
| IV-56 | (indan-1-yl-O-) | 1-isopropylimidazol-4-yl |
| IV-57 | (2,6-dichlorobenzyl-O-) | oxazol-4-yl |
| IV-58 | (2-F, 6-Cl-benzyl-NH-) | oxazol-4-yl |

TABLE 4-continued

| No. | X | Z |
|---|---|---|
| IV-59 | 2-F, 6-Cl styryl | oxazol-4-yl |
| IV-60 | indan-1-yloxy | oxazol-4-yl |
| IV-61 | 2,6-dichlorobenzyloxy | 1-methylpyrrol-3-yl |
| IV-62 | 2-F, 6-Cl benzylamino | 1-methylpyrrol-3-yl |
| IV-63 | 2-F, 6-Cl styryl | 1-isopropylpyrrol-3-yl |
| IV-64 | indan-1-yloxy | 1-isopropylpyrrol-3-yl |
| IV-65 | 2,6-dichlorobenzyloxy | cyclohexyl |
| IV-66 | 2-F, 6-Cl benzylamino | cyclohexyl |
| IV-67 | 2-F, 6-Cl styryl | 3,5-dimethylcyclohexyl |
| IV-68 | indan-1-yloxy | 3,5-dimethylcyclohexyl |
| IV-69 | 2,6-dichlorobenzyloxy | cyclopentyl |
| IV-70 | 2-F, 6-Cl benzylamino | cyclopentyl |
| IV-71 | 2-F, 6-Cl styryl | 3,4-dimethylcyclopentyl |
| IV-72 | indan-1-yloxy | 3,4-dimethylcyclopentyl |
| IV-73 | 2-F, 6-Cl styryl | 5-CF$_3$-2-(2-hydroxyethoxy)pyridin-3-yl |
| IV-74 | 2-F, 6-Cl (α-methyl)styryl | 5-CF$_3$-2-(2-hydroxyethoxy)pyridin-3-yl |
| IV-75 | 2-ethyl-3-CF$_3$-propenyl | 5-CF$_3$-2-(2-hydroxyethoxy)pyridin-3-yl |
| IV-76 | 2,6-dichlorobenzyloxy | 3-CF$_3$-phenyl |

TABLE 4-continued

| No. | X | Z |
|---|---|---|
| IV-77 | 2-Cl, 6-F benzyl-NH- | 3-CF3 phenyl |
| IV-78 | 2-Cl, 6-F phenyl-CH=CH- | 3-CF3 phenyl |
| IV-79 | 2-Cl, 6-F phenyl-CH2CH2- | 3-CF3 phenyl |
| IV-80 | 2,6-diCl benzyl-O- | 3-F, 5-CF3 phenyl |
| IV-81 | 2-Cl, 6-F benzyl-NH- | 3-F, 5-CF3 phenyl |
| IV-82 | (CF3CH2)2C=CH- | 5-CF3, 2-(OCH2CH2OH) pyridin-3-yl |
| IV-83 | 2-Cl, 6-F phenyl-C(CH3)=CH- | 5-CF3, 4-CH3, 2-(OCH2CH2OH) pyridin-3-yl |
| IV-84 | 2-Cl, 6-F phenyl-C(CH3)=CH- | 5-CF3, 2-(OCH2CH2OH) pyridin-3-yl |
| IV-85 | (CF3)(C2H5)C=CH- | 5-CF3, 2-(OCH2CH2OH) pyridin-3-yl |
| IV-86 | 2-Cl, 6-F phenyl-C(CH3)=CH- | 5-cyclopropyl, 2-(OCH2CH2OH) pyridin-3-yl |
| IV-87 | 2-Cl, 6-F phenyl-C(CH3)=CH- | 5-CF3, 2-(NHCH2CH2OH) pyridin-3-yl |
| IV-88 | 2-Cl, 6-F phenyl-C(CH3)=CH- | 5-CF3, 2-(OCHF2) pyridin-3-yl |
| IV-89 | cyclohexylidene-CH- | 5-CF3, 2-(OCH2CH2OH) pyridin-3-yl |
| IV-90 | cyclohexylidene-CH- | 3-CF3 phenyl |
| IV-91 | 4,4-diF-cyclohexylidene-CH- | 3-CF3 phenyl |
| IV-92 | (CF3)(C2H5)C=CH- | 5-CF3, 2-(NHCH2CH2OH) pyridin-3-yl |
| IV-93 | cyclohexyl-CH2- | 5-CF3, 2-(OCH2CH2OH) pyridin-3-yl |
| IV-94 | 2-Cl, 6-F phenyl-C(CH3)=CH- | 5-CF3, 2-OCH3 pyridin-3-yl |
| IV-95 | 2-Cl, 6-F phenyl-C(CH3)=CH- | 6-(OCH2CH2OH) 2,3-dihydro-1H-cyclopenta[c]pyridin-5-yl |
| IV-96 | 3-Cl, 2-OCH3 phenyl-C(CH3)=CH- | 5-CF3, 2-(OCH2CH2OH) pyridin-3-yl |

TABLE 4-continued

| No. | X | Z |
|---|---|---|
| IV-97 | 2-F, 6-Cl phenyl propenyl | 5-CF₃, 2-(OCH₂CF₃) pyridinyl |
| IV-98 | gem-dimethylcyclopentylidene methyl | 5-CF₃, 2-(OCH₂CH₂OH) pyridinyl |
| IV-99 | gem-dimethylcyclopentylidene methyl | 3-CF₃ phenyl |
| IV-100 | gem-difluorocyclohexylidene methyl | 3-CF₃ phenyl |
| IV-101 | 3-pentenyl (diethyl) | 5-CF₃, 2-(OCH₂CH₂OH) pyridinyl |
| IV-102 | 1-methylcyclohexyl methyl | 5-CF₃, 2-(OCH₂CH₂OH) pyridinyl |

Methods for preparing compounds described in this section are illustrated in the following synthetic Schemes. The Schemes are given for the purpose of illustrating the invention, and are not intended to limit the scope or spirit of the invention. Starting materials shown in the Schemes can be obtained from commercial sources or be prepared based on procedures described in the literature.

The synthetic route illustrated in Scheme 1 is a general method for preparing substituted 1,2,3,4-tetrahydroquinoline compounds F and G. Reaction of aniline A with diethyl 2-(ethoxymethylene)malonate B followed by thermally induced cyclization with acid affords the substituted ethyl 4-oxo-1,4-dihydroquinoline-3-carboxylate C. Treatment of compound C with phosphoryl trichloride affords the ethyl 4-chloroquinoline-3-carboxylate D. Reduction with borane in pyridine or with transition metal-mediated hydrogenation affords the ethyl 1,2,3,4-tetrahydroquinoline-3-carboxylate E, which can be reacted with a sulphonyl chloride or sulfamoyl chloride to provide the substituted sulfonamide-tetrahydroquinoline F. The ester group of F can be hydrolyzed to afford the substituted 1,2,3,4-tetrahydroquinoline-3-carboxylic acid G. Compound G can be obtained in enanteriomerically enriched form by chiral separation techniques described in the literature for carboxylic acids.

The reaction procedures in Scheme 1 are contemplated to be amenable to preparing a wide variety of 3-substituted 1,2,3,4-tetrahydroquinoline compounds having different substituents at the R, X, and 3-positions. For example, numerous substituted anilines are known in the literature and/or are commercially available or readily prepared from nitroaromatic compounds. Furthermore, if a functional group on a molecule would not be amenable to a reaction condition described in Scheme 1, it is contemplated that the functional group can first be protected using standard protecting group chemistry and strategies, and then the protecting group is removed after completing the desired synthetic transformation. See, for example, Greene, T. W.; Wuts, P. G. M. *Protective Groups in Organic Synthesis*, 2$^{nd}$ ed.; Wiley: New York, 1991, for further description of protecting chemistry and strategies. For example, if X is OMe, the methyl moiety can be removed from F with boron tribromide to afford a 6- or 7-hydroxytetrahydroquinoline. The resulting compound can be subjected to either alkylation with halides or with the Mitsunobu reaction to afford a wide variety of OR groups as X. In other embodiments, the —OH may be converted to triflate and be subjected to Pd-mediated catalyzed reactions to afford a wide variety of carbon linked substituents. In certain other embodiments, the ester group in compound F can be converted to another functional group using standard functional group manipulation procedures known in the art. See, for example, "Comprehensive Organic Synthesis" (B. M. Trost & I. Fleming, eds., 1991-1992).

SCHEME 1.

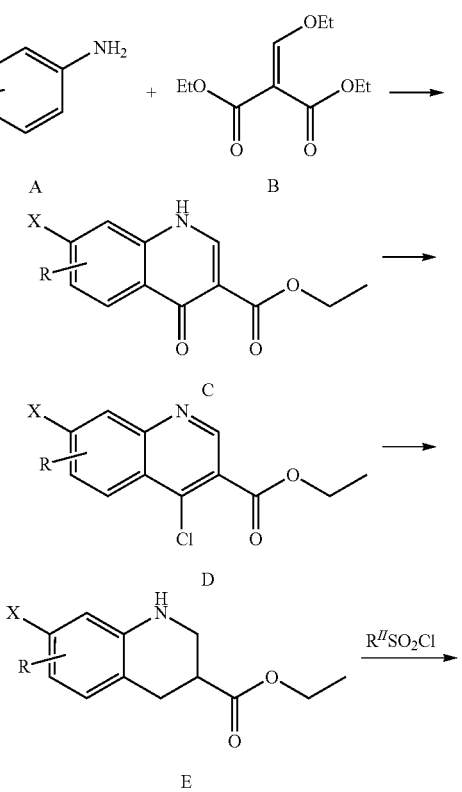

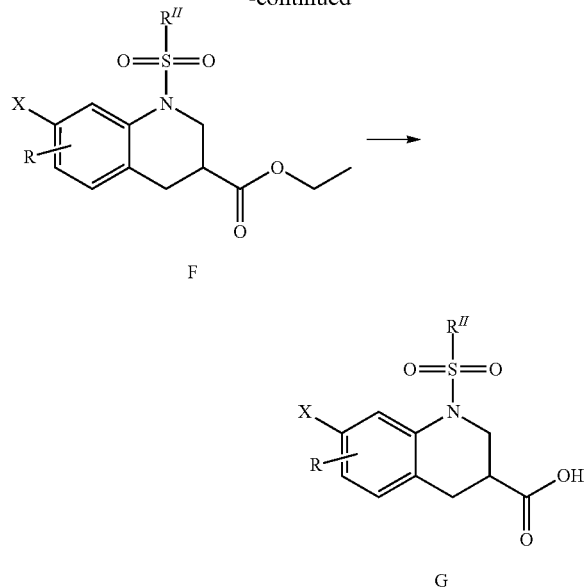

R may be, for example, hydrogen or a substituent, such as methyl or halogen; X may be for example an O-alkylene-cycloalkyl; and R″ may be an aromatic or heteroaromatic substituent.

Scheme 2 illustrates a general method for preparing substituted 1,2,3,4-tetrahydroquinoline compound F. Condensation of a substituted 2-nitrobenzaldehyde A with diethyl malonate affords α-β-unsaturated diester B. Reduction of B with sodium borohydride affords diester C. Reduction of the nitro moiety of C with either metal-mediated hydrogenation or dissolving metal reductions (for example Zn/AcOH or Fe in HCl) affords 2-oxo-1,2,3,4-tetrahydroquinoline-3-carboxylate D. Selective reduction of the 2-keto moiety of D affords ethyl 1,2,3,4-tetrahydroquinoline-3-carboxylate E. The ester group in E can be converted to additional functional groups via the methodology described above in connection with Scheme 1.

SCHEME 2.

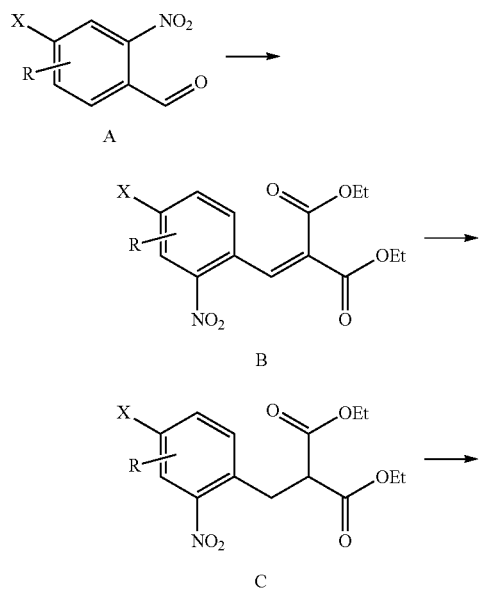

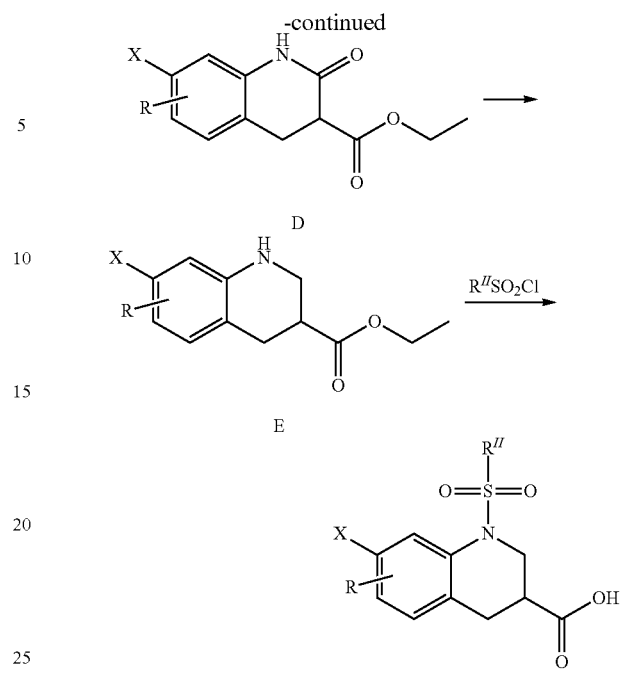

R may be, for example, hydrogen or a substituent, such as methyl or halogen; X may be for example a O-alkylene-cycloalkyl; and R″ may be an aromatic or heteroaromaticc substituent.

Scheme 3 illustrates a general method for preparing substituted (R)-2-alkyl-1-(aryl or heteroaryl sulfonyl)-1,2-dihydroquinoline-3-carboxylic acids D. A tandem Michael-aldol dehydration of a substituted N-(2-formylphenyl)(aryl or heteroaryl)sulfonamide A with a 3-substituted acrylaldehyde B catalyzed by the (S)-diphenylprolinol triethyl silyl ether (see, for example, W. Wang et al., *Org. Lett.* 9: 965-968, 2007; and A. Cordova et al., *Adv. Synth. Catal.* 349: 827-832, 2007) affords substituted (R)-2-alkyl-1-(aryl or heteroaryl sulfonyl)-1,2-dihydroquinoline-3-carbaldehyde C. Oxidation (see, for example, Y. K. Bae et al. *Synlett.* 24: 1848-1850, 2013; S. J. Williams et al. in WO2011/047432) of the aldehyde in C affords substituted (R)-2-alkyl-1-(aryl or heteroaryl sulfonyl)-1,2-dihydroquinoline-3-carboxylic acid D.

SCHEME 3.

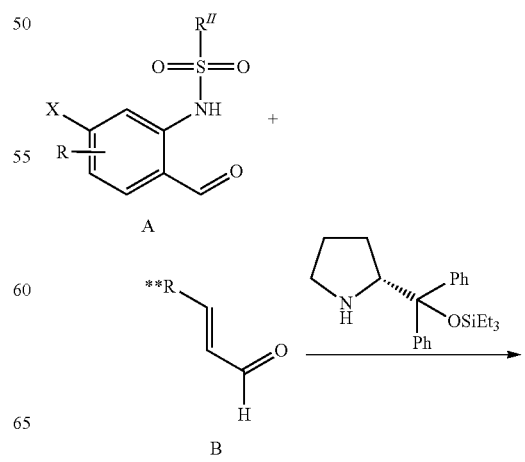

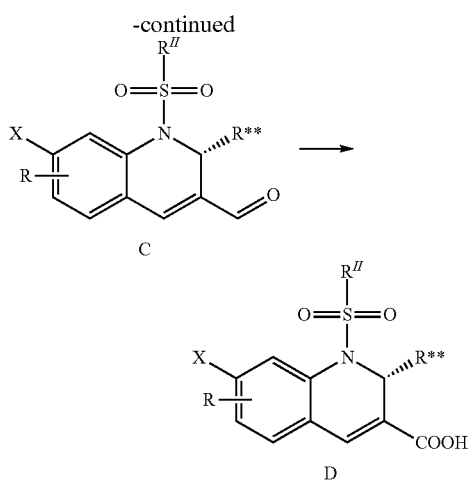

Scheme 4 illustrates a general method for preparing substituted (R)-(2-alkyl-1-(aryl or heteroaryl sulfonyl)-1,2-dihydroquinolin-3-yl)alkyl alcohol B. Reduction of the aldehyde in compound A with sodium borohydride in the presence of cerium (III) chloride (Y. Hamada et al., *Tetrahedron* 64: 11568-11579, 2008) yields compound B where R' is hydrogen. Addition of an alkyl magnesium or alkyl lithium halide in the presence of cerium (III) chloride affords the secondary alcohol B where R' is a lower alkyl (i.e., $C_{1-6}$ alkyl).

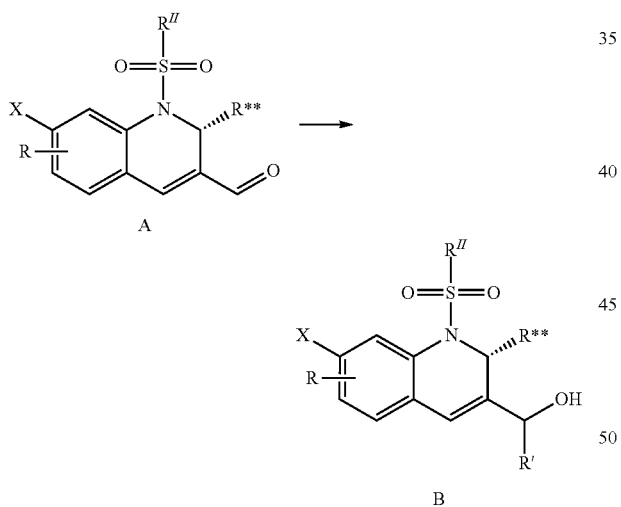

Scheme 5 illustrates a general procedure for preparing substituted (R)-3-(2-alkyl-1-(aryl or heteroaryl sulfonyl)-1,2-dihydroquinolin-3-yl)propanoic acid D. Treatment of allylic alcohol A with methane sulfonyl halide (or a tosyl halide or triflic anhydride may be used to activate the hydroxyl group, and alternatively the hydroxyl group may be converted to an allylic halide by methods known in the literature) affords compound B where the allylic hydroxyl is activated with a leaving group. When R' is the same as R'', an ester of an appropriate substituted (or unsubstituted) acetic acid is converted to an anion with an appropriate base (e.g., LDA, lithium hexamethyldisilazide, etc.) and is alkylated with B to yield compound C where variable Q is oxygen. When R' is not the same as R'', various chiral enolate chemistry methods from the literature may be used to provide a chiral acid (where variable Q may be, for example, oxygen or N(R''')). For example, the anion of an acyloxazolidinone may be utilized. Removal of the chiral auxiliary with an appropriate base (e.g., potassium carbonate, lithium hydroxide in the presence of peroxide) or an acid (for tert-butyl esters) affords (R)-3-(2-alkyl-1-(aryl or heteroaryl sulfonyl)-1,2-dihydroquinolin-3-yl)propanoic acid D.

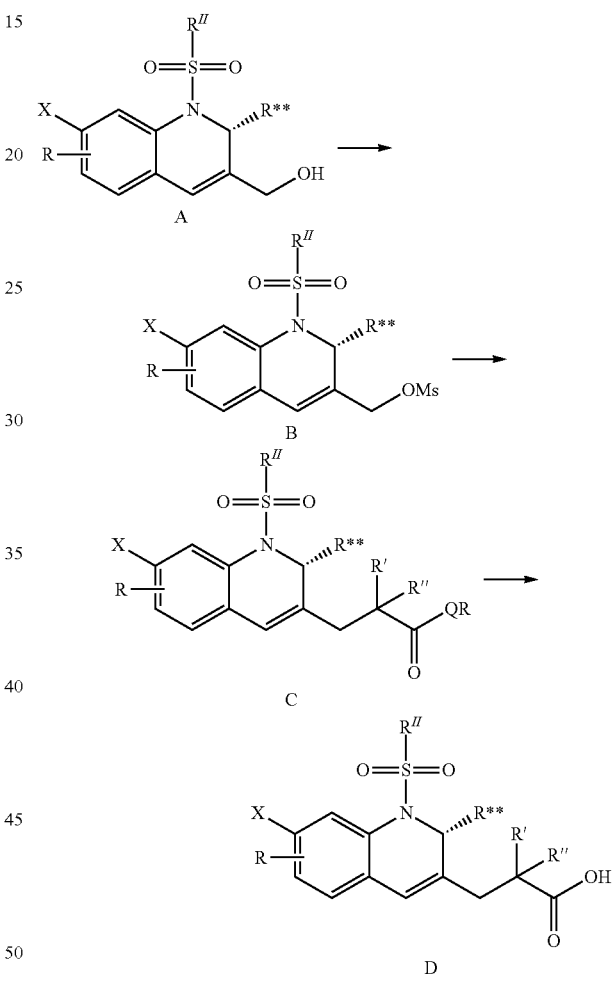

Scheme 6 illustrates a general procedure for preparing substituted (R)-(2-alkyl-1-(aryl or heteroarylsulfonyl)-1,2-dihydroquinolin-3-yl)alkylamines C and D. Mitsunobu reaction (D. L. Hughes et al. *Organic Reactions* 42: 1992) of allylic alcohol A with phthalamide affords substituted phthamide B. Treatment of compound B with hydrazine in an appropriate solvent (for example, ethanol or isopropanol; see, for example, H. Itoh et al. in *J. Org. Chem.* 43: 2320, 1978) affords (R)-(2-alkyl-1-(aryl or heteroarylsulfonyl)-1,2-dihydroquinolin-3-yl)alkylamine C. Reductive amination of the amine group in compound C (C. A. Maryanoff et al. *J. Org. Chem.* 61: 3849-3860, 1996) affords (R)-(2-alkyl-1-(aryl or heteroarylsulfonyl)-1,2-dihydroquinolin-3-yl)alkylamine D.

SCHEME 6.

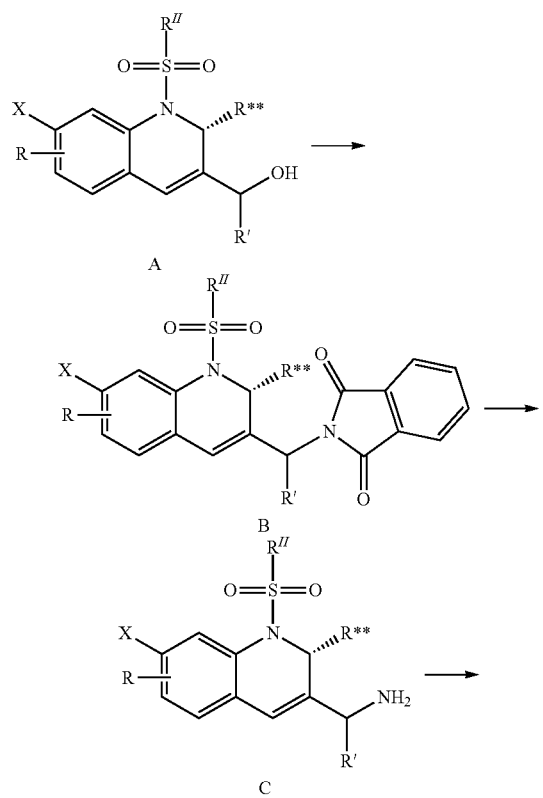

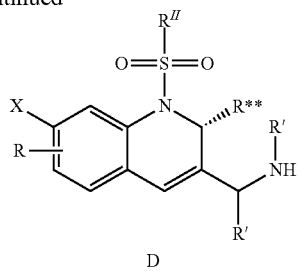

Scheme 7 illustrates a general procedure for preparing substituted (R)—N-((2-alkyl-1-(aryl or heteroarylsulfonyl)-1,2-dihydroquinolin-3-yl)alkyl)amide B, substituted (R)—N-((2-alkyl-1-(aryl or heteroarylsulfonyl)-1,2-dihydroquinolin-3-yl)alkyl)carbamate C, substituted (R)—N-((2-alkyl-1-(aryl or heteroarylsulfonyl)-1,2-dihydroquinolin-3-yl)alkyl)ureas or substituted (R)—N-((2-alkyl-1-(aryl or heteroarylsulfonyl)-1,2-dihydroquinolin-3-yl)alkyl)thiourea D, substituted (R)—N-((2-alkyl-1-(aryl or heteroarylsulfonyl)-1,2-dihydroquinolin-3-yl)alkyl)sulfonamide E, and substituted (R)—N-((2-alkyl-1-(aryl or heteroarylsulfonyl)-1,2-dihydroquinolin-3-yl)alkyl)sulfamide F. Reaction of substituted (R)-(2-alkyl-1-(aryl or heteroarylsulfonyl)-1,2-dihydroquinolin-3-yl)alkylamine A with an appropriate base and an acyl halide affords amide B. Alternatively, a coupling agent (e.g., a carbodiimide, PyBOP, treatment of the acid with a chloroformate to make a mixed anhydride, etc.) may be utilized to couple a wide variety of acids to form amide B. The amine A may also be coupled with a choroformate to afford compound C; with an isocyanate, carbamoyl choride, or isothiocyanate to afford D; with a sulfonyl halide to afford E; or with a sulfamoyl halide to afford F.

SCHEME 7.

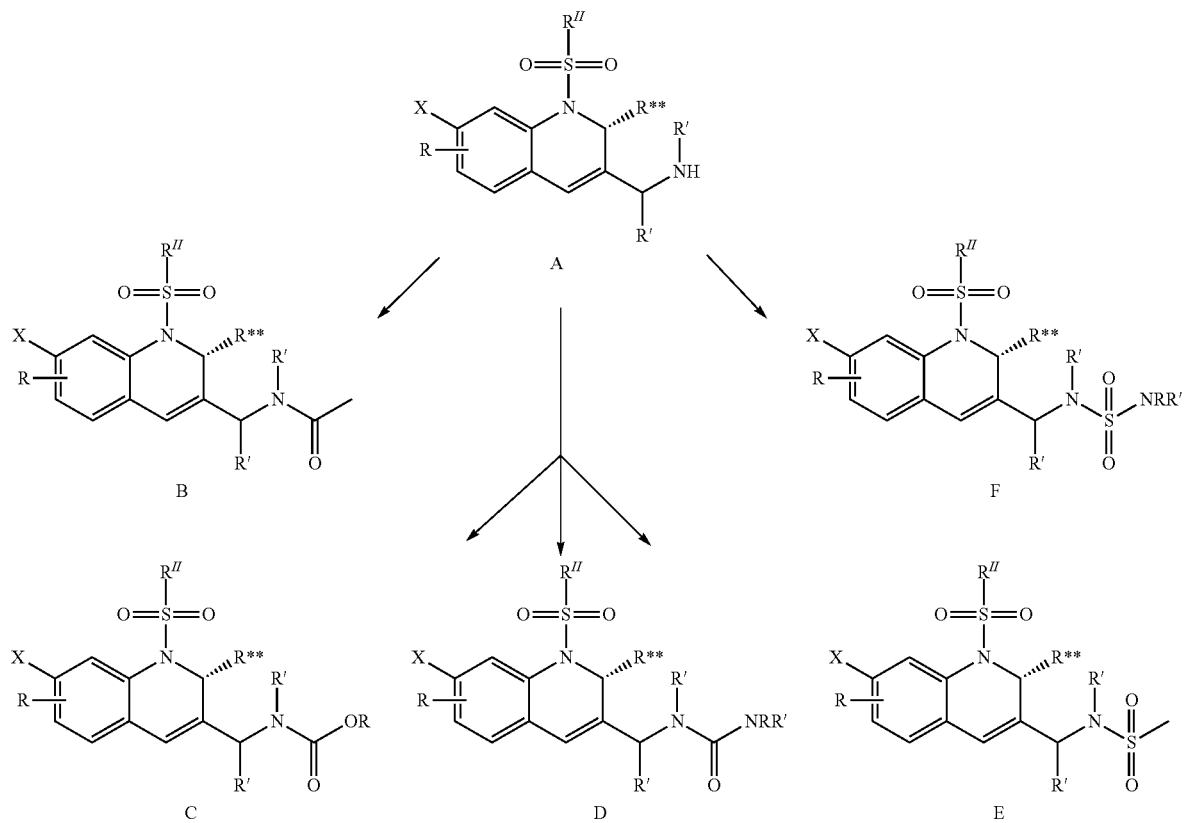

Scheme 8 illustrates a general method of preparing substituted cis-(2R,3)-3-substituted-2-alkyl-1-(aryl or heteroarylsulfonyl)-1,2,3,4-tetrahydroquinoline B. Hydrogenation of the substituted (R)-2-alkyl-1-(aryl or heteroarylsulfonyl)-1,2-dihydroquinoline A prepared via the above methods in the presence of a catalyst affords the substituted cis-(2R,3)-3-substituted-2-alkyl-1-(aryl or heteroarylsulfonyl)-1,2,3,4-tetrahydroquinoline B. The choice of the catalyst depends on the substituents X and R. In cases where dehalogenation or reductive removal of benzylic heteroatom is not an issue, Pd or Pt on C may be utilized. In other cases Rh and/or a heterogeneous catalyst which does not reduce these functionalities is more appropriate as is known to those skilled in the art.

SCHEME 8.

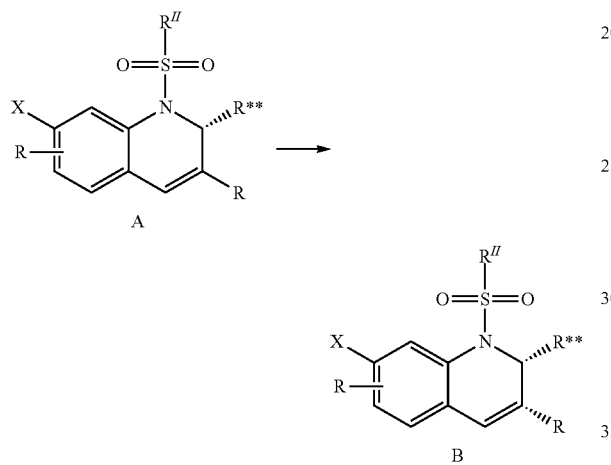

Scheme 9 is an alternative general method to prepare substituted 3-substituted-1-(aryl or heteroarylsulfonyl)-1,2,3,4-tetrahydroquinoline E. A tandem reaction combining radical and ionic cyclization of an halogenated aniline A and a substituted acrylate B affords substituted 3,4-dihydroquinolin-2-one C (N. Jiao et al. *Tetrahedron* 65: 1982-1987, 2009). Reduction of the amide group in C with a hydride (e.g., a borane or lithium aluminum hydride) affords substituted 1,2,3,4-tetrahydroquinoline D. Sulfonylation of D with a sulfonyl halide yields the substituted 3-substituted-1-(aryl or heteroarylsulfonyl)-1,2,3,4-tetrahydroquinoline E.

SCHEME 9.

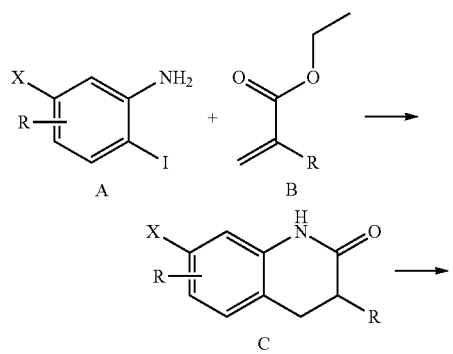

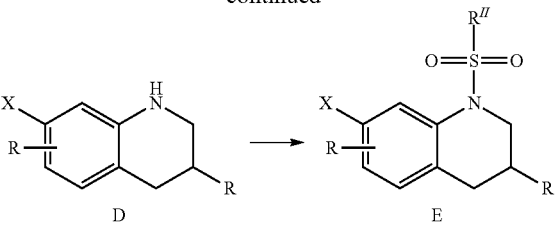

Scheme 10 illustrates an alternative general method to prepare chiral substituted 3-substituted-1-(aryl or heteroarylsulfonyl)-1,2,3,4-tetrahydroquinolines. Alkylation of an acylated oxazolidinedione B with a 2-nitrobenzylic halide A affords with high diastereomeric excess the 3-arylpropionamide C. Reduction of C with dissolving metal conditions affords chiral substituted 3,4-dihydroquinolin-2-one D which can be elaborated to the substituted 3-substituted-1-(aryl or heteroarylsulfonyl)-1,2,3,4-tetrahydroquinolines E and F based on procedures described above.

SCHEME 10.

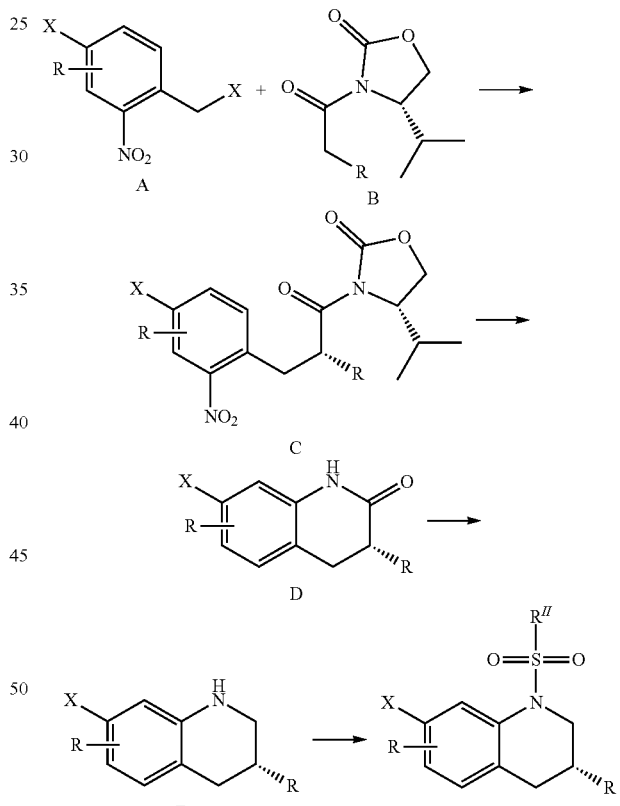

Scheme 11 illustrates an alternative general method of preparing substituted cis-2,3-disubstituted-1-(aryl or heteroarylsulfonyl)-1,2,3,4-tetrahydroquinoline E. Alkylation of β-ketoester B with 2-nitrobenzylic halide A affords substituted 2-(2-nitrobenzyl)-β-ketoester C. Reduction of C affords substituted ethyl cis-2-alkyl-1,2,3,4-tetrahydroquinoline-3-carboxylate D (R. A. Bunce et al. *J. Heterocyclic Chem.* 44: 1059-1064, 2007). This material can be sulfonylated as described above to afford the substituted cis-2,3-disubstituted-1-(aryl or heteroarylsulfonyl)-1,2,3,4-tetrahydroquinoline E.

SCHEME 11.

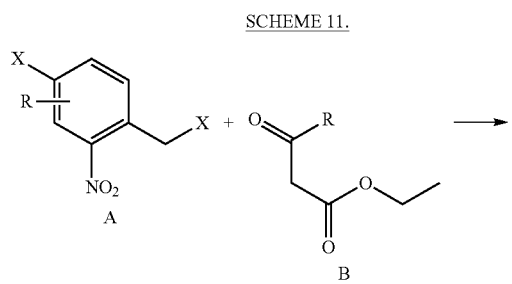

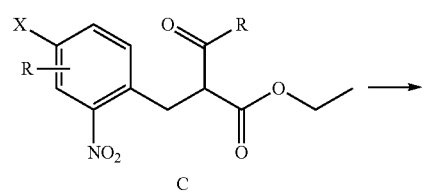

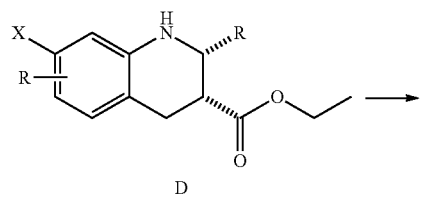

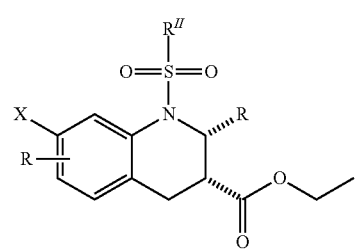

SCHEME 12.

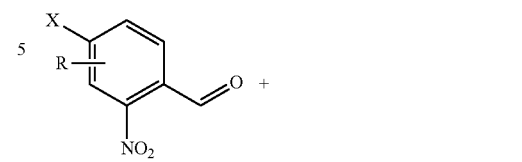

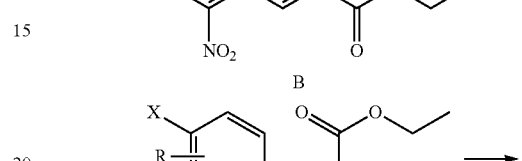

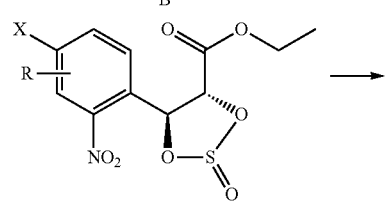

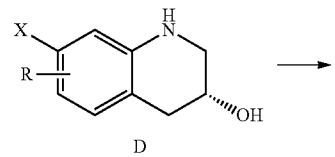

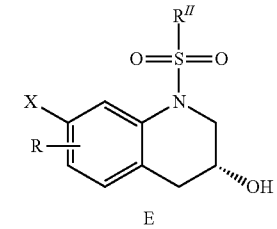

Scheme 12 illustrates a general method of preparing chiral substituted 1-(aryl or hetereoarylsulfonyl)-1,2,3,4-tetrahydroquinoline E substituted at the 3-position with an oxygen bearing group. Wittig reaction of 2-nitroaldehyde A forms α,β-unsaturated ester B, which is subjected to Os-catalyzed asymmetric dihydroxylation with the (DHQ)₂-PHAL ligand (see, for example, K. B. Sharpless et al. *Chem. Rev.* 94: 2483-2547, 1994) followed by treatment of the diol with thionyl chloride to form cyclic sulfite C (see, for example, K. B. Sharpless et al. *J. Am. Chem. Soc.* 110: 7538-7539, 1988). Sulfite C undergoes a one-pot cobalt chloride catalyzed reductive cyclization with sodium borohydride (see, for example, A. Sudalai et al. *Organic Letters* 11: 803-806, 2009) to form the substituted chiral 3-hydroxy-1,2,3,4-tetrahydroquinoline D. This material is sulfonylated as described above to afford chiral substituted 1-(aryl or hetereoarylsulfonyl)-3-hydroxy-1,2,3,4-tetrahydroquinoline E. The pendant hydroxyl may be alkylated (for example with 2-chloroacetic acid). When using a different, suitable ligand in the chiral osmylation, the enantiomers of C and then D and E can be produced. The hydroxyl group in E can be mesylated and displaced with azide, and the resulting azido product reduced to afford access to a wide variety of chiral 3-aminosubsituted-1,2,3,4-tetrahydroquinolines.

Scheme 13 illustrates a general method of forming substituted (E)-7-(2-aryl-alken-1-en-1-yl)-1-(aryl or heteroarylsulfonyl)-1,2,3,4-tetrahydroquinolines, substituted (E)-6-(2-aryl-alken-1-en-1-yl)-4-(aryl or heteroarylsulfonyl)-3,4-dihydro-2H-benzo[b][1,4]oxazines, and substituted (E)-N-alkyl-N-(3-(2-aryl-alken-1-en-1-yl)phenyl)(arene or heteroarene)sulfonamides. Copper(I)-catalyzed carboboration (R. Alfaro et al. *J. Am. Chem. Soc.* 134: 15165-15168, 2012) of an aryl-alkyne affords tri- and tetrasubstituted vinylboronates that are suitable for Pd-mediated stereoselective addition to the appropriate 7-halo or triflate-1,2,3,4-tetrahydroquinoline (variable A is CRR'), or 6-halo or triflate-3,4-dihydro-2H-benzo[b][1,4]oxazine (variable A is O) to afford the final product.

SCHEME 13.

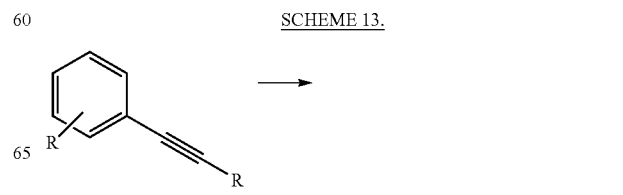

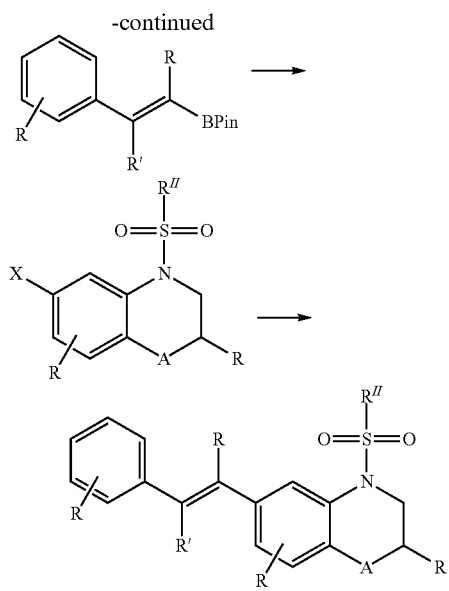

Scheme 14 illustrates a general method of forming chiral substituted 7-cyclopropyl-1-(aryl or heteroarylsulfonyl)-1,2,3,4-tetrahydroquinolines, 6-cyclopropyl-4-(aryl or heteroarylsulfonyl)-3,4-dihydro-2H-benzo[b][1,4]oxazines, or N-(3-cyclopropylphenyl)-N-alkyl(aryl or heteroaryl)sulfonamides C. Chiral cyclopropylboronic acids (M.-Z. Deng et al. *Angew. Chem. Ed.* 37: 2845-2847, 1998) A are added to the appropriate haloarenes or triflates B to afford compound C.

SCHEME 14.

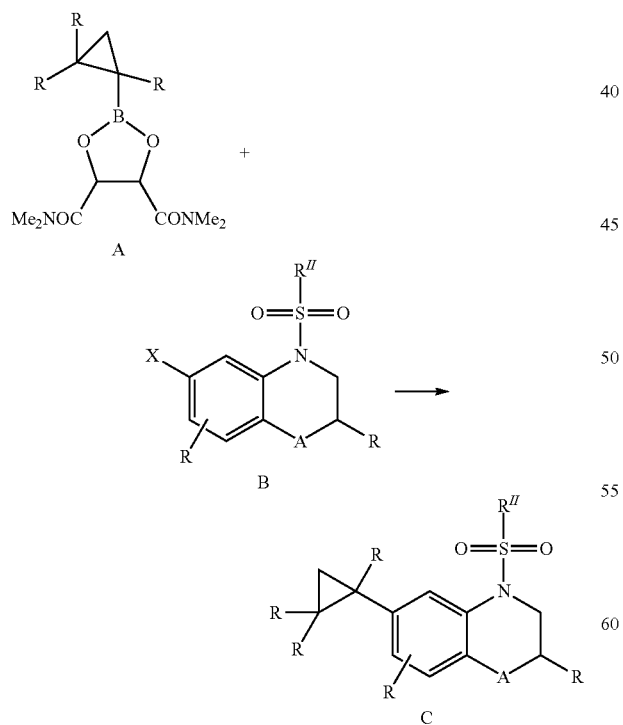

Scheme 15 illustrates a general method of forming chiral 3-substituted-1-(aryl or heteroarylsulfonyl)-1,2,3,4-tetrahydroquinolines (A is CRR') or chiral substituted benzoxazines (A is O). Esterification of the carboxylic acid A with a chiral allylic alcohol forms allylic ester B. Treatment of the enolate of ester B with TMSCl, followed by a Claisen rearrangement (see, for example, J. Kallmerten et al. *J. Org. Chem.* 52: 3889-3901, 1987) affords carboxylic acid C. Esterification of carboxylic acid C with an alcohol followed by a dissolving metal reduction affords lactam D. Reduction of lactam D with borane or lithium aluminum hydride affords tetrahydroquinoline or benzoxazine E, which is sulfonylated to afford the chiral 3-substituted-1-(aryl or heteroarylsulfonyl)-1,2,3,4-tetrahydroquinoline (A is CRR') or chiral substituted benzoxazine (A is O) F. The alkene of F, may be converted to other functional groups (for example to a COOH by oxidation).

Scheme 15.

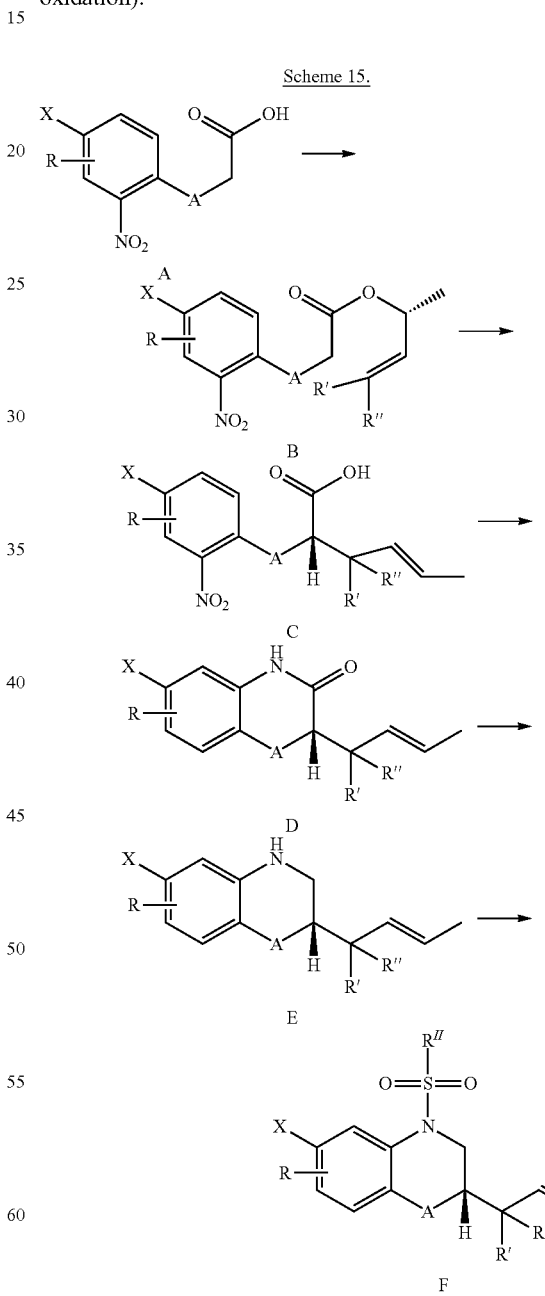

Scheme 16 is a general method for preparing various substituted benzoxazine compounds. Reaction of aryl sulfonamide A with an epoxide provides benzoxazine B.

SCHEME 16.

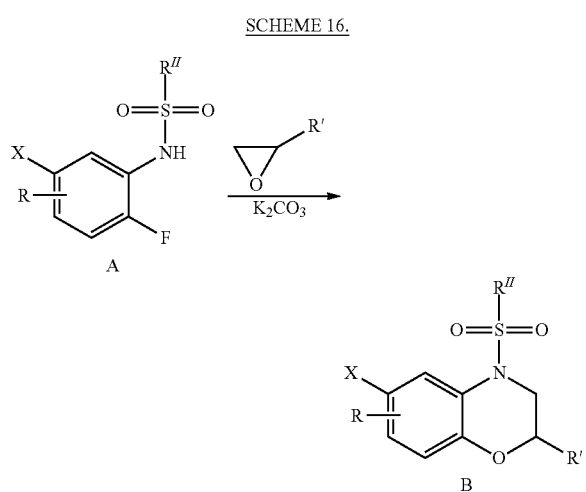

Scheme 17 is another general method for preparing various substituted benzoxazine compounds. Reaction of a 2-fluoro-nitrobenzene A with a 2-hydroxyester B provides 2-O-arylacetic acid ester C. Reduction of the nitro moiety in C with a dissolving metal in an acid forms benzoxazinone D. The amide group in benzoxazinone D can be reduced using, for example, lithium aluminum hydride (LiAlH$_4$) or a borane to provide benzoxazine E, which is treated with a sulfonyl halide and base to afford sulfonylated benzoxazine F.

SCHEME 17.

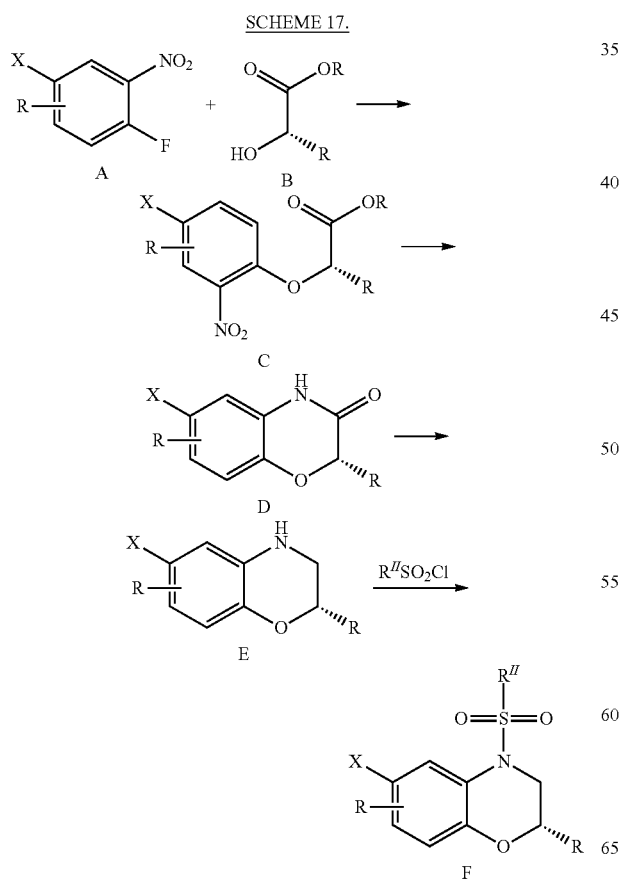

Scheme 18 is a general method for preparing various substituted benzoxazine compounds. Mitsunobu addition of sulfonamide A to chiral α-hydroxyester B affords O-aryl ether C. Treatment of compound C with DIBAL affords aldehyde D, to which vinyl magnesium bromide adds to form the anti-aminoalcohol E (see, for example, D. Gryko et al. *Tetrahedron: Asymmetry* 8: 4059-4067, 1997). Treatment of compound E with base affords benzoxazine F. The vinyl moiety in F is then converted to other alkenes via olefin metathesis chemistry which can be reduced to substituted alkanes, or oxidized to a hydroxyl group, a diol, a carboxylic acid, or other functional group.

SCHEME 18.

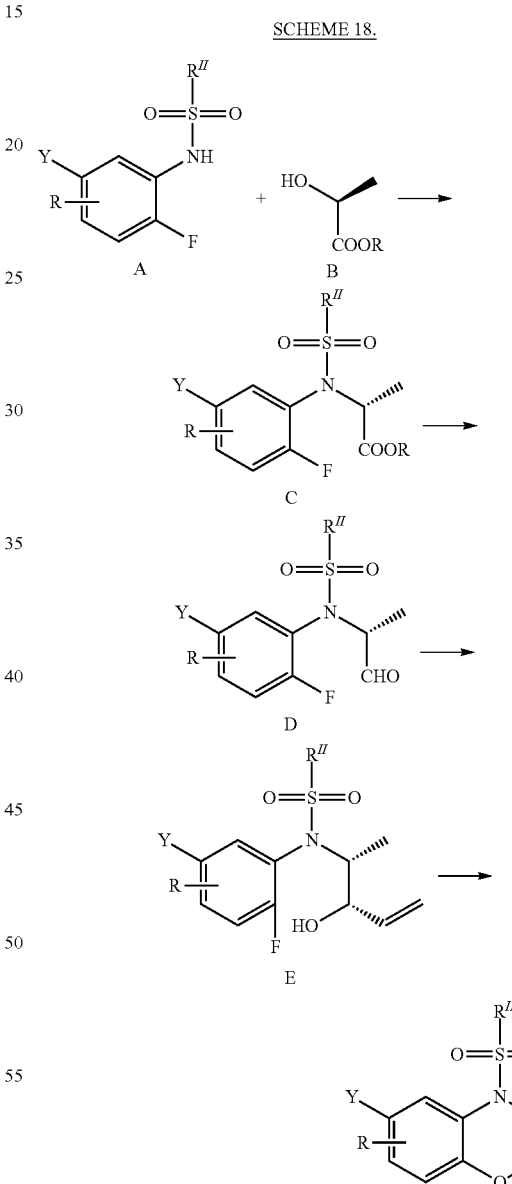

Scheme 19 is a general method for preparing various thioether substituted compounds. Palladium-mediated addition of a thiol A in presence of a base (such as Hunig's base) and a ligand (such as Xantphos) to the bromide B affords thioether C.

SCHEME 19.

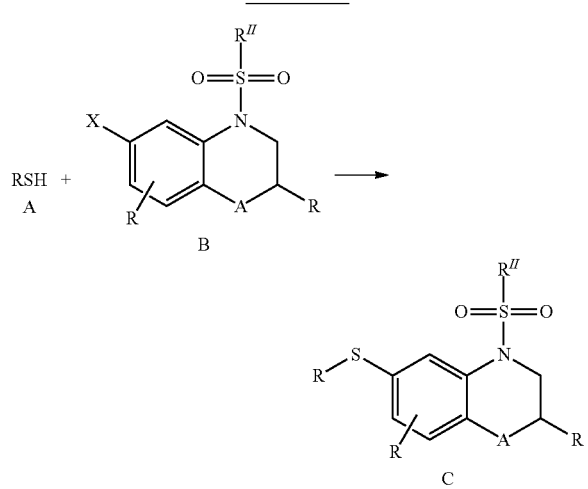

Heteroaryl-Amide RORγ Agonists

In certain embodiments, the RORγ agonist is one of the following or a pharmaceutically acceptable salt thereof:

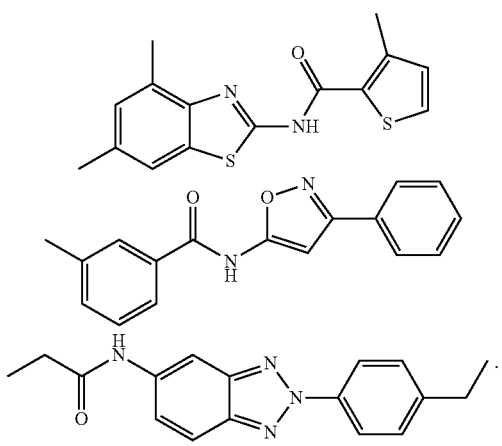

These heteroaryl-amide RORγ agonists are described in, for example, Zhang et al. in *Mol. Pharmacol.* (2012) vol. 82, pages 583-590.

Aryl-Amide RORγ Agonists

In certain embodiments, the RORγ agonist is the following compound or a pharmaceutically acceptable salt thereof:

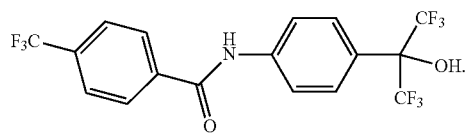

The above aryl-amide RORγ agonist is described in, for example, Wang et al. in *ACS Chem. Biol.* (2010), vol. 5, pages 1029-1034.

Aryl-Sulfone RORγ Agonists

In certain embodiments, the RORγ agonist is the following compound or a pharmaceutically acceptable salt thereof:

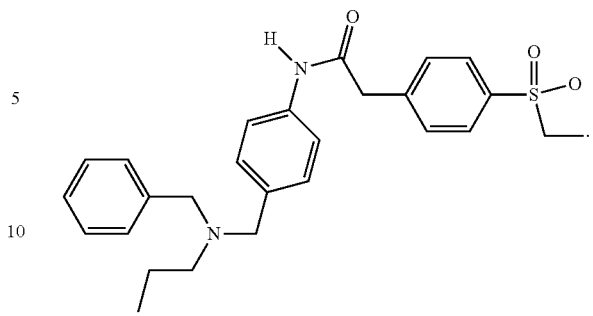

The above aryl-amide RORγ agonist is described in, for example, Yang et al. in *ACS Med. Chem. Lett.* (2014) vol 5, pages 65-68.

Polypeptide Agonist of RORγ

Exemplary polypeptides that are agonists of RORγ include, for example, NCOA1 (SRC1), NCOA2 (GRIP1), and NCOA3 (AIB1) each of which are described by Xie et al. in *Crit. Rev. Immunol.* (2006) vol. 26(6), pages 475-486; PPARGC1A (PGC1A) described by Liu et al. in *Nature* (2007) vol. 447(7143), pages 477-481; and CBP described by Jin et al. in *Mol. Endocrino* (2010) vol. 24(5), pages 923-929; each of which is hereby incorporated by reference.

Additional Features of RORγ Agonists

The RORγ agonist may be characterized according to its ability to increase activity of the retinoic acid receptor-related orphan receptor gamma. In certain embodiments, the RORγ agonist has an $EC_{50}$ of less than 10 mM, 1 mM, 100 µM, 10 µM, 1 µM, 100 nM, 10 nM, or 1 nM towards retinoic acid receptor-related orphan receptor gamma Procedures for testing the ability of a compound to increase activity of the retinoic acid receptor-related orphan receptor gamma are described in, for example, WO 2013/169864.

Because two isoforms of RORγ have been identified and are referred to as γ1 and γ2 (also referred to as RORγ t), the RORγ agonist may be characterized according to whether it has agonist activity at isoform γ1, isoform γ2, or both. In certain embodiments, the RORγ agonist is an agonist of at least RORγ t.

VIII. General Features of Therapeutic Methods Involving In Vivo Therapeutic Enhancement of Lymphocyte Cells and/or Dendritic Cells Another aspect of the invention relates to therapeutic methods in which an RORγ agonist is administered to a patient in an amount sufficient to elicit a therapeutic benefit from a population of cells in the patient, such as lymphocyte cells and/or dendritic cells. Without being bound by a particular theory, the RORγ agonist contacts lymphocyte cells and/or dendritic cells in the patient and increases the therapeutic benefit of the population of lymphocyte cells and/or dendritic cells, wherein the RORγ agonist contacted lymphocyte cells and/or dendritic cells treat the medical disorder. The lymphocyte cells in the patient preferably have a receptor specific for the medical disorder to be treated. Similarly, the dendritic cells in the patient preferably have a receptor specific for the medical disorder to be treated. General features of this therapeutic approach are described below.

First Exemplary Method of Treatment

One aspect of the invention provides a method of treating a medical disorder. The method comprises administering to a patient, in need thereof having a population of lymphocyte cells featuring a receptor specific for the medical disorder, an agonist of RORγ in an amount sufficient to elicit a therapeutic benefit from said population of lymphocyte cells to thereby treat the disorder. In certain embodiments, the method further comprises administering to the patient an antigen specific for the medical disorder (preferably prior to administering said agonist of RORγ).

The medical disorder may be a medical disorder described in Section VI herein. In certain embodiments, the medical disorder is a cancer, bacterial infection, fungal infection, or immune disorder. In certain other embodiments, the medical disorder is a cancer selected from the group consisting of solid tumor, lymphoma, and leukemia. In yet other embodiments, the medical disorder is a cancer selected from the group consisting of ovarian cancer, melanoma, colorectal cancer, lung cancer, breast cancer, prostate cancer, pancreatic cancer, renal cell carcinoma, leukemia, a B-cell lymphoma, and non-Hodgkin lymphoma.

The therapeutic methods are contemplated to provide medical benefits to human patients, such as adult human patients and pediatric human patients. The therapeutic methods are also contemplated to provide medical benefits to animal patients, such as veterinary animals.

The agonist of RORγ may be an agonist of RORγ described in Section VII herein. In certain embodiments, the agonist of RORγ is a small organic molecule. In certain other embodiments, the agonist of RORγ is a compound of Formula I described herein.

Second Exemplary Method of Treatment

Another aspect of the invention provides a method of treating a medical disorder, where the method comprises administering to a patient in need thereof an agonist of RORγ in an amount sufficient to increase a therapeutic benefit of a population of lymphocyte cells in the patient to thereby treat the disorder, wherein the patient has been administered a lymphocyte cell or will be administered a lymphocyte cell during the time period over which said agonist of RORγ exerts physiological activity.

The medical disorder may be a medical disorder described in Section VI herein. In certain embodiments, the medical disorder is a cancer, bacterial infection, fungal infection, or immune disorder. In certain other embodiments, the medical disorder is a cancer selected from the group consisting of solid tumor, lymphoma, and leukemia. In yet other embodiments, the medical disorder is a cancer selected from the group consisting of ovarian cancer, melanoma, colorectal cancer, lung cancer, breast cancer, prostate cancer, pancreatic cancer, renal cell carcinoma, leukemia, a B-cell lymphoma, and non-Hodgkin lymphoma.

The therapeutic methods are contemplated to provide medical benefits to human patients, such as adult human patients and pediatric human patients. The therapeutic methods are also contemplated to provide medical benefits to animal patients, such as veterinary animals.

The agonist of RORγ may be an agonist of RORγ described in Section VII herein. In certain embodiments, the agonist of RORγ is a small organic molecule. In certain other embodiments, the agonist of RORγ is a compound of Formula I described herein.

Third Exemplary Method of Treatment

One aspect of the invention provides a method of treating a medical disorder. The method comprises administering to a patient, in need thereof having a population of dendritic cells featuring a receptor specific for the medical disorder, and an agonist of RORγ in an amount sufficient to elicit a therapeutic benefit from said population of dendritic cells to thereby treat the disorder. In certain embodiments, the method further comprises administering to the patient an antigen specific for the medical disorder (preferably prior to administering said agonist of RORγ).

Fourth Exemplary Method of Treatment

Another aspect of the invention provides a method of treating a medical disorder, where the method comprises administering to a patient in need thereof an agonist of RORγ in an amount sufficient to increase a therapeutic benefit of a population of dendritic cells in the patient to thereby treat the disorder, wherein the patient has been administered a dendritic cell or will be administered a dendritic cell during the time period over which said agonist of RORγ exerts physiological activity.

IX. Combination Therapy

Another aspect of the invention provides for combination therapy. The RORγ agonist treated cells (e.g., lymphocyte cells and/or dendritic cells) and/or RORγ agonists can be used in combination with additional therapeutic agents to treat medical disorders, such as a cancer, bacterial infection, fungal infection, or immune disorder.

Exemplary therapeutic agents that may be used as part of a combination therapy in treating cancer, include, for example, mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustine, thymalfasin, sobuzoxane, nedaplatin, cytarabine, bicalutamide, vinorelbine, vesnarinone, aminoglutethimide, amsacrine, proglumide, elliptinium acetate, ketanserin, doxifluridine, etretinate, isotretinoin, streptozocin, nimustine, vindesine, flutamide, drogenil, butocin, carmofur, razoxane, sizofilan, carboplatin, mitolactol, tegafur, ifosfamide, prednimustine, picibanil, levamisole, teniposide, improsulfan, enocitabine, lisuride, oxymetholone, tamoxifen, progesterone, mepitiostane, epitiostanol, formestane, interferon-alpha, interferon-2 alpha, interferon-beta, interferon-gamma, colony stimulating factor-1, colony stimulating factor-2, denileukin diftitox, interleukin-2, and leutinizing hormone releasing factor.

An additional class of agents that may be used as part of a combination therapy in treating cancer is immune checkpoint inhibitors (also referred to as immune checkpoint blockers) Immune checkpoint inhibitors are a class of therapeutic agents that have the effect of blocking immune checkpoints. See, for example, Pardoll in *Nature Reviews Cancer* (2012) vol. 12, pages 252-264. Exemplary immune checkpoint inhibitors include agents that inhibit one or more of (i) cytotoxic T-lymphocyte-associated antigen 4 (CTLA4), (ii) programmed cell death protein 1 (PD1), (iii) PDL1, (iv) LAB3, (v) B7-H3, (vi) B7-H4, and (vii) TIM3. The CTLA4 inhibitor Ipilumumab has been approved by the United States Food and Drug Administration for treating melanoma.

Yet other agents that may be used as part of a combination therapy in treating cancer are monoclonal antibody agents that target non-checkpoint targets (e.g., herceptin) and non-cytoxic agents (e.g., tyrosine-kinase inhibitors).

In yet other embodiments, the second therapeutic agent used in the combination therapy is an antibody-drug-conjugate.

When performing therapy by administering lymphocyte cells (e.g., RORγ agonist treated lymphocyte cells) to a patient, there can be benefits to administering to the patient a lymphodepleting agent prior to administering the lymphocyte cells. Exemplary lymphodepleting agents include, for example, cyclophosphamide, fludarabine, cladribine, and denileukin diftitox. Further description of combination therapy using lymphocyte cells and a lymphodepleting agent can be found in, for example, U.S. Pat. No. 7,993,638, which is hereby incorporated by reference.

When performing therapy by administering lymphocyte cells (e.g., RORγ agonist treated lymphocyte cells) to a patient, there can be benefits to administering to the patient a cytokine. Exemplary cytokines include, for example, IL-1β, IL-2, IL-6, IL-7, IL-10, IL-12, IL-15, IL-18, IL-21, IL-23, or transforming growth factor beta. There can also be benefits to administering to the patient an agent that modulates the immune system, such as agent that reduces the amount of regulatory T cells in the patient (e.g., sunitinib or imatinib).

Exemplary therapeutic agents that may be used as part of a combination therapy in treating a bacterial infection, include, for example, amoxicillin, azithromycin, cefazolin, ceftriaxone, cefuroxime, cephalexin, ciprofloxacin, clindamycin, doxycycline, levofloxacin, linezolid, metronidazole, moxifloxacin, and penicillin.

Exemplary therapeutic agents that may be used as part of a combination therapy in treating a fungal infection, include, for example, 2-phenylphenol; 8-hydroxyquinoline sulphate; acibenzolar-S-methyl; aldimorph; amidoflumet; ampropylfos; ampropylfos-potassium; andoprim; anilazine; azaconazole; azoxystrobin; benalaxyl; benodanil; benomyl; benthiavalicarb-isopropyl; benzamacril; benzamacril-isobutyl; bilanafos; binapacryl; biphenyl; bitertanol; blasticidin-S; bromuconazole; butylamine; calcium polysulphide; capsimycin; captafol; captan; carbendazim; carboxin; carpropamid; carvone; chinomethionat; chlobenthiazone; chlorfenazole; chloroneb; chlorothalonil; chlozolinate; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulphamide, hexaconazole; hymexazole; imazalil; imibenconazole; iminoctadine triacetate; iminoctadine tris (albesil); iodocarb; ipconazole; iprobenfos; iprodione; iprovalicarb; irumamycin; isoprothiolane; isovaledione; kasugamycin; kresoxim-methyl; oxyfenthiin; paclobutrazole; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolenitrine; tetraconazole; thiabendazole; thicyofen; thifluzamide; thiophanate-methyl; thiram; tioxymid; tricyclazole; tridemorph; trifloxystrobin; triflumizole; triforine; triticonazole; uniconazole; validamycin A; vinclozolin; zineb; ziram; and zoxamide.

The amount of RORγ agonist treated lymphocyte cells, RORγ agonist treated dendritic cells, and/or RORγ agonist and additional therapeutic agent and the relative timing of administration may be selected in order to achieve a desired combined therapeutic effect. For example, when administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like The doses and dosage regimen of the active ingredients used in the combination therapy may be determined by an attending clinician. In certain embodiments, the RORγ agonist treated lymphocyte cells and/or RORγ agonist and the additional therapeutic agent(s) are administered in doses commonly employed when such agents are used as monotherapy for treating the disorder.

In certain embodiments, the RORγ agonist treated lymphocyte cells and/or RORγ agonist and the additional therapeutic agent(s) may act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

X. Pharmaceutical Compositions and Dosing Considerations

As indicated above, the invention provides pharmaceutical compositions, which comprise a therapeutic agent and a pharmaceutically acceptable carrier. The therapeutic agent may be a cell (e.g., a population of cells, particularly a population of lymphocyte cells that have been exposed to a RORγ agonist) and/or a RORγ agonist. Depending on the identity of the therapeutic agent and the desired route of administration, the pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient. The selected dosage level will depend upon a variety of factors including the activity of the therapeutic agent, the route of administration, the time of administration, the rate of excretion or metabolism of the particular therapeutic agent, the rate and extent of absorption, the duration of the treatment, other drugs, compounds and/or materials used in combination with the particular compound employed, the age, sex, weight, condition, general health and prior medical history of the patient being treated, and like factors well known in the medical arts. A physician or veterinarian having ordinary skill in the art can readily determine and prescribe the effective amount of the therapeutic agent required. For example, the physician or veterinarian could start doses of the therapeutic agent at levels lower than that required in order to achieve the desired therapeutic effect and gradually increase the dosage until the desired effect is achieved.

In general, a suitable daily dose of a therapeutic agent will be that amount of the agent which is the lowest dose effective to produce a therapeutic effect. Such an effective dose will generally depend upon the factors described above. Preferably, compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent, the effective amount may be less than when the agent is used alone.

If desired, the effective daily dose of the active agent may be administered as two, three, four, five, six or more sub-doses administered separately at appropriate intervals throughout the day, optionally, in unit dosage forms. Preferred dosing is one administration per day.

XI. Definitions

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name, and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "fluoroalkyl," "—O-alkyl," etc.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and include bicycloalkyls such as where two saturated carbocyclic rings are fused together. In certain embodiments, the cycloalkyls have about 5, 6 or 7 carbons in the ring structure. Exemplary alkyl groups include methyl, ethyl, n-propyl, isopropyl, n-butyl, sec-butyl, isobutyl, tert-butyl, cyclopropyl, and cyclobutyl.

The term "alkylene" refers to a diradical of an alkyl group. Exemplary alkylene groups include —$CH_2CH_2$—,

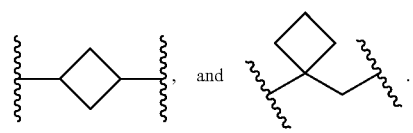

The term "cycloalkylene" refers to a diradical of a cycloalkyl group. Exemplary cycloalkylene groups include

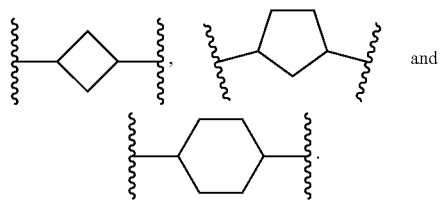

The term "haloalkyl" refers to an alkyl group that is substituted with at least one halogen. Exemplary haloalkyl groups include —$CH_2F$, —$CHF_2$, —$CF_3$, —$CH_2CF_3$, —$CF_2CF_3$, and the like.

The term "hydroxyalkyl" refers to an alkyl group that is substituted with at least one hydroxyl group. Exemplary hydroxyl alkyl groups include —$CH_2OH$, —$CH_2CH_2OH$, —$C(H)(OH)C(OH)H_2$, and the like.

The term "aralkyl" refers to an alkyl group substituted with an aryl group. Exemplary aralkyl groups include

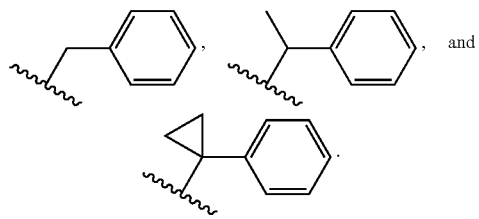

The term "heteroaralkyl" refers to an alkyl group substituted with a heteroaryl group.

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to a carbocyclic aromatic group. Representative aryl groups include phenyl, naphthyl, anthracenyl, and the like. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —$CO_2$alkyl, carbonyl, carboxyl, alkylthio, sulfonyl, sulfonamido, sulfonamide, ketone, aldehyde, ester, heterocyclyl, aryl or heteroaryl moieties, —$CF_3$, —CN, or the like. The term "aryl" also includes polycyclic aromatic ring systems having two or more carbocyclic rings in which two or more carbons are common to two adjoining rings (the rings are "fused rings") wherein all of the fused rings are aromatic rings, e.g., in a naphthyl group. In certain embodiments, the aryl is a mono or bicyclic, aromatic, 6-10 membered ring.

The term "heteroaryl" is art-recognized and refers to aromatic groups that include at least one ring heteroatom. In certain instances, a heteroaryl group contains 1, 2, 3, or 4 ring heteroatoms. Representative examples of heteroaryl groups include pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. Unless specified otherwise, the heteroaryl ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —$CO_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. The term "heteroaryl" also includes polycyclic aromatic ring systems having two or more rings in which two or more carbons are common to two adjoining rings (the rings are "fused rings") wherein all of the fused rings are heteroaromatic, e.g., in a naphthyridinyl group. In certain embodiments, the heteroaryl is a mono or bicyclic, aromatic, 5-10 membered ring containing 1-4 heteroatoms independent selected from nitrogen, oxygen, and sulfur.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

As used herein, the terms "heterocyclic" and "heterocyclyl" represent, for example, an aromatic or nonaromatic ring (e.g., a monocyclic or bicyclic ring) containing one or more heteroatoms. The heteroatoms can be the same or different from each other. Examples of heteratoms include, but are not limited to nitrogen, oxygen and sulfur. Aromatic and nonaromatic heterocyclic rings are well-known in the art. Some nonlimiting examples of aromatic heterocyclic rings include, but are not limited to, pyridine, pyrimidine, indole, purine, quinoline and isoquinoline. Nonlimiting examples of nonaromatic heterocyclic compounds include, but are not limited to, piperidine, piperazine, morpholine, pyrrolidine and pyrazolidine. Examples of oxygen containing heterocyclic rings include, but are not limited to, furan, oxirane, 2H-pyran, 4H-pyran, 2H-chromene, benzofuran, and 2,3-dihydrobenzo[b][1,4]dioxine. Examples of sulfur-containing heterocyclic rings include, but are not limited to, thiophene, benzothiophene, and parathiazine. Examples of nitrogen containing rings include, but are not limited to, pyrrole, pyrrolidine, pyrazole, pyrazolidine, imidazole, imidazoline, imidazolidine, pyridine, piperidine, pyrazine, piperazine, pyrimidine, indole, purine, benzimidazole, quinoline, isoquinoline, triazole, and triazine. Examples of heterocyclic rings containing two different heteroatoms include, but are not limited to, phenothiazine, morpholine, parathiazine, oxazine, oxazole, thiazine, and thiazole. The heterocyclic ring is optionally further substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the heterocyclyl group is a 3-7 membered ring that, unless specified otherwise, is substituted or unsubstituted.

The term "heterocycloalkyl" refers to a saturated heterocyclyl group having, for example, 3-7 ring atoms.

The terms "amine" and "amino" are art-recognized and refer to both unsubstituted and substituted amines, e.g., a moiety that may be represented by the general formulas:

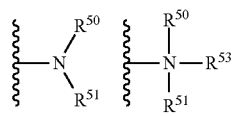

wherein $R^{50}$, $R^{51}$, $R^{52}$ and $R^{53}$ each independently represent a hydrogen, an alkyl, an alkenyl, —(CH$_2$)$_m$—$R^{61}$, or $R^{50}$ and $R^{51}$, taken together with the N atom to which they are attached complete a heterocycle having from 4 to 8 atoms in the ring structure; $R^{61}$ represents an aryl, a cycloalkyl, a cycloalkenyl, a heterocycle or a polycycle; and m is zero or an integer in the range of 1 to 8. In certain embodiments, only one of $R^{50}$ or $R^{51}$ may be a carbonyl, e.g., $R^{50}$, $R^{51}$ and the nitrogen together do not form an imide. In other embodiments, $R^{50}$ and $R^{51}$ (and optionally $R^{52}$) each independently represent a hydrogen, an alkyl, an alkenyl, or —(CH$_2$)$_m$—$R^{61}$.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and —O—(CH$_2$)$_m$—$R^{61}$, where m and $R^{61}$ are described above.

The term "oxo" is art-recognized and refers to a "=O" substituent. For example, a cyclopentane substituted with an oxo group is cyclopentanone.

The symbol "〜〜" indicates a point of attachment.

The term "substituted" means that one or more hydrogens on the atoms of the designated group are replaced with a selection from the indicated group, provided that the atoms' normal valencies under the existing circumstances are not exceeded, and that the substitution results in a stable compound. Combinations of substituents and/or variables are permissible only if such combinations result in stable compounds. The terms "stable compound" or "stable structure" refer to a compound that is sufficiently robust to survive isolation to a useful degree of purity from a reaction mixture, and formulation into an efficacious therapeutic agent.

When any substituent or variable occurs more than one time in any constituent or the compound of the invention, its definition on each occurrence is independent of its definition at every other occurrence, unless otherwise indicated.

It should also be noted that any carbon as well as heteroatom with unsatisfied valences in the text, schemes, examples and tables herein is assumed to have the sufficient number of hydrogen atom(s) to satisfy the valences.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is H$_2$O.

Certain compounds contained in compositions of the present invention may exist in particular geometric or stereoisomeric forms. Further, certain compounds described herein may be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. The compounds may contain one or more stereogenic centers. For example, asymmetric carbon atoms may be present in a substituent such as an alkyl group. All such isomers, as well as mixtures thereof, are intended to be included in this invention, such as, for example, racemic mixtures, single enantiomers, diastereomeric mixtures and individual diastereomers. Additional asymmetric centers may be present depending upon the nature of the various substituents on the molecule. Each such asymmetric center will independently produce two optical isomers, and it is intended that all of the possible optical isomers, diastereomers in mixtures, and pure or partially purified compounds are included within the ambit of this invention.

Diastereomeric mixtures can be separated into their individual diastereomers on the basis of their physical chemical differences by methods known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Alternatively, a particular enantiomer of a compound of the present invention may be prepared by asymmetric synthesis. Still further, where the molecule contains a basic functional group (such as amino) or an acidic functional group (such as carboxylic acid) diastereomeric salts are formed with an appropriate optically-active acid or base, followed by resolution of the diastereomers thus formed by fractional crystallization or chromatographic means known in the art, and subsequent recovery of the pure enantiomers.

Individual stereoisomers of the compounds of the invention may, for example, be substantially free of other isomers, or may be admixed, for example, as racemates or with all other, or other selected, stereoisomers. Chiral center(s) in a compound of the present invention can have the S or R configuration as defined by the IUPAC 1974 Recommendations. Further, to the extent a compound described herein may exist as a atropisomer (e.g., substituted biaryls), all forms of such atropisomer are considered part of this invention.

The term "small organic molecule" refers to an organic molecule having a molecule weight less than about 2000 g/mol. In certain embodiments, the small organic molecule comprises (i) from about 2 to about 75 carbon atoms, (ii) from about 2 to about 120 hydrogen atoms, and (iii) from about 0 to about 10 oxygen and/or nitrogen atoms. In certain embodiments, the small organic molecule has molecule weight less than about 1000 g/mol, 500 g/mol, 400 g/mol, or 250 g/mol. In yet other embodiments, the small organic molecule has molecule weight in the range of about 100 g/mol to about 1500 g/mol, about 100 g/mol to about 1000 g/mol, or about 100 g/mol to about 500 g/mol.

The terms "subject" and "patient" are used interchangeable and refer to organisms to be treated by the methods of the present invention. Such organisms preferably include, but are not limited to, mammals (e.g., murines, simians, equines, bovines, porcines, canines, felines, and the like), and most preferably includes humans. In certain embodiments, the patient is a veterinary animal, such as a canine or feline.

The term "IC$_{50}$" is art-recognized and refers to the concentration of a compound that is required for 50% inhibition of its target.

As used herein, the term "effective amount" refers to the amount of a compound sufficient to effect beneficial or desired results (e.g., a therapeutic, ameliorative, inhibitory or preventative result). An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, Pa. [1975].

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate (also known as toluenesulfonate), undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. Further examples of salts include, but are not limited to: ascorbate, borate, nitrate, phosphate, salicylate, and sulfate. Further, acids which are generally considered suitable for the formation of pharmaceutically useful salts from basic pharmaceutical compounds are discussed, for example, by P. Stahl et al., Camille G. (eds.) *Handbook of Pharmaceutical Salts. Properties, Selection and Use*. (2002) Zurich: Wiley-VCH; S. Berge et al., *Journal of Pharmaceutical Sciences* (1977) 66(1) 1-19; P. Gould, *International J. of Pharmaceutics* (1986) 33 201-217; Anderson et al., *The Practice of*

Medicinal Chemistry (1996), Academic Press, New York; and in The Orange Book (Food & Drug Administration, Washington, D.C. on their website). These disclosures are incorporated herein by reference.

Additional exemplary basic salts include, but are not limited to ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

In addition, when a compound of the invention contains both a basic moiety (such as, but not limited to, a pyridine or imidazole) and an acidic moiety (such as, but not limited to, a carboxylic acid) zwitterions ("inner salts") may be formed. Such acidic and basic salts used within the scope of the invention are pharmaceutically acceptable (i.e., non-toxic, physiologically acceptable) salts. Such salts of the compounds of the invention may be formed, for example, by reacting a compound of the invention with an amount of acid or base, such as an equivalent amount, in a medium such as one in which the salt precipitates or in an aqueous medium followed by lyophilization.

The present invention includes the compounds of the invention in all their isolated forms (such as any solvates, hydrates, stereoisomers, and tautomers thereof). Further, the invention includes compounds in which one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques known to those skilled in the art or by processes analogous to those described in the Schemes and Examples herein using appropriate isotopically-enriched reagents and/or intermediates.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

The terms "a" and "an" as used herein mean "one or more" and include the plural unless the context is inappropriate.

As a general matter, compositions specifying a percentage are by weight unless otherwise specified.

EXAMPLES

The invention now being generally described, will be more readily understood by reference to the following examples, which are included merely for purposes of illustration of certain aspects and embodiments of the present invention, and are not intended to limit the invention. Starting materials described herein can be obtained from commercial sources or may be readily prepared from commercially available materials using transformations known to those of skill in the art.

Example 1—Synthesis of (S)-6-((2-Chloro-6-fluorophenoxy)methyl)-2-methyl-4-((3-(trifluoromethyl)phenyl)sulfonyl)-3,4-dihydro-2H-benzo[b][1,4]oxazine

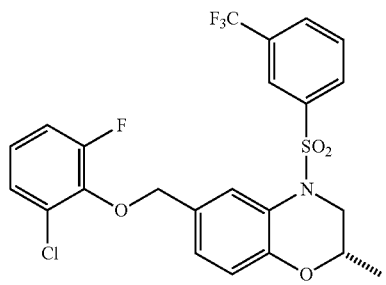 [SMILES: C[C@H]1CN(S(=O)(=O)c2cccc(C(F)(F)F)c2)c2cc(COc3c(F)cccc3Cl)ccc2O1]

Part I—Synthesis of Methyl (S)-4-((1-methoxy-1-oxopropan-2-yl)oxy)-3-nitrobenzoate

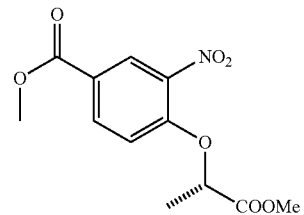 [SMILES: COC(=O)c1ccc(O[C@@H](C)C(=O)OC)c([N+](=O)[O-])c1]

Methyl-4-hydroxy-3-nitrobenzoate (3 g, 13.76 mmol), methyl-(R)-lactate (1.433 g, 13.8 mmol), and triphenylphosphine (4.33 g, 16.5 mmol) were suspended in dichloromethane (36 mL), and diisopropyl azodicarboxylate (3.25 mL, 16.51 mmol) was added dropwise. The reaction mixture was stirred at room temperature for an hour, and then the crude was washed with water, dried ($Na_2SO_4$), and concentrated to provide a residue. The residue was purified via MPLC eluting with a gradient of ethyl acetate in hexanes, followed by a second MPLC purification eluting with dichloromethane to afford methyl (S)-4-((1-methoxy-1-oxopropan-2-yl)oxy)-3-nitrobenzoate (2.56 g, 66%) as a light yellow oil. $^1$H-NMR (400 MHz, DMSO-$d_6$) δ 8.37 (s, 1H), 8.12 (d, 1H), 7.36 (d, 1H), 5.40 (q, 1H), 3.83 (s, 3H), 3.65 (s, 3H), 1.54 (d, 3H).

Part II—Synthesis of Methyl (S)-2-methyl-3-oxo-3,4-dihydro-2H-benzo[b][1,4]oxazine-6-carboxylate

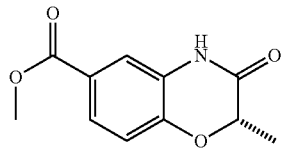

Methyl (S)-4-((1-methoxy-1-oxopropan-2-yl)oxy)-3-nitrobenzoate (2.38 g, 8.42 mmol) was dissolved in acetic acid (30 mL) and powdered iron (2.35 g, 42.1 mmol) was added. The mixture was heated to 70° C. for two hours. Then, the resulting suspension was filtered through a pad of celite, and the material was washed through with ethyl acetate. The filtrate was then partitioned between ethyl acetate and water, and the organic phase was washed a second time with water, washed with brine, and concentrated to provide a residue. The residue was purified by MPLC, eluting with a gradient of hexanes and ethyl acetate (85:15 to 3:7) to afford methyl (S)-2-methyl-3-oxo-3,4-dihydro-2H-benzo[b][1,4]oxazine-6-carboxylate (1.16 g, 62%) as a white solid. $^1$H-NMR (400 MHz, DMSO-$d_6$) δ 10.81 (s, 1H), 7.52 (m, 2H), 7.02 (d, 1H), 4.77 (q, 1H), 3.79 (s, 3H), 1.42 (d, 3H).

Part III—Synthesis of (S)-(2-Methyl-3,4-dihydro-2H-benzo[b][1,4]oxazin-6-yl)methanol

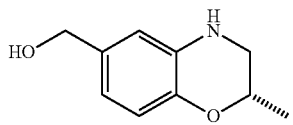

To a solution of methyl (S)-2-methyl-3-oxo-3,4-dihydro-2H-benzo[b][1,4]oxazine-6-carboxylate (1.16 g, 5.24 mmol) in anhydrous THF (26 mL) at ambient temperature was carefully added 1M solution of lithium aluminum hydride in diethyl ether (20.98 mL, 20.98 mmol). The mixture was heated in an oil bath at 50° C. overnight. The resulting crude mixture was carefully treated with water (0.75 mL), then 15% NaOH solution (0.75 mL), and then water (2.25 mL). The resulting mixture was stirred vigorously for several minutes, and then filtered. The filtrate was concentrated to afford the title compound (0.96 g, 102%) which was used without purification. $^1$H-NMR (400 MHz, DMSO-$d_6$) δ 6.50 (m, 2H), 6.36 (d, 1H), 5.66 (s, 1H), 4.86 (t, 1H), 4.26 (d, 2H), 4.01 (m, 1H), 3.24 (m, 1H), 2.87 (m, 1H), 1.22 (d, 3H).

Part IV—Synthesis of (S)-(2-Methyl-4-((3-(trifluoromethyl)phenyl)sulfonyl)-3,4-dihydro-2H-benzo[b][1,4]oxazin-6-yl)methanol

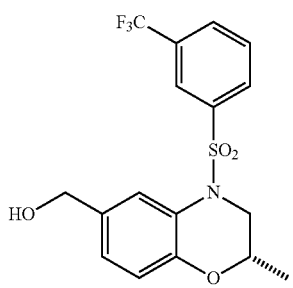 [SMILES: C[C@H]1CN(S(=O)(=O)c2cccc(C(F)(F)F)c2)c2cc(CO)ccc2O1]

(S)-(2-Methyl-3,4-dihydro-2H-benzo[b][1,4]oxazin-6-yl)methanol (0.9 g, 5.02 mmol), 3-(trifluoromethyl)benzenesulfonyl chloride (3.07 g, 12.5 mmol), and potassium carbonate (2.08 g, 15.1 mmol) were suspended in acetone, and the mixture was shaken at room temperature for 18 hours. Next, the crude was filtered, and the filtrate was concentrated onto silica gel and purified by chromatography delivering the title compound. $^1$H-NMR (400 MHz, DMSO-$d_6$) δ 8.08 (d, 1H), 7.97 (m, 2H), 7.81 (t, 1H), 7.65 (s, 1H), 6.99 (d, 1H), 6.74 (d, 1H), 5.18 (bs, 1H), 4.40 (s, 2H), 4.35 (d, 1H), 3.45 (m, 1H), 3.22 (m, 1H), 1.18 (d, 3H).

Part V—Synthesis of (S)-6-((2-Chloro-6-fluorophenoxy)methyl)-2-methyl-4-((3-(trifluoromethyl)phenyl)sulfonyl)-3,4-dihydro-2H-benzo[b][1,4]oxazine

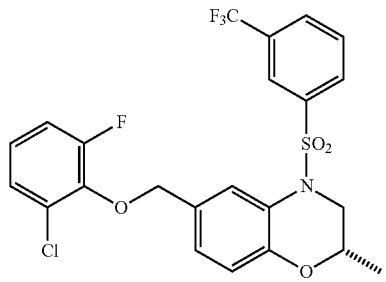 [SMILES: C[C@H]1CN(S(=O)(=O)c2cccc(C(F)(F)F)c2)c2cc(COc3c(F)cccc3Cl)ccc2O1]

(S)-(2-Methyl-4-((3-(trifluoromethyl)phenyl)sulfonyl)-3,4-dihydro-2H-benzo[b][1,4]oxazin-6-yl)methanol (1.28 g, 3.304 mmol), 2-chloro-6-fluorophenol (0.484 g, 3.304 mmol), and triphenylphosphine (1.04 g, 3.965 mmol) were suspended in dichloromethane (7 mL), and diisopropylazodicarboxylate (0.78 mL, 3.965 mmol) was added dropwise. The reaction mixture was stirred at room temperature for one hour, then washed with water, dried (Na$_2$SO$_4$) and concentrated to provide a residue. The residue was purified via MPLC, eluting with a gradient of 0-5% methanol in dichloromethane to afford the title compound (1.3 g, 73%). $^1$H-NMR (400 MHz, DMSO-$d_6$) δ 8.08 (d, 1H), 7.94 (m, 2H), 7.80 (m, 2H), 7.27 (m, 2H), 7.13 (m, 2H), 6.80 (d, 1H), 5.03 (s, 2H), 4.36 (d, 1H), 3.49 (m, 1H), 3.25 (m, 1H), 1.19 (d, 3H).

Example 2—Synthesis of (S,E)-3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanoic acid

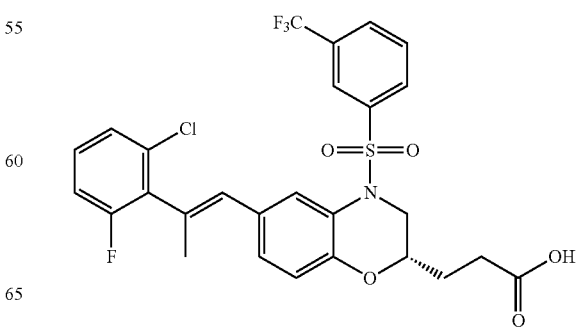

Part I—Synthesis of dimethyl (R)-2-hydroxypentanedioate

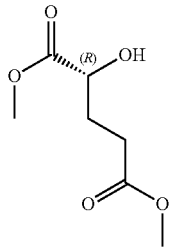

To a mixture of (2R)-5-oxotetrahydro-2-furancarboxylic acid (25 g, 192 mmol) in methanol (300 mL) was added concentrated hydrogen chloride (0.5 mL) and the mixture was refluxed overnight. Then, the reaction mixture was cooled to ambient temperature, solid sodium bicarbonate was added, and the resulting mixture was slurried for 20 minutes. Next, the mixture was filtered and concentrated to obtain dimethyl (R)-2-hydroxypentanedioate (34.7 g, 100%).

Part II—Synthesis of dimethyl (S)-2-(4-bromo-2-nitrophenoxy)pentanedioate

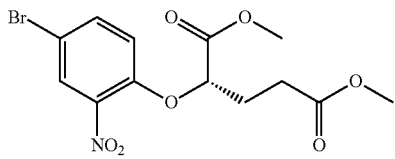 [SMILES: COC(=O)CC[C@H](Oc1ccc(Br)cc1[N+](=O)[O-])C(=O)OC]

To a solution of dimethyl (R)-2-hydroxypentanedioate (33.8 g, 192 mmol), 4-bromo-2-nitrophenol (50.2 g, 230 mmol), and triphenylphosphine (60.4 g, 230 mmol) in dichloromethane (300 mL) with activated molecular sieves at 0° C. was added a solution of diisopropyl azodicarboxylate (45.4 mL, 230 mmol) in dichloromethane (50 mL) dropwise. The resulting mixture was stirred at 0° C. for 20 minutes, then stirred at ambient temperature overnight. Next, the reaction mixture was concentrated and triphenylphosphine oxide was removed by running the mixture through a large pad of silica, eluting with dichloromethane (~6 L). The eluted material was a mixture of the title compound and a small amount of residual phenol. Accordingly, the eluted material was redissolved in ethyl acetate, washed four times with 1M sodium hydroxide, then washed with brine, dried (Na₂SO₄), and concentrated to yield dimethyl (S)-2-(4-bromo-2-nitrophenoxy)pentanedioate (62.84 g, 87%) as a clear oil.

Part III—Synthesis of methyl (S)-3-(6-bromo-3-oxo-3,4-dihydro-2H-benzo[b][1,4]oxazin-2-yl)propanoate

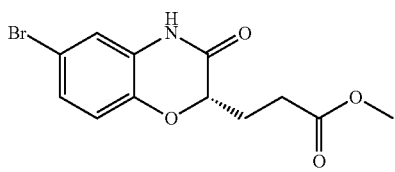 [SMILES: COC(=O)CC[C@@H]1Oc2ccc(Br)cc2NC1=O]

In a flask equipped with a mechanical stirrer was charged dimethyl (S)-2-(4-bromo-2-nitrophenoxy)pentanedioate (62.84 g, 167 mmol) and acetic acid (500 mL), followed by powdered iron (46.7 g, 835 mmol) at ambient temperature. Then, the reaction mixture was heated to 60° C. for 2 hours. Next, the reaction mixture was filtered hot through a pad of celite, washing with ethyl acetate (900 mL). The filtrates were washed three times with water, washed with brine, dried (Na₂SO₄), and concentrated to yield methyl (S)-3-(6-bromo-3-oxo-3,4-dihydro-2H-benzo[b][1,4]oxazin-2-yl)propanoate (48.06 g, 92%) as a white solid.

Part IV—Synthesis of methyl (S)-3-(6-bromo-3,4-dihydro-2H-benzo[b][1,4]oxazin-2-yl)propanoate

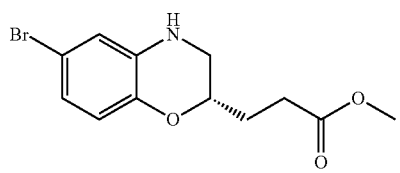 [SMILES: COC(=O)CC[C@H]1CNc2cc(Br)ccc2O1]

To methyl (S)-3-(6-bromo-3-oxo-3,4-dihydro-2H-benzo[b][1,4]oxazin-2-yl)propanoate (24.46 g, 77.9 mmol) in anhydrous tetrahydrofuran (200 mL) at 0° C. was added borane-methyl sulfide complex (19.5 mL, 195 mmol) dropwise. The reaction mixture was heated to 50° C. for 1 hour. Then, the reaction mixture was cooled to 0° C., and next carefully quenched with methanol (150 mL). The resulting mixture was heated to 60° C. for 60 minutes, and then concentrated to provide a residue. The residue was partitioned between water and ethyl acetate. The organic layer was washed with brine, dried (Na₂SO₄), and concentrated. The resulting mixture was purified by column chromatography eluting with a gradient of 5-50% ethyl acetate in hexanes to yield methyl (S)-3-(6-bromo-3,4-dihydro-2H-benzo[b][1,4]oxazin-2-yl)propanoate (17.97 g, 77%) as a white solid.

Part V—Synthesis of (S)-methyl 3-(6-bromo-4-((3-(trifluoromethyl)phenyl)sulfonyl)-3,4-dihydro-2H-benzo[b][1,4]oxazin-2-yl)propanoate

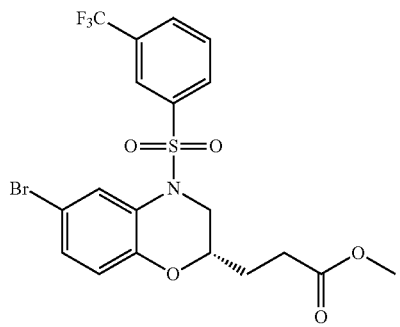 [SMILES: COC(=O)CC[C@H]1CN(S(=O)(=O)c2cccc(C(F)(F)F)c2)c2cc(Br)ccc2O1]

To a solution of (S)-3-(6-bromo-3,4-dihydro-2H-benzo[b][1,4]oxazin-2-yl)propanoate (10.0 g, 33.3 mmol) in pyridine (60 mL) was added 3-(trifluoromethyl)benzenesulfonyl chloride (8.96 g, 36.6 mmol). The mixture was heated at 50° C. for four hours, cooled, and concentrated to provide a residue. The residue was partitioned between ethyl acetate and 1N HCl. The organic layer was separate and then washed twice with 1N HCl, brine, and dried (Na$_2$SO$_4$). To the resulting solution was added activated charcoal, and the resulting mixture was slurried then filtered through celite. The filtrate was concentrated onto a small amount of silica and the resulting residue was purified via MPLC eluting with a gradient of ethyl acetate in hexanes. The major UV component was concentrated to afford (S)-methyl 3-(6-bromo-4-((3-(trifluoromethyl)phenyl)sulfonyl)-3,4-dihydro-2H-benzo[b][1,4]oxazin-2-yl)propanoate (14.75 g, 87%).

Part VI—Synthesis of 1-chloro-2-ethynyl-3-fluorobenzene

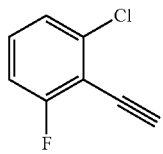

2-Chloro-6-fluorobenzaldehyde (2.00 g, 12.61 mmol) was dissolved in methanol (84 mL), and dimethyl (diazomethyl) phosphonate (2.39 mL, 15.77 mmol) was added followed by potassium carbonate (4.36 g, 31.53 mmol). The reaction mixture was stirred at room temperature overnight. Then, the crude mixture was diluted with methyl tert-butyl ether, washed with water, washed with brine, dried (Na$_2$SO$_4$), and concentrated to afford 1-chloro-2-ethynyl-3-fluorobenzene (1.83 g, 94%). $^1$H-NMR (400 MHz, DMSO-d$_6$) δ 7.45 (m, 2H), 7.32 (t, 1H), 4.86 (s, 1H).

Part VII—Synthesis of (E)-2-(2-(2-chloro-6-fluorophenyl)prop-1-en-1-yl)-4,4,5,5-tetramethyl-1,3,2-dioxaborolane

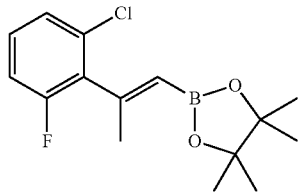 [SMILES: C/C(=C\B1OC(C)(C)C(C)(C)O1)c1c(F)cccc1Cl]

Bis(pinacolato)diborane (5.82 g, 22.92 mmol), copper (I) chloride (0.21 g, 2.08 mmol), and 4,5-bis(diphenylphosphino)-9,9-dimethylxanthene (1.21 g, 2.08 mmol) were suspended in THF (208 mL) and the mixture was degassed with nitrogen, and stirred for five minutes. Then, a solution of sodium tert-butoxide (2.202 g, 22.92 mmol) in minimal THF was added, and the mixture stirred for an additional five minutes. Next, 1-chloro-2-ethynyl-3-fluorobenzene (3.22 g, 20.83 mmol) and methyl iodide (11.83 g, 83.33 mmol) were added to the reaction mixture, and the resulting mixture was stirred at room temperature overnight. The crude product mixture was concentrated onto silica gel and purified by MPLC eluting with a gradient of 0-5% ethyl acetate in hexanes to afford (E)-2-(2-(2-chloro-6-fluorophenyl)prop-1-en-1-yl)-4,4,5,5-tetramethyl-1,3,2-dioxaborolane (2.41 g, 39%). $^1$H-NMR (400 MHz, DMSO-d$_6$) δ 7.31 (m, 2H), 7.20 (t, 1H), 5.18 (s, 1H), 2.15 (s, 3H), 1.23 (s, 12H).

Part VIII—Synthesis of (S,E)-methyl 3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanoate

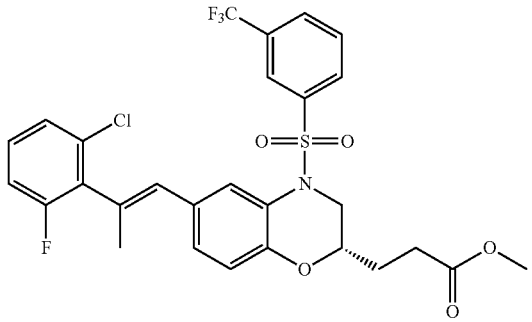 [SMILES: COC(=O)CC[C@H]1CN(S(=O)(=O)c2cccc(C(F)(F)F)c2)c2cc(/C=C(\C)c3c(F)cccc3Cl)ccc2O1]

A mixture of (S)-methyl 3-(6-bromo-4-((3-(trifluoromethyl)phenyl)sulfonyl)-3,4-dihydro-2H-benzo[b][1,4]oxazin-2-yl)propanoate (7.46 g, 14.7 mmol), (E)-2-(2-(2-chloro-6-fluorophenyl)prop-1-en-1-yl)-4,4,5,5-tetramethyl-1,3,2-dioxaborolane (6.09 g, 20.5 mmol), potassium carbonate (2.84 g, 20.5 mmol) in dioxane (80 mL) and water (20 mL) was degassed and was placed under an atmosphere of nitrogen. To the reaction mixture was added [1,1'-bis(diphenylphosphino)ferrocene]dichloropalladium(II) complex with dichloromethane (1.12 g, 1.47 mmol) and the resulting mixture was heated to 70° C. for five hours. Next, toluene (100 mL) and a 20% solution of sodium bisulfite in water (50 mL) were added to the reaction mixture. The resulting mixture was stirred at 60° C. for an additional fifteen minutes. Next, the reaction mixture was cooled, and then diluted with toluene (150 mL). The organic layer was washed with a 20% aqueous solution of sodium bisulfite, water, brine, dried (Na$_2$SO$_4$), and added activated charcoal. The resulting mixture was slurried, and then filtered through a pad of celite. The filtrate was concentrated onto a small amount of silica and the residue was purified by MPLC eluting with a gradient of 0-30% ethyl acetate in hexanes to afford (S,E)-methyl 3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanoate (6.8 g, 77%). $^1$H-NMR (400 MHz, DMSO-d$_6$) δ 8.11 (d, 1H), 8.03 (d, 1H), 7.99 (s, 1H), 7.86 (t, 1H), 7.68 (d, 1H), 7.38 (m, 2H), 7.27 (m, 1H), 7.11 (dd, 1H), 6.87 (d, 1H), 6.37 (s, 1H), 4.37 (d, 1H), 3.57 (s, 3H), 3.49 (m, 1H), 3.3 (m, 1H), 2.48 (m, 2H), 2.08 (s, 3H), 1.9 (m, 1H), 1.76 (m, 1H). (ES, m/z): (M+Na)$^+$=620.09, 622.10.

Part IX—Synthesis of (S,E)-3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanoic acid

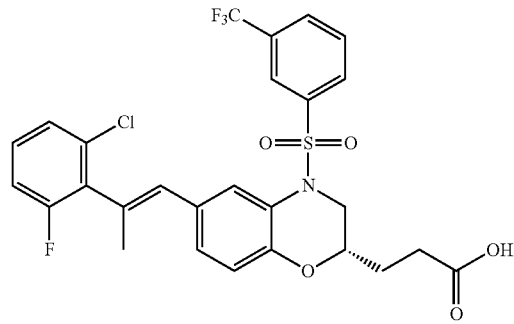 [SMILES: C/C(=C\c1ccc2c(c1)N(S(=O)(=O)c1cccc(C(F)(F)F)c1)C[C@H](CCC(=O)O)O2)c1c(F)cccc1Cl]

To a solution of (S,E)-methyl 3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanoate (5.74 g, 9.60 mmol) in methanol (100 mL) and tetrahydrofuran (10 mL) was added 2M sodium hydroxide (14.4 mL, 28.8 mmol) in water. The reaction mixture was stirred at ambient temperature for 16 hours. Then, the volume of the reaction mixture was reduced under vacuum. Next, the reaction mixture was acidified solution by addition of 1M hydrogen chloride solution in water. The resulting mixture was extracted with ethyl acetate, the extracts were combined and was with brine, then dried with sodium sulfate, filtered and concentrated to provide the title compound. (5.54 g, 99%).

Preparation of Sodium Salt of (S,E)-3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanoic acid The carboxylic acid reaction product above was converted to the sodium salt by redissolving the carboxylic acid in methanol (100 mL), then adding one equivalent of a 2.962M sodium hydroxide (3.203 mL, 9.487 mmol) solution in water. The reaction mixture was stirred twenty minutes. The reaction mixture was then concentrated, and added methanol and concentrated three times. The resulting residue was dried in a vacuum oven to afford the sodium salt of (S,E)-3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanoic acid (5.50 g, 98%) as a white solid. $^1$H-NMR (400 MHz, DMSO-$d_6$) δ 8.1 (m, 2H), 7.89 (m, 2H), 7.69 (s, 1H), 7.37 (m, 2H), 7.26 (m, 1H), 7.08 (dd, 1H), 6.85 (d, 1H), 6.36 (s, 1H), 4.40 (d, 1H), 3.55 (m, 1H), 3.3 (m, 1H), 2.08 (s, 3H), 1.92 (m, 2H), 1.70 (m, 2H). (ES, m/z): $(M+H)^+$=606.15, 608.15.

Example 3—Synthesis of (S,E)-3-(6-(2-chloro-6-(trifluoromethyl)styryl)-4-((3-(trifluoromethyl)phenyl)sulfonyl)-3,4-dihydro-2H-benzo[b][1,4]oxazin-2-yl)propanoic acid

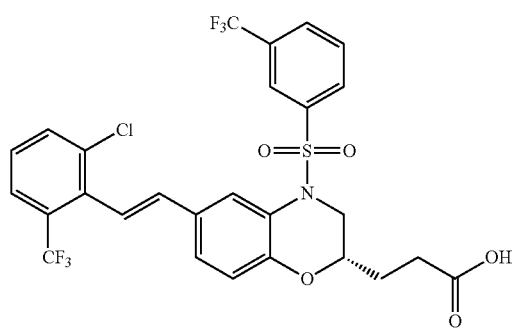 [SMILES: O=C(O)CC[C@H]1CN(S(=O)(=O)c2cccc(C(F)(F)F)c2)c2cc(/C=C/c3c(Cl)cccc3C(F)(F)F)ccc2O1]

Part I—Synthesis of 1-chloro-2-ethynyl-3-(trifluoromethyl)benzene

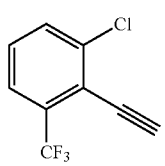

To a solution of 2-chloro-6-(trifluoromethyl)benzaldehyde (10.0 g, 47.9 mmol) in methanol (100 mL) was added dimethyl (diazomethyl)phosphonate (11.05 g, 57.5 mmol). The reaction mixture was cooled to 0° C., and potassium carbonate (16.6 g, 119 mmol) was added. The reaction mixture was stirred at room temperature overnight. The resulting crude mixture was diluted with ether, washed with water, washed with brine, dried ($MgSO_4$), and concentrated to afford 1-chloro-2-ethynyl-3-(trifluoromethyl)benzene (9.17 g, 93%).

Part II—Synthesis of (E)-2-(2-chloro-6-(trifluoromethyl)styryl)-4,4,5,5-tetramethyl-1,3,2-dioxaborolane

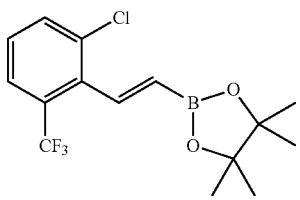 [SMILES: CC1(C)OB(/C=C/c2c(Cl)cccc2C(F)(F)F)OC1(C)C]

To [2,3-bis(1-adamatyl)imidazolidin-2-yl]-chloro-copper (0.99 g, 2.23 mmol) and sodium tert-butoxide (0.215 g, 2.23 mmol) suspended in THF (40 mL) was added bis(pinacoato)diboron (11.36 g, 44.7 mmol). The mixture was stirred for 30 minutes, and then a solution of 1-chloro-2-ethynyl-3-(trifluoromethyl)benzene (9.15 g, 44.7 mmol) in THF (40 mL) and methanol (1.58 g, 49.2 mmol) was added. The resulting mixture was stirred overnight, and then filtered through celite. The filtrate was concentrated and the resulting residue was purified via MPLC eluting with a gradient of 0-10% ethyl acetate in hexanes to afford (E)-2-(2-chloro-6-(trifluoromethyl)styryl)-4,4,5,5-tetramethyl-1,3,2-dioxaborolane (11.23 g, 76%).

Part III—Synthesis of (S,E)-methyl 3-(6-(2-chloro-6-(trifluoromethyl)styryl)-4-((3-(trifluoromethyl)phenyl)sulfonyl)-3,4-dihydro-2H-benzo[b][1,4]oxazin-2-yl)propanoate

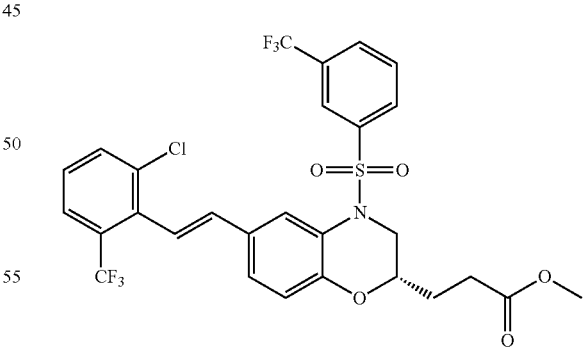

A mixture of (S)-methyl 3-(6-bromo-4-((3-(trifluoromethyl)phenyl)sulfonyl)-3,4-dihydro-2H-benzo[b][1,4]oxazin-2-yl)propanoate (2.00 g, 3.93 mmol), (E)-2-(2-chloro-6-(trifluoromethyl)styryl)-4,4,5,5-tetramethyl-1,3,2-dioxaborolane (1.83 g, 5.51 mmol), potassium carbonate (0.65 g, 4.72 mmol) in dioxane (40 mL) and water (6 mL) was degassed and was placed under an atmosphere of nitrogen. To this mixture was added [1,1'-bis(diphenylphosphino)ferrocene]-dichloropalladium(II), complex with dichloromethane (0.30 g, 0.39 mmol) and the resulting mixture was heated to 70° C. overnight. Then, the reaction mixture was cooled, and partitioned between ethyl acetate and water. The organic layer was washed with brine, dried (Na₂SO₄) and concentrated onto a small amount of silica. The resulting residue was purified by MPLC eluting with a gradient of 0-30% ethyl acetate in hexanes to afford (S,E)-methyl 3-(6-(2-chloro-6-(trifluoromethyl)styryl)-4-((3-(trifluoromethyl)phenyl)sulfonyl)-3,4-dihydro-2H-benzo[b][1,4]oxazin-2-yl)propanoate (2.0 g, 80%). ¹H-NMR (400 MHz, DMSO-d₆) δ 8.10 (d, 1H), 8.06 (d, 1H), 8.0 (s, 1H), 7.85 (m, 2H), 7.75 (m, 2H), 7.54 (t, 1H), 7.38 (dd, 1H), 6.98 (m, 1H), 6.88 (d, 1H), 6.78 (m, 1H), 4.37 (d, 1H), 3.58 (s, 3H), 3.40 (m, 1H), 3.3 (m, 1H), 2.42 (m, 2H), 1.9 (m, 1H), 1.75 (m, 1H). (ES, m/z): (M+Na)⁺=656.08, 658.07.

Part IV—Synthesis of (S,E)-3-(6-(2-chloro-6-(trifluoromethyl)styryl)-4-((3-(trifluoromethyl)phenyl)sulfonyl)-3,4-dihydro-2H-benzo[b][1,4]oxazin-2-yl)propanoic acid

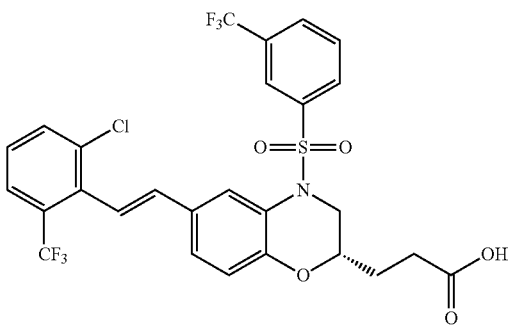 [SMILES: O=C(O)CC[C@H]1CN(S(=O)(=O)c2cccc(C(F)(F)F)c2)c2cc(/C=C/c3c(Cl)cccc3C(F)(F)F)ccc2O1]

To a solution of (S,E)-methyl 3-(6-(2-chloro-6-(trifluoromethyl)styryl)-4-((3-(trifluoromethyl)phenyl)sulfonyl)-3,4-dihydro-2H-benzo[b][1,4]oxazin-2-yl)propanoate (11.8 g, 18.6 mmol) in methanol (100 mL) and tetrahydrofuran (30 mL) was added 2M sodium hydroxide (27.9 mL, 55.8 mmol) in water. The reaction mixture was stirred at ambient temperature for 16 hours. Then, the volume of the reaction mixture was reduced under vacuum. The resulting mixture was acidified by adding a solution with 1M hydrogen chloride solution in water. The resulting mixture was extracted with ethyl acetate, the combined extracts were washed with brine, dried with sodium sulfate, filtered and concentrated. The resulting solids were redissolved using dichloromethane and then precipitated using hexanes. The solids were filtered off and dried under vacuum to provide the title compound. (8.73 g, 76%).

Preparation of Sodium Salt of (S,E)-3-(6-(2-chloro-6-(trifluoromethyl)styryl)-4-((3-(trifluoromethyl)phenyl)sulfonyl)-3,4-dihydro-2H-benzo[b][1,4]oxazin-2-yl)propanoic acid The carboxylic acid produce from the above reaction was converted to the sodium salt by redissolving in methanol (100 mL), then adding one equivalent of a 3.109M sodium hydroxide (4.529 mL, 14.082 mmol) solution in water. The resulting mixture was stirred ten minutes, then concentrated, and added methanol and concentrated three times. The resulting residue was dried in a vacuum oven to afford the sodium salt of (S,E)-3-(6-(2-chloro-6-(trifluoromethyl)styryl)-4-((3-(trifluoromethyl)phenyl)sulfonyl)-3,4-dihydro-2H-benzo[b][1,4]oxazin-2-yl)propanoic acid (8.70 g, 99%) as a white solid. ¹H-NMR (400 MHz, DMSO-d₆) δ 8.15 (d, 1H), 8.08 (d, 1H), 7.88 (m, 3H), 7.78 (m, 2H), 7.55 (t, 1H), 7.34 (d, 1H), 6.98 (m, 1H), 6.84 (d, 1H), 6.78 (m, 1H), 4.40 (d, 1H), 3.60 (m, 1H), 3.3 (m, 1H), 1.92 (m, 2H), 1.70 (m, 2H). (ES, m/z): (M+Na)⁺=641.93, 643.93.

Example 4—Compound Agonist Activity Towards RORγ

Exemplary compounds were tested for ability to increase RORγ activity using (i) a RORγ-Ligand Binding Domain (LBD) TR-FRET Assay, and (ii) a Gal4-RORγ Luciferase Reporter Assay in HEK-293T Cells. Assay procedures and results are described below.

Part I—Procedures for RORγ-Ligand Binding Domain TR-FRET Assay

HIS-tagged RORγ-LBD protein was expressed in SF9 cells using a baculovirus expression system. The lysate was diluted in assay buffer (50 mM Tris pH 7.0, 50 mM KCl, 1 mM EDTA, 0.1 mM DTT, 0.01% BSA) to obtain RORγ-LBD final concentration of ~3 nM in a 384-well assay plate (need to titrate for each batch of protein).

A stock of biotinylated-LXXLL peptide from coactivator SRC1 (Biotin-CPSSHSSLTERHKILHRLLQEGSPS) was prepared in assay buffer and added to each well (200 nM final concentration). A solution of Europium tagged anti-HIS antibody (0.6 nM final concentration) and APC-conjugated streptavidin (30 nM final concentration) were also added to each well. RORγ antagonist ursolic acid was also included at a final concentration of 2 μM. Compounds were diluted in DMSO and further diluted in assay buffer with a final DMSO concentration at 1%.

The final assay mixture was incubated overnight at 4° C. or 2 hours at room temperature, and the fluorescence signal was measured on an Envision plate reader: (Excitation filter=340 nm; APC emission=665 nm; Europium emission=615 nm; dichroic mirror=D400/D630; delay time=100 μs, integration time=200 μs). 50% Effective concentration (EC₅₀) values for test compounds were calculated from the quotient of the fluorescence signal at 665 nm divided by the fluorescence signal at 615 nm. The quotient of the fluorescence signals in the absence of ursolic acid or test compound is set as 100. Max Response is defined as the upper plateau in the signal as determined by line-fit using a 4-parameter logistic model in PRISM (GraphPad).

Part II—Procedures for Gal4-RORγ Luciferase Reporter Assay in HEK-293T Cells

Transfection of HEK-293 Cells

In the following protocol, HEK-293 cells were transfected with a construct comprising the Gal4 DNA binding domain fused to the ligand binding domain of RORγ (Gal4-RORγ-LBD) in a pcDNA3.1neo plasmid, and also with a reporter construct comprising pGL4.31 Gal4-luciferase (Promega). Control cells were prepared similarly using empty pcDNA3.1neo and pGL4.31 vectors.

Trans-IT reagent (Mirus, 60 μL) at room temperature was added drop wise to OptiMEM (Invitrogen, 1.5 ml). This reagent mixture was mixed by inversion then incubated for 5 to 30 minutes at room temperature. It then was added to a solution of both expression vectors (5 μg each), mixed, and incubated at room temperature for about 20 minutes. HEK-293 cells were harvested from incubation flasks by removing the media, treating with TrypLE Express (Invitrogen), and incubating until the cells detached from the bottom of the flask (approximately 2-5 minutes). 10 Million cells were collected by centrifugation and re-suspended in 10 mL of Dulbecco's Modified Eagle Medium, High Glucose (DMEM, Invitrogen) containing 10% Fetal Bovine Serum and 100 IU each of penicillin and streptomycin. The re-suspended cells and the transfection mixture were added to a T75 flask, mixed and incubated overnight at 37° C. and 5% $CO_2$.

Assay for RORγ Activity

The cells were harvested as described above, counted, and centrifuged to obtain the desired number of cells, then re-suspended in complete growth media at $0.75 \times 10^6$ cells/mL. The RORγ antagonist, ursolic acid, was added to the cells at a final concentration of 2 μM. Cells were plated at 20 μL of cell suspension/well (10,000-15,000 cells/well) in white tissue culture treated 384 well plates. Test compounds were dissolved at 10 mM in DMSO then diluted into complete growth medium to 5× the final intended test concentration. These drug stock solutions, 5 μL/well were added to the tissue culture plate. The final DMSO concentration was 0.2%. The plates were briefly centrifuged then incubated overnight at 37° C. and 5% $CO_2$. To conduct the assay, the tissue culture plates were allowed to equilibrate to room temperature and One-Glo luciferase reagent (Promega, 25 μL/well) was added. The plates were briefly centrifuged then incubated at room temperature for 10 minutes. The luciferase intensity was read on an Envision plate reader (Perkin Elmer). RORγ activity was determined relative to controls and plotted as a function of test compound concentration using PRISM (GraphPad) to determine a 50% effective concentration ($EC_{50}$). The luciferase signal in the absence of ursolic acid or test compound is defined at 100. The Max Response is the upper plateau in the signal as determined by line-fit using a 4-parameter logistic model in PRISM (GraphPad).

Part III—Results

Experimental results are provided in Table 1 below. The symbol "++++" indicates an $EC_{50}$ less than 0.5 μM. The symbol "+++" indicates an $EC_{50}$ in the range of 0.5 μM to 5 μM. The symbol "++" indicates an $EC_{50}$ in the range of greater than 5 μM to 10 μM. The symbol "+" indicates an $EC_{50}$ greater than 10 μM. The symbol "N/A" indicates that no data was available. The symbol "**" indicates a value greater than 200. The symbol "*" indicates a value in the range of greater than 150 to 200. The symbol "**" indicates a value in the range of greater than 90 to 150. The symbol "*" indicates a value in the range of 70 to 90.

TABLE 1

Assay Results for Sulfonamido Compounds.

| Compound No. | Compound Structure | TR-FRET Assay | | Gal4-RORγ Assay | |
|---|---|---|---|---|---|
| | | Average $EC_{50}$ | Average Max Response | Average $EC_{50}$ | Average Max Response |
| 1 | | ++++ | **** | +++ | ** |
| 2 | | ++++ | *** | ++++ | ** |

TABLE 1-continued

Assay Results for Sulfonamido Compounds.

| Compound No. | Compound Structure | TR-FRET Assay | | Gal4-RORγ Assay | |
|---|---|---|---|---|---|
| | | Average $EC_{50}$ | Average Max Response | Average $EC_{50}$ | Average Max Response |
| 3 | 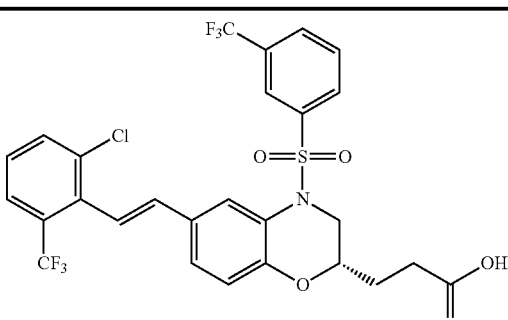 | ++++ | ** | +++ | * |

Example 5—Treatment of EG7 Tumors Using Adoptively Transferred Tc17 Cells Treated Ex Vivo with an RORγ Agonist EG7 tumors in mice were treated using adoptively transferred Tc17 cells treated ex vivo with an RORγ agonist. Experimental procedures and results are described below.

Part I—Procedures for Adoptive Transfer of Tc17 Cells to Mice Bearing EG7 Tumors EG7 cells (EL4 cells with OVA expression) were grown in RPMI 1640 medium (Invitrogen)/10% heat-inactivated FBS (Hyclone), penicillin-streptomycin, and 50 mM β-mercaptoethanol (Invitrogen); harvested; washed with phosphate-buffered saline (PBS); and then implanted at $1 \times 10^6$ cells/mouse in PBS into the flank of mice subcutaneously. Implanted tumor cells grow into visible tumor in about one week. Mice are provided food and water ab libitum throughout the duration of the experiment.

Three to five days after tumor cell transplantation, Tc17 differentiation culture is set up. Splenocytes (at $2 \times 10^6$/ml) isolated from OTI TCR transgenic mice are differentiated into Tc17 cells in the presence of 50 ng/ml ovalbumin peptide (peptide sequence: SIINFEKL), 1.25 ng/ml TGFβ and 10 ng/ml IL-6 (R&D systems). RORγ agonist is added in the culture at the desired concentration (10 μM for Compound 1 and 5 μM for Compounds 2 and 3, where compound structures are as shown in Table 1 in Example 4) and cells are differentiated into Tc17 for 4 or 5 days. A small aliquot of cells are assayed for IL17A production using intracellular staining to verify the differentiation of Tc17 cells.

When a tumor becomes visible, tumor volume is assessed by caliper measurement of the length and width and tumor volume is calculated $(0.5 \times (length \times (width)^2))$. When the tumor becomes visible in most mice (typically 7-10 days after implantation), mice are randomized by tumor volume (tumor volume is <500 mm³) and divided into three groups. Differentiated Tc17 cells (with or without RORγ agonist) are counted, washed with phosphate buffered saline (PBS), and then the cells are injected into tumor-bearing mice at $5 \times 10^6$ cells/mouse intraperitoneally or intravenously using a PBS carrier to deliver the cells. A control group receives vehicle PBS alone.

After T cell transfer, tumor volume was assessed every 2 to 3 days. In studies where survival is assessed, mice that are alive and have tumor volume smaller than 3000 mm³ are considered survivors.

Part II—Results

Figure 2:
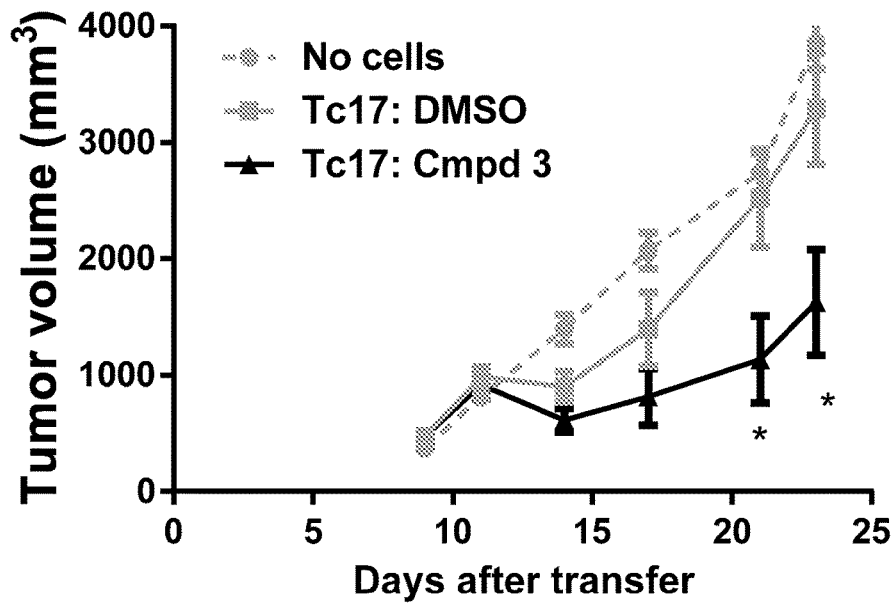
FIG. 2 provides graphs showing results from an assay evaluating change in tumor volume over time and mouse survival rates for mice bearing EG7 tumors that have been exposed to Tc17 cells, where the Tc17 cells have been exposed ex vivo to an RORγ agonist, as further described in Example 5. Part A provides results for tumors exposed to Tc17 cells previously exposed ex vivo to RORγ agonist compound 3 at a concentration of 5 μM, and provides results from control assays where * indicates p<0.03 vs. DMSO treated Tc17 cells. Part B shows percent survival of the mice over the duration of the experiment using compound 3.
Figure 2:
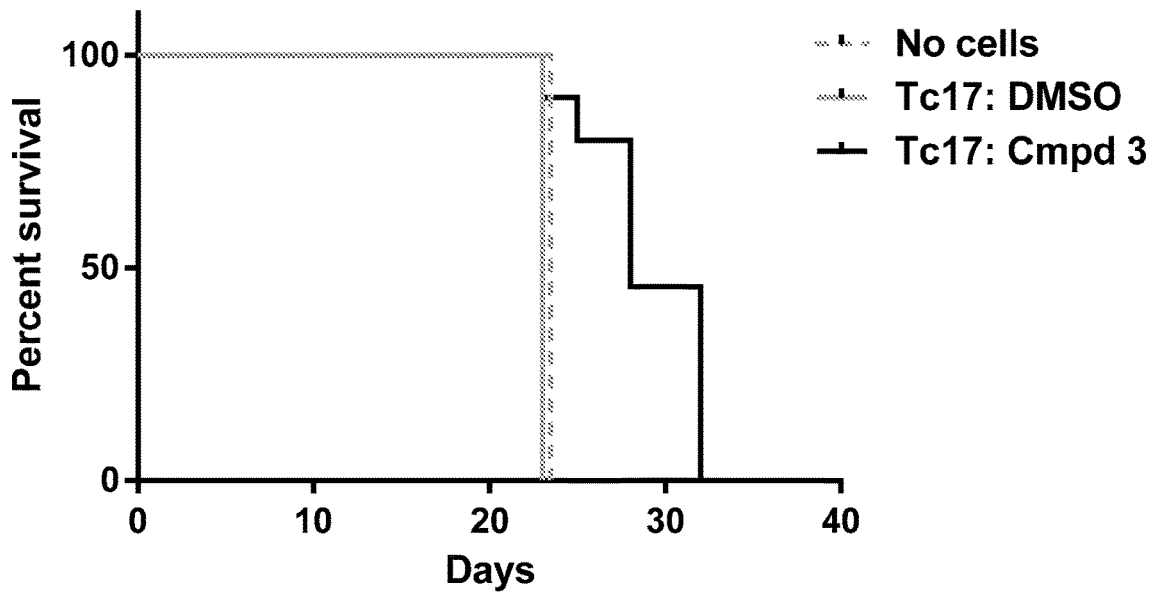

Experimental results are shown in FIGS. 1 and 2. FIG. 1 provides line graphs of results from an assay evaluating change in tumor volume over time in (i) mice bearing EG7 tumors that have been exposed to Tc17 cells, where the Tc17 cells have been exposed ex vivo to RORγ agonist compound 1 or 2, (ii) mice bearing EG7 tumors that have been exposed to Tc17 cells, where the Tc17 cells have been exposed ex vivo to DMSO but not to an RORγ agonist compound, and (iii) mice bearing EG7 tumors where Tc17 cells have not been administered to the mice. Part A provides results for tumors exposed to Tc17 cells previously exposed ex vivo to RORγ agonist compound 1 at a concentration of 10 μM, and provides results from control assays where * indicates $p<0.004$ vs. DMSO treated Tc17 cells. Part B provides results for tumors exposed to Tc17 cells previously exposed ex vivo to RORγ agonist compound 2 at a concentration of 5 μM, and provides results from control assays where * indicates $p<0.002$ vs. DMSO treated Tc17 cells.

FIG. 2 provides graphs showing results from an assay evaluating change in tumor volume over time and mouse survival rates for (i) mice bearing EG7 tumors that have been exposed to Tc17 cells, where the Tc17 cells have been exposed ex vivo to RORγ agonist compound 3, (ii) mice bearing EG7 tumors that have been exposed to Tc17 cells, where the Tc17 cells have been exposed ex vivo to DMSO but not to an RORγ agonist compound, and (iii) mice bearing EG7 tumors where Tc17 cells have not been administered to the mice. Part A provides results for tumors exposed to Tc17 cells previously exposed ex vivo to RORγ agonist compound 3 at a concentration of 5 μM, and provides results from control assays where * indicates $p<0.03$ vs. DMSO treated Tc17 cells. Part B shows percent survival of the mice over the duration of the experiment using compound 3. Data in FIG. 2 demonstrate that adoptive transfer of Tc17 cells treated ex vivo with compound 3 increases percent survival of mice having an EG7 tumor. The structure of compounds 1, 2, and 3 are provided in Table 1 in Example 4.

Example 6—Treatment of B16F10 Tumors Using Adoptively Transferred Lymphocyte Cells Treated Ex Vivo with an RORγ Agonist B16F10 tumors in mice were treated using adoptively transferred lymphocyte cells that been treated ex vivo with an RORγ agonist. Experimental procedures and results are described below.

Part I—Procedures for Adoptive Transfer of Cells to Mice Bearing a B16F10 Tumor Splenocytes from Trp1 transgenic as well as C57BL/6 mice were isolated. Briefly, spleens were homogenized, passed through a 70 μm filter and washed with phosphate buffered saline (PBS). Red blood cells were lysed by incubating splenocytes in an ACK solution (i.e., an aqueous solution of ammonium chloride and potassium bicarbonate, such as 155 mM ammonium chloride and 10 mM potassium bicarbonate) on ice for 5 minutes. Cells were washed twice with PBS and resuspended in RPMI 1640 media supplemented with 10% fetal bovine serum, glutamine, and penicillin/streptomycin at a ratio of 5:1 Trp1 to C57BL/6 splenocytes.

To obtain CD4+Th0 T lymphocytes, Trp1 splenocytes were cultured with irradiated C57BL/6 splenocytes in the presence of 100 IU/ml IL-2 and Trp1 peptide. For assays measuring the effect of Compound 3, Compound 3 was added to the culture media to achieve a 10 μM concentration of Compound 3. The culture was performed for seven days at a temperature of 37° C. in a humidified $CO_2$ incubator. Compound 3 has the following structure:

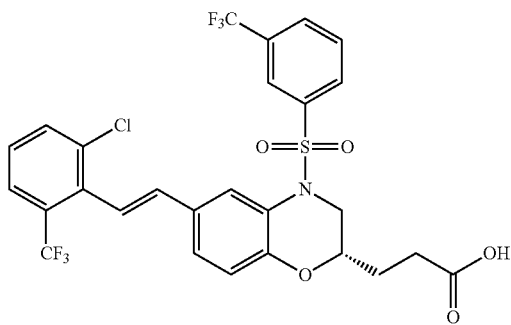 [SMILES: O=C(O)CC[C@H]1CN(S(=O)(=O)c2cccc(C(F)(F)F)c2)c2cc(/C=C/c3c(Cl)cccc3C(F)(F)F)ccc2O1]

Figure 3:
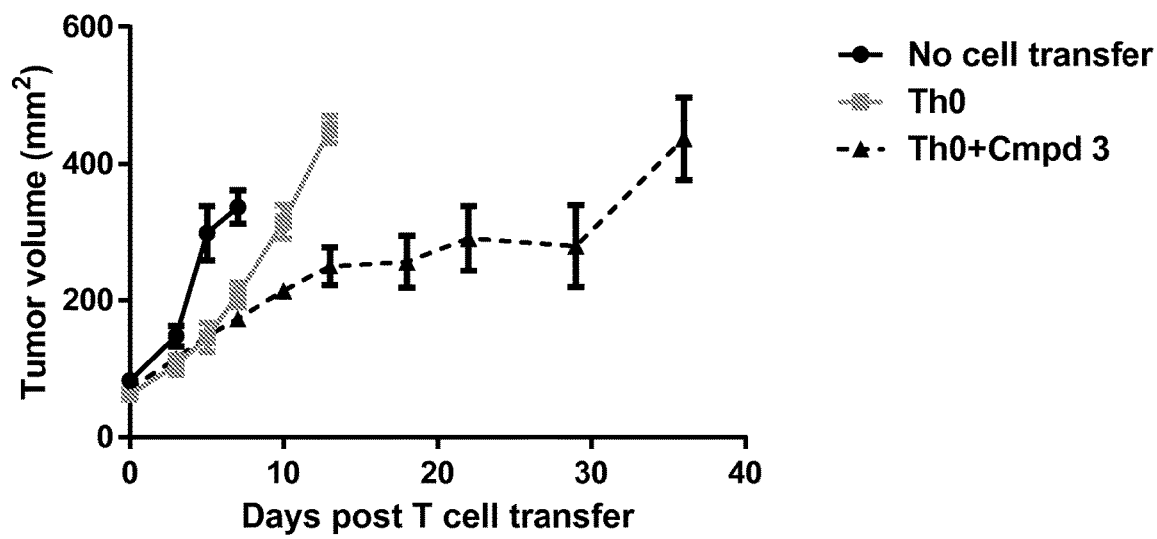
FIG. 3 provides graphs showing results from an assay evaluating change in tumor volume over time and mouse survival rates for mice bearing a B16F10 tumor that have been exposed to Th0 cells, where the Th0 cells have been exposed ex vivo to RORγ agonist Compound 3, and showing results from control assays as further described in Example 6.
Figure 3:
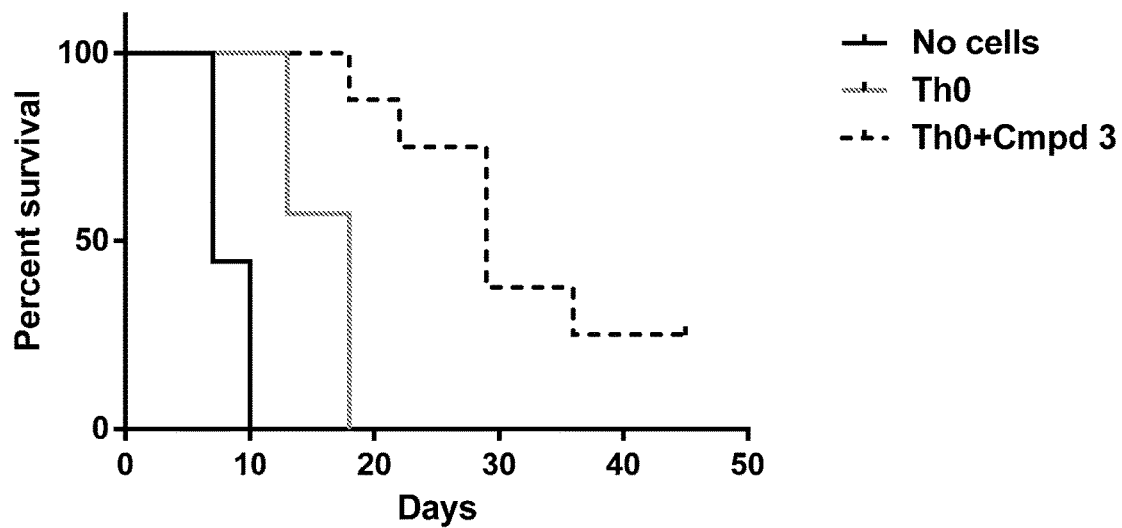

Cells were expanded for 7 days in the presence of 100 IU/ml of IL-2, peptide, and Compound 3. Next, approximately 250,000 cells were injected intraperitoneally into mice bearing a B16F10 tumor of approximately 50-100 mm² in size. The carrier liquid when injecting the cells was phosphate buffered saline. Tumor volume was monitored twice a week for the duration of the study (FIG. 3). Ethical tumor volume limit was set at 400 mm² which established the time of death for survival purposes.

Figure 4:
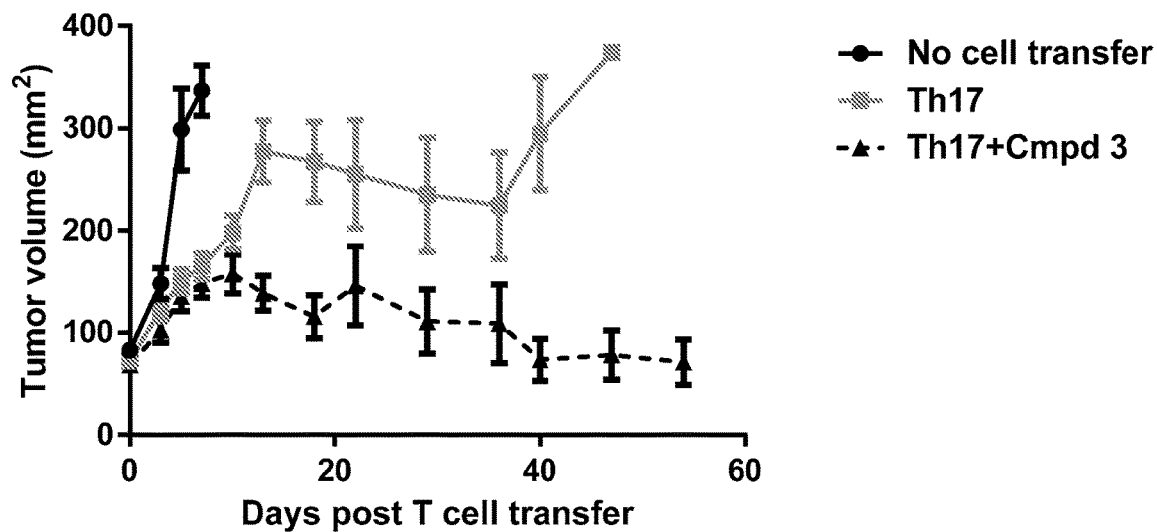
FIG. 4 provides graphs showing results from an assay evaluating change in tumor volume over time and mouse survival rates for mice bearing a B16F10 tumor that have been exposed to Th17 cells, where the Th17 cells have been exposed ex vivo to RORγ agonist Compound 3, and showing results from control assays as further described in Example 6.
Figure 4:
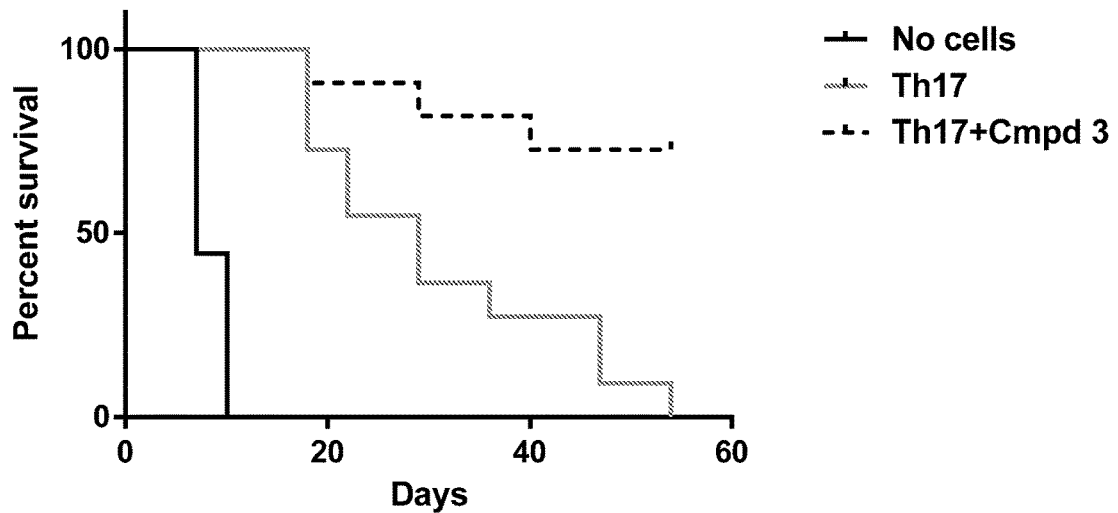

A similar protocol was employed to generate Th17-polarized CD4+ T lymphocytes with the modification that the resulting Trp1 splenocytes and C57BL/6 splenocytes were co-cultured in the presence of Trp1 peptide, 30 ng/ml human TGFβ1, 100 ng/ml human IL-6, 10 ng/ml human IL-1β, 100 ng/ml human IL-21, 10 μg/ml anti-mouse IFNγ and 10 μg/ml anti-mouse IL-4. For assays measuring the effect of Compound 3, Compound 3 was added to the culture media to achieve a concentration of 10 μM of Compound 3. Cells were cultured for 7 days in the presence of 100 IU/ml IL-2. Approximately, 250,000 cells were injected intraperitoneally into mice bearing B16F10 tumors of approximately 50-100 mm² in size. Tumor volume was monitored twice a week for the duration of the study (FIG. 4).

Figure 5:
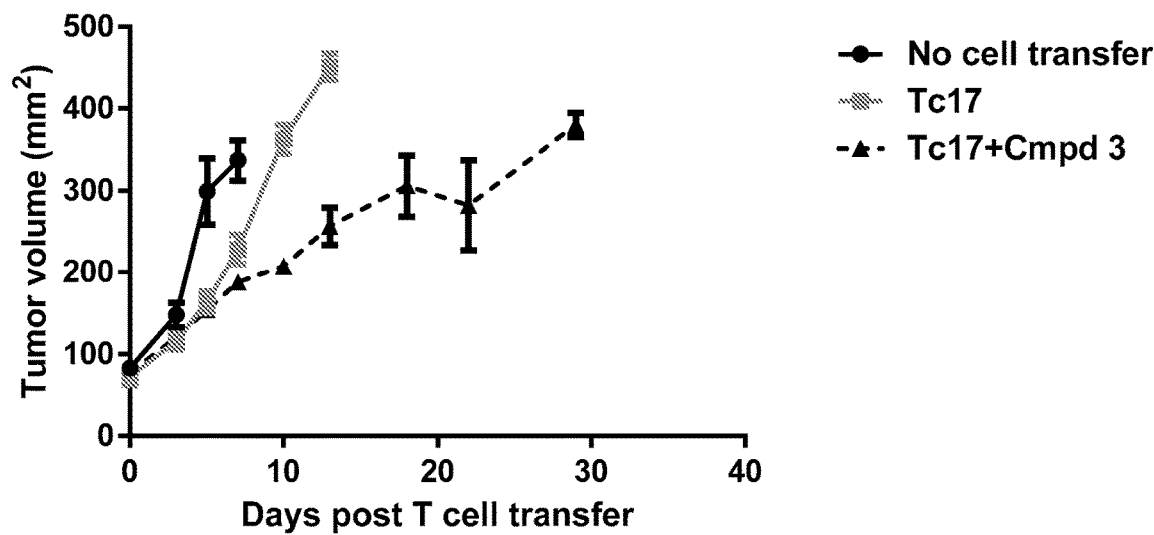
FIG. 5 provides graphs showing results from an assay evaluating change in tumor volume over time and mouse survival rates for mice bearing a B16F10 tumor that have been exposed to Tc17 cells, where the Tc17 cells have been exposed ex vivo to RORγ agonist Compound 3, and showing results from control assays as further described in Example 6.
Figure 5:
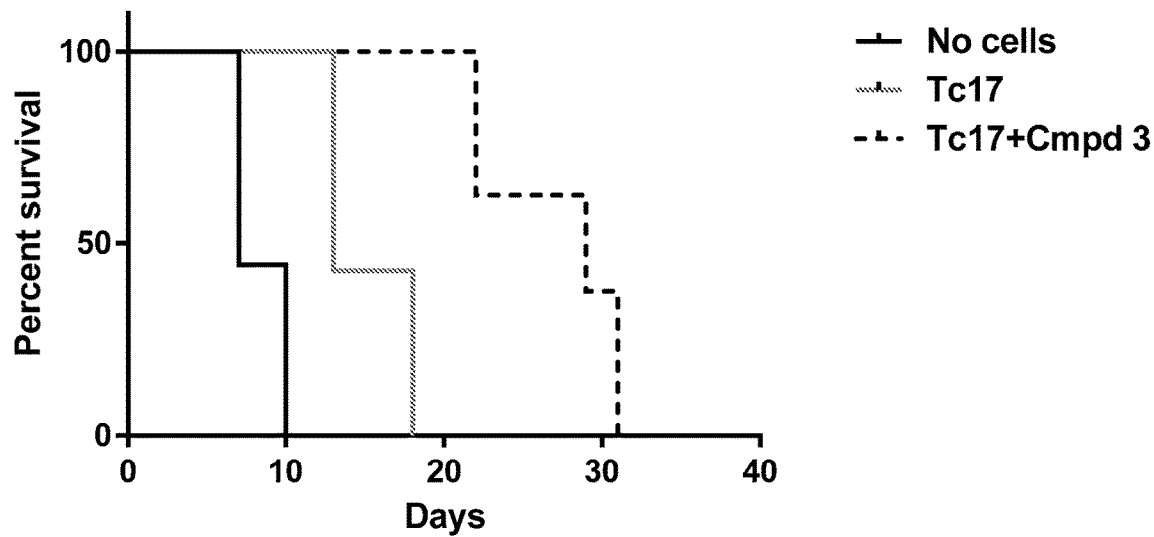

To generate CD8+Tc17 T lymphocytes, the same protocol was employed as per the Th17 cells except splenocytes from PMEL1 mice were used (FIG. 5).

Figure 6:
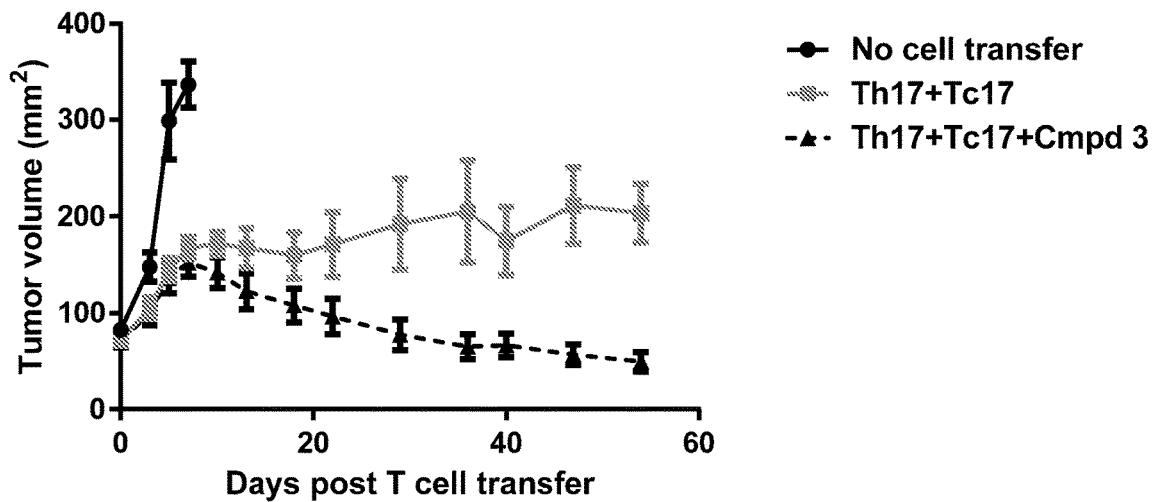
FIG. 6 provides graphs showing results from an assay evaluating change in tumor volume over time and mouse survival rates for mice bearing a B16F10 tumor that have been exposed to a mixture of Th17 cells and Tc17 cells, where the mixture of Th17 cells and Tc17 cells have been exposed ex vivo to RORγ agonist Compound 3, and showing results from control assays as further described in Example 6.
Figure 6:
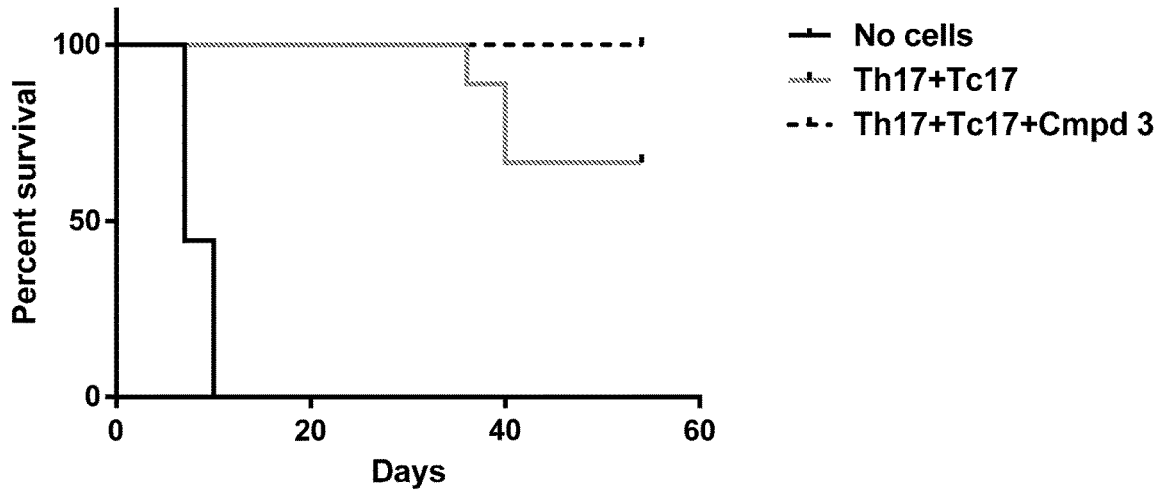

Co-transfer of approximately 125,000 Th17 and 125,000 Tc17 cells exposed to Compound 3 also was performed (FIG. 6).

Part II—Results

Experimental results are shown in FIGS. 3-6, which depict change in tumor volume over the duration of the experiment and percent survival statistics for the mice. FIG. 3 provides line graphs showing results from an assay evaluating change in tumor volume over time and mouse survival rates for (i) mice bearing a B16F10 tumor that have been exposed to Th0 cells, where the Th0 cells have been exposed ex vivo to RORγ agonist Compound 3, (ii) mice bearing a B16F10 tumor that have been exposed to Th0 cells, where the Th0 cells have not been exposed ex vivo to RORγ agonist Compound 3, and (iii) mice bearing a B16F10 tumor where Th0 cells have not been administered to the mice. The data show that percent survival of the mice was better in mice that received Th0 cells exposed ex vivo to RORγ agonist Compound 3 than mice receiving Th0 cells that had not been exposed ex vivo to the RORγ agonist Compound 3. Also, tumor volume was less at, for example, days 10, 20, and 30 post-administration of cells to the tumor in mice that received Th0 cells exposed ex vivo to the RORγ agonist Compound 3 than mice receiving Th0 cells that had not been exposed ex vivo to the RORγ agonist Compound 3.

FIG. 4 provides line graphs showing results from an assay evaluating change in tumor volume over time and mouse survival rates for (i) mice bearing a B16F10 tumor that have been exposed to Th17 cells, where the Th17 cells have been exposed ex vivo to RORγ agonist Compound 3, (ii) mice bearing a B16F10 tumor that have been exposed to Th17 cells, where the Th17 cells have not been exposed ex vivo to an RORγ agonist compound, and (iii) mice bearing a B16F10 tumor where Th17 cells have not been administered to the mice. The data show that percent survival of the mice was better in mice that received Th17 cells exposed ex vivo to the RORγ agonist Compound 3 than mice receiving Th17 cells that had not been exposed ex vivo to the RORγ agonist Compound 3. Also, tumor volume was less at, for example, days 10, 20, and 30 post-administration of cells to the tumor in mice that received Th17 cells exposed ex vivo to the RORγ agonist Compound 3 than mice receiving Th17 cells that had not been exposed ex vivo to the RORγ agonist Compound 3.

FIG. 5 provides line graphs showing results from an assay evaluating change in tumor volume over time and mouse survival rates for (i) mice bearing a B16F10 tumor that have been exposed to Tc17 cells, where the Tc17 cells have been exposed ex vivo to RORγ agonist compound 3, (ii) mice bearing a B16F10 tumor that have been exposed to Tc17 cells, where the Tc17 cells have not been exposed ex vivo to an RORγ agonist compound, and (iii) mice bearing a B16F10 tumor where Tc17 cells have not been administered to the mice. The data show that percent survival of the mice was better in mice that received Tc17 cells exposed ex vivo to RORγ agonist Compound 3 than mice receiving Tc17 cells that had not been exposed ex vivo to the RORγ agonist Compound 3. Also, tumor volume was less at, for example, days 10, 20, and 30 post-administration of cells to the tumor in mice that received Tc17 cells exposed ex vivo to RORγ agonist Compound 3 than mice receiving Tc17 cells that had not been exposed ex vivo to the RORγ agonist Compound 3.

FIG. 6 provides graphs showing results from an assay evaluating change in tumor volume over time and mouse survival rates for (i) mice bearing a B16F10 tumor that have been exposed to a mixture of Th17 cells and Tc17 cells, where both the Th17 cells and the Tc17 cells had been exposed ex vivo to RORγ agonist compound 3, (ii) mice bearing a B16F10 tumor that have been exposed to a mixture of Th17 cells and Tc17 cells, where neither the Th17 nor the Tc17 cells had been exposed ex vivo to an RORγ agonist compound, and (iii) mice bearing a B16F10 tumor where neither Th17 nor Tc17 cells were administered to the mice. The data show that percent survival of the mice was better in mice that received the mixture of Th17 cells and Tc17 cells exposed ex vivo to RORγ agonist Compound 3 than mice receiving a mixture of Th17 cells and Tc17 cells that had not been exposed ex vivo to RORγ agonist Compound 3. Also, tumor volume was less at, for example, days 10, 20, and 30 post administration of cells to the tumor in mice that received a mixture of Th17 cells and Tc17 cells exposed ex vivo to the RORγ agonist Compound 3 than mice receiving a mixture of Th17 cells and Tc17 cells that had not been exposed ex vivo to the RORγ agonist Compound 3.

Example 7—Synthesis of (S)-2-(6-((2-Chloro-6-fluorophenoxy)methyl)-4-((3-(trifluoromethyl)phenyl)sulfonyl)-3,4-dihydro-2H-benzo[b][1,4]oxazin-2-yl)ethan-1-ol

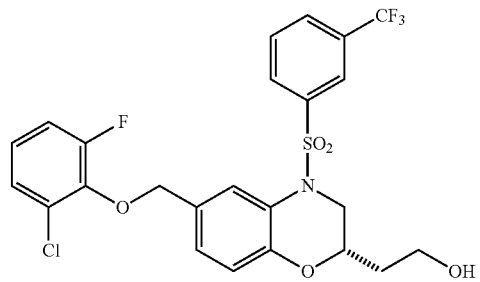 [SMILES: O=S(=O)(c1cccc(C(F)(F)F)c1)N1C[C@H](CCO)Oc2ccc(COc3c(F)cccc3Cl)cc21]

Part I—Synthesis of Methyl (R)-3-Nitro-4-((2-oxotetrahydrofuran-3-yl)oxy)benzoate

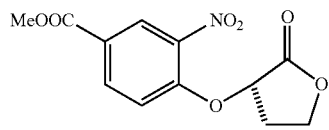 [SMILES: COC(=O)c1ccc(O[C@H]2CCOC2=O)c([N+](=O)[O-])c1]

Methyl 4-hydroxy-3-nitrobenzoate (2.0 g, 10.2 mmol), (3R)-3-hydroxytetrahydrofuran-2-one (1.036 g, 10.2 mmol), and triphenylphosphine (3.19 g, 12.2 mmol) were suspended in dichloromethane (25 mL), the reaction vessel was cooled in an ice bath, and diisopropyl azodicarboxylate (2.40 mL, 12.2 mmol) was added dropwise to the reaction mixture. The reaction mixture was stirred at room temperature for one hour, then washed with water, dried (Na$_2$SO$_4$), and concentrated. The concentrate was purified via MPLC (Two columns: the first column eluting first with dichloromethane, the second column to purify further eluting with a gradient of 15-70% ethyl acetate in hexanes) to afford methyl (R)-3-nitro-4-((2-oxotetrahydrofuran-3-yl)oxy)benzoate (2.15 g, 75%). $^1$H-NMR (400 MHz, DMSO-d$_6$) δ 8.38 (s, 1H), 8.20 (d, 1H), 7.62 (d, 1H), 5.71 (t, 1H), 4.44 (t, 1H), 4.28 (m, 1H), 3.84 (s, 3H), 2.80 (m, 1H), 2.35 (m, 1H).

Part II—Synthesis of Methyl (S)-2-(2-hydroxyethyl)-3-oxo-3,4-dihydro-2H-benzo[b][1,4]oxazine-6-carboxylate

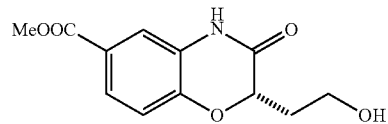

Methyl (R)-3-nitro-4-((2-oxotetrahydrofuran-3-yl)oxy)benzoate (2.15 g, 7.65 mmol) was dissolved in acetic acid (25 mL) and powdered iron (2.14 g, 38.2 mmol) was added. The reaction mixture was heated to 70° C. for two hours. Then, the suspension was filtered through a pad of Celite. The filtrate was partitioned between ethyl acetate and water. The organic phase was washed with saturated sodium bicarbonate, washed with brine, and then concentrated to provide a residue. The residue was purified via MPLC eluting with a gradient of 15-70% ethyl acetate in hexanes to afford methyl (S)-2-(2-hydroxyethyl)-3-oxo-3,4-dihydro-2H-benzo[b][1,4]oxazine-6-carboxylate. $^1$H-NMR (400 MHz, DMSO-d$_6$) δ 10.81 (bs, 1H), 7.52 (d, 1H), 7.47 (s, 1H), 7.02 (d, 1H), 4.75 (m, 1H), 4.63 (t, 1H), 3.78 (s, 3H), 3.55 (m, 2H), 1.95 (m, 1H), 1.80 (m, 1H).

Part III—Synthesis of Methyl (S)-2-(2-((tert-butyldimethylsilyl)oxy)ethyl)-3-oxo-3,4-dihydro-2H-benzo[b][1,4]oxazine-6-carboxylate

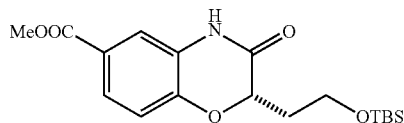 [SMILES: COC(=O)c1ccc2c(c1)NC(=O)[C@H](CCO[Si](C)(C)C(C)(C)C)O2]

Methyl (S)-2-(2-hydroxyethyl)-3-oxo-3,4-dihydro-2H-benzo[b][1,4]oxazine-6-carboxylate (1.24 g, 4.94 mmol), tert-butyldimethylsilyl chloride (0.967 g, 6.42 mmol), and imidazole (0.672 g, 9.87 mmol) were suspended in DMF (16 mL), and stirred at room temperature overnight. The resulting mixture was partitioned between water and ethyl acetate, and the organic layer was washed twice with water, washed with brine, dried (Na$_2$SO$_4$), and concentrated to provide a residue. The residue was purified via MPLC, eluting with a gradient of 5-30% ethyl acetate in hexanes to afford methyl (S)-2-(2-((tert-butyldimethylsilyl)oxy)ethyl)-3-oxo-3,4-dihydro-2H-benzo[b][1,4]oxazine-6-carboxylate (1.20 g, 67%). ¹H-NMR (400 MHz, DMSO-d₆) δ 10.82 (bs, 1H), 7.52 (d, 1H), 7.46 (s, 1H), 7.01 (d, 1H), 4.70 (m, 1H), 3.79 (s, 3H), 3.73 (m, 2H), 2.00 (m, 1H), 1.87 (m, 1H), 0.81 (s, 9H), 0.00 (s, 6H).

Part IV—Synthesis of (S)-2-(6-(Hydroxymethyl)-3,4-dihydro-2H-benzo[b][1,4]oxazin-2-yl)ethan-1-ol

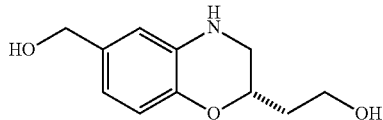 [SMILES: OCC[C@H]1CNc2cc(CO)ccc2O1]

Methyl (S)-2-(2-((tert-butyldimethylsilyl)oxy)ethyl)-3-oxo-3,4-dihydro-2H-benzo[b][1,4]oxazine-6-carboxylate (1.2 g, 3.283 mmol) was dissolved in anhydrous THF (16 mL) and a 1M solution of lithium aluminum hydride in ether (13.1 mL, 13.1 mmol) was added. The mixture was heated in an oil bath at 50° C. overnight. Then, the crude mixture was carefully treated with water (0.5 mL), 15% NaOH (0.5 mL), and then treated again with water (1.5 mL). The resulting mixture was stirred vigorously for several minutes and then filtered. The filtrate was concentrated onto silica gel and purified by MPLC delivering (S)-2-(6-(hydroxymethyl)-3,4-dihydro-2H-benzo[b][1,4]oxazin-2-yl)ethan-1-ol as a clear oil (0.62 g, 90%). ¹H-NMR (400 MHz, DMSO-d₆) δ 6.51 (m, 2H), 6.36 (d, 1H), 5.65 (bs, 1H), 4.85 (t, 1H), 4.51 (t, 1H), 4.23 (d, 2H), 4.02 (m, 1H), 3.53 (m, 2H), 3.27 (m, 1H), 2.92 (m, 1H), 1.67 (m, 2H).

Part V—Synthesis of (S)-2-(6-(Hydroxymethyl)-4-((3-(trifluoromethyl)phenyl)sulfonyl)-3,4-dihydro-2H-benzo[b][1,4]oxazin-2-yl)ethan-1-ol

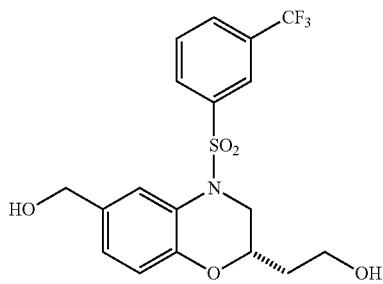 [SMILES: O=S(=O)(c1cccc(C(F)(F)F)c1)N1C[C@H](CCO)Oc2ccc(CO)cc21]

(S)-2-(6-(Hydroxymethyl)-3,4-dihydro-2H-benzo[b][1,4]oxazin-2-yl)ethan-1-ol (0.62 g, 2.96 mmol) and 3-(trifluoromethyl)benzenesulfonyl chloride (1.812 g, 7.408 mmol) were suspended in acetone (30 mL), and potassium carbonate (1.23 g, 8.89 mmol) was added. The mixture was stirred at room temperature overnight. Then, the crude mixture was then filtered, and the filtrate was concentrated onto silica gel and purified by MPLC affording (5)-2-(6-(hydroxymethyl)-4-((3-(trifluoromethyl)phenyl)sulfonyl)-3,4-dihydro-2H-benzo[b][1,4]oxazin-2-yl)ethan-1-ol (0.8 g, 65%). ¹H-NMR (400 MHz, DMSO-d₆) δ 8.06 (d, 1H), 7.92 (m, 2H), 7.80 (t, 1H), 7.64 (s, 1H), 6.98 (d, 1H), 6.73 (d, 1H), 5.15 (t, 1H), 4.55 (t, 1H), 4.39 (m, 3H), 3.43 (m, 3H), 3.26 (m, 1H), 1.61 (m, 2H).

Part VI—Synthesis of (S)-2-(6-((2-Chloro-6-fluorophenoxy)methyl)-4-((3-(trifluoromethyl)phenyl)sulfonyl)-3,4-dihydro-2H-benzo[b][1,4]oxazin-2-yl)ethan-1-ol

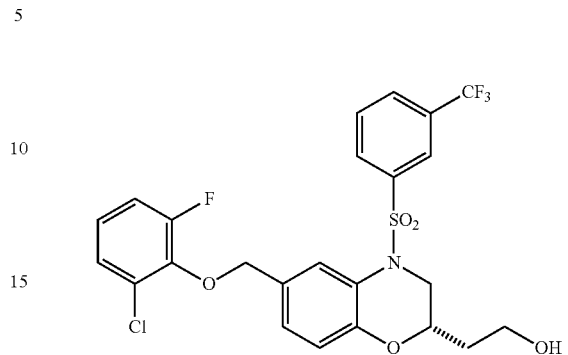

(S)-2-(6-(Hydroxymethyl)-4-((3-(trifluoromethyl)phenyl)sulfonyl)-3,4-dihydro-2H-benzo[b][1,4]oxazin-2-yl)ethan-1-ol (0.1 g, 0.24 mmol), 2-chloro-6-fluorophenol (0.035 g, 0.24 mmol), and triphenylphosphine (0.075 g, 0.287 mmol) were suspended in dichloromethane (3 mL), and diisopropylazodicarboxylate (0.057 mL, 0.287 mmol) was added dropwise. The reaction mixture was stirred at room temperature for one hour, washed with water, dried (Na₂SO₄) and concentrated to provide a residue. The residue was purified by MPLC twice (2 columns: first, eluting with a gradient of 10-40% ethyl acetate in hexanes; second eluting with dichloromethane) to afford (S)-2-(6-((2-chloro-6-fluorophenoxy)methyl)-4-((3-(trifluoromethyl)phenyl)sulfonyl)-3,4-dihydro-2H-benzo[b][1,4]oxazin-2-yl)ethan-1-ol (0.125 g, 89%). ¹H-NMR (400 MHz, DMSO-d₆) δ 8.07 (d, 1H), 7.93 (s, 1H), 7.84 (d, 1H), 7.78 (m, 2H), 7.27 (m, 2H), 7.13 (m, 2H), 6.81 (d, 1H), 5.05 (s, 2H), 4.56 (t, 1H), 4.40 (d, 1H), 3.43 (m, 3H), 3.25 (m, 1H), 1.64 (m, 2H).

Example 8—Synthesis of (S)-2-(6-((2-Chloro-6-fluorophenoxy)methyl)-4-((3-(trifluoromethyl)phenyl)sulfonyl)-3,4-dihydro-2H-benzo[b][1,4]oxazin-2-yl)acetic acid

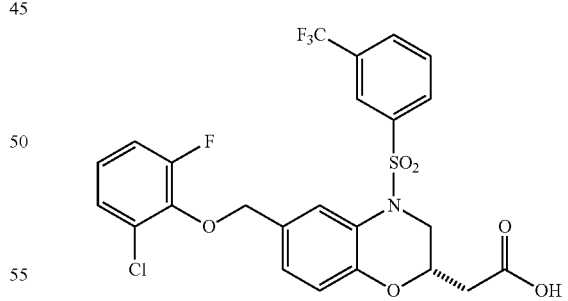

(S)-2-(6-((2-Chloro-6-fluorophenoxy)methyl)-4-((3-(trifluoromethyl)phenyl) sulfonyl)-3,4-dihydro-2H-benzo[b][1,4]oxazin-2-yl)ethan-1-ol (30 mg, 0.055 mmol) was dissolved in acetone (2 mL) and Jones' reagent was added dropwise until the orange color remained. Then, isopropyl alcohol was added dropwise until the orange color was gone. Next, the solution was decanted, and concentrated, then re-dissolved in methanol and purified by preparative HPLC eluting with a gradient of water (containing 0.05% trifluoroacetic acid) and acetonitrile to afford (S)-2-(6-((2-chloro- 6-fluorophenoxy)methyl)-4-((3-(trifluoromethyl)phenyl)sulfonyl)-3,4-dihydro-2H-benzo[b][1,4]oxazin-2-yl)acetic acid (10 mg, 33%) as a white solid. ¹H-NMR (400 MHz, DMSO-d₆) δ 8.10 (m, 1H), 7.96 (s, 1H), 7.81 (m, 3H), 7.27 (m, 2H), 7.13 (m, 2H), 6.80 (d, 1H), 6.49 (bs, 1H), 5.04 (s, 2H), 4.45 (d, 1H), 3.63 (m, 1H), 3.33 (m, 1H), 2.78 (dd, 1H), 2.58 (dd, 1H).

Example 9—Synthesis of (S)-3-(6-(2-Chloro-6-fluorophenethyl)-4-((3-(trifluoromethyl)phenyl)sulfonyl)-3,4-dihydro-2H-benzo[b][1,4]oxazin-2-yl)propanenitrile

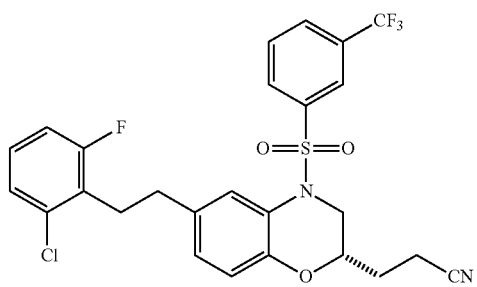 [SMILES: N#CCC[C@H]1CN(S(=O)(=O)c2cccc(C(F)(F)F)c2)c2cc(CCc3c(F)cccc3Cl)ccc2O1]

Part I—Synthesis of (R)-3-(4-Bromo-2-nitrophenoxy)dihydrofuran-2(3H)-one

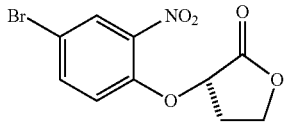 [SMILES: O=C1OCC[C@@H]1Oc1ccc(Br)cc1[N+](=O)[O-]]

4-Bromo-2-nitrophenol (3 g, 13.76 mmol), (3R)-3-hydroxytetrahydrofuran-2-one (1.405 g, 13.76 mmol), and triphenylphosphine (4.33 g, 16.51 mmol) were suspended in dichloromethane (36 mL), and diisopropylazodicarboxylate (3.25 mL, 16.5 mmol) was added dropwise. The reaction mixture was stirred at room temperature for one hour, washed with water, dried (Na₂SO₄), and concentrated onto silica gel. The residue on the silica gel was purified by MPLC (2 columns: first, dichloromethane; second, a gradient of EtOAc/hexanes) affording (R)-3-(4-bromo-2-nitrophenoxy)dihydrofuran-2(3H)-one as a white solid (1.93 g, 46%). ¹H-NMR (400 MHz, DMSO-d₆) δ 8.12 (s, 1H), 7.86 (d, 1H), 7.47 (d, 1H), 5.55 (t, 1H), 4.42 (m, 1H), 4.26 (m, 1H), 2.75 (m, 1H), 2.30 (m, 1H).

Part II—Synthesis of (S)-6-Bromo-2-(2-hydroxyethyl)-2H-benzo[b][1,4]oxazin-3(4H)-one

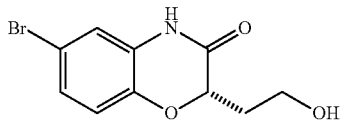 [SMILES: O=C1Nc2cc(Br)ccc2O[C@H]1CCO]

(R)-3-(4-Bromo-2-nitrophenoxy)dihydrofuran-2(3H)-one (1.93 g, 6.39 mmol) was dissolved in acetic acid and powdered iron (1.784 g, 31.95 mmol) was added. The resulting mixture was heated to 70° C. for two hours. The resulting suspension was filtered through a pad of Celite, and the pad was washed with ethyl acetate. The combined filtrates were partitioned between ethyl acetate and water, and the organic phase was washed a second time with water, washed with brine, and concentrated to provide a residue. The residue was purified via MPLC eluting with a gradient of 15-70% ethyl acetate in hexanes to afford (S)-6-bromo-2-(2-hydroxyethyl)-2H-benzo[b][1,4]oxazin-3(4H)-one as a white solid (1.32 g, 76%). ¹H-NMR (400 MHz, DMSO-d₆) δ 10.73 (bs, 1H), 7.04 (d, 1H), 6.98 (s, 1H), 6.90 (d, 1H), 4.62 (m, 2H), 3.53 (m, 2H), 1.91 (m, 1H), 1.88 (m, 1H).

Part III—Synthesis of (S)-2-(6-Bromo-3,4-dihydro-2H-benzo[b][1,4]oxazin-2-yl)ethan-1-ol

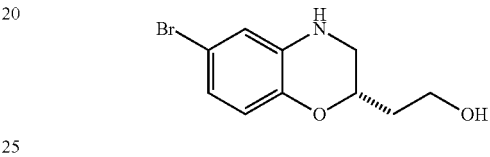

(S)-6-Bromo-2-(2-hydroxyethyl)-2H-benzo[b][1,4]oxazin-3(4H)-one (1.32 g, 4.85 mmol) was dissolved in anhydrous THF (49 mL) under nitrogen at ambient temperature and borane-dimethylsulfide complex (1.47 g, 19.41 mmol) was added dropwise. The reaction mixture was heated to reflux for 90 minutes. Then, the reaction mixture was cooled in an ice bath and subsequently methanol was added to the reaction mixture to quench the reaction. The resulting solution was heated to reflux for 20 minutes, and then concentrated to provide a residue. The residue was partitioned between ethyl acetate and water, washed with brine, dried (Na₂SO₄), and concentrated to provide crude product. The crude product was purified by MPLC eluting with a gradient of 15-70% ethyl acetate in hexanes to afford (S)-2-(6-bromo-3,4-dihydro-2H-benzo[b][1,4]oxazin-2-yl)ethan-1-ol (1.05 g, 84%).

Part IV—Synthesis of (S)-6-Bromo-2-(2-((tert-butyldimethylsilyl)oxy)ethyl)-3,4-dihydro-2H-benzo[b][1,4]oxazine

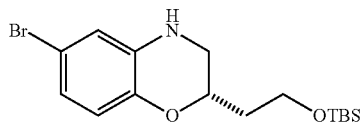 [SMILES: CC(C)(C)[Si](C)(C)OCC[C@H]1CNc2cc(Br)ccc2O1]

(S)-2-(6-Bromo-3,4-dihydro-2H-benzo[b][1,4]oxazin-2-yl)ethan-1-ol (0.28 g, 1.085 mmol), tert-butyldimethylchlorosilane (0.196 g, 1.302 mmol), and imidazole (0.148 g, 2.17 mmol) were dissolved in DMF (4 mL), and the reaction mixture was stirred at room temperature overnight. Next, the reaction mixture was partitioned between water and ethyl acetate, and the organic layer was washed twice more with water, washed with brine, dried (Na₂SO₄), and concentrated onto silica gel. The residue on the silica gel was purified by MPLC eluting with a gradient of 5-30% ethyl acetate in hexanes to afford (S)-6-bromo-2-(2-((tert-butyldimethylsilyl)oxy)ethyl)-3,4-dihydro-2H-benzo[b][1,4]oxazine (0.19 g, 47%). ¹H-NMR (400 MHz, DMSO-d₆) δ 6.66 (s, 1H), 6.52 (s, 2H), 6.06 (bs, 1H), 4.02 (q, 1H), 3.72 (m, 2H), 3.33 (m, 1H), 2.94 (m, 1H), 1.70 (q, 2H), 0.82 (s, 9H), 0.01 (s, 6H).

Part V—Synthesis of (S)-2-(6-Bromo-4-((3-(trifluoromethyl)phenyl)sulfonyl)-3,4-dihydro-2H-benzo[b][1,4]oxazin-2-yl)ethan-1-ol

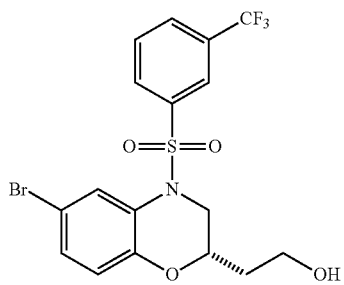 [SMILES: O=S(=O)(c1cccc(C(F)(F)F)c1)N1C[C@H](CCO)Oc2ccc(Br)cc21]

(S)-6-Bromo-2-(2-((tert-butyldimethylsilyl)oxy)ethyl)-3,4-dihydro-2H-benzo[b][1,4]oxazine (1.04 g, 2.79 mmol), 3-(trifluoromethyl)benzenesulfonyl chloride (1.025 g, 4.19 mmol), and potassium carbonate (0.772 g, 5.586 mmol) were suspended in acetone (28 mL), and the mixture was shaken at room temperature for 18 hours. The crude material was filtered, and the filtrate was concentrated onto silica gel and purified by chromatography delivering (S)-2-(6-bromo-4-((3-(trifluoromethyl)phenyl)sulfonyl)-3,4-dihydro-2H-benzo[b][1,4]oxazin-2-yl)ethan-1-ol (1.61 g, 99%). It is noted that the silyl protecting group did not hydrolyze immediately, but after several days at room temperature degradation to the alcohol was observed. $^1$H-NMR (400 MHz, DMSO-$d_6$) δ 8.11 (d, 1H), 7.95 (m, 2H), 7.84 (t, 1H), 7.78 (s, 1H), 7.25 (d, 1H), 6.80 (d, 1H), 4.56 (s, 1H), 3.39 (d, 1H), 3.41 (m, 3H), 3.28 (m, 1H), 1.63 (m, 2H).

Part VI—Synthesis of (S)-2-(6-Bromo-4-((3-(trifluoromethyl)phenyl)sulfonyl)-3,4-dihydro-2H-benzo[b][1,4]oxazin-2-yl)ethyl 4-methylbenzenesulfonate

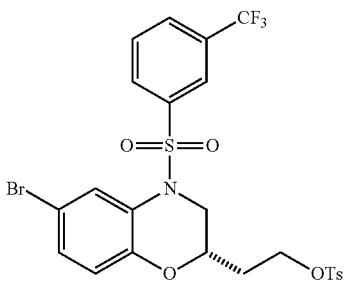 [SMILES: Cc1ccc(S(=O)(=O)OCC[C@H]2CN(S(=O)(=O)c3cccc(C(F)(F)F)c3)c3cc(Br)ccc3O2)cc1]

(S)-2-(6-Bromo-4-((3-(trifluoromethyl)phenyl)sulfonyl)-3,4-dihydro-2H-benzo[b][1,4]oxazin-2-yl)ethan-1-ol (0.13 g, 0.28 mmol) was dissolved in dichloromethane (6 mL) and triethylamine (0.058 mL, 0.42 mmol) was added followed by tosyl chloride (0.056 g, 0.293 mmol). The reaction mixture was stirred at room temperature overnight. Then, an additional 56 mg of tosyl chloride and triethylamine (60 μL) were added, and the reaction mixture was stirred for one additional day. Then, the crude solution was washed with dilute HCl, washed with brine, dried (Na$_2$SO$_4$), and concentrated onto silica gel for purification by chromatography to afford (S)-2-(6-bromo-4-((3-(trifluoromethyl)phenyl)sulfonyl)-3,4-dihydro-2H-benzo[b][1,4]oxazin-2-yl)ethyl 4-methylbenzenesulfonate as a white solid (0.14 g, 81%). $^1$H-NMR (400 MHz, DMSO-$d_6$) δ 8.12 (d, 1H), 7.98 (m, 2H), 7.87 (t, 1H), 7.76 (s, 1H), 7.59 (d, 2H), 7.33 (d, 2H), 7.24 (dd, 1H), 6.54 (d, 1H), 4.33 (dd, 1H), 4.08 (m, 1H), 4.00 (m, 1H), 3.24 (m, 2H), 2.32 (s, 3H), 1.97 (m, 1H), 1.70 (m, 1H).

Part VII—Synthesis of (S)-3-(6-Bromo-4-((3-(trifluoromethyl)phenyl)sulfonyl)-3,4-dihydro-2H-benzo[b][1,4]oxazin-2-yl)propanenitrile

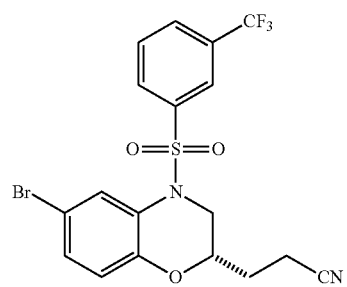

(S)-2-(6-Bromo-4-((3-(trifluoromethyl)phenyl)sulfonyl)-3,4-dihydro-2H-benzo[b][1,4]oxazin-2-yl)ethyl 4-methylbenzenesulfonate (0.14 g, 0.226 mmol) was dissolved in DMSO (1 mL) and potassium cyanide (0.016 g, 0.248 mmol) was added. After one hour, additional potassium cyanide (17 mg) was added, and stirring was continued overnight. Then, the crude material was then partitioned between water and ethyl acetate. The organic phase was washed a second time, then washed with brine, dried (Na$_2$SO$_4$), and concentrated to afford (S)-3-(6-bromo-4-((3-(trifluoromethyl)phenyl)sulfonyl)-3,4-dihydro-2H-benzo[b][1,4]oxazin-2-yl)propanenitrile (0.09 g, 84%). $^1$H-NMR (400 MHz, DMSO-$d_6$) δ 8.09 (d, 1H), 8.00 (m, 2H), 7.84 (t, 1H), 7.78 (s, 1H), 7.27 (d, 1H), 6.82 (d, 1H), 4.40 (d, 1H), 3.37 (m, 2H), 2.56 (m, 2H), 1.92 (m, 1H), 1.72 (m, 1H).

Part VIII—Synthesis of (S)-3-(6-(2-Chloro-6-fluorophenethyl)-4-((3-(trifluoromethyl)phenyl)sulfonyl)-3,4-dihydro-2H-benzo[b][1,4]oxazin-2-yl)propanenitrile

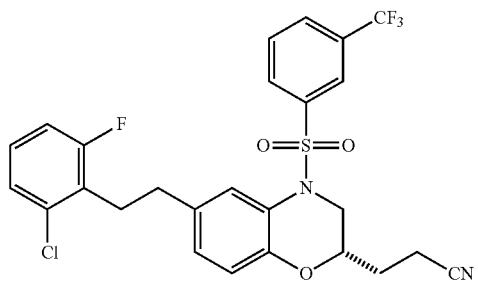 [SMILES: N#CCC[C@H]1CN(S(=O)(=O)c2cccc(C(F)(F)F)c2)c2cc(CCc3c(F)cccc3Cl)ccc2O1]

1-Chloro-3-fluoro-2-vinylbenzene (40 mg, 0.257 mmol) was dissolved in THF (2 mL) and the solution was cooled in an ice bath. A 0.5 M solution of 9-borabicyclo[3.3.1]nonane in toluene (0.52 mL, 0.26 mmol) was then added, and the reaction mixture was stirred at room temperature for five hours. (S)-3-(6-Bromo-4-((3-(trifluoromethyl)phenyl)sulfonyl)-3,4-dihydro-2H-benzo[b][1,4]oxazin-2-yl)propanenitrile (61 mg, 0.129 mmol) was mixed with triethylamine (0.027 mL, 0.193 mmol), and [1,1'-bis(diphenylphosphino) ferrocene] dichloropalladium (II) complex with dichloromethane (10 mg, 0.013 mmol) in degassed DMF (1.9 mL) and water (0.19 mL). The olefin solution was then added, and the reaction mixture was heated to 50° C. overnight. Next, the reaction mixture was cooled to room temperature, and partitioned between water and ethyl acetate. The organic phase was washed with brine, dried ($Na_2SO_4$), and concentrated to provide a residue. The residue was purified by MPLC eluting with a gradient of 10-40% ethyl acetate in hexanes to afford (S)-3-(6-(2-chloro-6-fluorophenethyl)-4-((3-(trifluoromethyl)phenyl)sulfonyl)-3,4-dihydro-2H-benzo[b][1,4]oxazin-2-yl)propanenitrile (20 mg, 28%). $^1$H-NMR (400 MHz, DMSO-$d_6$) δ 8.07 (d, 1H), 7.94 (m, 2H), 7.82 (t, 1H), 7.47 (s, 1H), 7.28 (m, 2H), 7.15 (m, 1H), 6.86 (dd, 1H), 6.73 (d, 1H), 4.39 (d, 1H), 3.33 (m, 2H), 2.92 (t, 2H), 2.73 (t, 2H), 2.56 (m, 2H), 1.92 (m, 1H), 1.73 (m, 1H).

Example 10—Synthesis of (S,E)-3-(6-(2-(2-Chloro-6-fluorophenyl)prop-1-en-1-yl)-4-((3-(trifluoromethyl)phenyl)sulfonyl)-3,4-dihydro-2H-benzo[b][1,4]oxazin-2-yl)propanenitrile

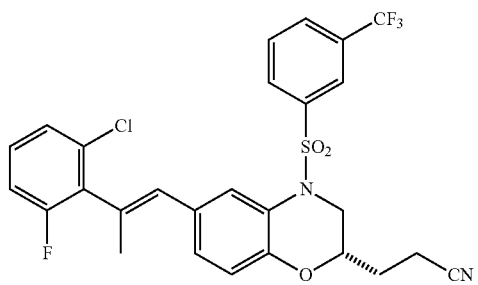 [SMILES: C/C(=C\c1ccc2c(c1)N(S(=O)(=O)c1cccc(C(F)(F)F)c1)C[C@H](CCC#N)O2)c1c(F)cccc1Cl]

Part I—Synthesis of 1-Chloro-2-ethynyl-3-fluorobenzene

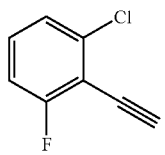

2-Chloro-6-fluorobenzaldehyde (2 g, 12.61 mmol) was dissolved in methanol (84 mL), and dimethyl (diazomethyl) phosphonate (2.39 mL, 15.77 mmol) was added followed by potassium carbonate (4.36 g, 31.53 mmol). The reaction mixture was stirred at room temperature overnight. Then, the crude mixture was diluted with methyl tert-butyl ether, washed with water, washed with brine, dried ($Na_2SO_4$), and concentrated to afford 1-chloro-2-ethynyl-3-fluorobenzene (1.83 g, 94%). $^1$H-NMR (400 MHz, DMSO-$d_6$) δ 7.45 (m, 2H), 7.32 (t, 1H), 4.86 (s, 1H).

Part II—Synthesis of (E)-2-(2-(2-Chloro-6-fluorophenyl)prop-1-en-1-yl)-4,4,5,5-tetramethyl-1,3,2-dioxaborolane

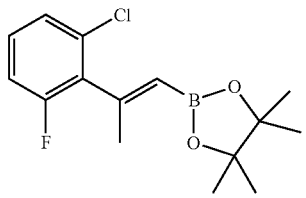 [SMILES: C/C(=C\B1OC(C)(C)C(C)(C)O1)c1c(F)cccc1Cl]

Bis(pinacolato)diborane (5.82 g, 22.92 mmol), copper (I) chloride (0.21 g, 2.08 mmol), and 4,5-bis(diphenylphosphino)-9,9-dimethylxanthene (1.21 g, 2.08 mmol) were suspended in THF (208 mL) and the mixture was degassed with nitrogen, and stirred for five minutes. A solution of sodium tert-butoxide (2.202 g, 22.92 mmol) in minimal THF was then added, and the mixture stirred for an additional five minutes. 1-Chloro-2-ethynyl-3-fluorobenzene (3.22 g, 20.83 mmol) and methyl iodide (11.83 g, 83.33 mmol) were then added to the reaction mixture, and the resulting mixture was stirred at room temperature overnight. Next, the crude product mixture was concentrated onto silica gel and purified by MPLC eluting with a gradient of 0-5% ethyl acetate in hexanes to afford (E)-2-(2-(2-chloro-6-fluorophenyl)prop-1-en-1-yl)-4,4,5,5-tetramethyl-1,3,2-dioxaborolane (2.41 g, 39%). $^1$H-NMR (400 MHz, DMSO-$d_6$) δ 7.31 (m, 2H), 7.20 (t, 1H), 5.18 (s, 1H), 2.15 (s, 3H), 1.23 (s, 12H).

Part III—Synthesis of (S,E)-3-(6-(2-(2-Chloro-6-fluorophenyl)prop-1-en-1-yl)-4-((3-(trifluoromethyl)phenyl)sulfonyl)-3,4-dihydro-2H-benzo[b][1,4]oxazin-2-yl)propanenitrile

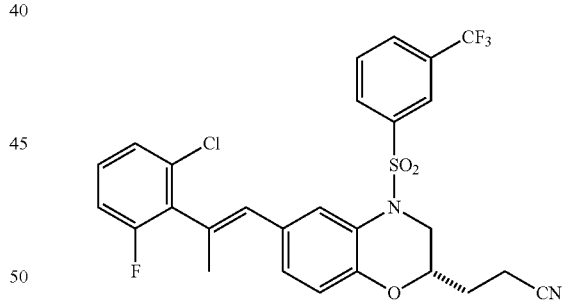

(S)-3-(6-Bromo-4-((3-(trifluoromethyl)phenyl)sulfonyl)-3,4-dihydro-2H-benzo[b][1,4]oxazin-2-yl)propanenitrile (40 mg, 0.084 mmol), (E)-2-(2-(2-chloro-6-fluorophenyl)prop-1-en-1-yl)-4,4,5,5-tetramethyl-1,3,2-dioxaborolane (25 mg, 0.084 mmol), THF (3 mL), and sodium hydroxide (10 mg, 0.252 mmol) were combined in a vial, and the mixture was degassed by bubbling nitrogen. Tetrakis(triphenylphosphine)palladium (10 mg, 0.008 mmol) was added to the reaction mixture, and the resulting mixture was shaken at 70° C. overnight. Then, the crude mixture was partitioned between water and ethyl acetate. The organic phase was then washed with brine, dried ($Na_2SO_4$), and concentrated onto silica gel and purified by chromatography to afford (S,E)-3-(6-(2-(2-chloro-6-fluorophenyl)prop-1-en-1-yl)-4-((3-(trifluoromethyl)phenyl)sulfonyl)-3,4-dihydro-2H-benzo[b][1, 4]oxazin-2-yl)propanenitrile as a yellow oil (31 mg, 65%). ¹H-NMR (400 MHz, DMSO-d₆) δ 8.03 (m, 3H), 7.82 (m, 2H), 7.67 (s, 1H), 7.35 (m, 4H), 7.11 (d, 1H), 6.89 (d, 1H), 6.38 (s, 1H), 4.42 (d, 1H), 3.40 (m, 3H), 2.60 (m, 3H), 2.07 (s, 3H), 1.96 (m, 2H), 1.78 (m, 2H), 1.20 (m, 2H), 1.02 (s, 3H).

Example 11—Synthesis of (S)-3-(6-(2-Chloro-6-fluorophenethyl)-4-((3-(trifluoromethyl)phenyl)sulfonyl)-3,4-dihydro-2H-benzo[b][1,4]oxazin-2-yl)propanoic acid

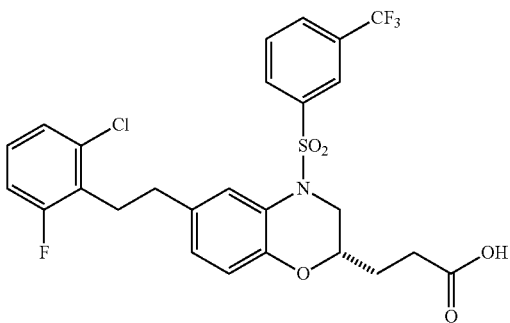 [SMILES: O=C(O)CC[C@H]1CN(S(=O)(=O)c2cccc(C(F)(F)F)c2)c2cc(CCc3c(F)cccc3Cl)ccc2O1]

Part I—Synthesis of (S)-3-(6-(2-Chloro-6-fluorophenethyl)-4-((3-(trifluoromethyl)phenyl)sulfonyl)-3,4-dihydro-2H-benzo[b][1,4]oxazin-2-yl)propanal

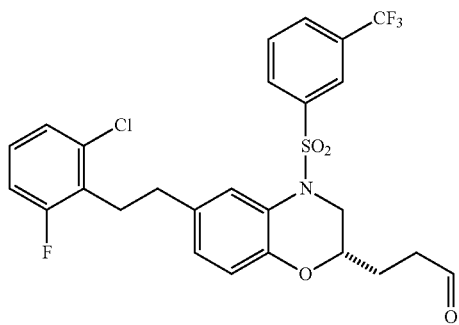 [SMILES: O=CCC[C@H]1CN(S(=O)(=O)c2cccc(C(F)(F)F)c2)c2cc(CCc3c(F)cccc3Cl)ccc2O1]

A solution of (S)-3-(6-(2-chloro-6-fluorophenethyl)-4-((3-(trifluoromethyl)phenyl)sulfonyl)-3,4-dihydro-2H-benzo[b][1,4]oxazin-2-yl)propanenitrile (80 mg, 0.145 mmol) in dichloromethane (6 mL) contained in a reaction vessel was cooled by placing the reaction vessel in an ice bath, and a 1 M solution of diisobutylaluminum hydride solution in dichloromethane (0.44 mL, 0.44 mmol) was added to the reaction vessel. The reaction mixture was stirred at 0° C. for an hour, then at room temperature for two additional hours. Then, the reaction was quenched by adding Rochelle's salt solution to the reaction mixture, and the resulting mixture was stirred at room temperature for two hours. Next, the phases of the resulting mixture were separated, and the organic phase was dried (Na₂SO₄), concentrated onto silica gel and purified by chromatography eluting with a gradient of 5-30% ethyl acetate in hexanes to afford (S)-3-(6-(2-chloro-6-fluorophenethyl)-4-((3-(trifluoromethyl)phenyl)sulfonyl)-3,4-dihydro-2H-benzo[b][1,4]oxazin-2-yl)propanal (21 mg, 26%). MS (ESI+) (M+Na)⁺ 577.99.

Part II—Synthesis of (S)-3-(6-(2-Chloro-6-fluorophenethyl)-4-((3-(trifluoromethyl)phenyl)sulfonyl)-3,4-dihydro-2H-benzo[b][1,4]oxazin-2-yl)propanoic acid

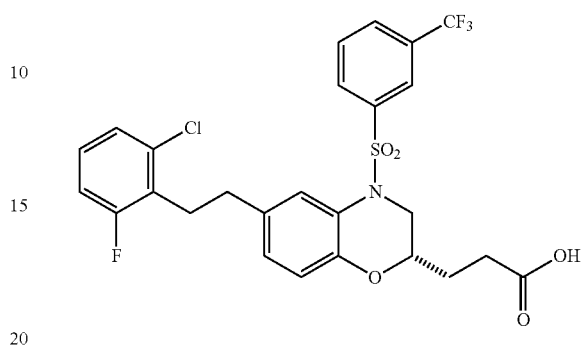

(S)-3-(6-(2-Chloro-6-fluorophenethyl)-4-((3-(trifluoromethyl)phenyl)sulfonyl)-3,4-dihydro-2H-benzo[b][1,4]oxazin-2-yl)propanal (0.038 mmol) was dissolved in tert-butanol (1 mL), and 2-methyl-2-butene (8 mg, 0.113 mmol) was added. To this mixture, a solution of sodium chlorite (3 mg, 0.038 mmol) and sodium phosphate monobasic (7 mg, 0.057 mmol) in water (1 mL) was added dropwise over several minutes, and the reaction mixture was stirred at room temperature overnight. Then, the reaction mixture was concentrated to remove the tert-butanol. The remaining aqueous mixture was diluted with water, and the solution was extracted with hexanes. The aqueous solution was acidified with 3 M HCl, and the mixture was extracted three times with ethyl acetate. The organic extracts were combined then dried (Na₂SO₄), and concentrated to provide a residue. The residue was purified by preparative HPLC providing (S)-3-(6-(2-chloro-6-fluorophenethyl)-4-((3-(trifluoromethyl)phenyl)sulfonyl)-3,4-dihydro-2H-benzo[b][1,4]oxazin-2-yl)propanoic acid. ¹H-NMR (400 MHz, DMSO-d₆) δ 12.13 (bs, 1H), 8.07 (d, 1H), 7.93 (m, 2H), 7.82 (t, 1H), 7.45 (s, 1H), 7.27 (m, 2H), 7.14 (m, 1H), 6.84 (dd, 1H), 6.70 (d, 1H), 4.31 (d, 1H), 3.28 (m, 2H), 2.91 (t, 2H), 2.72 (t, 2H), 2.27 (m, 2H), 1.78 (m, 1H), 1.65 (m, 1H). MS (ESI+) (M+Na)⁺ 593.99

Example 12—Synthesis of (7-((2-Chloro-6-fluorobenzyl)oxy)-1-((3-(trifluoromethyl)phenyl)sulfonyl)-1,2,3,4-tetrahydroquinolin-3-yl)methanol

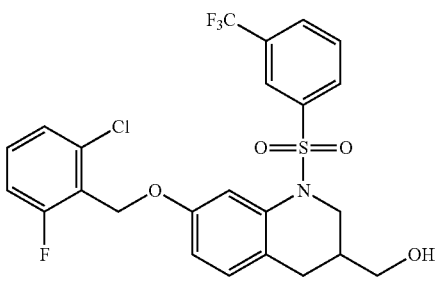 [SMILES: O=S(=O)(c1cccc(C(F)(F)F)c1)N1CC(CO)Cc2ccc(OCc3c(F)cccc3Cl)cc21]

Part I—Synthesis of Diethyl 2-(4-methoxy-2-nitrobenzylidene)malonate

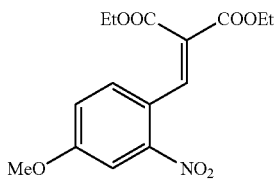

4-Methoxy-2-nitrobenzaldehyde (10 g, 55.20 mmol) was dissolved in ethanol (110 mL), and diethyl malonate (9.73 g, 60.72 mmol) was added followed by piperidine (0.94 g, 11.04 mmol) and acetic acid (0.663 g, 11.04 mmol). The reaction mixture was then heated at reflux overnight. Next, the reaction mixture was concentrated, and the resulting residue was partitioned between 1N HCl and ethyl acetate. The organic phase was washed with 10% sodium carbonate solution, washed with brine, dried (Na$_2$SO$_4$), and concentrated to provide a residue. The residue was purified by MPLC eluting with a gradient of 5-15% ethyl acetate in hexanes to afford diethyl 2-(4-methoxy-2-nitrobenzylidene) malonate as an oil (10.01 g, 56%).

Part II—Synthesis of Diethyl 2-(4-methoxy-2-nitrobenzyl)malonate

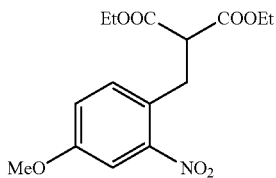 [SMILES: CCOC(=O)C(Cc1ccc(OC)cc1[N+](=O)[O-])C(=O)OCC]

Diethyl 2-(4-methoxy-2-nitrobenzylidene)malonate (10.01 g, 30.96 mmol) was dissolved in ethanol (103 mL) and the solution was cooled to 0° C. To this mixture, sodium borohydride (1.347 g, 35.606 mmol) was added, and the reaction mixture was stirred while the reaction vessel was placed in the ice bath for one hour. Next, the reaction was neutralized by adding aqueous ammonium chloride to the reaction mixture, and the resulting crude was partitioned between water and ethyl acetate. The organic phase was then washed with brine, dried (Na$_2$SO$_4$), and concentrated to afford diethyl 2-(4-methoxy-2-nitrobenzyl)malonate (9.51 g, 94%).

Part III—Synthesis of Ethyl 7-methoxy-2-oxo-1,2,3,4-tetrahydroquinoline-3-carboxylate

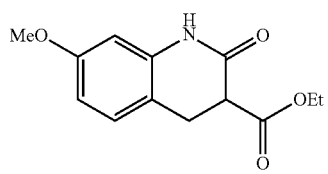 [SMILES: CCOC(=O)C1Cc2ccc(OC)cc2NC1=O]

Diethyl 2-(4-methoxy-2-nitrobenzyl)malonate (9.51 g, 29.23 mmol) was dissolved in acetic acid (147 mL) and powdered iron (6.53 g, 116.94 mmol) was added. The reaction mixture was heated to 60° C. for two hours. Then, the crude solution was filtered through a plug of Celite, and the filtrate was concentrated to provide a residue. The residue was partitioned between water and ethyl acetate. The organic phase was then washed with brine, and dried (Na$_2$SO$_4$), and concentrated to afford ethyl 7-methoxy-2-oxo-1,2,3,4-tetrahydroquinoline-3-carboxylate as a light yellow solid (5.72 g, 78%).

Part IV—Synthesis of Ethyl 7-hydroxy-2-oxo-1,2,3,4-tetrahydroquinoline-3-carboxylate

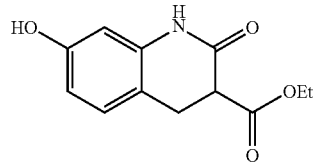 [SMILES: CCOC(=O)C1Cc2ccc(O)cc2NC1=O]

Ethyl 7-methoxy-2-oxo-1,2,3,4-tetrahydroquinoline-3-carboxylate (2 g, 8.02 mmol) was dissolved in dichloromethane (80 mL) and the solution was cooled to −78° C. to the mixture, a 1M solution of boron tribromide in THF (24.1 mL, 24.1 mmol) was added dropwise, and then the reaction mixture was stirred at −20° C. for one hour. To the resulting crude mixture ethanol was added, and solid sodium bicarbonate was added. Next, the resulting mixture was poured into a separatory funnel and diluted with dichloromethane. The organic phase was washed with brine, dried (Na$_2$SO$_4$), and concentrated to afford ethyl 7-hydroxy-2-oxo-1,2,3,4-tetrahydroquinoline-3-carboxylate (1.71 g, 91%). MS (ESI+) (M+H)$^+$236.14.

Part V—Synthesis of Ethyl 7-((2-chloro-6-fluorobenzyl)oxy)-2-oxo-1,2,3,4-tetrahydroquinoline-3-carboxylate

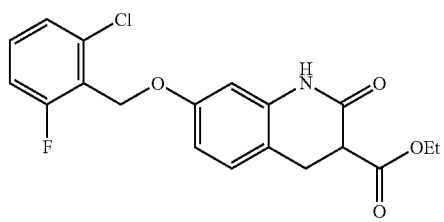 [SMILES: CCOC(=O)C1Cc2ccc(OCc3c(F)cccc3Cl)cc2NC1=O]

Ethyl 7-hydroxy-2-oxo-1,2,3,4-tetrahydroquinoline-3-carboxylate (1.5 g, 6.38 mmol), 2-chloro-6-fluorobenzyl alcohol (1.075 g, 6.70 mmol), and triphenylphosphine (2.01 g, 7.65 mmol) were suspended in dichloromethane (64 mL), and diisopropyl azodicarboxylate (1.51 mL, 7.65 mmol) was added dropwise. The reaction mixture was stirred at room temperature for one hour, and then the crude was washed with water, dried (Na$_2$SO$_4$), and concentrated to provide a residue. The residue was purified by MPLC eluting with a gradient of 10-30% ethyl acetate in hexanes to afford ethyl 7-((2-chloro-6-fluorobenzyl)oxy)-2-oxo-1,2,3,4-tetrahydroquinoline-3-carboxylate as a solid (1.4 g, 58%).

Part VI—Synthesis of (7-((2-Chloro-6-fluorobenzyl)oxy)-1,2,3,4-tetrahydroquinolin-3-3-yl)methanol

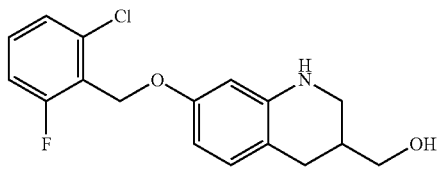 [SMILES: OCC1CNc2cc(OCc3c(F)cccc3Cl)ccc2C1]

Ethyl 7-((2-chloro-6-fluorobenzyl)oxy)-2-oxo-1,2,3,4-tetrahydroquinoline-3-carboxylate (1.4 g, 3.706 mmol) was dissolved in THF (37 mL) and borane dimethylsulfide complex (1.408 g, 18.53 mmol) was added. The reaction mixture was heated at reflux for two hours. Then, the crude solution was cooled by placing the reaction vessel in an ice bath, and the reaction carefully quenched by adding methanol to the reaction mixture. The resulting mixture was then refluxed for ten minutes, cooled and concentrated to provide a residue. The residue was partitioned between ethyl acetate and water. The organic phase was washed with brine, dried ($Na_2SO_4$), and concentrated to provide a residue. The residue was purified via MPLC to afford (7-((2-chloro-6-fluorobenzyl)oxy)-1,2,3,4-tetrahydroquinolin-3-yl)methanol as a light yellow oil (0.48 g, 40%).

Part VII—Synthesis of (7-((2-Chloro-6-fluorobenzyl)oxy)-1-((3-(trifluoromethyl)phenyl)sulfonyl)-1,2,3,4-tetrahydroquinolin-3-yl)methanol

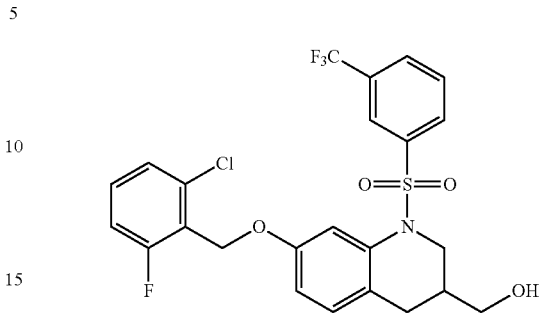

(7-((2-Chloro-6-fluorobenzyl)oxy)-1,2,3,4-tetrahydroquinolin-3-yl)methanol (0.1 g, 0.311 mmol) was dissolved in pyridine (2 mL) and 3-(trifluoromethyl) benzenesulfonyl chloride (84 mg, 0.342 mmol) was added. The reaction mixture was heated to 50° C. overnight. Then, the reaction mixture was diluted in ethyl acetate, washed three times with 1 N HCl, washed with brine, dried ($Na_2SO_4$), and then concentrated to provide a residue. The residue was purified by MPLC to afford (7-((2-chloro-6-fluorobenzyl)oxy)-1-((3-(trifluoromethyl)phenyl) sulfonyl)-1,2,3,4-tetrahydroquinolin-3-yl)methanol (51 mg, 31%).

Example 13—Preparation of Additional 1,2,3,4-Tetrahydroquinolin-3-yl)methanol Compounds Compounds in the table below were prepared based on experimental procedures described in Example 12 and the detailed description.

| No. | Structure | Name | Observed m/z |
|---|---|---|---|
| 13A | 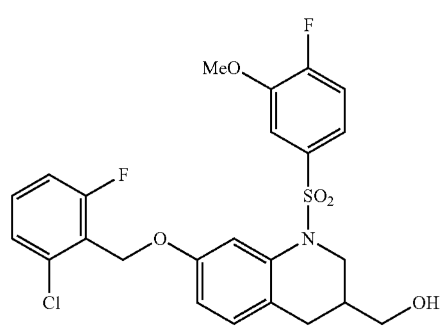 [SMILES: COc1cc(S(=O)(=O)N2CC(CO)Cc3ccc(OCc4c(F)cccc4Cl)cc32)ccc1F] | (7-((2-chloro-6-fluorobenzyl)oxy)-1-((4-fluoro-3-methoxyphenyl)sulfonyl)-1,2,3,4-tetrahydroquinolin-3-yl)methanol | 510 (M + H)+ |
| 13B | 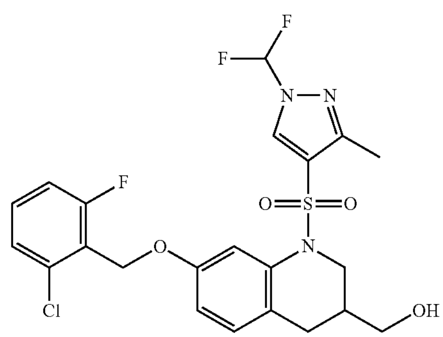 [SMILES: Cc1nn(C(F)F)cc1S(=O)(=O)N1CC(CO)Cc2ccc(OCc3c(F)cccc3Cl)cc21] | (7-((2-chloro-6-fluorobenzyl)oxy)-1-((1-(difluoromethyl)-3-methyl-1H-pyrazol-4-yl)sulfonyl)-1,2,3,4-tetrahydroquinolin-3-yl)methanol | 516 (M + H)+ |

| No. | Structure | Name | Observed m/z |
|---|---|---|---|
| 13C | 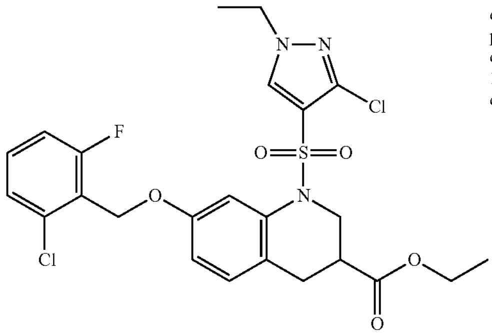 [SMILES: CCOC(=O)C1Cc2ccc(OCc3c(F)cccc3Cl)cc2N(S(=O)(=O)c2cn(CC)nc2Cl)C1] | ethyl 1-((3-chloro-1-ethyl-1H-pyrazol-4-yl)sulfonyl)-7-((2-chloro-6-fluorobenzyl)oxy)-1,2,3,4-tetrahydroquinoline-3-carboxylate | 556 (M + H)+ |

Example 14—Synthesis of 7-((2-Chloro-6-fluorobenzyl)oxy)-1-((3-(trifluoromethyl)phenyl)sulfonyl)-1,2,3,4-tetra hydroquinoline-3-carboxylic acid

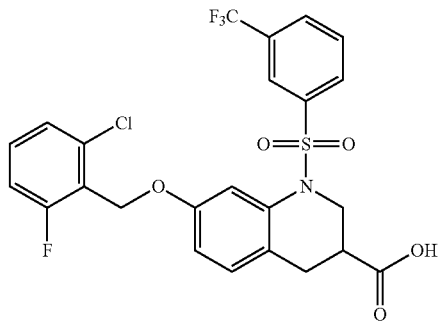 [SMILES: O=C(O)C1Cc2ccc(OCc3c(F)cccc3Cl)cc2N(S(=O)(=O)c2cccc(C(F)(F)F)c2)C1]

(7-((2-Chloro-6-fluorobenzyl)oxy)-1-((3-(trifluoromethyl)phenyl)sulfonyl)-1,2,3,4-tetrahydroquinolin-3-yl)methanol (43 mg, 0.081 mmol) was dissolved in acetone (4 mL), and Jones' reagent was added dropwise until the orange color persisted. The mixture was stirred at room temperature for two hours, then the reaction was quenched by addition of isopropyl alcohol to the reaction mixture, and the resulting mixture was concentrated to provide a residue. The residue was partitioned between 1 N HCl and ethyl acetate/THF. The organic phase was washed with brine, dried ($Na_2SO_4$), and concentrated to provide a residue. The residue was purified by MPLC eluting with a gradient of 0-10% methanol in dichloromethane to afford 7-((2-chloro-6-fluorobenzyl)oxy)-1-((3-(trifluoromethyl)phenyl)sulfonyl)-1,2,3,4-tetrahydroquinoline-3-carboxylic acid (19 mg, 43%). $^1$H-NMR (400 MHz, DMSO-$d_6$) δ 12.25 (bs, 1H), 8.08 (d, 1H), 7.95 (d, 1H), 7.80 (m, 2H), 7.48 (m, 1H), 7.40 (m, 1H), 7.28 (t, 1H), 7.18 (s, 1H), 7.07 (d, 1H), 6.83 (d, 1H), 5.08 (s, 2H), 4.19 (d, 1H), 3.67 (m, 1H), 2.53 (m, 3H). MS (ESI+) (M+Na)+565.95.

Example 15—Preparation of Additional 1,2,3,4-Tetrahydroquinoline-3-carboxylic acids Compounds in the table below were prepared based on experimental procedures described in Example 14 and the detailed description.

| No. | Structure | Name | Observed m/z |
|---|---|---|---|
| 15A | 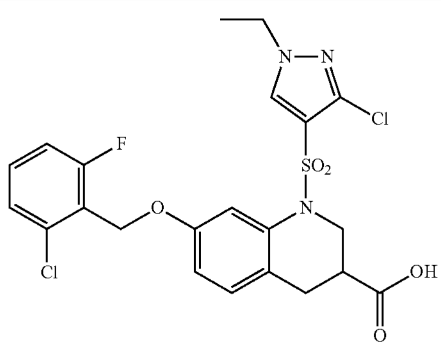 [SMILES: CCn1cc(S(=O)(=O)N2CC(C(=O)O)Cc3ccc(OCc4c(F)cccc4Cl)cc32)c(Cl)n1] | 1-((3-chloro-1-ethyl-1H-pyrazol-4-yl)sulfonyl)-7-((2-chloro-6-fluorobenzyl)oxy)-1,2,3,4-tetrahydroquinoline-3-carboxylic acid | 528 (M + H)+ |

| No. | Structure | Name | Observed m/z |
|---|---|---|---|
| 15B | 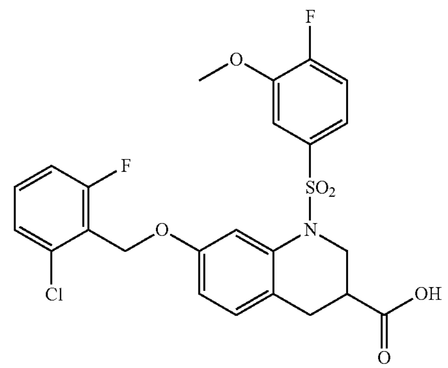 [SMILES: COc1cc(S(=O)(=O)N2CC(C(=O)O)Cc3ccc(OCc4c(F)cccc4Cl)cc32)ccc1F] | 7-((2-chloro-6-fluorobenzyl)oxy)-1-((4-fluoro-3-methoxyphenyl)sulfonyl)-1,2,3,4-tetrahydroquinoline-3-carboxylic acid | 524 (M + H)+ |
| 15C | 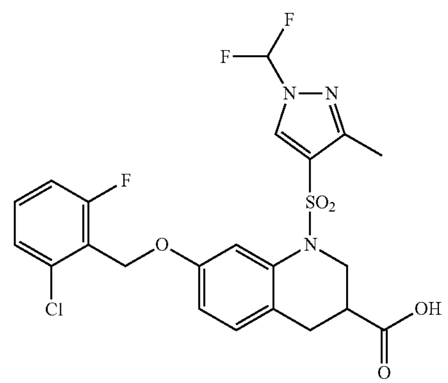 [SMILES: Cc1nn(C(F)F)cc1S(=O)(=O)N1CC(C(=O)O)Cc2ccc(OCc3c(F)cccc3Cl)cc21] | 7-((2-chloro-6-fluorobenzyl)oxy)-1-((1-(difluoromethyl)-3-methyl-1H-pyrazol-4-yl)sulfonyl)-1,2,3,4-tetrahydroquinoline-3-carboxylic acid | 530 (M + H)+ |
| 15D | 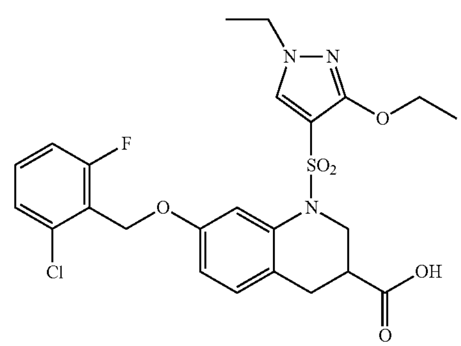 [SMILES: CCOc1nn(CC)cc1S(=O)(=O)N1CC(C(=O)O)Cc2ccc(OCc3c(F)cccc3Cl)cc21] | 7-((2-chloro-6-fluorobenzyl)oxy)-1-((3-ethoxy-1-ethyl-1H-pyrazol-4-yl)sulfonyl)-1,2,3,4-tetrahydroquinoline-3-carboxylic acid | 538 (M + H)+ |
| 15E | 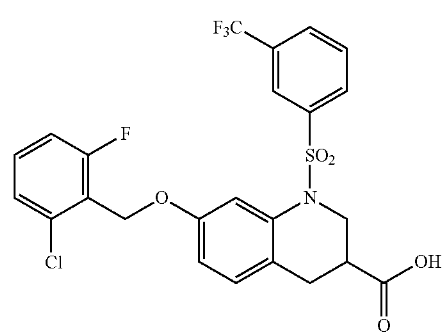 [SMILES: O=C(O)C1Cc2ccc(OCc3c(F)cccc3Cl)cc2N(S(=O)(=O)c2cccc(C(F)(F)F)c2)C1] | 7-((2-fluoro-6-(trifluoromethyl)benzyl)oxy)-1-((3-(trifluoromethyl)phenyl)sulfonyl)-1,2,3,4-tetrahydroquinoline-3-carboxylic acid | 578 (M + H)+ |

| No. | Structure | Name | Observed m/z |
|---|---|---|---|
| 15F | 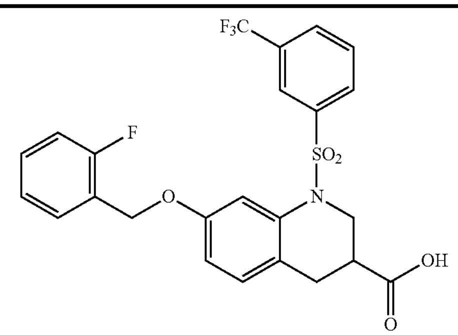 | 7-((2-fluorobenzyl)oxy)-1-((3-(trifluoromethyl)phenyl)sulfonyl)-1,2,3,4-tetrahydroquinoline-3-carboxylic acid | 510 (M + H)+ |
| 15G | 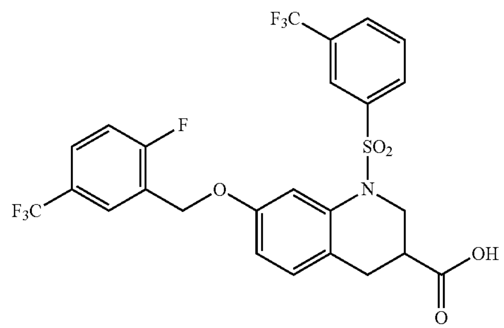 [SMILES: O=C(O)C1Cc2ccc(OCc3cc(C(F)(F)F)ccc3F)cc2N(S(=O)(=O)c2cccc(C(F)(F)F)c2)C1] | 7-((2-fluoro-5-(trifluoromethyl)benzyl)oxy)-1-((3-(trifluoromethyl)phenyl)sulfonyl)-1,2,3,4-tetrahydroquinoline-3-carboxylic acid | 578 (M + H)+ |

Example 16—Synthesis of Ethyl 7-(2-chloro-6-fluorophenethyl)-1-((3-(trifluoromethyl)phenyl)sulfonyl)-1,2,3,4-tetra hydroquinoline-3-carboxylate

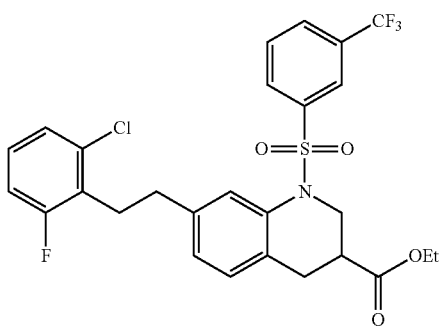 [SMILES: CCOC(=O)C1Cc2ccc(CCc3c(F)cccc3Cl)cc2N(S(=O)(=O)c2cccc(C(F)(F)F)c2)C1]

Part I—Synthesis of Ethyl 7-bromo-4-oxo-1,4-dihydroquinoline-3-carboxylate

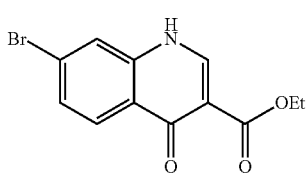 [SMILES: CCOC(=O)c1c[nH]c2cc(Br)ccc2c1=O]

3-Bromoaniline (10 g, 58.13 mmol) and diethyl 2-(ethoxymethylene)malonate (12.57 g, 58.13 mmol) were suspended in ethanol (60 mL), and the reaction mixture was heated to reflux overnight. Then, the crude mixture was concentrated, and the resulting residue was re-suspended in diphenyl ether. Next, the suspension was heated to 250° C. for 90 minutes. The mixture was then cooled to about 35-40° C. and filtered through a sintered glass funnel. The isolated solid was washed with 2:1 ethyl acetate:hexanes, and recrystallized from 70% ethanol affording ethyl 7-bromo-4-oxo-1,4-dihydroquinoline-3-carboxylate as a white solid (5.11 g, 30%).

Part II—Synthesis of Ethyl 7-bromo-4-chloroquinoline-3-carboxylate

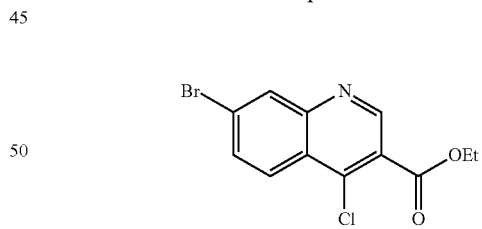

Ethyl 7-bromo-4-oxo-1,4-dihydroquinoline-3-carboxylate (5.11 g, 17.3 mmol) was dissolved in thionyl chloride (70 mL), and DMF (0.5 mL) was added. The reaction mixture was heated to reflux overnight. The resulting solution was concentrated to provide a residue, and the residue was carefully treated with a saturated sodium carbonate solution. The resulting mixture was slurried, and then filtered. The solid isolated by filtration was washed with water, and dried in a vacuum oven to produce a yellow solid. The yellow solid was then loaded onto silica gel and purified by MPLC eluting with a gradient of 5-80% ethyl acetate in hexanes to afford ethyl 7-bromo-4-chloroquinoline-3-carboxylate as a white solid (4.12 g, 76%).

Part III—Synthesis of Ethyl 4-chloro-7-(2-chloro-6-fluorophenethyl)quinoline-3-carboxylate

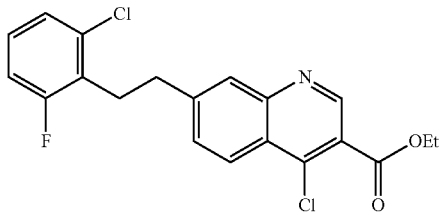 [SMILES: CCOC(=O)c1cnc2cc(CCc3c(F)cccc3Cl)ccc2c1Cl]

1-Chloro-3-fluoro-2-vinyl benzene (996 mg, 6.358 mmol) was dissolved in THF (16 mL) and the reaction vessel containing the solution was cooled in an ice bath. To this solution, a 0.5 M solution of 9-borabicyclo[3.3.1] nonane in toluene (12.7, 6.35 mmol) was added, and the resulting mixture allowed to warm to room temperature where it was held for six days. Ethyl 7-bromo-4-chloroquinoline-3-carboxylate (1 g, 3.179 mmol) was mixed with triethylamine (0.665 mL, 4.769 mmol), and [1,1'-bis(diphenylphosphino)ferrocene] dichloropalladium (II) complex with dichloromethane (243 mg, 0.318 mmol) in degassed DMF (18 mL) and water (2 mL). The olefin solution was then added to the reaction mixture, and the resulting reaction mixture was heated to 50° C. overnight. Next, the reaction mixture was cooled to room temperature, and partitioned between water and ethyl acetate. The organic phase was washed with brine, dried (Na$_2$SO$_4$), and concentrated to provide a residue. The residue was purified by MPLC eluting with a gradient of 10-30% ethyl acetate in hexanes to afford ethyl 4-chloro-7-(2-chloro-6-fluorophenethyl)quinoline-3-carboxylate (610 mg, 49%). MS (ESI+) (M+H)$^+$391.99.

Part IV—Synthesis of Ethyl 7-(2-chloro-6-fluorophenethyl)-1,2,3,4-tetrahydroquinoline-3-carboxylate

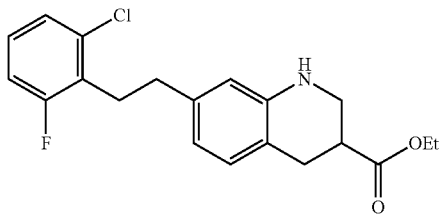 [SMILES: CCOC(=O)C1CNc2cc(CCc3c(F)cccc3Cl)ccc2C1]

Ethyl 4-chloro-7-(2-chloro-6-fluorophenethyl)quinoline-3-carboxylate (230 mg, 0.586 mmol) was dissolved in acetic acid (4 mL) and a 8M solution of borane pyridine complex (0.147 mL, 1.173 mmol) was added. The reaction mixture was stirred at room temperature for 18 hours. Then, the reaction mixture was concentrated to provide a residue. To the residue was added 1 M sodium carbonate. The resulting mixture was extracted three times with dichloromethane. The organic extracts were combined, dried (Na$_2$SO$_4$), and concentrated to provide a residue. The residue was purified by MPLC to afford ethyl 7-(2-chloro-6-fluorophenethyl)-1,2,3,4-tetrahydroquinoline-3-carboxylate (80 mg, 38%). MS (ESI+) (M+H)$^+$362.08.

Part V—Synthesis of Ethyl 7-(2-chloro-6-fluorophenethyl)-1-((3-(trifluoromethyl)phenyl)sulfonyl)-1,2,3,4-tetrahydroquinoline-3-carboxylate

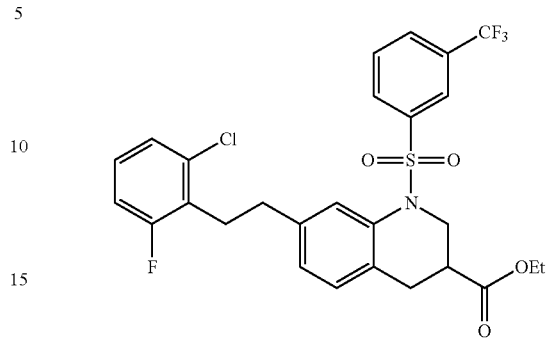

Ethyl 7-(2-chloro-6-fluorophenethyl)-1,2,3,4-tetrahydroquinoline-3-carboxylate (115 mg, 0.318 mmol) and 3-(trifluoromethyl)benzenesulfonyl chloride (311 mg, 1.271 mmol) were dissolved in acetone (2 mL), and potassium carbonate (220 mg, 1.59 mmol) was added. The mixture was shaken at room temperature overnight. Additional aliquots of 3-(trifluoromethyl)benzenesulfonyl chloride (311 mg, 1.271 mmol), and potassium carbonate (220 mg, 1.59 mmol) were then added, and the reaction mixture stirred for an additional five hours. Next, the reaction mixture was filtered, and the filtrate was concentrated onto silica gel and purified by MPLC providing ethyl 7-(2-chloro-6-fluorophenethyl)-1-((3-(trifluoromethyl)phenyl) sulfonyl)-1,2,3,4-tetrahydroquinoline-3-carboxylate (76 mg, 0.1093 mmol). MS (ESI+) (M+Na)$^+$592.04.

Example 17—Synthesis of Ethyl (E)-7-(2-(2-chloro-6-fluorophenyl)prop-1-en-1-yl)-1-((3-(trifluoromethyl)phenyl)sulfonyl)-1,2,3,4-tetrahydroquinoline-3-carboxylate

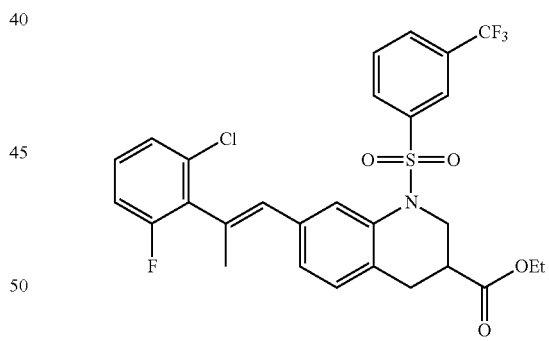

Part I—Synthesis of Ethyl (E)-7-(2-(2-chloro-6-fluorophenyl)prop-1-en-1-yl)-2-oxo-1,2,3,4-tetrahydroquinoline-3-carboxylate

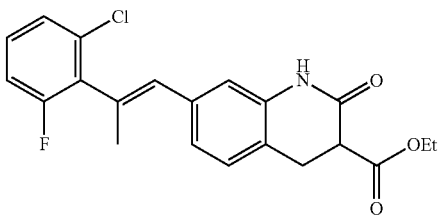 [SMILES: CCOC(=O)C1Cc2ccc(/C=C(\C)c3c(F)cccc3Cl)cc2NC1=O]

Ethyl 7-bromo-2-oxo-1,2,3,4-tetrahydroquinoline-3-carboxylate (1.7 g, 5.702 mmol), (E)-2-(2-(2-chloro-6-fluorophenyl)prop-1-en-1-yl)-4,4,5,5-tetramethyl-1,3,2-dioxaborolane (2.20 g, 7.413 mmol), dioxane (40 mL), water (10 mL), and potassium carbonate (946 mg, 6.843 mmol) were combined in a vial, and the mixture was degassed by bubbling nitrogen in. To this mixture was added [1,1'-bis(diphenylphosphino)ferrocene] dichloropalladium (II) complex with dichloromethane (435 mg, 0.57 mmol), and the resulting mixture was shaken at 70° C. for 45 minutes. Next, the crude mixture was partitioned between water and ethyl acetate. The organic phase was then washed with brine, dried (Na$_2$SO$_4$), and concentrated onto silica gel. This residue was purified by MPLC eluting with a gradient of 5-20% ethyl acetate in hexanes to afford ethyl (E)-7-(2-(2-chloro-6-fluorophenyl)prop-1-en-1-yl)-2-oxo-1,2,3,4-tetrahydroquinoline-3-carboxylate as a white solid (1.75 g, 79%). MS (ESI+) (M+K)$^+$425.95.

Part II—Synthesis of Ethyl (E)-7-(2-(2-chloro-6-fluorophenyl)prop-1-en-1-yl)-1,2,3,4-tetrahydroquinoline-3-carboxylate

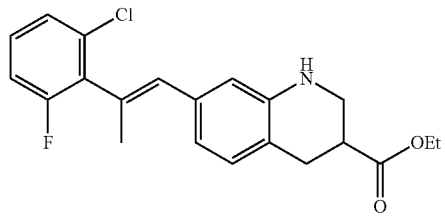 [SMILES: CCOC(=O)C1CNc2cc(/C=C(\C)c3c(F)cccc3Cl)ccc2C1]

Ethyl (E)-7-(2-(2-chloro-6-fluorophenyl)prop-1-en-1-yl)-2-oxo-1,2,3,4-tetrahydroquinoline-3-carboxylate (1.06 g, 2.733 mmol) was dissolved in THF (60 mL) and the reaction vessel containing the solution was cooled in an ice bath. Borane dimethylsulfide complex (1.367 mL, 13.67 mmol) was added dropwise to the reaction mixture, and the reaction mixture was stirred at room temperature overnight. Then, the reaction was quenched by adding methanol (10 mL) to the reaction mixture, and the resulting mixture was heated to reflux for ten minutes. Then, the crude was concentrated, and next purified by chromatography providing ethyl (E)-7-(2-(2-chloro-6-fluorophenyl)prop-1-en-1-yl)-1,2,3,4-tetrahydroquinoline-3-carboxylate (0.39 g, 38%).

Part III—Synthesis of Ethyl (E)-7-(2-(2-chloro-6-fluorophenyl)prop-1-en-1-yl)-1-((3-(trifluoromethyl)phenyl)sulfonyl)-1,2,3,4-tetrahydroquinoline-3-carboxylate

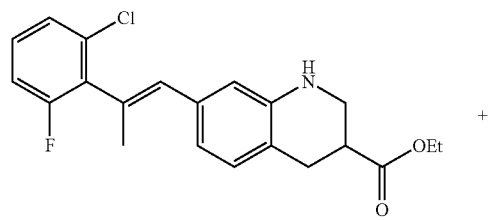

+

-continued

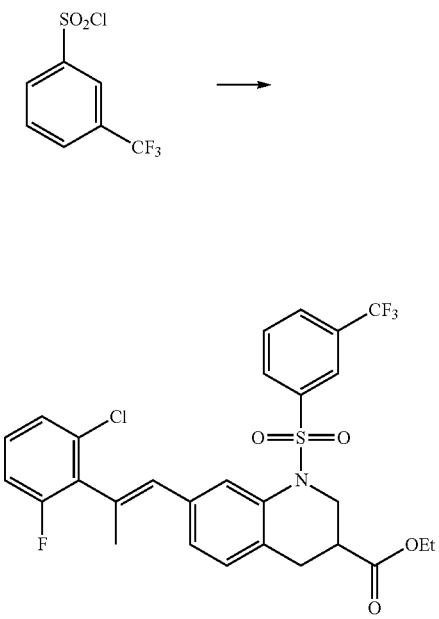

Ethyl (E)-7-(2-(2-chloro-6-fluorophenyl)prop-1-en-1-yl)-1,2,3,4-tetrahydroquinoline-3-carboxylate (460 mg, 1.23 mmol) was dissolved in pyridine (8 mL) and 3-(trifluoromethyl)benzenesulfonyl chloride (361 mg, 1.477 mmol) was added. The reaction mixture was heated to 50° C. overnight. Then, the reaction mixture was diluted with ethyl acetate. The resulting organic mixture was washed three times with 1 N HCl, washed with brine, dried (Na$_2$SO$_4$), and concentrated to provide a residue. The residue was purified by chromatography to afford ethyl (E)-7-(2-(2-chloro-6-fluorophenyl)prop-1-en-1-yl)-1-((3-(trifluoromethyl)phenyl)sulfonyl)-1,2,3,4-tetrahydroquinoline-3-carboxylate (540 mg, 75%).

Example 18—Synthesis of (E)-7-(2-(2-Chloro-6-fluorophenyl)prop-1-en-1-yl)-1-((3-(trifluoromethyl)phenyl)sulfonyl)-1,2,3,4-tetrahydroquinoline-3-carboxylic acid and It's Sodium Salt

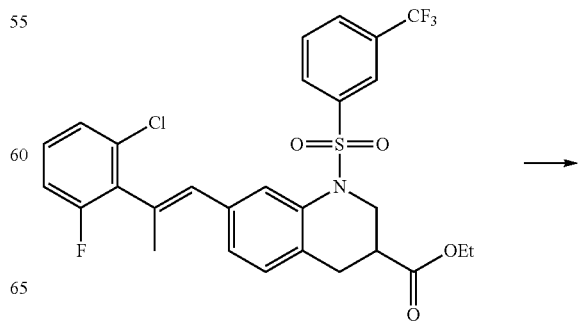

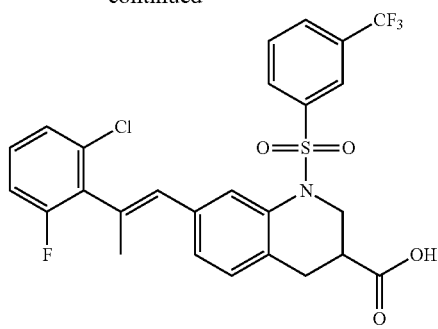

Ethyl (E)-7-(2-(2-chloro-6-fluorophenyl)prop-1-en-1-yl)-1-((3-(trifluoromethyl)phenyl)sulfonyl)-1,2,3,4-tetrahydroquinoline-3-carboxylate (540 mg, 0.928 mmol) was dissolved in THF (9 mL) and water (9 mL), and lithium hydroxide (44 mg, 1.856 mmol) was added. The resulting mixture was stirred at room temperature for 3 hours. The reaction mixture was diluted with ethyl acetate, and then 1 N HCl (1 mL) was added. The organic phase was washed with brine, dried ($Na_2SO_4$), and concentrated to provide a residue. The residue was purified by MPLC eluting with a gradient of 0-10% methanol in dichloromethane to afford (E)-7-(2-(2-chloro-6-fluorophenyl)prop-1-en-1-yl)-1-((3-(trifluoromethyl)phenyl)sulfonyl)-1,2,3,4-tetrahydroquinoline-3-carboxylic acid as a white solid (430 mg, 84%). $^1$H-NMR (400 MHz, DMSO-$d_6$) δ 12.73 (bs, 1H), 8.07 (d, 1H), 7.99 (d, 1H), 7.82 (m, 2H), 7.52 (s, 1H), 7.36 (m, 2H), 7.25 (m, 1H), 7.18 (d, 1H), 7.11 (d, 1H), 6.38 (s, 1H), 4.21 (d, 1H), 4.05 (m, 1H), 3.75 (m, 1H), 3.13 (s, 3H), 2.60 (m, 3H), 2.02 (s, 3H).

Preparation of sodium (E)-7-(2-(2-chloro-6-fluorophenyl)prop-1-en-1-yl)-1-((3-(trifluoromethyl)phenyl)sulfonyl)-1,2,3,4-tetrahydroquinoline-3-carboxylate

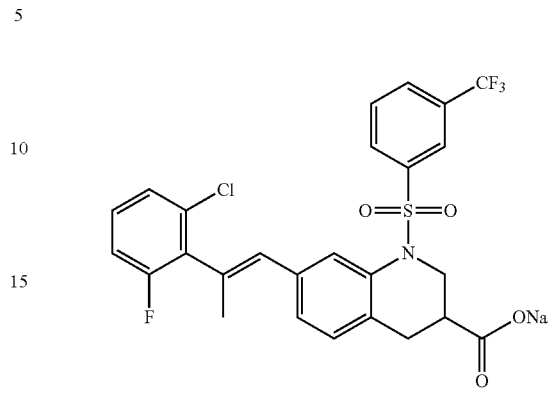

(E)-7-(2-(2-Chloro-6-fluorophenyl)prop-1-en-1-yl)-1-((3-(trifluoromethyl)phenyl)sulfonyl)-1,2,3,4-tetrahydroquinoline-3-carboxylic acid (388 mg, 0.7 mmol) was dissolved in 10 mL of 1:1 MeOH:THF, and a sodium hydroxide solution (0.219 mL of 3.2 M NaOH in water) was added. The solution was then concentrated, and held under vacuum for 18 hours to afford the title compound as a white solid (380 mg, 94%).

Example 19—Preparation of Additional Aryl-alkenylene 1,2,3,4-Tetrahydroquinolines Compounds in the table below were prepared based on experimental procedures described in Example 17 and 18 and the detailed description using the appropriate vinyl boronate.

| No. | Structure | Name | Observed m/z |
|---|---|---|---|
| 19A | 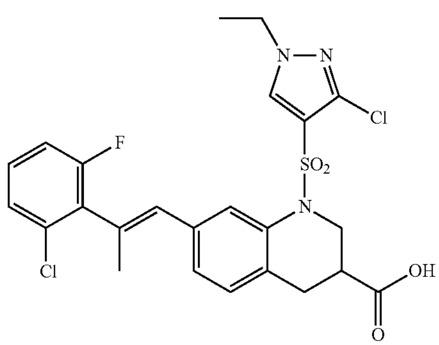 [SMILES: CCn1cc(S(=O)(=O)N2CC(C(=O)O)Cc3ccc(/C=C(\C)c4c(F)cccc4Cl)cc32)c(Cl)n1] | (E)-1-((3-chloro-1-ethyl-1H-pyrazol-4-yl)sulfonyl)-7-(2-(2-chloro-6-fluorophenyl)prop-1-en-1-yl)-1,2,3,4-tetrahydroquinoline-3-carboxylic acid | 538 (M + H)⁺ |
| 19B | 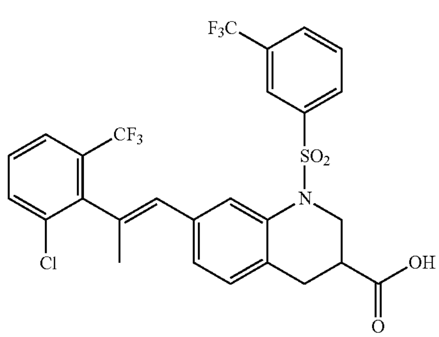 [SMILES: C/C(=C\c1ccc2c(c1)N(S(=O)(=O)c1cccc(C(F)(F)F)c1)CC(C(=O)O)C2)c1c(Cl)cccc1C(F)(F)F] | (E)-7-(2-(2-chloro-6-(trifluoromethyl)phenyl)prop-1-en-1-yl)-1-((3-(trifluoromethyl)phenyl)sulfonyl)-1,2,3,4-tetrahydroquinoline-3-carboxylic acid | 604 (M + H)⁺ |

| No. | Structure | Name | Observed m/z |
|---|---|---|---|
| 19C | 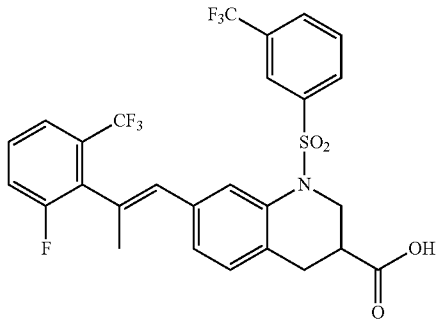 [SMILES: C/C(=C\c1ccc2c(c1)N(S(=O)(=O)c1cccc(C(F)(F)F)c1)CC(C(=O)O)C2)c1c(F)cccc1C(F)(F)F] | (E)-7-(2-(2-fluoro-6-(trifluoromethyl)phenyl)prop-1-en-1-yl)-1-((3-(trifluoromethyl)phenyl)sulfonyl)-1,2,3,4-tetrahydroquinoline-3-carboxylic acid | 588 (M + H)+ |
| 19D | 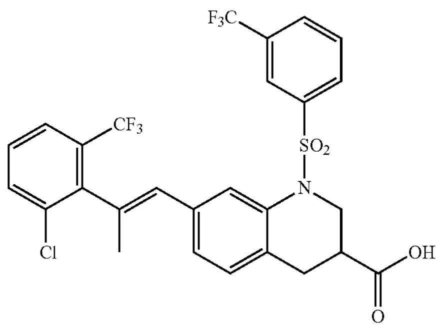 | (E)-7-(2-chloro-6-(trifluoromethyl)styryl)-1-((3-(trifluoromethyl)phenyl)sulfonyl)-1,2,3,4-tetrahydroquinoline-3-carboxylic acid | 590 (M + H)+ |

Example 20—Synthesis of (S)—N-((6-((2-Chloro-6-fluorobenzyl)amino)-4-((3-(trifluoromethyl)phenyl)sulfonyl)-3,4-dihydro-2H-benzo[b][1,4]oxazin-2-yl)methyl)acetamide

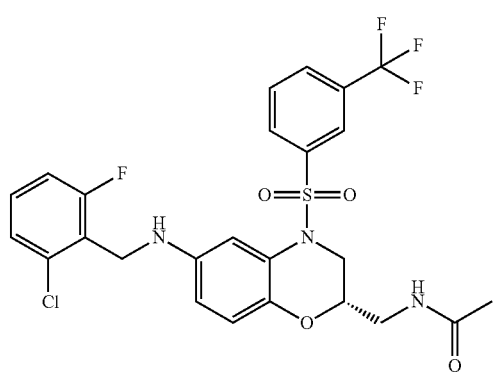 [SMILES: CC(=O)NC[C@H]1CN(S(=O)(=O)c2cccc(C(F)(F)F)c2)c2cc(NCc3c(F)cccc3Cl)ccc2O1]

Part I—Synthesis of 2-[[(2S)-3-Chloro-2-hydroxypropyl]amino]-4-nitrophenol

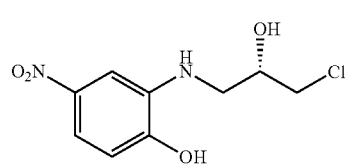 [SMILES: O=[N+]([O-])c1ccc(O)c(NC[C@H](O)CCl)c1]

A solution of 2-amino-4-nitrophenol (250 g, 1.62 mol) and (2S)-2-(chloromethyl)oxirane (330.0 g, 3.57 mol) in ethanol/water (2500/25 mL) was stirred for twelve hours at 60° C. in an oil bath. The resulting mixture was cooled and concentrated to afford 2-[[(2S)-3-chloro-2-hydroxypropyl]amino]-4-nitrophenol as a brown oil.

Part II—Synthesis of [(2R)-6-Nitro-3,4-dihydro-2H-1,4-benzoxazin-2-yl]methanol

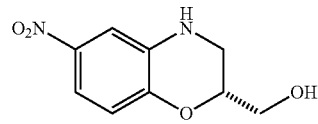 [SMILES: O=[N+]([O-])c1ccc2c(c1)NC[C@H](CO)O2]

A solution of 2-[[(2S)-3-chloro-2-hydroxypropyl]amino]-4-nitrophenol (400 g, 1.62 mol) in ethanol (2.5 L) and potassium carbonate (134.5 g, 973 mmol) was stirred for twelve hours at 90° C. in an oil bath. Then, the mixture was filtered, and the filtrate was concentrated to provide a residue. The residue was diluted with water (1.5 L) and extracted three times with ethyl acetate (1 L). The organic layers were combined and then washed with brine, dried (Na₂SO₄), and concentrated to provide a residue. The residue was purified via MPLC over silica gel eluting with ethyl acetate/petroleum ether (1:1) to afford [(2R)-6-nitro-3,4-dihydro-2H-1,4-benzoxazin-2-yl]methanol as a red solid.

Part III—Synthesis of ((R)-2-Hydroxymethyl-3,4-dihydro-2H-benzo[1,4]oxazin-6-yl)-carbamic acid tert-butyl ester

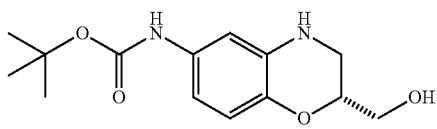 [SMILES: CC(C)(C)OC(=O)Nc1ccc2c(c1)NC[C@H](CO)O2]

The atmosphere above a solution of [(2R)-6-nitro-3,4-dihydro-2H-1,4-benzoxazin-2-yl]methanol (137 g, 652 mmol), palladium carbon (13.7 g), and di-tert-butyl dicarbonate (157 g, 717 mmol) in methanol (1400 mL) was exchanged with hydrogen. The resulting solution was stirred for twelve hours at room temperature. Next, the mixture was filtered, and the filtrate was concentrated to provide a crude product that was purified by re-crystallization from ether to afford ((R)-2-hydroxymethyl-3,4-dihydro-2H-benzo[1,4]oxazin-6-yl)-carbamic acid tert-butyl ester as an off-white solid. LRMS (ESI) calculated for $C_{14}H_{20}N_2O_4$ 280. Found: 225 $(M-C_4H_8+H)^+$; 281 $(M+H)^+$. $^1$H-NMR (400 MHz, CDCl$_3$): δ 6.92 (s, 1H), 6.71 (d, 1H), 6.41 (dd, 1H), 6.26 (s, 1H), 4.20-4.21 (m, 1H), 3.76-3.86 (m, 2H), 3.26-3.35 (m, 2H), 1.53 (s, 9H).

Part IV—Synthesis of (R)-tert-Butyl (2-((1,3-dioxoisoindolin-2-yl)methyl)-3,4-dihydro-2H-benzo[b][1,4]oxazin-6-yl)carbamate

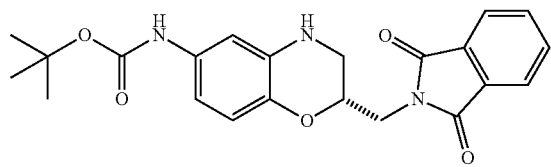 [SMILES: CC(C)(C)OC(=O)Nc1ccc2c(c1)NC[C@H](CN1C(=O)c3ccccc3C1=O)O2]

At 0° C., diisopropyl azodicarboxylate (1.38 mL, 7.12 mmol) was added slowly to a solution of (R)-tert-butyl (2-(hydroxymethyl)-3,4-dihydro-2H-benzo[b][1,4]oxazin-6-yl)carbamate (1.9 g, 6.78 mmol), triphenylphosphine (1.78 g, 6.78 mmol), and phthalimide (1.00 g, 6.78 mmol) in THF (20 mL). The reaction mixture was stirred at room temperature overnight. Then, the reaction mixture was partitioned between ethyl acetate and water. The organic layer was dried (MgSO$_4$) and concentrated to provide a residue. The residue was purified by column chromatography on silica, eluting with 50% ethyl acetate in hexane to afford (R)-tert-butyl (2-((1,3-dioxoisoindolin-2-yl)methyl)-3,4-dihydro-2H-benzo[b][1,4]oxazin-6-yl)carbamate as a yellow solid.

Part V—Synthesis of (S)-tert-Butyl (2-(aminomethyl)-3,4-dihydro-2H-benzo[b][1,4]oxazin-6-yl)carbamate

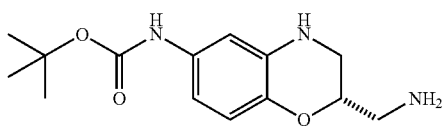 [SMILES: CC(C)(C)OC(=O)Nc1ccc2c(c1)NC[C@H](CN)O2]

Hydrazine hydrate (2.00 g, 40.0 mmol) was added to a stirred mixture of (R)-tert-butyl (2-((1,3-dioxoisoindolin-2-yl)methyl)-3,4-dihydro-2H-benzo[b][1,4]oxazin-6-yl)carbamate (2.25 g, 5.50 mmol) in ethanol (20 mL). After sixteen hours, the reaction mixture was concentrated, and the resulting residue was triturated with dichloromethane. The resulting mixture was filtered, and the filtrate was concentrated to provide a residue. The residue was crystallized to obtain (S)-tert-butyl (2-(aminomethyl)-3,4-dihydro-2H-benzo[b][1,4]oxazin-6-yl)carbamate.

Part VI—Synthesis of (R)-tert-Butyl (2-(acetamidomethyl)-3,4-dihydro-2H-benzo[b][1,4]oxazin-6-yl)carbamate

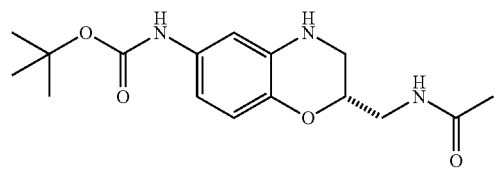 [SMILES: CC(=O)NC[C@H]1CNc2cc(NC(=O)OC(C)(C)C)ccc2O1]

To a stirred solution of (S)-tert-butyl (2-(aminomethyl)-3,4-dihydro-2H-benzo[b][1,4]oxazin-6-yl)carbamate (7.9 g, 28.3 mmol), (benzotriazol-1-yloxy)tris (dimethylamino) phosphonium hexafluorophosphate (13.8 g, 31.1 mmol), and acetic acid (1.6 mL, 28.3 mmol) in THF (141 mL) was added N,N'-diisopropylethylamine (19.8 mL, 113 mmol). After two hours, the mixture was partitioned between isopropanol/chloroform (1:3, v/v) and saturated sodium bicarbonate. The organic layer was isolated, dried (MgSO$_4$), and concentrated to afford (R)-tert-butyl (2-(acetamidomethyl)-3,4-dihydro-2H-benzo[b][1,4]oxazin-6-yl)carbamate.

Part VII—Synthesis of tert-Butyl (S)-(2-(acetamidomethyl)-4-((3-(trifluoromethyl)phenyl)sulfonyl)-3,4-dihydro-2H-benzo[b][1,4]oxazin-6-yl)carbamate

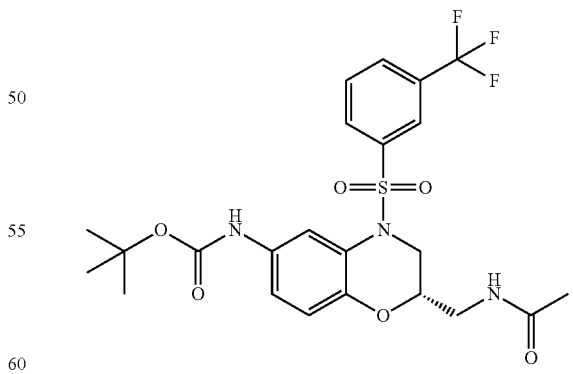

To a solution of tert-butyl (R)-(2-(acetamidomethyl)-3,4-dihydro-2H-benzo[b][1,4]oxazin-6-yl)carbamate (0.3 g, 0.93 mmol) in pyridine (4 mL) was added 3-(trifluoromethyl)benzenesulfonyl chloride (0.27 g, 1.1 mmol). The solution was stirred at 60° C. for two hours. The resulting mixture was diluted with ethyl acetate, washed with 1M hydrochloric acid (3×), washed with brine, dried (Na₂SO₄) and concentrated. The concentrate was purified by column chromatography eluting with a gradient of ethyl acetate in hexanes. Fractions containing the title compound in pure form were combined and concentrated to provide the title compound (120 mg, 24%).

Part VIII—Synthesis of (S)—N-((6-Amino-4-((3-(trifluoromethyl)phenyl)sulfonyl)-3,4-dihydro-2H-benzo[b][1,4]oxazin-2-yl)methyl)acetamide

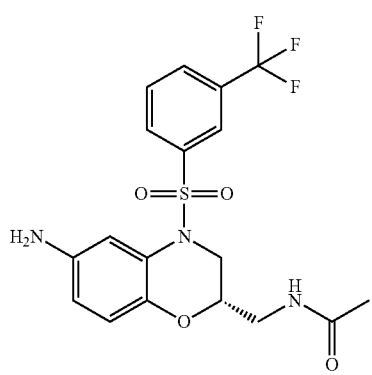 [SMILES: CC(=O)NC[C@H]1CN(S(=O)(=O)c2cccc(C(F)(F)F)c2)c2cc(N)ccc2O1]

To a solution of tert-butyl (S)-(2-(acetamidomethyl)-4-((3-(trifluoromethyl) phenyl)sulfonyl)-3,4-dihydro-2H-benzo[b][1,4]oxazin-6-yl)carbamate (0.12 g, 0.23 mmol) in dichloromethane (3 mL) was added trichloroacetic acid (3 mL), and the reaction mixture was stirred at ambient temperature for 2 hours. Then, the reaction mixture was concentrated in vacuo. The resulting concentrate was partitioned between ethyl acetate and saturated sodium bicarbonate. The organic layer was separated, washed with brine, dried (Na₂SO₄) and concentrated to provide the title compound (100 mg, 24%).

Part IX—Synthesis of (S)—N-((6-((2-Chloro-6-fluorobenzyl)amino)-4-((3-(trifluoromethyl)phenyl)sulfonyl)-3,4-dihydro-2H-benzo[b][1,4]oxazin-2-yl)methyl)acetamide

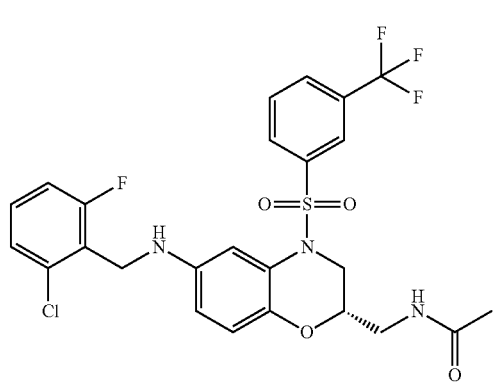 [SMILES: CC(=O)NC[C@H]1CN(S(=O)(=O)c2cccc(C(F)(F)F)c2)c2cc(NCc3c(F)cccc3Cl)ccc2O1]

To a solution of 2-chloro-6-fluorobenzaldehyde (20 mg, 0.13 mmol) and (S)—N-((6-amino-4-((3-(trifluoromethyl)phenyl)sulfonyl)-3,4-dihydro-2H-benzo[b][1,4]oxazin-2-yl)methyl)acetamide (50 mg, 0.12 mmol) in 1,2-dichloroethane (0.5 mL) was added sodium triacetoxyborohydride (32 mg, 0.15 mmol). The resulting mixture was stirred at ambient temperature overnight. Then, the reaction mixture was concentrated, and the concentrate was subjected to preparatory HPLC. Fractions containing the title compound in pure form were combined and concentrated to provide the title compound (24 mg, 36%). ¹H-NMR (400 MHz, DMSO-d₆) δ 8.07-8.00 (m, 2H), 7.92 (m, 1H), 7.86 (s, 1H), 7.80 (t, 1H), 7.38 (m, 2H), 7.22 (m, 1H), 7.04 (m, 1H), 6.59 (d, 1H), 6.46 (m, 1H), 4.27 (m, 1H), 4.22 (m, 2H), 3.3-3.0 (m, 3H), 1.80 (s, 3H).

Example 21—Preparation of (S)—N-((4-((3-Chloro-1-ethyl-1H-pyrazol-4-yl)sulfonyl)-6-((2-chloro-6-fluorobenzyl)amino)-3,4-dihydro-2H-benzo[b][1,4]oxazin-2-yl)methyl)acetamide

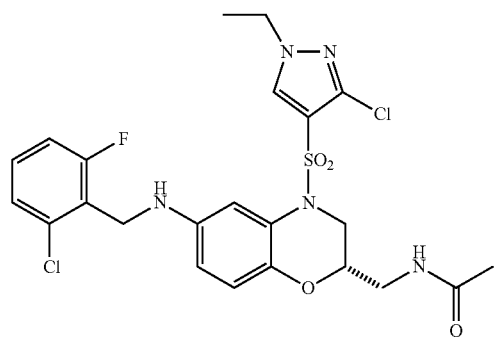 [SMILES: CCn1cc(S(=O)(=O)N2C[C@H](CNC(C)=O)Oc3ccc(NCc4c(F)cccc4Cl)cc32)c(Cl)n1]

The title compound was prepared based on experimental procedures described in Example 20 and the detailed description. (ES, m/z): (M+H)⁺556.

Example 22—Preparation of Additional Benzylamino-3,4-dihydro-2H-benzo[b][1,4]oxazin-2-yl Compounds Compounds in the table below were prepared based on experimental procedures described in Examples 18 and 20 and the detailed description.

| No. | Structure | Name | Observed m/z |
|---|---|---|---|
| 22A | 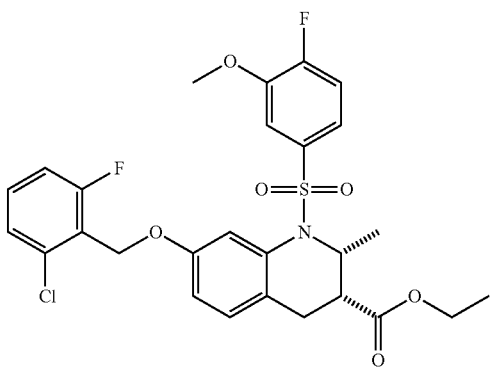 | (S)-2-(6-((2-chloro-6-fluorobenzyl)amino)-4-((3-(trifluoromethyl)phenyl)sulfonyl)-3,4-dihydro-2H-benzo[b][1,4]oxazin-2-yl)acetic acid | 559 (M + H)+ |
| 22B | 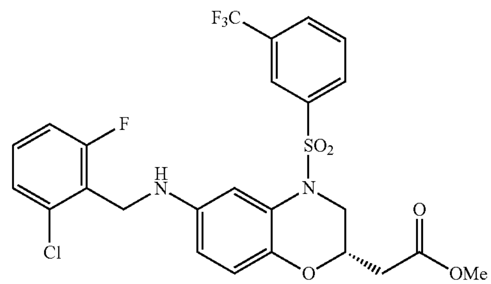 [SMILES: COC(=O)C[C@H]1CN(S(=O)(=O)c2cccc(C(F)(F)F)c2)c2cc(NCc3c(F)cccc3Cl)ccc2O1] | (S)-methyl 2-(6-((2-chloro-6-fluorobenzyl)amino)-4-((3-(trifluoromethyl)phenyl)sulfonyl)-3,4-dihydro-2H-benzo[b][1,4]oxazin-2-yl)acetate | 573 (M + H)+ |

Example 23—Synthesis of Racemic (2R,3R)-Ethyl 7-((2-chloro-6-fluorobenzyl)oxy)-1-((4-fluoro-3-methoxyphenyl)sulfonyl)-2-methyl-1,2,3,4-tetrahydroquinoline-3-carboxylate Part I—Synthesis of Ethyl 2-(4-acetoxy-2-nitrobenzyl)-3-oxobutanoate

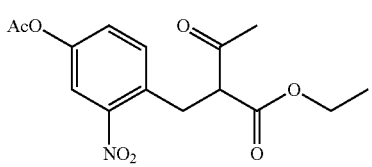 [SMILES: CCOC(=O)C(Cc1ccc(OC(C)=O)cc1[N+](=O)[O-])C(C)=O]

Ethyl 3-oxobutanoate (2.83 g, 21.7 mmol) was added to a mixture of THF (100 mL) and 60% sodium hydride in mineral oil (870 mg, 21.7 mmol). The resulting solution was stirred for an hour at 0° C. Then, a solution of 4-(bromomethyl)-3-nitrophenyl acetate (4.58 g, 16.71 mmol) in THF (20 mL) was added dropwise to the reaction mixture. The resulting solution was stirred for an additional three hours at room temperature. Then, the reaction was quenched by the addition of water (30 mL) to the reaction mixture. The resulting solution was extracted three times with ethyl acetate and the organic layers were combined. The organic solution was washed with water, washed with brine, dried (Na$_2$SO$_4$) and concentrated to provide a residue. The residue was purified via MPLC eluting with ethyl acetate/petroleum ether (1:10) to afford ethyl 2-[[4-(acetyloxy)-2-nitrophenyl]methyl]-3-oxobutanoate (3.75 g, 69%) as a colorless oil.

Part II—Synthesis of Racemic (2R,3R)-Ethyl 7-acetoxy-2-methyl-1,2,3,4-tetrahydroquinoline-3-carboxylate

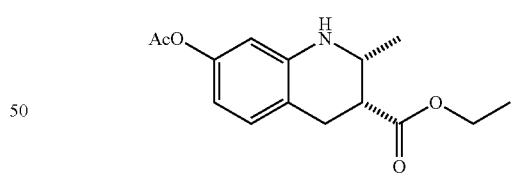

In a 100-mL high-pressure reactor was placed ethyl 2-[[4-(acetyloxy)-2-nitrophenyl]methyl]-3-oxobutanoate (3.75 g, 11.60 mmol), ethyl acetate (80 mL), palladium carbon 10% containing water (380 mg, 0.10 equiv). The resulting solution was stirred for 20 hours at 40° C. under 10 atmospheres of hydrogen gas pressure. Then, the reaction mixture was cooled, the pressure in the reaction vessel was released, and the reaction mixture was filtered through Celite. The filtrate was concentrated to provide a residue that was purified via MPLC eluting with ethyl acetate/petroleum ether (1:10) to afford racemic (2R,3R)-ethyl 7-acetoxy-2-methyl-1,2,3,4-tetrahydroquinoline-3-carboxylate (1.3 g, 40%) as a colorless oil.

Part III—Synthesis of Racemic (2R,3R)-Ethyl 7-acetoxy-1-((4-fluoro-3-methoxyphenyl)sulfonyl)-2-methyl-1,2,3,4-tetrahydroquinoline-3-carboxylate

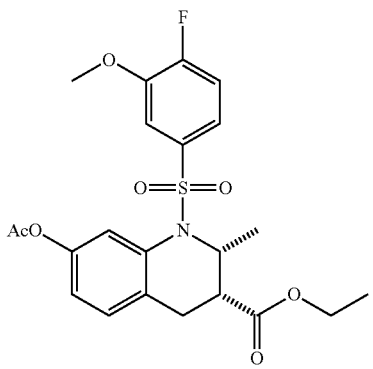 [SMILES: CCOC(=O)[C@@H]1Cc2ccc(OC(C)=O)cc2N(S(=O)(=O)c2ccc(F)c(OC)c2)[C@@H]1C]

A solution of racemic (2R,3R)-ethyl 7-(acetyloxy)-2-methyl-1,2,3,4-tetrahydroquinoline-3-carboxylate (750 mg, 2.70 mmol), dichloromethane (30 mL), triethylamine (1.37 g, 13.54 mmol), 4-fluoro-3-methoxybenzene-1-sulfonyl chloride (1.1 g, 4.90 mmol) was refluxed for 18 hours. Then, the reaction mixture was cooled and water was added to quench the reaction. The resulting mixture was extracted twice with ethyl acetate. The organic extracts were combined and washed twice with water, washed with brine, dried (Na$_2$SO$_4$) and concentrated to provide a residue. The residue was purified via MPLC eluting with ethyl acetate/petroleum ether (1:10) to afford racemic (2R,3R)-ethyl 7-acetoxy-1-(4-fluoro-3-methoxyphenyl)sulfonyl)-2-methyl-1,2,3,4-tetrahydroquinoline-3-carboxylate (730 mg, 58%) as light yellow oil.

Part IV—Synthesis of Racemic (2R,3R)-Ethyl 1-((4-fluoro-3-methoxyphenyl)sulfonyl)-7-hydroxy-2-methyl-1,2,3,4-tetrahydroquinoline-3-carboxylate

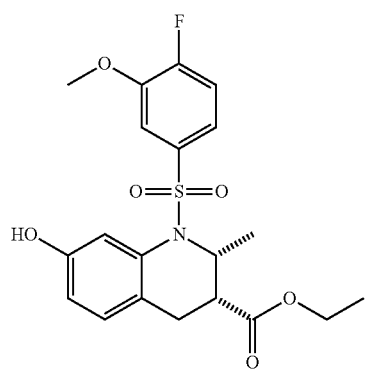 [SMILES: CCOC(=O)[C@@H]1Cc2ccc(O)cc2N(S(=O)(=O)c2ccc(F)c(OC)c2)[C@@H]1C]

To a solution of racemic (2R,3R)-ethyl 7-acetoxy-1-((4-fluoro-3-methoxyphenyl)sulfonyl)-2-methyl-1,2,3,4-tetrahydroquinoline-3-carboxylate (620 mg, 1.33 mmol) in methanol (20 mL) was added acetyl chloride (1.0 mL, 13.3 mmol). The resulting solution was stirred for one hour at room temperature, concentrated and diluted in water (30 ml). The pH value of the resulting solution was adjusted to 4-5 by adding saturated sodium bicarbonate. Next, the reaction mixture was extracted three times with ethyl acetate. The organic extracts were combined and washed with water, washed with brine, dried (Na$_2$SO$_4$) and concentrated to provide a residue. The residue was purified via MPLC eluting with ethyl acetate/petroleum ether (1:10) to afford racemic (2R,3R)-ethyl 1-((4-fluoro-3-methoxyphenyl)sulfonyl)-7-hydroxy-2-methyl-1,2,3,4-tetrahydroquinoline-3-carboxylate (560 mg, 99%) as a light yellow oil.

Part V—Synthesis of Racemic (2R,3R)-Ethyl 7-((2-chloro-6-fluorobenzyl)oxy)-1-((4-fluoro-3-methoxyphenyl)sulfonyl)-2-methyl-1,2,3,4-tetrahydroquinoline-3-carboxylate

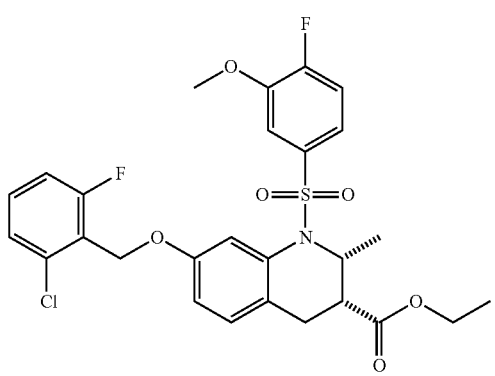 [SMILES: CCOC(=O)[C@@H]1Cc2ccc(OCc3c(F)cccc3Cl)cc2N(S(=O)(=O)c2ccc(F)c(OC)c2)[C@@H]1C]

To a solution of racemic (2R,3R)-ethyl 1-((4-fluoro-3-methoxyphenyl)sulfonyl)-7-hydroxy-2-methyl-1,2,3,4-tetrahydroquinoline-3-carboxylate (130 mg, 0.31 mmol), (2-chloro-6-fluorophenyl)methanol (59 mg, 0.37 mmol), and triphenyl phosphine (120 mg, 0.46 mmol) in THF (10 mL) was added diisopropyl azodicarboxylate (93 mg, 0.46 mmol) dropwise. The resulting solution was stirred for one hour at room temperature and then partitioned between ethyl acetate and water. The organic layer was washed twice with water, washed with brine, dried (Na$_2$SO4) and concentrated to provide a residue. The residue was applied onto a silica gel column that was eluted using ethyl acetate/petroleum ether (1:10) to afford racemic (2R,3R)-ethyl 7-((2-chloro-6-fluorobenzyl)oxy)-1-((4-fluoro-3-methoxyphenyl)sulfonyl)-2-methyl-1,2,3,4-tetrahydroquinoline-3-carboxylate (94 mg, 54%) as a white solid. $^1$H-NMR (400 MHz, CDCl$_3$): δ 7.63 (s, 1H), 7.40-7.20 (m, 3H), 7.17-7.00 (m, 4H), 6.83 (d, J=8.4 Hz, 1H), 5.20 (s, 2H), 5.00-4.90 (m, 1H), 4.25-4.20 (m, 2H), 3.74 (s, 3H), 2.90-2.80 (m, 1H), 2.60 (dd, J=18.0, 6.4 Hz, 1H), 2.30-2.20 (m, 1H), 1.12 (d, J=6.8 Hz, 3H). (ES, m/z:) (M+H)$^+$566.1.

Example 24—Synthesis of Racemic (2R,3R)-Ethyl 7-((2,3-dihydro-1H-inden-1-yl)oxy)-1-((4-fluoro-3-methoxyphenyl)sulfonyl)-2-methyl-1,2,3,4-tetrahydroquinoline-3-carboxylate

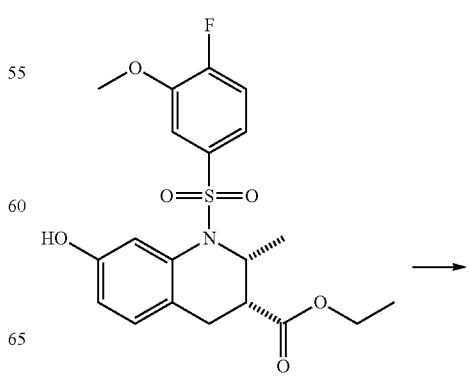

-continued

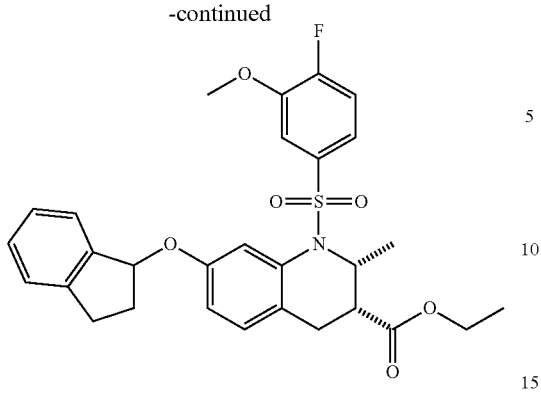

The title compound was prepared based on procedures described above. $^1$H-NMR (400 MHz, CDCl$_3$) δ 7.61 (dd, 1H), 7.50 (d, 1H), 7.40-7.45 (m, 2H), 7.09-7.31 (m, 4H), 7.01 (d, 1H), 6.82 (t, 1H), 5.79 (dd, 1H), 4.92 (m, 1H), 4.17 (m, 2H), 3.75 (s, 3H), 3.16 (m, 1H), 2.88-3.00 (m, 2H), 2.58 (m, 2H), 2.15-2.28 (m, 2H), 1.28 (t, 3H), 1.07 (d, 3H). (ES, m/z:) 562 (M+Na).$^+$ Example 25—Synthesis of Racemic (2R,3R)-7-((2-Chloro-6-fluorobenzyl)oxy)-1-((4-fluoro-3-methoxy-phenyl)sulfonyl)-2-methyl-1,2,3,4-tetrahydroquinoline-3-carboxylic acid

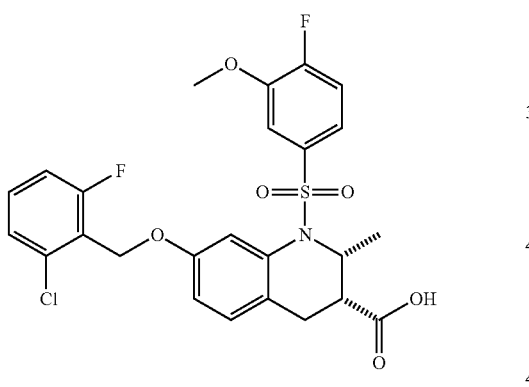

To a solution of racemic (2R,3R)-ethyl 7-((2-chloro-6-fluorobenzyl)oxy)-1-((4-fluoro-3-methoxyphenyl)sulfonyl)-2-methyl-1,2,3,4-tetrahydroquinoline-3-carboxylate (70 mg, 0.12 mmol) in THF (3 mL) and water (1.5 mL) was added lithium hydroxide monohydrate (21 mg, 0.50 mmol). The resulting solution was stirred overnight at room temperature. Next, the reaction mixture was diluted with water (15 mL) and the pH of the mixture was adjusted to 4-5 by adding concentrated hydrogen chloride to the mixture. Next, the mixture was extracted three times with ethyl acetate. The organic extracts were combined, washed brine, dried (Na$_2$SO$_4$) and concentrated to provide a residue. The residue was purified by reverse phase HPLC eluting with a gradient of water (containing 0.05% trifluoroacetic acid) and acetonitrile to afford racemic (2R,3R)-7-((2-chloro-6-fluorobenzyl)oxy)-1-((4-fluoro-3-methoxyphenyl)sulfonyl)-2-methyl-1,2,3,4-tetrahydroquinoline-3-carboxylic acid (40 mg, 60%) as a white solid. $^1$H-NMR (400 MHz, CDCl$_3$): δ 7.64 (s, 1H), 7.40-7.20 (m, 3H), 7.17-7.00 (m, 4H), 6.84 (dd, J=8.4, 2.4 Hz, 1H), 5.21 (s, 2H), 5.04-4.96 (m, 1H), 3.75 (s, 3H), 2.95-2.80 (m, 1H), 2.64 (dd, J=18.0, 6.4 Hz, 1H), 2.30-2.20 (m, 1H), 1.12 (d, J=6.8 Hz, 3H). (ES, m/z:) (M+H)$^+$538.3.

Example 26—Preparation of Racemic (2R,3R)-7-((2,3-Dihydro-1H-inden-1-yl)oxy)-1-((4-fluoro-3-methoxy-phenyl)sulfonyl)-2-methyl-1,2,3,4-tetrahydroquinoline-3-carboxylic acid

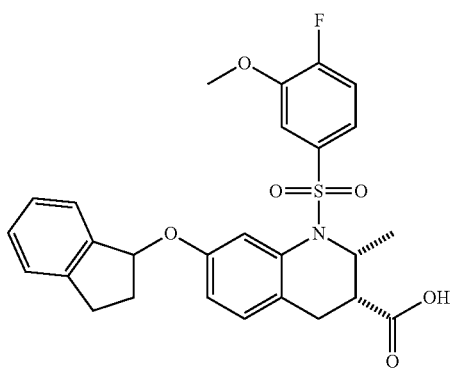 [SMILES: COc1cc(S(=O)(=O)N2c3cc(OC4CCc5ccccc54)ccc3C[C@@H](C(=O)O)[C@H]2C)ccc1F]

The title compound was prepared based on the experimental procedures described in Examples 23-25 and the detailed description. (ES, m/z): (M+H)$^+$512.

Example 27—Synthesis of 7-((2-Chloro-6-fluorobenzyl)oxy)-1-((4-fluoro-3-methoxyphenyl)sulfonyl)-1,2,3,4-tetrahydroquinoline

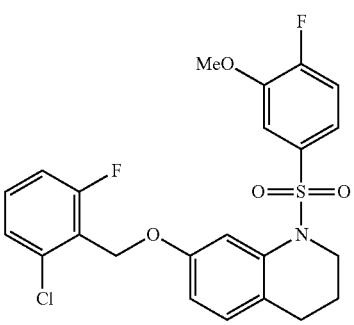 [SMILES: COc1cc(S(=O)(=O)N2CCCc3ccc(OCc4c(F)cccc4Cl)cc32)ccc1F]

Part I—Synthesis of 1-((4-Fluoro-3-methoxyphenyl) sulfonyl)-1,2,3,4-tetrahydroquinolin-7-ol

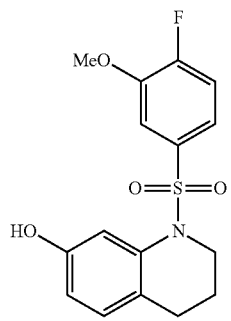

To a solution of 1,2,3,4-tetrahydroquinolin-7-ol (2.5 g, 16.76 mmol) in dichloromethane (100 mL) was added pyridine (2.6 g, 32.9 mmol) and 4-fluoro-3-methoxybenzene-1-sulfonyl chloride (5.6 g, 24.93 mmol, 1.50 equiv). The mixture was stirred for one hour at room temperature.

Then, methanol (2 mL) was added to the reaction mixture, and the resulting mixture was concentrated to provide a residue. The residue was purified via MPLC eluting with dichloromethane/ethyl acetate (2:1) to afford 1-[(4-fluoro-3-methoxybenzene)sulfonyl]-1,2,3,4-tetrahydroquinolin-7-ol (7.0 g) as a red oil.

Part II—Synthesis of 7-((2-Chloro-6-fluorobenzyl)oxy)-1-((4-fluoro-3-methoxyphenyl)sulfonyl)-1,2,3,4-tetrahydroquinoline

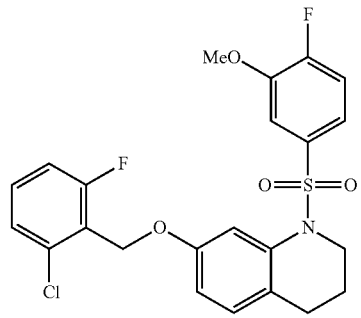 [SMILES: COc1cc(S(=O)(=O)N2CCCc3ccc(OCc4c(F)cccc4Cl)cc32)ccc1F]

To a solution of 1-[(4-fluoro-3-methoxybenzene)sulfonyl]-1,2,3,4-tetrahydroquinolin-7-ol (150 mg, 0.44 mmol), (2-chloro-6-fluorophenyl)methanol (71 mg, 0.44 mmol), triphenylphosphine (140 mg, 0.53 mmol), in anhydrous THF (5 mL) was added diisopropyl azodicarboxylate (108 mg, 0.53 mmol) dropwise at 0° C. The resulting solution was stirred overnight at 25° C., and then concentrated to provide a residue. The residue was purified by MPLC eluting with petroleum ether:ethyl acetate (3:1). The fraction containing the major component was further purified by Prep-HPLC eluting with a gradient of water (containing 0.05% trifluoroacetic acid) and acetonitrile (50.0% to 90.0% in 8 minutes) to afford the title compound (41.5 mg, 19%) as a white solid. $^1$H-NMR (400 MHz, CDCl$_3$) δ 7.61-7.60 (d, 1H), 7.36-7.28 (m, 3H), 7.15-7.02 (m, 3H), 6.96-6.94 (d, 1H), 6.81-6.78 (d, 1H), 5.21 (s, 2H), 3.84-3.81 (t, 2H), 3.71 (s, 3H), 2.44-2.40 (t, 2H), 1.67-1.58 (m, 2H). (ES, m/z): (M+H)$^+$: 480.

Example 28—Synthesis of (S)-Methyl 3-(7-((2-chloro-6-fluorobenzyl)oxy)-1-((4-fluoro-3-methoxyphenyl)sulfonyl)-1,2,3,4-tetrahydroquinolin-3-yl)-2,2-dimethylpropanoate

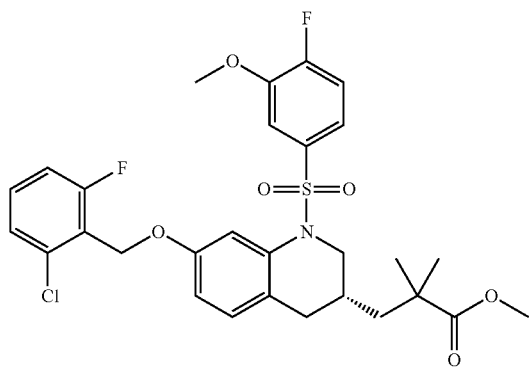 [SMILES: COC(=O)C(C)(C)C[C@@H]1Cc2ccc(OCc3c(F)cccc3Cl)cc2N(S(=O)(=O)c2ccc(F)c(OC)c2)C1]

Part I—Synthesis of 2,2-Dimethyl-5-oxo-5-[(4S)-2-oxo-4-(propan-2-yl)-1,3-oxazolidin-3-yl]pentanoic acid

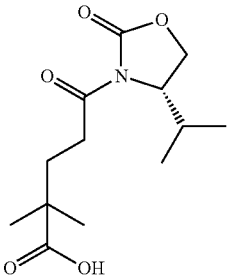 [SMILES: CC(C)[C@H]1COC(=O)N1C(=O)CCC(C)(C)C(=O)O]

To a mixture of (4S)-4-(propan-2-yl)-1,3-oxazolidin-2-one (5 g, 38.7 mmol) and lithium chloride (1.79 g, 42.6 mmol) in tetrahydrofuran (15 mL) was added triethylamine (6.97 mL, 50.1 mmol) dropwise. To this mixture was added 3,3-dimethyloxane-2,6-dione (5.78 g, 40.66 mmol) in portions. The resulting solution was stirred for two hours at room temperature, and then the reaction was quenched by the addition of brine (15 mL) to the reaction solution. The pH value of the solution was adjusted to pH 1 by adding hydrogen chloride (1 mol/L). Next, the resulting solution was extracted three times dichloromethane, organic layers were combined, and then concentrated to afford 2,2-dimethyl-5-oxo-5-[(4S)-2-oxo-4-(propan-2-yl)-1,3-oxazolidin-3-yl]pentanoic acid (11.32 g) as a colorless oil which was used without any further purification.

Part II—Synthesis of 2,2-Dimethyl-5-oxo-5-[(4S)-2-oxo-4-(propan-2-yl)-1,3-oxazolidin-3-yl]pentanoate

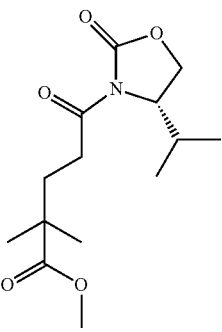 [SMILES: COC(=O)C(C)(C)CCC(=O)N1C(=O)OC[C@@H]1C(C)C]

To a solution of 2,2-dimethyl-5-oxo-5-[(4S)-2-oxo-4-(propan-2-yl)-1,3-oxazolidin-3-yl]pentanoic acid (11.29 g, 41.61 mmol) in acetonitrile (78.7 mL) and methanol (7.9 mL) was added 2M solution of trimethylsilyl diazomethane in hexanes (41.6 mL) dropwise with stirring at 0° C. The resulting solution was stirred for 2 h at 0° C. in an ice bath, and then the reaction solution was concentrated to provide a residue. The residue was purified using MPLC eluting with ethyl acetate/petroleum ether (1:2) as eluent to yield methyl 2,2-dimethyl-5-oxo-5-[(4S)-2-oxo-4-(propan-2-yl)-1,3-oxazolidin-3-yl]pentanoate (2.27 g, 19%) as a light yellow oil.

Part III—Synthesis of (4S)-4-[(4-Hydroxy-2-nitrophenyl)methyl]-2,2-dimethyl-5-oxo-5-[(4S)-2-oxo-4-(propan-2-yl)-1,3-oxazolidin-3-yl]pentanoate

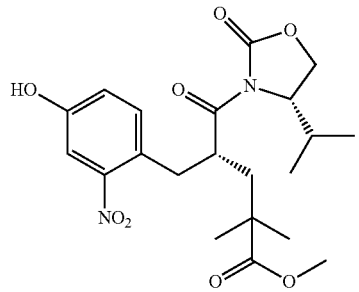 [SMILES: COC(=O)C(C)(C)C[C@H](Cc1ccc(O)cc1[N+](=O)[O-])C(=O)N1C(=O)OC[C@@H]1C(C)C]

To a solution of methyl 2,2-dimethyl-5-oxo-5-[(4S)-2-oxo-4-(propan-2-yl)-1,3-oxazolidin-3-yl]pentanoate (2.27 g, 7.96 mmol) in anhydrous tetrahydrofuran (22.8 mL) was added a 1M solution of LiHMDS in THF (8.9 mL) at −78° C., and the reaction mixture stirred for 10 minutes. To this was added a solution of 4-(bromomethyl)-3-nitrophenyl acetate (2.18 g, 7.95 mmol) in tetrahydrofuran (11.4 mL) dropwise with stirring. The resulting solution was stirred overnight at room temperature, and then the reaction was quenched by the addition of saturated ammonium chloride (100 mL) to reaction mixture. The resulting solution was extracted three times with dichloromethane, organic layers were combined, then concentrated to provide a residue. The residue was purified using MPLC eluting with ethyl acetate/petroleum ether (1:1) to afford methyl (4S)-4-[(4-hydroxy-2-nitrophenyl)methyl]-2,2-dimethyl-5-oxo-5-[(4S)-2-oxo-4-(propan-2-yl)-1,3-oxazolidin-3-yl]pentanoate (1.84 g, 53%) as a yellow oil.

Part IV—Synthesis of (S)-Methyl 3-(7-hydroxy-2-oxo-1,2,3,4-tetrahydroquinolin-3-yl)-2,2-dimethylpropanoate

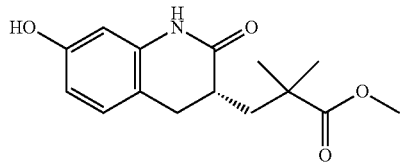 [SMILES: COC(=O)C(C)(C)C[C@@H]1Cc2ccc(O)cc2NC1=O]

A mixture of methyl (4S)-4-[(4-hydroxy-2-nitrophenyl)methyl]-2,2-dimethyl-5-oxo-5-[(4S)-2-oxo-4-(propan-2-yl)-1,3-oxazolidin-3-yl]pentanoate (1.84 g, 4.22 mmol), acetic acid (17.1 mL) and zinc (4 g, 50.6 mmol) was stirred for thirty minutes at 70° C. where the reaction vessel was placed in an oil bath. Next, the reaction was quenched by the addition of saturated sodium bicarbonate (100 mL) to the reaction mixture. The resulting mixture was extracted three times with dichloromethane, the organic layers were combined, then concentrated to provide a residue. The residue was purified via MPLC eluting with a gradient of 2:1 to 1:2 of petroleum ether to ethyl acetate to afford (S)-methyl 3-(7-hydroxy-2-oxo-1,2,3,4-tetrahydroquinolin-3-yl)-2,2-dimethylpropanoate (1.27 g) as a yellow oil.

Part V—Synthesis of (S)-Methyl 3-(7-hydroxy-1,2,3,4-tetrahydroquinolin-3-yl)-2,2-dimethylpropanoate

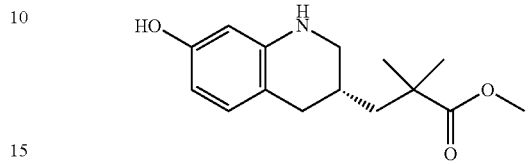

To a solution of (S)-methyl 3-(7-hydroxy-2-oxo-1,2,3,4-tetrahydroquinolin-3-yl)-2,2-dimethylpropanoate (1.25 g, 4.51 mmol) in tetrahydrofuran (30 mL) was added a 1M solution of borane in THF (20.1 mL) dropwise with stirring at 0° C. The resulting solution was stirred for four hours at room temperature. Then, the reaction was quenched by adding water (100 mL) to the reaction mixture. The resulting mixture was extracted with three times with dichloromethane. The organic layers were combined, then concentrated to provide a residue. The residue was purified using MPLC eluting with a gradient of petroleum ether:ethyl acetate of 4:1 to 1:1 to afford (S)-methyl 3-(7-hydroxy-1,2,3,4-tetrahydroquinolin-3-yl)-2,2-dimethylpropanoate (640 mg, 54%) as a yellow oil.

Part VI—Synthesis of (S)-methyl 3-(1-((4-fluoro-3-methoxyphenyl)sulfonyl)-7-hydroxy-1,2,3,4-tetrahydroquinolin-3-yl)-2,2-dimethylpropanoate

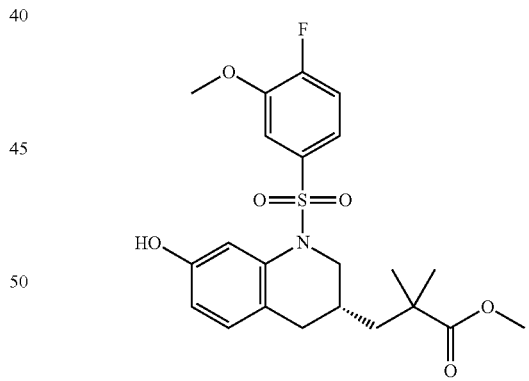

A solution (S)-methyl 3-(7-hydroxy-1,2,3,4-tetrahydroquinolin-3-yl)-2,2-dimethylpropanoate (189 mg, 0.72 mmol), pyridine (0.45 mL, 5.59 mmol), 4-fluoro-3-methoxybenzene-1-sulfonyl chloride (171.4 mg, 0.76 mmol) in dichloromethane (0.11 mL) was stirred for one hour at room temperature and then concentrated to provide a residue. The residue was purified by MPLC eluting with a gradient of 4:1 to 1:1 petroleum ether:ethyl acetate to afford (S)-methyl 3-(1-((4-fluoro-3-methoxyphenyl)sulfonyl)-7-hydroxy-1,2,3,4-tetrahydroquinolin-3-yl)-2,2-dimethylpropanoate (302 mg, 93%) as a dark red solid.

Part VII—Synthesis of (S)-Methyl 3-(7-((2-chloro-6-fluorobenzyl)oxy)-1-((4-fluoro-3-methoxyphenyl)sulfonyl)-1,2,3,4-tetrahydroquinolin-3-yl)-2,2-dimethylpropanoate

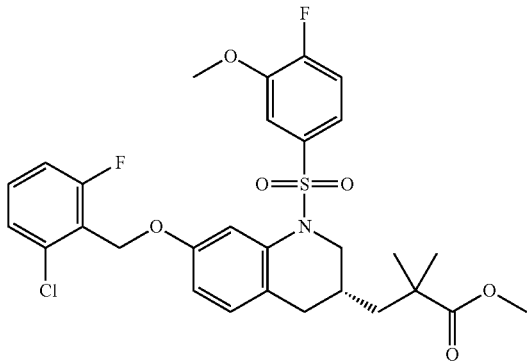 [SMILES: COC(=O)C(C)(C)C[C@@H]1Cc2ccc(OCc3c(F)cccc3Cl)cc2N(S(=O)(=O)c2ccc(F)c(OC)c2)C1]

A mixture of (S)-methyl 3-(1-((4-fluoro-3-methoxyphenyl)sulfonyl)-7-hydroxy-1,2,3,4-tetrahydroquinolin-3-yl)-2,2-dimethylpropanoate (260 mg, 0.58 mmol), potassium carbonate (79.5 mg, 0.58 mmol), and 2-(bromomethyl)-1-chloro-3-fluorobenzene (0.080 mL, 0.58 mmol) in N,N-dimethylformamide (1.0 mL) was stirred overnight at room temperature. Then, the resulting solution was diluted with water. The resulting mixture was extracted three times dichloromethane, the organic layers were combined, then concentrated to provide a residue. The residue was purified by MPLC eluting with a gradient of 10:1 to 2:1 petroleum ether:ethyl acetate. The major component was further purified by preparative HPLC with water (containing 0.05% trifluoroacetic acid) and acetonitrile (58.0% to 88.0% in 8 minutes) to afford (S)-methyl 3-(7-((2-chloro-6-fluorobenzyl)oxy)-1-((4-fluoro-3-methoxyphenyl)sulfonyl)-1,2,3,4-tetrahydroquinolin-3-yl)-2,2-dimethylpropanoate (338 mg, 99%) as a yellow oil. $^1$H-NMR (400 MHz, CDCl$_3$) δ 1.17 (s, 3H), 1.19 (s, 3H), 1.43-1.53 (m, 3H), 2.11 (dd, J=10.8 Hz, 16.8 Hz, 1H), 2.50 (dd, J=5.2 Hz, 16.4 Hz, 1H), 3.01 (dd, J=10.8 Hz, 13.6 Hz, 1H), 3.72 (s, 3H), 3.74 (s, 3H), 4.19 (dd, J=1.6 Hz, 13.2 Hz, 1H), 5.20 (d, J=1.6 Hz, 2H), 6.78 (dd, J=2.4 Hz, 8.4 Hz, 1H), 6.92 (d, J=8.4 Hz, 1H), 7.06-7.15 (m, 3H), 7.23-7.26 (m, 1H), 7.28-7.36 (m, 2H), 7.62 (d, J=2.4 Hz, 1H). (ES, m/z): (M+H)$^+$594.

Example 29—Synthesis of (S)-3-(7-((2-Chloro-6-fluorobenzyl)oxy)-1-((4-fluoro-3-methoxyphenyl)sulfonyl)-1,2,3,4-tetrahydroquinolin-3-yl)-2,2-dimethylpropanoic acid

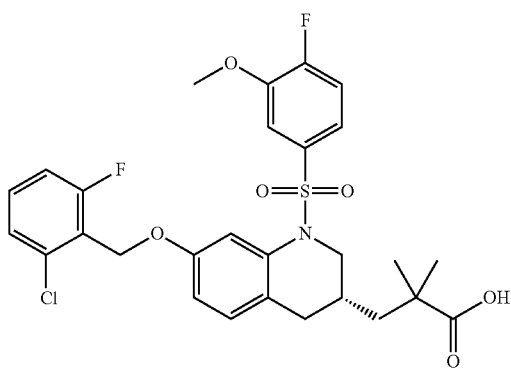 [SMILES: COc1cc(S(=O)(=O)N2C[C@H](CC(C)(C)C(=O)O)Cc3ccc(OCc4c(F)cccc4Cl)cc32)ccc1F]

A mixture of (S)-methyl 3-(7-((2-chloro-6-fluorobenzyl)oxy)-1-((4-fluoro-3-methoxyphenyl)sulfonyl)-1,2,3,4-tetrahydroquinolin-3-yl)-2,2-dimethylpropanoate (200 mg, 0.34 mmol), dioxane (1.5 mL), methanol (0.8 mL), water (0.8 mL), and lithium hydroxide monohydrate (282 mg, 6.73 mmol) was stirred for four hours at 50° C. The pH value of the solution was adjusted to pH 6 with hydrogen chloride (1 mol/L). The resulting solution was extracted three times with dichloromethane, the organic layers were combined, then concentrated to provide a crude product that was purified by Prep-HPLC eluting with a gradient of water (containing 0.05% TFA) and acetonitrile (55.0% to 80.0% in 8 minutes) to afford (S)-3-(7-((2-chloro-6-fluorobenzyl)oxy)-1-((4-fluoro-3-methoxyphenyl)sulfonyl)-1,2,3,4-tetrahydroquinolin-3-yl)-2,2-dimethylpropanoic acid (85.5 mg, 44%) as a white solid. $^1$H-NMR (400 MHz, CD$_3$OH) δ 1.15 (s, 3H), 1.18 (s, 3H), 1.41-1.57 (m, 3H), 2.22-2.10 (m, 1H), 2.59-2.51 (m, 1H), 3.03 (dd, J=10.8 Hz, 13.8 Hz), 3.69 (s, 3H), 4.31 (dd, J=2.1 Hz, 13.8 Hz, 1H), 5.22 (d, J=1.8 Hz, 2H), 6.84 (dd, J=2.7 Hz, 8.4 Hz, 1H), 6.99 (d, J=8.4 Hz, 1H), 7.04 (dd, J=1.8 Hz, 7.8 Hz, 1H), 7.15-7.45 (m, 5H), 7.53 (s, 1H). (ES, m/z): (M+H)$^+$580.

Example 30—Synthesis of the Sodium Salt of (S,E)-1-(3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanoyl)piperidine-4-carboxylic acid

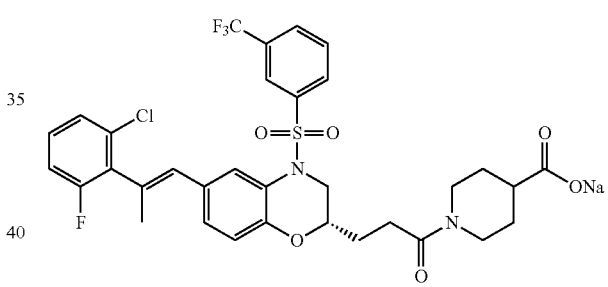

Part I—Synthesis of ethyl (S,E)-1-(3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanoyl)piperidine-4-carboxylate

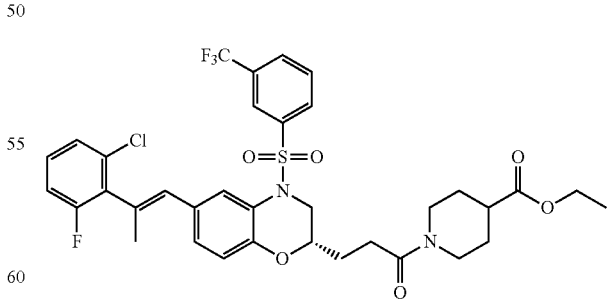

In a round bottomed flask was combined (S,E)-3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanoic acid (0.20 g, 0.34 mmol), N,N-diisopropylethylamine (0.12 mL, 0.69 mmol), and ethyl isonipecotate (81 mg, 0.51 mmol) in N,N-dimethylformamide (3 mL). Added benzotriazol-1-yl-oxytripyrrolidinophosphonium hexafluorophosphate (0.19 g, 0.49 mmol) and stirred the reaction at ambient temperature for 3 hours. The solution was diluted with ethyl acetate, washed with 1M aqueous hydrogen chloride, water, brine, dried (Na₂SO₄) and concentrated. The mixture was purified by column chromatography eluting with a gradient of 20-100% ethyl acetate in hexanes. Pure fractions were combined and concentrated to afford ethyl (S,E)-1-(3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanoyl)piperidine-4-carboxylate (0.25 g, 93%).

Part II—Synthesis of Sodium Salt of (S,E)-1-(3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanoyl)piperidine-4-carboxylic acid

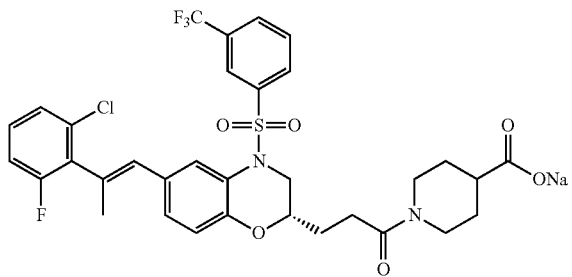

To a solution of ethyl (S,E)-1-(3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanoyl)piperidine-4-carboxylate (0.25 g, 0.35 mmol) in ethanol (5 mL) and tetrahydrofuran (2 mL) was added 2M sodium hydroxide (0.52 mL, 1.04 mmol) in water. The reaction was stirred at ambient temperature for 16 hours. Acidified solution with 1M hydrogen chloride solution in water. Extracted with ethyl acetate, washed combined extracts with brine, dried (Na₂SO₄) and concentrated to a solid (113 mg, 72%), which was (S,E)-1-(3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanoyl)piperidine-4-carboxylic acid having the following chemical formula:

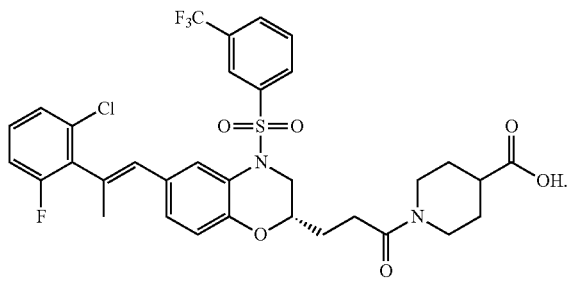 [SMILES: C/C(=C\c1ccc2c(c1)N(S(=O)(=O)c1cccc(C(F)(F)F)c1)C[C@H](CCC(=O)N1CCC(C(=O)O)CC1)O2)c1c(F)cccc1Cl]

The resulting solid carboxylic acid compound from above was converted to the sodium salt by redissolving the compound in methanol (2 mL), then adding one equivalent of a 2.962M sodium hydroxide (55 μL) solution in water. The mixture was stirred twenty minutes, then the mixture was concentrated, and then methanol was added and subsequently concentrated three times. The resulting residue was dried in a vacuum oven to afford the sodium salt of (S,E)-1-(3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanoyl)piperidine-4-carboxylic acid (110 mg, 94%) as a white solid. ¹H-NMR (400 MHz, DMSO-d₆) δ 8.10 (d, 1H), 8.0 (m, 2H), 7.86 (t, 1H), 7.70 (s, 1H), 7.38 (m, 2H), 7.28 (m, 1H), 7.10 (dd, 1H), 6.88 (d, 1H), 6.37 (s, 1H), 4.41 (m, 1H), 4.03 (m, 1H), 3.68 (m, 1H), 3.48 m, 1H), 3.4 (m, 2H), 3.0 (m, 1H), 2.75 (m, 1H), 2.37 (m, 2H), 2.09 (s, 3H), 2.02 (m, 1H), 1.84 (m, 1H), 1.7 (m, 2H), 1.45 (m, 1H), 1.35 (m, 1H). MS (ESI+)×717.26 (M+Na)⁺.

Example 31—Additional Compounds

The following additional compounds were prepared based on procedures above.

TABLE 8

| No. | Chemical Structure |
|---|---|
| 31A | 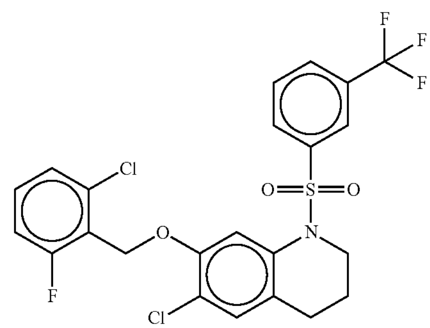 |
| 31B | 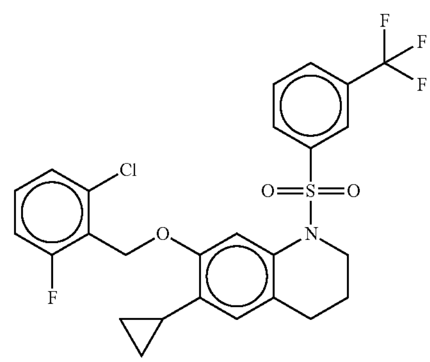 |
| 31C | 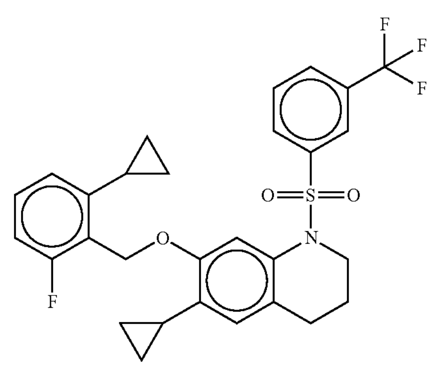 |

TABLE 8-continued

| No. | Chemical Structure |
|-----|-------------------|
| 31D | 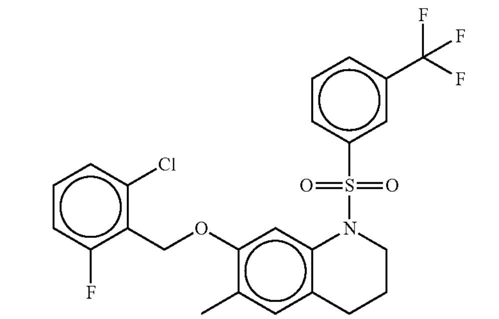 |
| 31E | 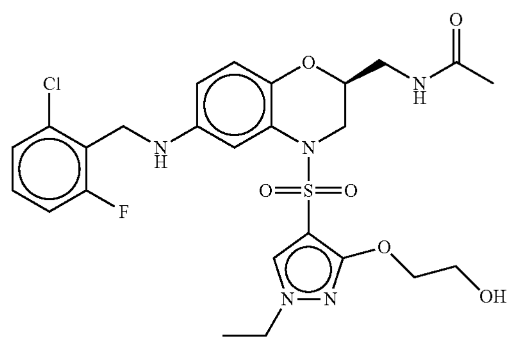 |
| 31F | 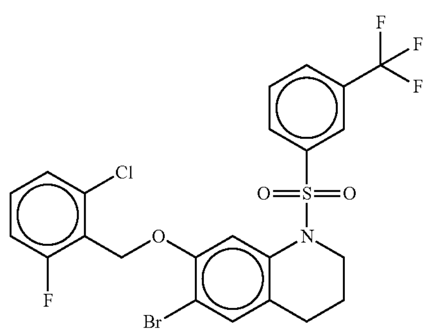 |
| 31G | 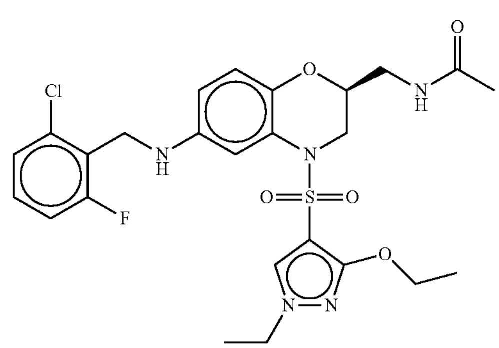 |
| 31H | |
| 31I | |

Example 32—Compound Agonist Activity Towards RORγ

Compounds from Examples 7-31 were tested for ability to increase RORγ activity using the RORγ-Ligand Binding Domain (LBD) TR-FRET Assay according to the procedures described in Example 4. Each of the compounds tested had (i) an average $EC_{50}$<5 μM in the TR-FRET Assay and (ii) an average Max Response ≥80 in the TR-FRET Assay.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A method of delivering to a patient a RORγ agonist treated lymphocyte cell, comprising administering to a patient in need thereof a pharmaceutical composition comprising said cell that has been exposed ex vivo to an agonist of RORγ.

2. The method of claim 1, further comprising culturing a lymphocyte cell with an agonist of RORγ to provide the cell that has been exposed ex vivo to an agonist of RORγ.

3. The method of claim 2, wherein the culturing comprises exposing the lymphocyte cell to a cytokine.

4. The method of claim 3, wherein the cytokine is IL-1β, IL-2, IL-6, IL-7, IL-10, IL-12, IL-15, IL-18, IL-21, IL-23, or transforming growth factor beta.

5. The method of claim 4, wherein the lymphocyte cell is a T cell.

6. The method of claim 4, wherein the lymphocyte cell is a CD8$^+$ T cell, CD4$^+$ T cell, or T$_H$17 cell.

7. The method of claim 4, wherein the lymphocyte cell is a Tc17 cell, natural killer T cell, or γδ T cell.

8. The method of claim 2, wherein the culturing comprises exposing the lymphocyte cell to an antigen associated with a medical disorder.

9. The method of claim 8, wherein the antigen comprises cancer tissue.

10. The method of claim 2, further comprising obtaining a lymphocyte cell from said patient for use in the culturing step.

11. The method of claim 2, further comprising obtaining a lymphocyte cell from a subject that produces cells allogenic to cells of the patient, for use in the culturing step.

12. The method of claim 1, wherein the lymphocyte cell is obtained from blood, cancer tissue, bone marrow, the spleen, a lymph node, or the thymus.

13. The method of claim 1, wherein the lymphocyte cell is obtained from a population of human peripheral blood mononuclear cells.

14. The method of claim 1, wherein the lymphocyte cell is obtained from a lymph node in proximity to a tumor or site of infection.

15. The method of claim 1, wherein the lymphocyte cell is obtained from cancer tissue.

16. The method of claim 1, wherein the lymphocyte cell is a tumor-infiltrating-lymphocyte cell.

17. The method of claim 1, wherein the cell expresses a receptor for an antigen specific for a medical disorder.

18. The method of claim 17, wherein the medical disorder is a cancer, bacterial infection, fungal infection, or immune disorder.

19. The method of claim 1, wherein the lymphocyte cell is a T cell.

20. The method of claim 1, wherein the lymphocyte cell is a CD8$^+$ T cell, CD4$^+$ T cell, or T$_H$17 cell.

21. The method of claim 1, wherein the lymphocyte cell is a natural killer cell.

22. The method of claim 1, wherein the lymphocyte cell is a Tc17 cell, natural killer T cell, or γδ T cell.

23. The method of claim 1, wherein the lymphocyte cell is a genetically altered cell.

24. The method of claim 1, wherein the administering comprises injecting into the patient the pharmaceutical composition.

25. The method of claim 1, further comprising administering to the patient one or more agents selected from the group consisting of a cytokine and an agonist of RORγ.

26. The method of claim 1, wherein the patient is a human.

27. The method of claim 1, wherein the agonist of RORγ is a small organic molecule.

28. The method of claim 1, wherein the agonist of RORγ is a compound of Formula I:

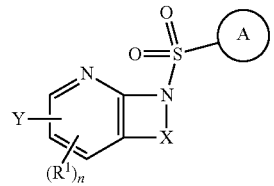

or a pharmaceutically acceptable salt or solvate thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, $C_{1-6}$alkyl, $C_{1-6}$haloalkyl, $C_{1-6}$hydroxyalkyl, $C_{1-6}$alkoxy, $C_{1-6}$haloalkoxy, —N(R$^4$)(R$^5$), —CO$_2$R$^6$, —C(O)R$^6$, —CN, —C$_{1-4}$alkylene-C$_{1-4}$alkoxy, —C$_{1-4}$alkylene-N(R$^4$)(R$^5$), —C$_{1-4}$alkylene-CO$_2$R$^6$, —O—C$_{1-6}$alkylene-N(R$^4$)(R$^5$), —N(R$^4$)C(O)—C$_{1-6}$alkylene-N(R$^4$)(R$^5$), —S(O)$_p$C$_{1-6}$alkyl, —SO$_2$N(R$^4$)(R$^5$), —N(R$^4$)SO$_2$(C$_{1-6}$alkyl), —C(O)N(R$^4$)(R$^5$), and —N(R$^4$)C(O)N(R$^4$)(R$^5$);

X is —O—[C(R$^6$)(R$^7$)]—[C(R$^6$)$_2$]$_m$-ψ, —O—C(R$^6$)$_2$—C(R$^6$)(R$^7$)—C(R$^6$)$_2$-ψ, —O—C(R$^6$)$_2$—C(R$^6$)(R$^7$)-ψ, —C(R$^6$)$_2$—[C(R$^6$)(R$^7$)]—[C(R$^6$)$_2$]$_m$-ψ, —C(O)—[C(R$^6$)(R$^7$)]—[C(R$^6$)$_2$]$_m$-ψ, —C(R$^6$)$_2$—N(R$^8$)—[C(R$^6$)(R$^7$)]—[C(R$^6$)$_2$]m-ψ, —C(R$^6$)=N-ψ, —C(R$^6$)$_2$C(R$^6$)=N-ψ, —N=C(R$^6$)-ψ, or —N=C(R$^6$)C(R$^6$)$_2$-ψ; wherein ψ is a bond to the sulfonamide ring nitrogen atom in Formula I;

Y is —N(R$^2$)(R$^3$) or —O-aralkyl, wherein said aralkyl is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N(R$^4$)(R$^5$), —CN, —CO$_2$—C$_{1-6}$alkyl, —C(O)—C$_{1-6}$alkyl, —C(O)N(R$^4$)(R$^5$), —S(O)$_p$C$_{1-6}$alkyl, —SO$_2$N(R$^4$)(R$^5$), and —N(R$^4$)SO$_2$(C$_{1-6}$alkyl);

R$^1$ represents independently for each occurrence hydrogen, halogen, or $C_{1-6}$alkyl;

R$^2$ is —C(O)-aryl, —C(O)-aralkyl, —C(O)—[C(R$^6$)$_2$]$_m$-cycloalkyl, —C(O)—[C(R$^6$)$_2$]$_m$-heterocyclyl, —C(O)—C$_{1-8}$alkyl, —C(O)—C$_{1-6}$alkylene-C$_{1-6}$alkoxyl, —C(O)—C$_{1-6}$alkylene-cycloalkyl, or —C(O)—C$_{1-6}$ alkylene-heterocycloalkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$alkyl, $C_{1-6}$haloalkyl, —N(R$^4$)(R$^5$), —CN, —CO$_2$—C$_{1-6}$alkyl, —C(O)—C$_{1-6}$alkyl, —C(O)N(R$^4$)(R$^5$), —S(O)$_p$C$_{1-6}$alkyl, —SO$_2$N(R$^4$)(R$^5$), and —N(R$^4$)SO$_2$(C$_{1-6}$alkyl);

R$^3$ is hydrogen or $C_{1-6}$alkyl;

R$^4$ and R$^5$ each represent independently for each occurrence hydrogen or $C_{1-6}$alkyl; or R$^4$ and R$^5$ taken together with the nitrogen atom to which they are attached form a 3-7 membered heterocyclic ring;

R$^6$ represents independently for each occurrence hydrogen or $C_{1-6}$alkyl;

R$^7$ is hydrogen, hydroxyl, $C_{1-6}$hydroxyalkyl, $C_{1-6}$alkyl, $C_{1-6}$haloalkyl, —CO$_2$R$^6$, $C_{1-6}$ alkylene-CO$_2$R$^6$, $C_{1-4}$hydroxyalkylene-CO$_2$R$^6$, —N(R$^4$)(R$^5$), $C_{1-6}$alkylene-N(R$^4$)(R$^5$), $C_{1-6}$hydroxyalkylene-N(R$^4$)(R$^5$), —N(R$^4$)C(O)R$^9$, $C_{1-6}$alkylene-N(R$^4$)C(O)R$^9$, $C_{1-6}$alkylene-C(O)N(R$^4$)(R$^5$), —N(R$^4$)CO$_2$—C$_{1-6}$ alkyl, or C$_{1-6}$alkylene-N(R$^4$)(C(O)N(R$^4$)(R$^5$); or R$^7$ is heterocycloalkyl or C$_{1-4}$alkylene-heterocycloalkyl, wherein the heterocycloalkyl is optionally substituted with 1, 2, or 3 substituents independently selected from the group consisting of oxo, halogen, hydroxyl, C$_{1-6}$alkyl, C$_{1-6}$haloalkyl, C$_{1-6}$hydroxyalkyl, C$_{1-6}$alkoxy, and C$_{1-6}$haloalkoxy;

R$^8$ is hydrogen, C$_{1-6}$alkyl, or —C(O)—C$_{1-6}$alkyl;

R$^9$ is hydrogen, C$_{1-6}$alkyl, C$_{1-6}$hydroxyalkyl, C$_{1-6}$ alkylene-N(R$^4$)(R$^5$), or C$_{1-6}$alkylene-N(R$^4$)C(O)—C$_{1-6}$alkyl;

n is 1 or 2; and m and p each represent independently for each occurrence 0, 1, or 2.

29. The method of claim 1, wherein the agonist of RORγ is a compound of Formula I*:

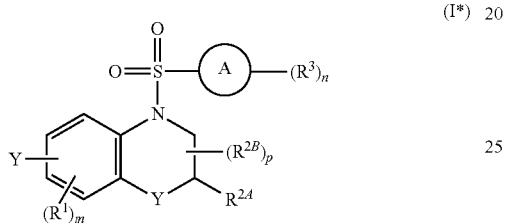

(I*)

or a pharmaceutically acceptable salt thereof; wherein:

A is phenylene, 5-6 membered heteroarylene, or C$_{3-6}$ heterocycloalkylene;

R$^1$ represents independently for each occurrence halogen, C$_{1-6}$ alkyl, C$_{1-6}$ haloalkyl, or C$_{3-6}$ cycloalkyl;

R$^{2A}$ is one of the following:
(i) hydrogen, C$_{1-6}$ alkyl, C$_{1-3}$ haloalkyl, C$_{3-6}$ cycloalkyl, —(C$_{1-6}$ alkylene)-(C$_{3-6}$ cycloalkyl), —O—(C$_{1-6}$ alkylene)-CO$_2$R$^4$, —O—(C$_{1-6}$ alkylene)-C(O)—(C$_{1-6}$ alkyl), —N(R$^4$)—(C$_{1-6}$ alkylene)-CO$_2$R$^4$, or —N(R$^4$)—(C$_{1-6}$ alkylene)-C(O)—(C$_{1-6}$ alkyl), wherein the C$_{1-6}$ alkyl, C$_{3-6}$ cycloalkyl, and C$_{1-6}$ alkylene are optionally substituted with 1 or 2 substituents independently selected from the group consisting of —CO$_2$R$^4$, —C(O)N(R$^4$)(R$^5$), —C(O)—N(R$^4$)—(C$_{1-4}$ alkylene)-CO$_2$R$^4$, —N(R$^4$)C(O)R$^8$, —CN, halogen, hydroxyl, C$_{1-6}$ alkoxy, C$_{1-6}$ haloalkoxy, C$_{1-6}$ haloalkyl, —N(R$^4$)(R$^5$), —N(R$^4$)C(O)N(R$^4$)(R$^5$), —N(R$^4$)CO$_2$R$^9$, —N(R$^4$)S(O)$_2$R$^9$, and —N(R$^4$)S(O)$_2$N(R$^4$)(R$^5$); or
(ii) —CO$_2$R$^4$, —N(R$^4$)C(O)R$^9$, —N(R$^4$)CO$_2$R$^9$, —N(R$^4$)C(O)N(R$^4$)(R$^5$), —N(R$^4$)C(O)N(R$^4$)(heteroaryl), —N(R$^4$)S(O)$_2$R$^9$, —N(R$^4$)(R$^5$), or —OH;

R$^{2B}$ is C$_{1-6}$ alkyl, C$_{1-3}$ haloalkyl, or fluoro;

R$^3$ represents independently for each occurrence hydrogen, C$_{1-6}$ haloalkyl, halogen, hydroxyl, C$_{1-6}$ alkyl, C$_{3-6}$ cycloalkyl, C$_{1-6}$ alkoxy, C$_{1-6}$ haloalkoxy, —N(R$^4$)(R$^8$), —O—(C$_{1-6}$ hydroxyalkyl), or —O—(C$_{1-6}$ alkylene)-CO$_2$R$^4$; or two vicinal occurrences of R$^3$ are taken together with intervening atoms to form a 4-6 membered ring;

R$^4$ and R$^5$ each represent independently for each occurrence hydrogen, C$_{1-6}$ alkyl, or C$_{3-6}$ cycloalkyl; or an occurrence of R$^4$ and R$^5$ attached to the same nitrogen atom are taken together with the nitrogen atom to which they are attached to form a 3-8 membered heterocyclic ring;

R$^6$ and R$^7$ each represent independently for each occurrence hydrogen, fluoro, or C$_{1-6}$ alkyl; or R$^6$ and R$^7$ are taken together with the carbon atom to which they are attached to form a 3-6 membered carbocyclic ring; or R$^6$ and a vicinal occurrence of R$^{2B}$ are taken together to form a bond;

R$^8$ represents independently for each occurrence C$_{1-6}$ alkyl, C$_{3-6}$ cycloalkyl, —(C$_{1-6}$ alkylene)-(C$_{3-6}$ cycloalkyl), or aryl, each of which is optionally substituted with 1, 2, or 3 substituents independently selected from the group consisting of halogen, hydroxyl, or —CO$_2$R$^4$; or R$^8$ is —CO$_2$R$^4$;

R$^9$ represents independently for each occurrence C$_{1-6}$ alkyl, C$_{3-6}$ cycloalkyl, —(C$_{1-6}$ alkylene)-(C$_{3-6}$ cycloalkyl), C$_{1-6}$ haloalkyl, or C$_{1-6}$ hydroxyalkyl;

X is one of the following:
(i) —O-aralkyl, —O-heteroaralkyl, —O-phenyl, —O-heteroaryl, —O— (partially unsaturated bicyclic carbocyclyl), —O—(C$_{1-6}$ alkylene)-(C$_{3-6}$ cycloalkyl), —O—(C$_{3-6}$ cycloalkyl), —N(R$^4$)-aralkyl, —N(R$^4$)-phenyl, —N(R$^4$)-(partially unsaturated bicyclic carbocyclyl), or —N(R$^4$)—(C$_{1-6}$ alkylene)-(C$_{3-6}$ cycloalkyl), each of which is optionally substituted with 1, 2, or 3 substituents independently selected from the group consisting of halogen, C$_{1-6}$ haloalkyl, C$_{1-6}$ alkyl, C$_{3-6}$ cycloalkyl, C$_{1-6}$ alkoxy, C$_{1-6}$ haloalkoxy, —S—(C$_{1-6}$ alkyl), hydroxyl, cyano, —C(O)R$^9$, and —SO$_2$R$^9$;
(ii) —S-aralkyl, —S-heteroaralkyl, —S-phenyl, —S-heteroaryl, —S-(partially unsaturated bicyclic carbocyclyl), —S—(C$_{1-6}$ alkylene)-(C$_{3-6}$ cycloalkyl), or —S—(C$_{3-6}$ cycloalkyl), each of which is optionally substituted with 1, 2, or 3 substituents independently selected from the group consisting of halogen, C$_{1-6}$ haloalkyl, C$_{1-6}$ alkyl, C$_{3-6}$ cycloalkyl, C$_{1-6}$ alkoxy, C$_{1-6}$ haloalkoxy, —S—(C$_{1-6}$ alkyl), hydroxyl, cyano, —C(O)R$^9$, and —SO$_2$R$^9$;
(iii) —(C$_{2-6}$ alkenylene)-phenyl, —(C$_{2-6}$ alkenylene)-heteroaryl, —(C$_{2-6}$ alkenylene)-(partially unsaturated 8-10 membered bicyclic ring containing 0-3 heteroatoms), —(C$_{1-6}$ alkylene)-phenyl, —(C$_{1-6}$ alkylene)-heteroaryl, —(C$_{1-6}$ alkylene)-(partially unsaturated bicyclic heterocyclyl), —(C$_{1-6}$ alkylene)-(partially unsaturated bicyclic oxo-heterocyclyl), —(C$_{1-6}$ alkylene)-(C$_3$-C$_6$ cycloalkyl), -(5-6 membered heterocycloalkylene)-phenyl, or —(C$_{3-6}$ cycloalkylene)-phenyl, each of which is optionally substituted with 1, 2, or 3 substituents independently selected from the group consisting of halogen, C$_{1-6}$ haloalkyl, C$_{1-6}$ alkyl, C$_{3-6}$ cycloalkyl, C$_{1-6}$ alkoxy, C$_{1-6}$ haloalkoxy, —S—(C$_{1-6}$ alkyl), hydroxyl, cyano, —C(O)R$^9$, and —SO$_2$R$^9$;
(iv) —(C$_{2-6}$ alkenylene)-(C$_{1-6}$ alkyl), —(C$_{2-6}$ alkenylene)-(C$_{3-6}$ cycloalkyl), or

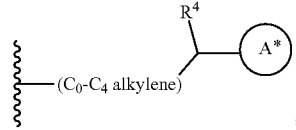

each of which is optionally substituted with 1, 2, or 3 substituents independently selected from the group consisting of halogen, C$_{1-6}$ haloalkyl, C$_{1-6}$ alkyl, C$_{3-6}$ cycloalkyl, C$_{1-6}$ alkoxy, C$_{1-6}$ haloalkoxy, —S—(C$_{1-6}$ alkyl), hydroxyl, cyano, —CO$_2$R$^4$, and —SO$_2$R$^9$, wherein A* is a 5-8 membered, partially saturated carbocyclic or heterocyclic ring; or
(v) —(C$_{1-6}$ alkylene)-Z$^1$ or —(C$_{2-6}$ alkenylene)-Z$^1$, wherein Z$^1$ is —O-aralkyl, —O— heteroaralkyl, —O- phenyl, —O-heteroaryl, —O— (partially unsaturated bicyclic carbocyclyl), —O—($C_{1-6}$ alkylene)-($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), —N($R^4$)—($C_{1-6}$ alkylene)-($C_{3-6}$ cycloalkyl), or —N($R^4$)—($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, —S—($C_{1-6}$ alkyl), hydroxyl, cyano, —C(O)$R^9$, and —SO$_2R^9$;

Y is —C($R^6$)($R^7$)—, —O—, —C(O)—, or —S(O)$_p$—;

m and p each represent independently for each occurrence 0, 1, or 2; and n is 1, 2, or 3.

30. The method of claim 29, wherein A is phenylene or 5-6 membered heteroarylene.

31. The method of claim 30, wherein $R^1$ represents independently for each occurrence halogen or $C_{1-6}$ alkyl.

32. The method of claim 30, wherein $R^{24}$ is $C_{1-6}$ alkyl substituted with 1 or 2 substituents independently selected from the group consisting of —CO$_2R^4$, —C(O)N($R^4$)($R^5$), —C(O)—N($R^4$)—($C_{1-4}$ alkylene)-CO$_2R^4$, —N($R^4$)C(O)$R^8$, —CN, halogen, hydroxyl, $C_{1-6}$ alkoxy, $C_{1-6}$ haloalkoxy, $C_{1-6}$ haloalkyl, —N($R^4$)($R^5$), —N($R^4$)C(O)N($R^4$)($R^5$), —N($R^4$)CO$_2R^9$, —N($R^4$)S(O)$_2R^9$, and —N($R^4$)S(O)$_2$N($R^4$)($R^5$).

33. A method of treating a medical disorder, comprising administering to a patient in need thereof a lymphocyte cell that has been exposed ex vivo to an agonist of RORγ to treat the medical disorder.

34. The method of claim 33, wherein the lymphocyte cell is a T cell.

35. The method of claim 33, wherein the lymphocyte cell is a CD8$^+$ T cell, CD4$^+$ T cell, or $T_H17$ cell.

36. The method of claim 33, wherein the lymphocyte cell is a Tc17 cell, natural killer T cell, or γδ T cell.

37. The method of claim 33, wherein the medical disorder is cancer.

* * * * *